United States Patent [19]

Niwa et al.

[11] Patent Number: 5,840,533
[45] Date of Patent: Nov. 24, 1998

[54] TISSUE PLASMINOGEN ACTIVATOR

[75] Inventors: Mineo Niwa, Muko; Yoshimasa Saito, Osaka; Hitoshi Sasaki, Amagasaki; Masako Hayashi; Jouji Notani, both of Takatsuki; Masakazu Kobayashi, Ikeda, all of Japan

[73] Assignee: Fujisawa Pharmaceutical Co., Ltd., Osaka, Japan

[21] Appl. No.: 811,949

[22] Filed: Mar. 5, 1997

Related U.S. Application Data

[62] Division of Ser. No. 412,859, Mar. 29, 1995, Pat. No. 5,648,250, which is a continuation of Ser. No. 238,796, May 6, 1994, abandoned, which is a continuation of Ser. No. 131,672, Oct. 5, 1993, abandoned, which is a continuation of Ser. No. 991,714, Dec. 16, 1992, abandoned, which is a continuation of Ser. No. 879,736, May 6, 1992, abandoned, which is a continuation of Ser. No. 711,410, Jun. 5, 1991, abandoned, which is a continuation of Ser. No. 227,149, Aug. 2, 1988, abandoned.

[30] Foreign Application Priority Data

Aug. 3, 1987 [GB] United Kingdom .................. 8718298
Oct. 26, 1987 [GB] United Kingdom .................. 8725052
Nov. 13, 1987 [GB] United Kingdom .................. 8726683

[51] Int. Cl.$^6$ .......................... C12P 21/02; C07H 21/04; C12N 15/58; C12N 15/70
[52] U.S. Cl. ...................... 435/69.1; 435/172.3; 435/212; 435/320.1; 514/12; 530/23.2
[58] Field of Search ...................................... 435/212, 69.1, 435/320.1, 172.3; 536/23.2; 514/12

[56] References Cited

U.S. PATENT DOCUMENTS 5,648,250 7/1997 Niwa et al. ......................... 435/172.3

FOREIGN PATENT DOCUMENTS 0093619 11/1983 European Pat. Off. .
0196920 10/1986 European Pat. Off. .
0199574 10/1986 European Pat. Off. .
8401786 5/1984 WIPO .

OTHER PUBLICATIONS van Zonneveld et al. (1986), Proc. Natl. Acad. Sci. USA, 83: 4670–4674.

*Primary Examiner*—Nancy Degen
*Attorney, Agent, or Firm*—Oblon, Spivak, McClelland, Maier & Neustadt, P.C.

[57] ABSTRACT

The invention relates to a new tissue plasminogen activator which has strong activity for converting plasminogen into plasmin that degrades the fibrin network of blood clots to form soluble products and therefore is useful as a thrombolytic agent. The invention also relates to a DNA sequence encoding the amino acid sequence for the tissue plasminogen activator, to a process for producing the plasminogen activator, and to a pharmaceutical composition comprising the new tissue plasminogen activator.

4 Claims, 58 Drawing Sheets

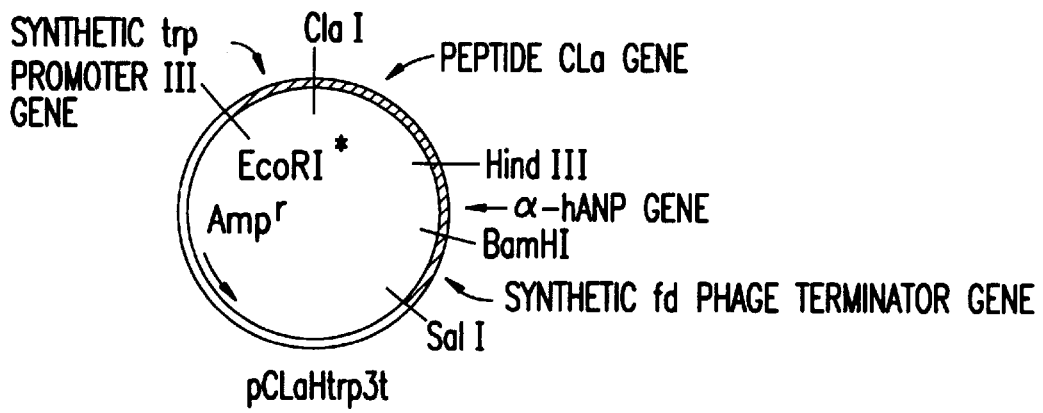
DIGESTION WITH BamHI AND Hind III
LIGATION WITH DNA FRAGMENT (27bp)
TRANSFORMATION OF E. coli DH-1 AND CULTIVATION
ISOLATION OF PLASMID pHVBB
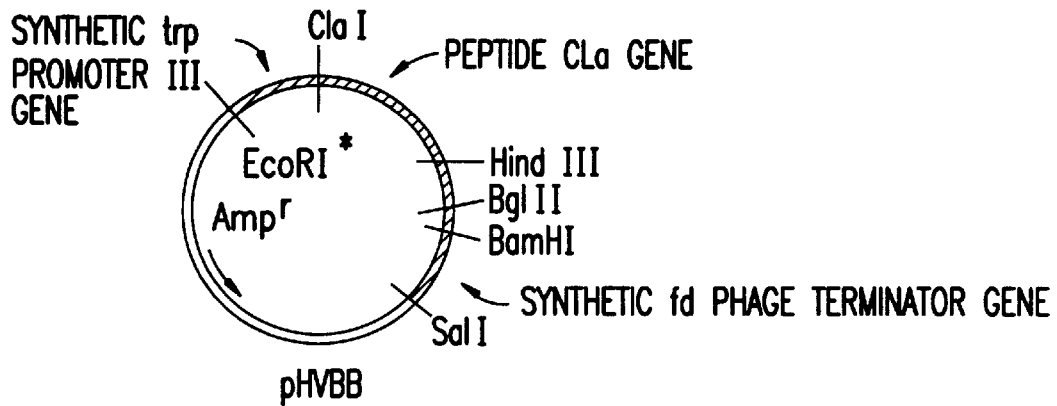
FIG.1

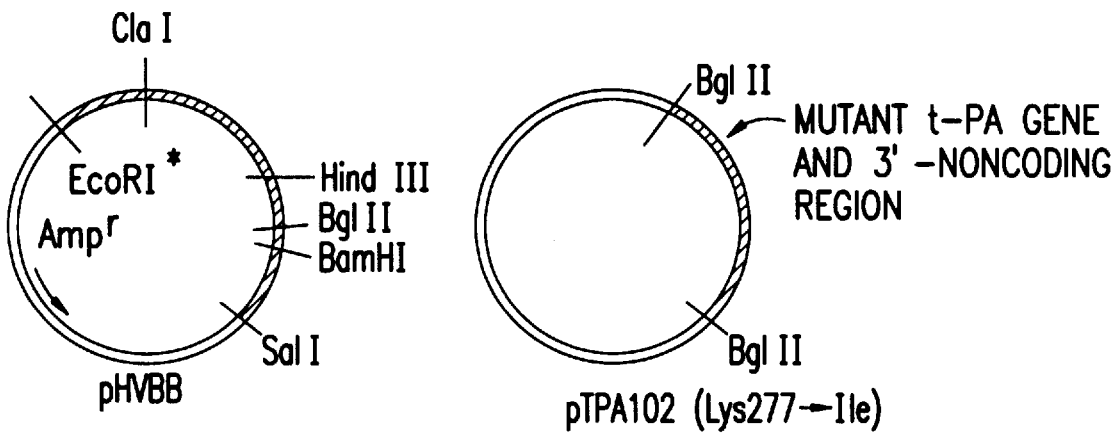
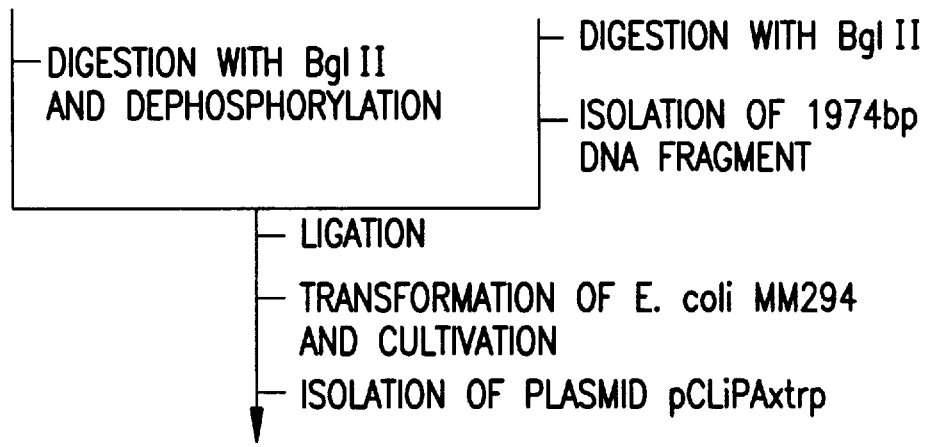
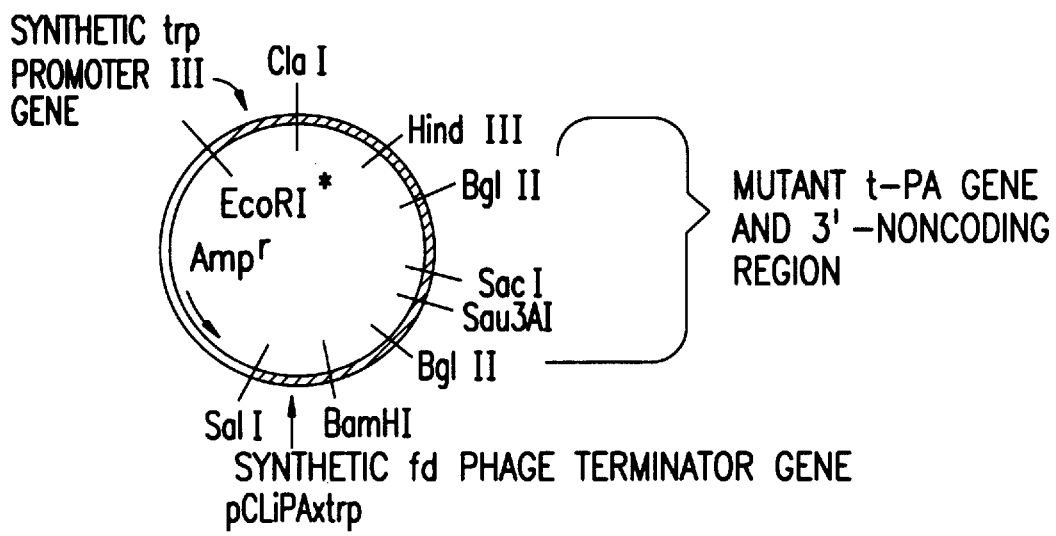
FIG.2

```
              (Bgl II)
Coding chains:5'- GATCTTACCAAGTGATCTGCAGAGATGAAAAAACGCAGATGATATACCAG
                  SerTyrGlnValIleCysArgAspGluLysThrGlnMetIleTyrGln
                 |→ Mutant t-PA                 10
```

```
CAACATCAGTCATGGCTGCGCCCTGTGCTCAGAAGCAACCGGGTGGAATATTGCTGGTGC
GlnHisGlnSerTrpLeuArgProValLeuArgSerAsnArgValGluTyrCysTrpCys
         20                              30

AACAGTGGCAGGGCACAGTGCCACTCAGTGCCTGTCAAAAGTTGCAGCGAGCCAAGGTGT
AsnSerGlyArgAlaGlnCysHisSerValProValLysSerCysSerGlyProArgCys
         40                              50

TTCAACGGGGGCACCTGCCAGCAGGCCCTGTACTTCTCAGATTTCGTGTGCCAGTGCCCC
PheAsnGlyGlyThrCysGlnGlnAlaLeuTyrPheSerAspPheValCysGlnCysPro
         60                              70
                                                    (AvaII)
GAAGGATTTGCTGGGAAGTGCTGTGAAATAGATACCAGGGCCACGTGCTACGAGGACCAG
GluGlyPheAlaGlyLysCysCysGluIleAspThrArgAlaThrCysTyrGluAspGln
         80                              90
                                     (BbeI)
GGCATCAGCTACAGGGGCACGTGGAGCACAGCGGAGAGTGGCGCCGAGTGCACCAACTGG
GlyIleSerTyrArgGlyThrTrpSerThrAlaGluSerGlyAlaGluCysThrAsnTrp
         100                             110

AACAGCAGCGCGTTGGCCCAGAAGCCCTACAGCGGGCGGAGGCCAGACGCCATCAGGCTG
AsnSerSerAlaLeuAlaGlnLysProTyrSerGlyArgArgProAspAlaIleArgLeu
         120                            .130

GGCCTGGGGAACCACAACTACTGCAGAAACCCAGATCGAGACTCAAAGCCCTGGTGCTAC
GlyLeuGlyAsnHisAsnTyrCysArgAsnProAspArgAspSerLysPorTrpCysTyr
         140                             150
                                                     (DdeI)
GTCTTTAAGGCGGGGAAGTACAGCTCAGAGTTCTGCAGCACCCCTGCCTGCTCTGAGGGA
ValPheLysAlaGlyLysTyrSerSerGluPheCysSerThrProAlaCysSerGluGly
         160                             170

AACAGTGACTGCTACTTTGGGAATGGGTCAGCCTACCGTGGCACGCACAGCCTCACCGAG
AsnSerAspCysTyrPheGlyAsnGlySerAlaTyrArgGlyThrHisSerLeuThrGlu
         180                             190
                    (EcoRI)
TCGGGTGCCTCCTGCCTCCCGTGGAATTCCATGATCCTGATAGGCAAGGTTTACACAGCA
SerGlyAlaSerCysLeuProTrpAsnSerMetIleLeuIleGlyLysValTyrThrAla
         200                             210
```

FIG.3A

```
CAGAACCCCAGTGCCCAGGCACTGGGCCTGGGCAAACATAATTACTGCCGGAATCCTGAT
GlnAsnProSerAlaGlnAlaLeuGlyLeuGlyLysHisAsnTyrCysArgAsnProAsp
         220                              230

GGGGATGCCAAGCCCTGGTGCCACGTGCTGAAGAACCGCAGGCTGACGTGGGAGTACTGT
GlyAspAlaLysProTrpCysHisValLeuLysAsnArgArgLeuThrTrpGluTyrCys
         240                              250

GATGTGCCCTCCTGCTCCACCTGCGGCCTGAGACAGTACAGCCAGCCTCAGTTTCGCATC
AspValProSerCysSerThrCysGlyLeuArgGlnTyrSerGlnProGlnPheArgIle
         260                              270

ATAGGAGGCCTCTTCGCCGACATCGCCTCCCACCCCTGGCAGGCTGCCATCTTTGCCAAG
IleGlyGlyLeuPheAlaAspIleAlaSerHisProTrpGlnAlaAlaIlePheAlaLys
         280                              290

CACAGGAGGTCGCCCGGAGAGCGGTTCCTGTGCGGGGGCATACTCATCAGCTCCTGCTGG
HisArgArgSerProGlyGluArgPheLeuCysGlyGlyIleLeuIleSerSerCysTrp
         300                              310

ATTCTCTCTGCCGCCCACTGCTTCCAGGAGAGGTTTCCGCCCCACCACCTGACGGTGATC
IleLeuSerAlaAlaHisCysPheGlnGluArgPheProProHisHisLeuThrValIle
         320                              330

TTGGGCAGAACATACCGGGTGGTCCCTGGCGAGGAGGAGCAGAAATTTGAAGTCGAAAAA
LeuGlyArgThrTyrArgValValProGlyGluGluGluGlnLysPheGluValGluLys
         340                              350
              (EcoRI)
TACATTGTCCATAAGGAATTCGATGATGACACTTACGACAATGACATTGCGCTGCTGCAG
TyrIleValHisLysGluPheAspAspAspThrTyrAspAsnAspIleAlaLeuLeuGln
         360                              370

CTGAAATCGGATTCGTCCCGCTGTGCCCAGGAGAGCAGCGTGGTCCGCACTGTGTGCCTT
LeuLysSerAspSerSerArgCysAlaGlnGluSerSerValValArgThrValCysLeu
         380                              390
                                        (Sac I)
CCCCCGGCGGACCTGCAGCTGCCGGACTGGACGGAGTGTGAGCTCTCCGGCTACGGCAAG
ProProAlaAspLeuGlnLeuProAspTrpThrGluCysGluLeuSerGlyTyrGlyLys
         400                              410

CATGAGGCCTTGTCTCCTTTCTATTCGGAGCGGCTGAAGGAGGCTCATGTCAGACTGTAC
HisGluAlaLeuSerProPheTyrSerGluArgLeuLysGluAlaHisValArgLeuTyr
         420                              430
```

FIG.3B

```
CCATCCAGCCGCTGCACATCACAACATTTACTTAACAGAACAGTCACCGACAACATGCTG
ProSerSerArgCysThrSerGlnHisLeuLeuAsnArgThrValThrAspAsnMetLeu
         440                                    450

TGTGCTGGAGACACTCGGAGCGGCGGGCCCCAGGCAAACTTGCACGACGCCTGCCAGGGC
CysAlaGlyAspThrArgSerGlyGlyProGlnAlaAsnLeuHisAspAlaCysGlnGly
         460                                    470

GATTCGGGAGGCCCCCTGGTGTGTCTGAACGATGGCCGCATGACTTTGGTGGGCATCATC
AspSerGlyGlyProLeuValCysLeuAsnAspGlyArgMetThrLeuValGlyIleIle
         480                                    490

AGCTGGGGCCTGGGCTGTGGACAGAAGGATGTCCCGGGTGTGTACACAAAGGTTACCAAC
SerTrpGlyLeuGlyCysGlyGlnLysAspValProGlyValTyrThrLysValThrAsn
         500                                    510

TACCTAGACTGGATTCGTGACAACATGCGACCGTGACCAGGAACACCCGACTCCTCAAAA
TyrLeuAspTrpIleArgAspAsnMetArgPro***|→  Noncoding (Sau3AI)
GCAAATGAGATCCCGCCTCTTCTTCTTCAGAAGACACTGCAAAGGCGCAGTGCTTCTCTA

CAGACTTCTCCAGACCCACCACACCGCAGAAGCGGGACGAGACCCTACAGGAGAGGGAAG

AGTGCATTTTCCCAGATACTTCCCATTTTGGAAGTTTTCAGGACTTGGTCTGATTTCAGG

ATACTCTGTCAGATGGGAAGACATGAATGCACACTAGCCTCTCCAGGAATGCCTCCTCCC

TGGGCAGAAGTGGCCATGCCACCCTGTTTTCGCTAAAGCCCAACCTCCTGACCTGTCACC

GTGAGCAGCTTTGGAAACAGGACCACAAAAATGAAAGCATGTCTCAATAGTAAAAGAAAC (Bgl II)
AAGA -3'
```

FIG.3C

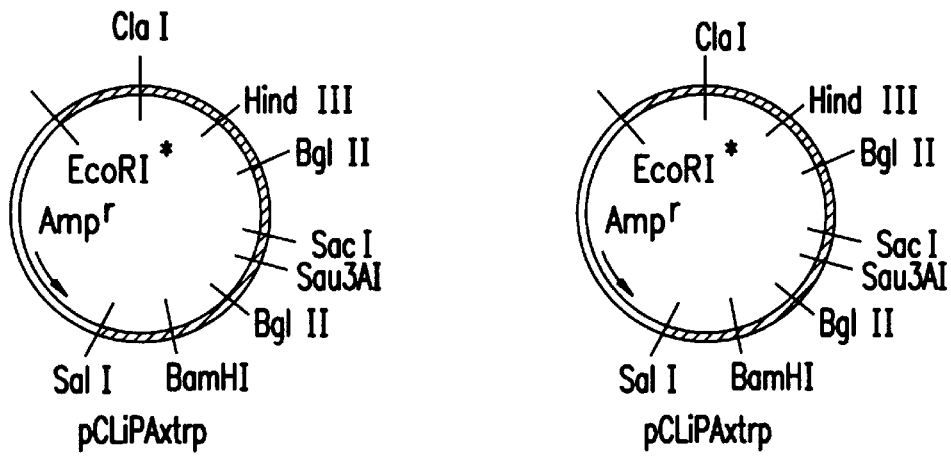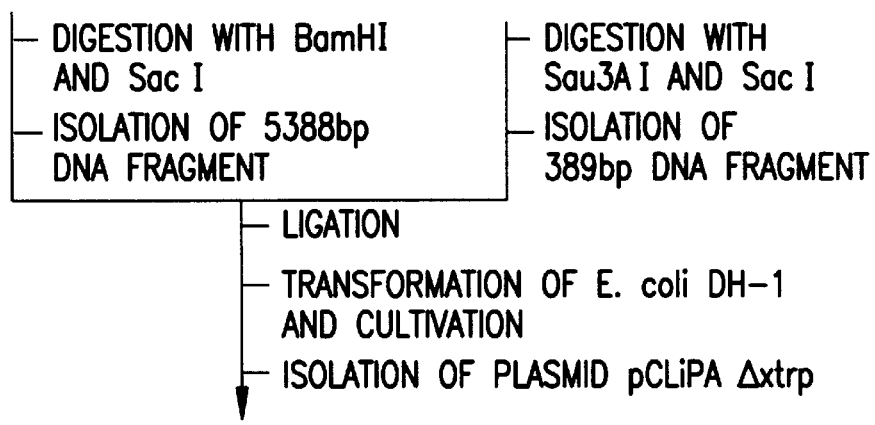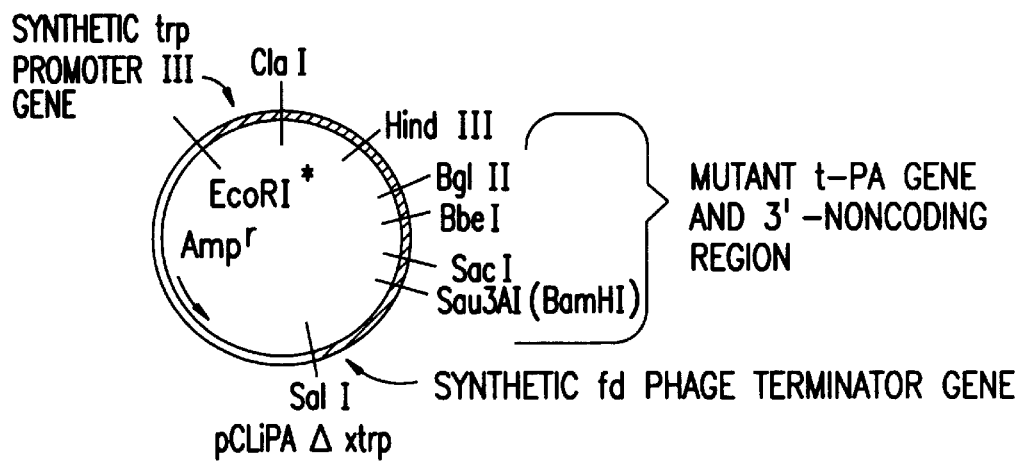
FIG.4

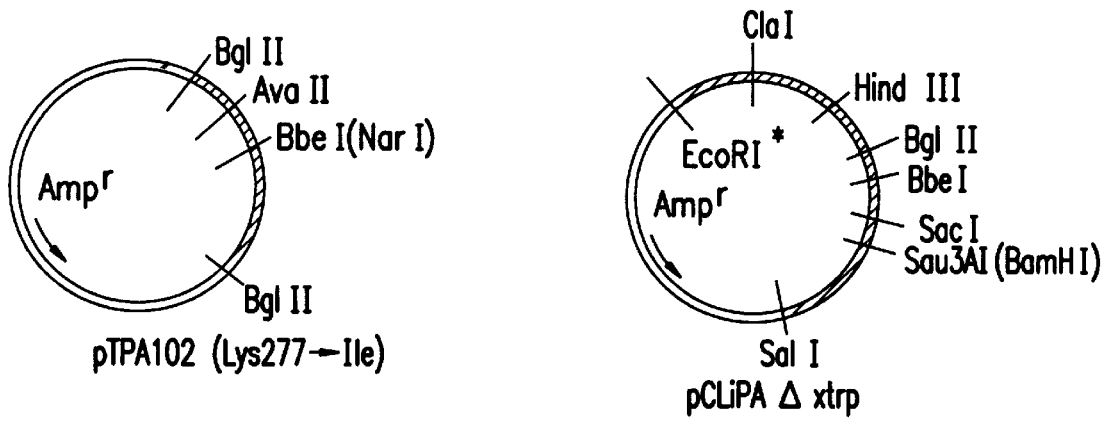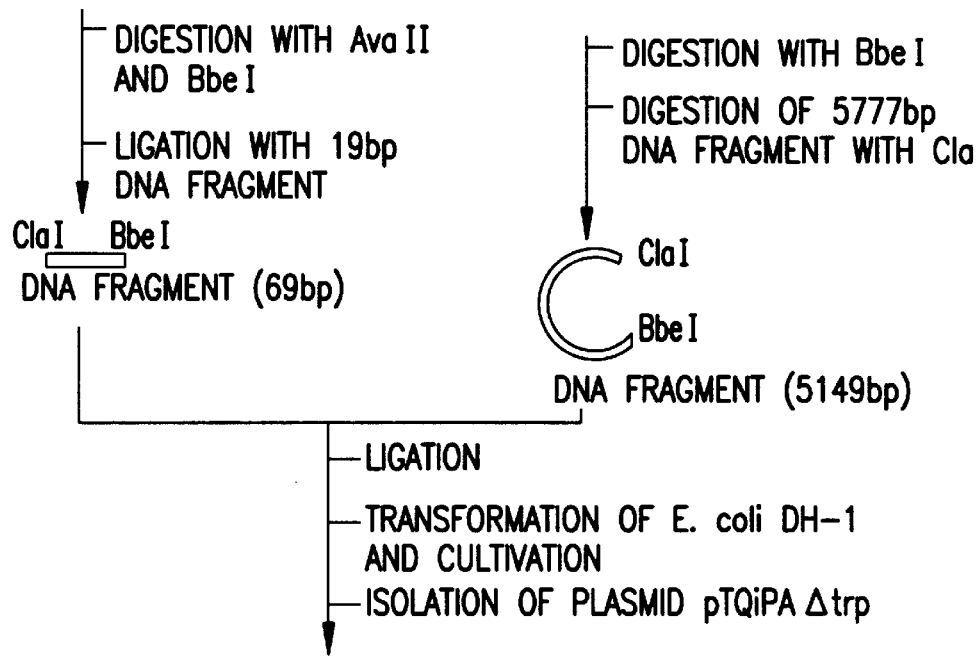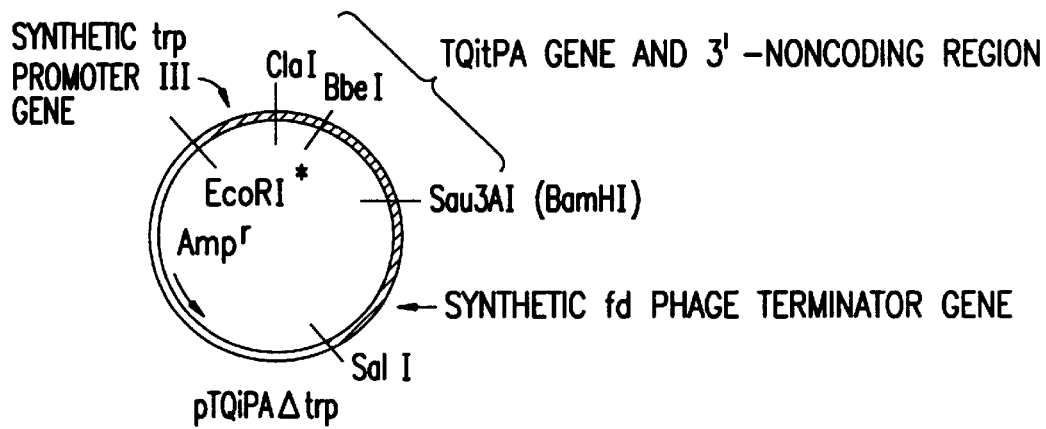
FIG.5

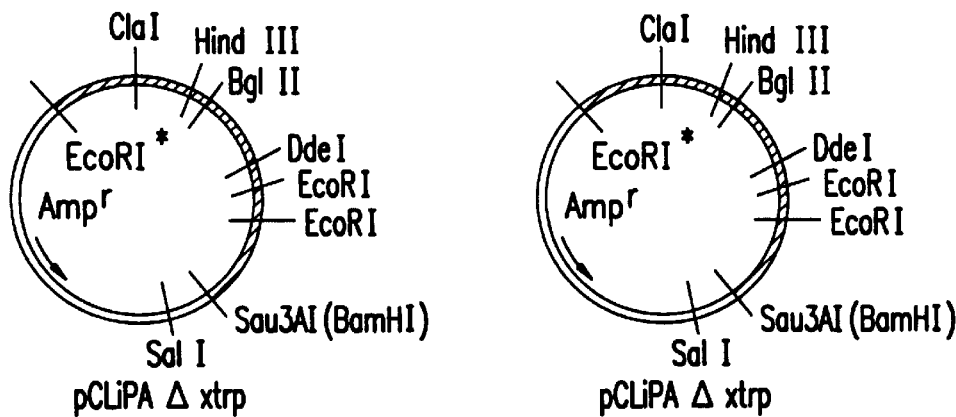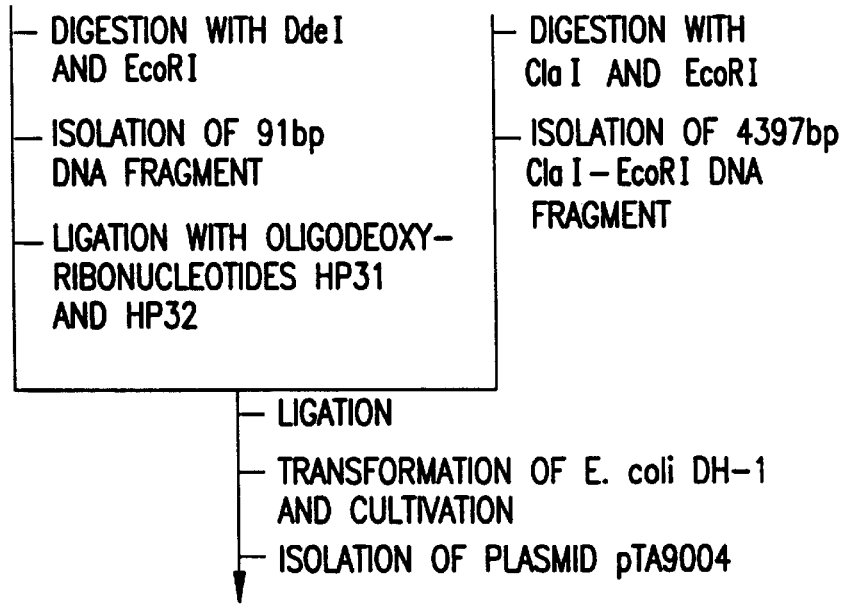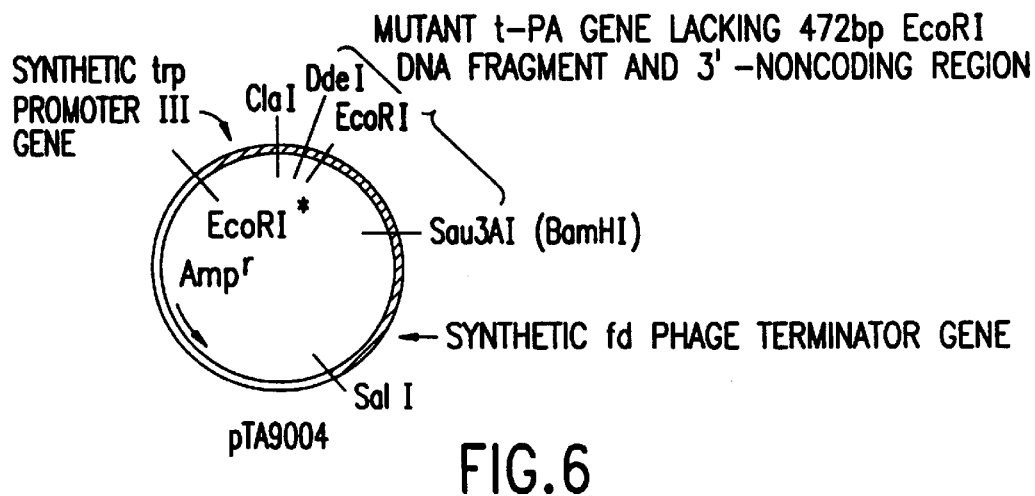
FIG.6

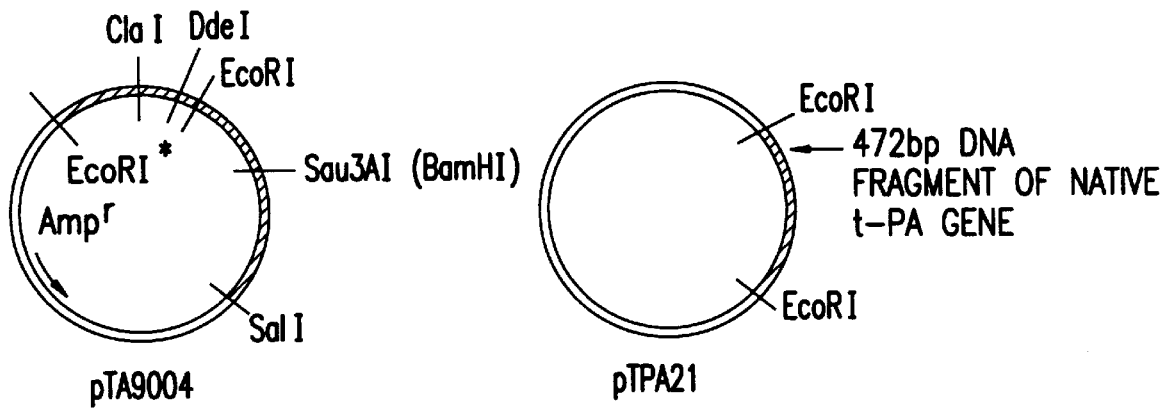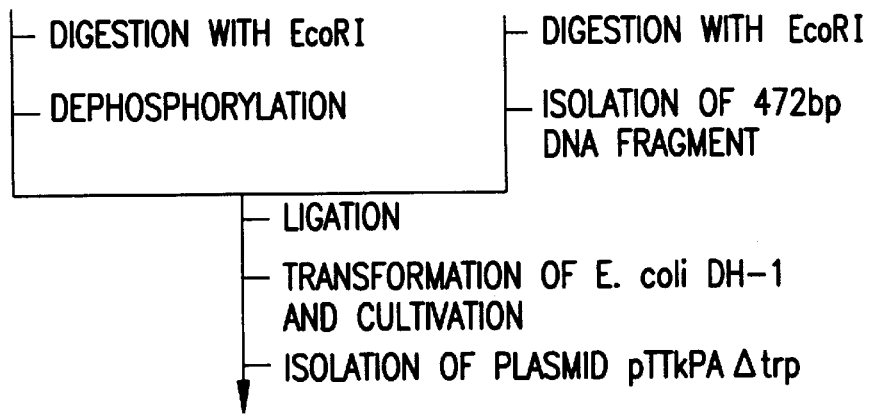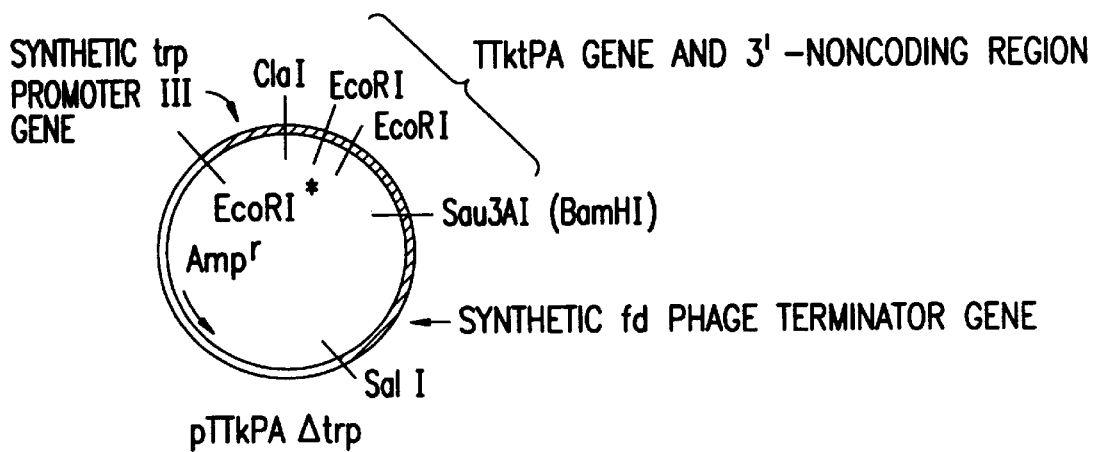
FIG.7

```
                          (EcoRI)
Coding chain:      5'- AATTCCATGATCCTGATAGGCAAGGTTTACACAGCA
Amino acid sequence:   AsnSerMetIleLeuIleGlyLysValTyrThrAla CAGAACCCCAGTGCCCAGGCACTGGGCCTGGGCAAACATAATTACTGCCGGAATCCTGAT
GlnAsnProSerAlaGlnAlaLeuGlyLeuGlyLysHisAsnTyrCysArgAsnProAsp GGGGATGCCAAGCCCTGGTGCCACGTGCTGAAGAACCGCAGGCTGACGTGGGAGTACTGT
GlyAspAlaLysProTrpCysHisValLeuLysAsnArgArgLeuThrTrpGluTyrCys GATGTGCCCTCCTGCTCCACCTGCGGCCTGAGACAGTACAGCCAGCCTCAGTTTCGCATC
AspValProSerCysSerThrCysGlyLeuArgGlnTyrSerGlnProGlnPheArgIle AAAGGAGGGCTCTTCGCCGACATCGCCTCCCACCCCTGGCAGGCTGCCATCTTTGCCAAG
LysGlyGlyLeuPheAlaAspIleAlaSerHisProTrpGlnAlaAlaIlePheAlaLys CACAGGAGGTCGCCCGGAGAGCGGTTCCTGTGCGGGGGCATACTCATCAGCTCCTGCTGG
HisArgArgSerProGlyGluArgPheLeuCysGlyGlyIleLeuIleSerSerCysTrp ATTCTCTCTGCCGCCCACTGCTTCCAGGAGAGGTTTCCGCCCCACCACCTGACGGTGATC
IleLeuSerAlaAlaHisCysPheGlnGluArgPheProProHisHisLeuThrValIle TTGGGCAGAACATACCGGGTGGTCCCTGGCGAGGAGGAGCAGAAATTTGAAGTCGAAAAA
LeuGlyArgThrTyrArgValValProGlyGluGluGluGlnLysPheGluValGluLys
                    (EcoRI)
TACATTGTCCATAAGG  -3'
TyrIleValHisLys
```

FIG.8

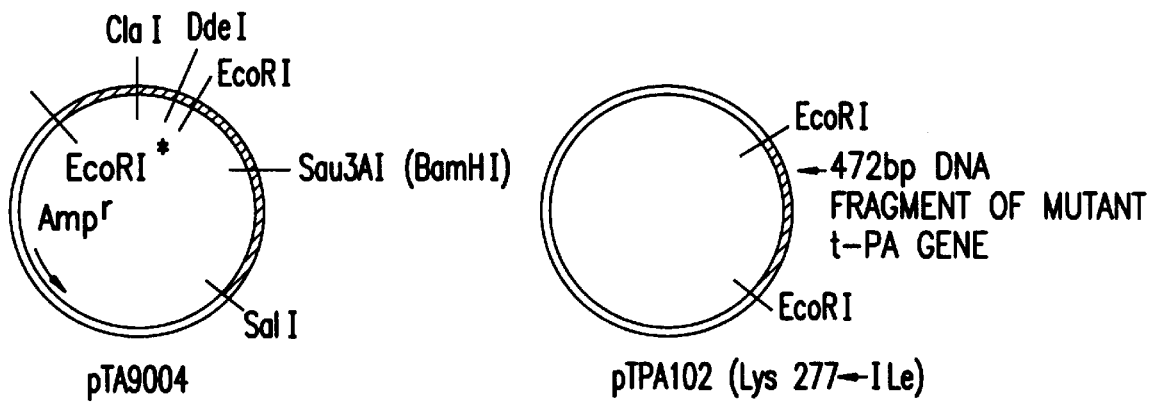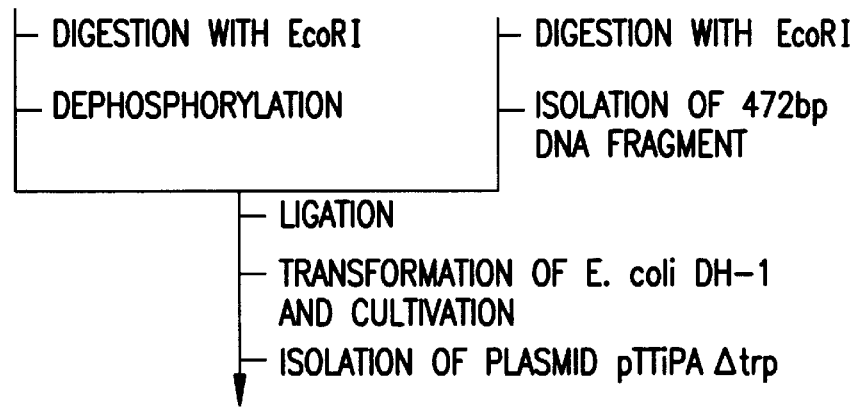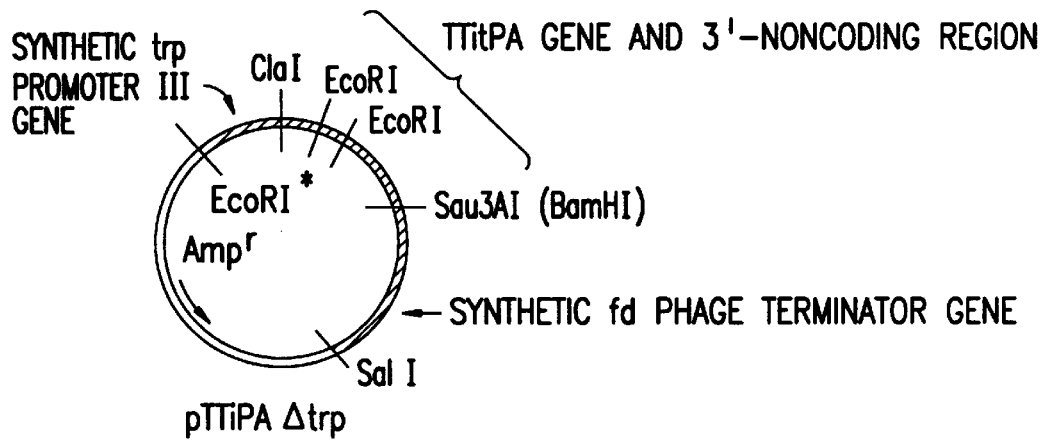
FIG.9

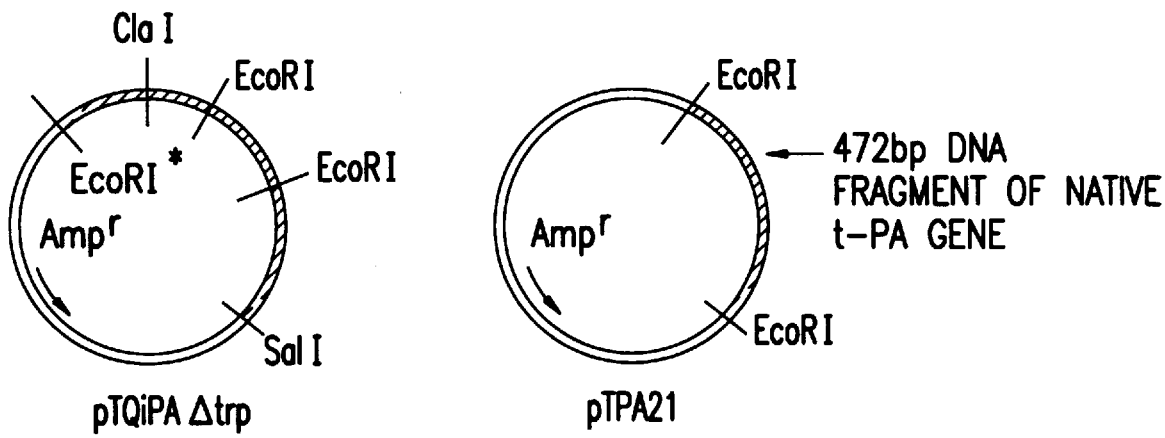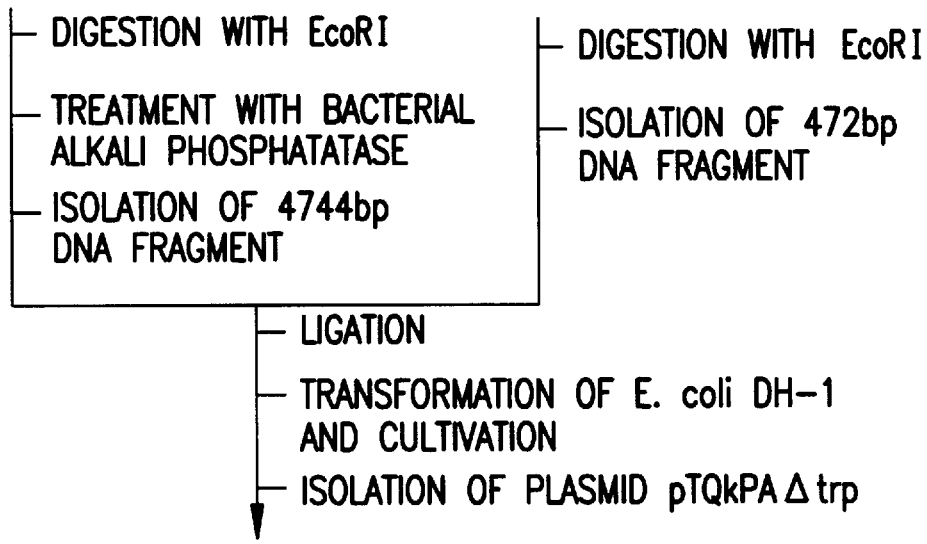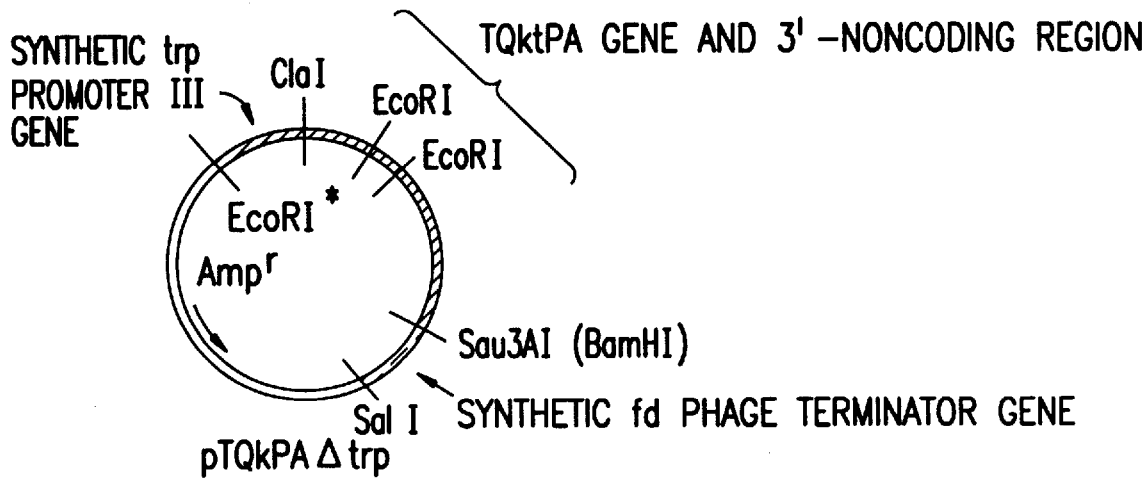
FIG.10

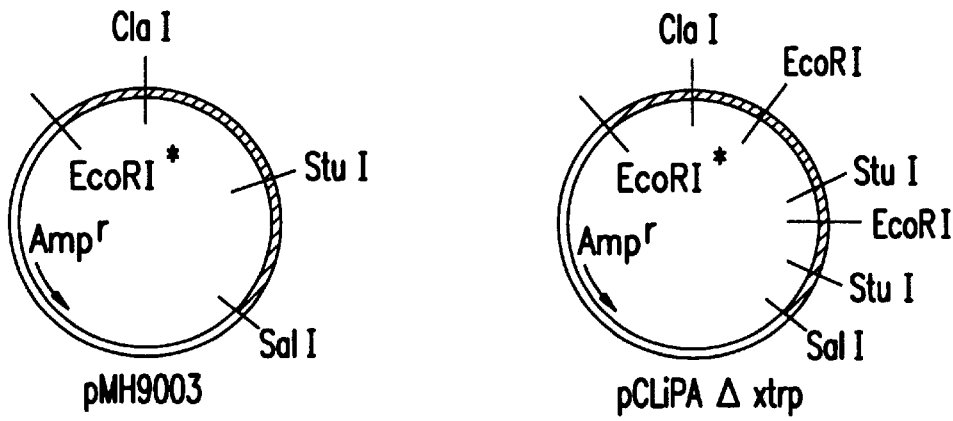
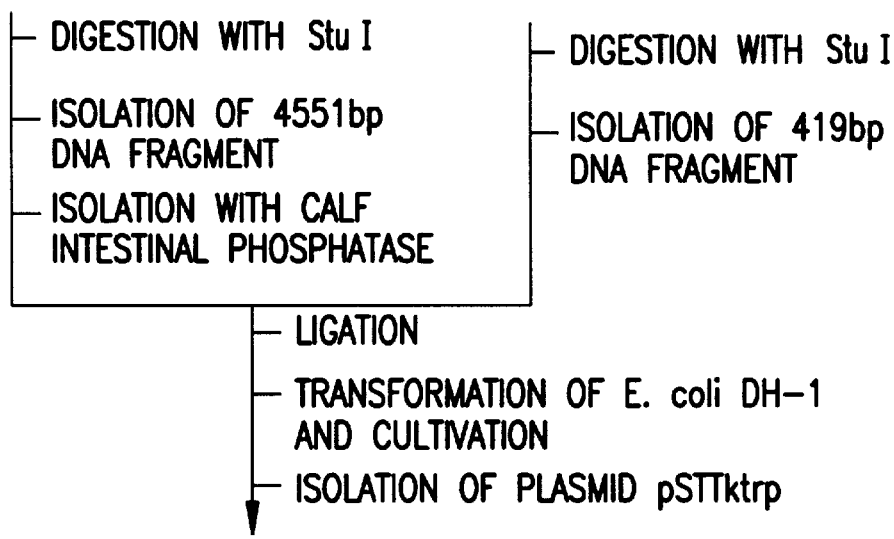
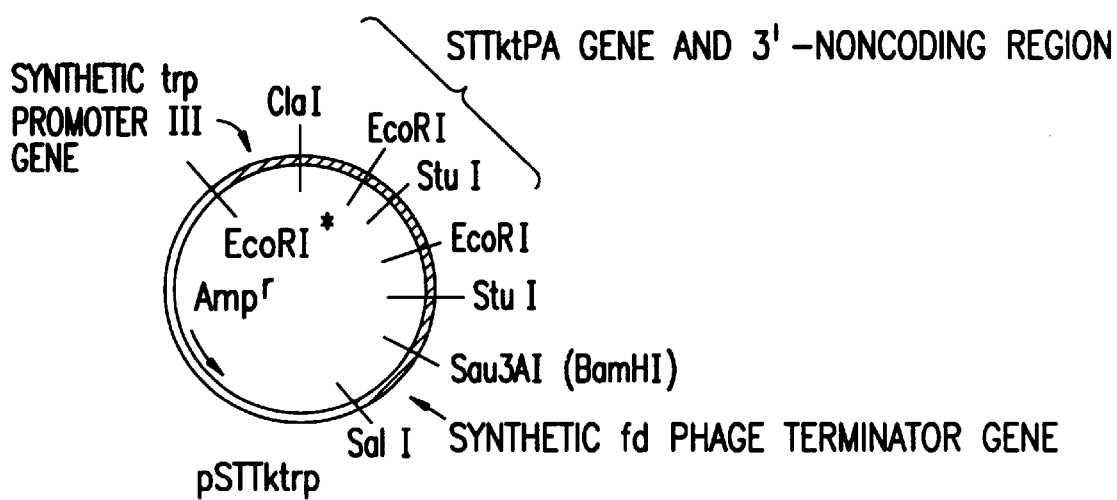
FIG.12

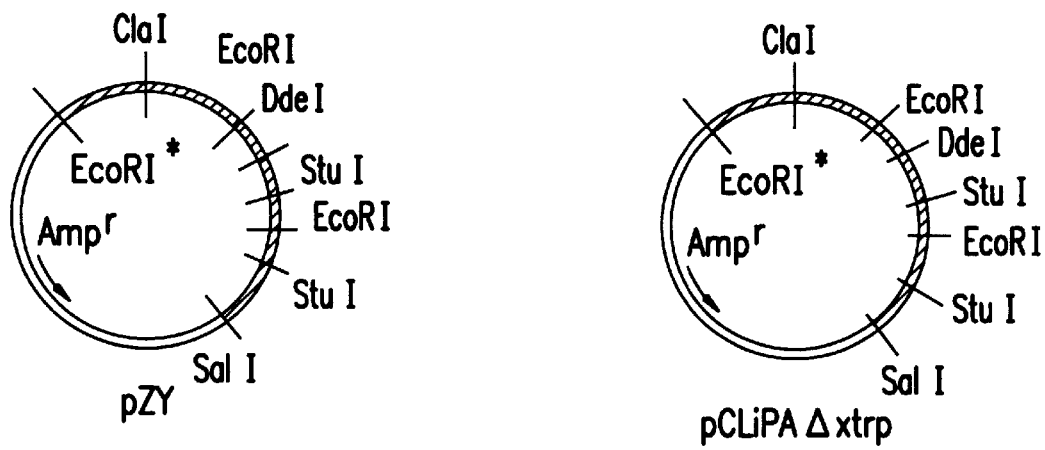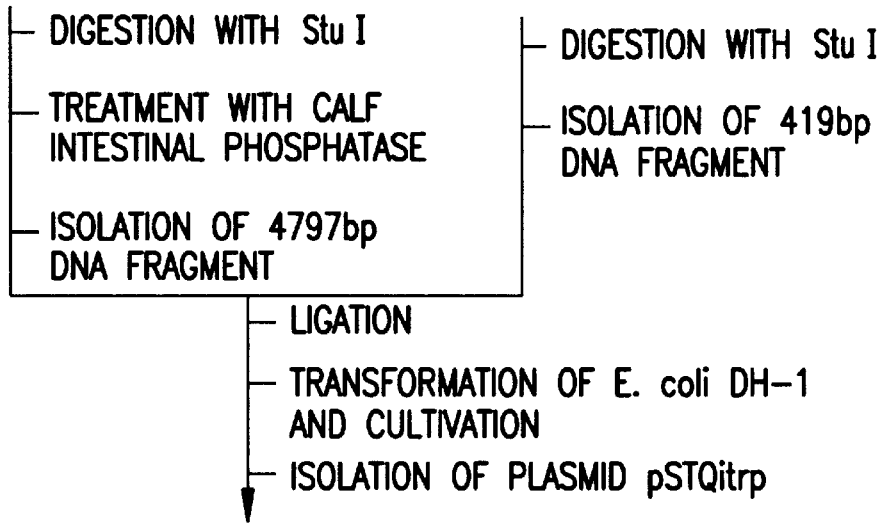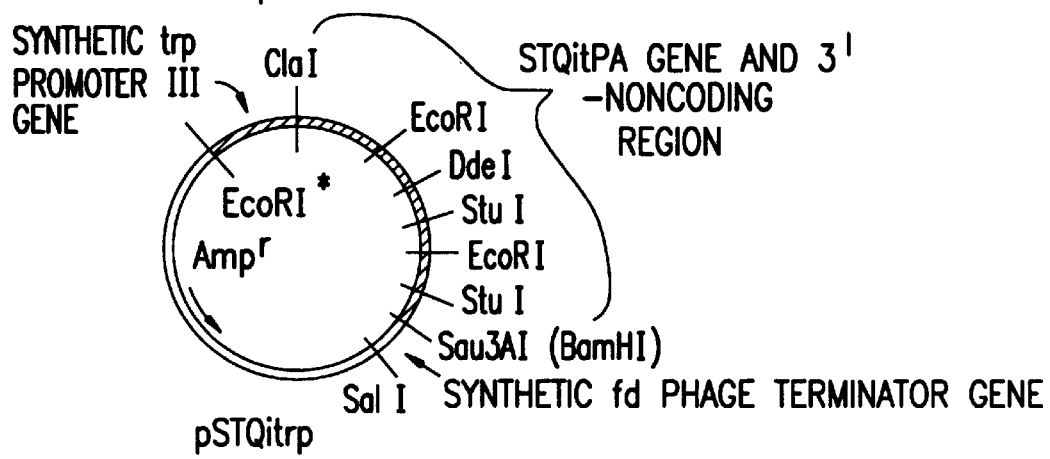
FIG.14

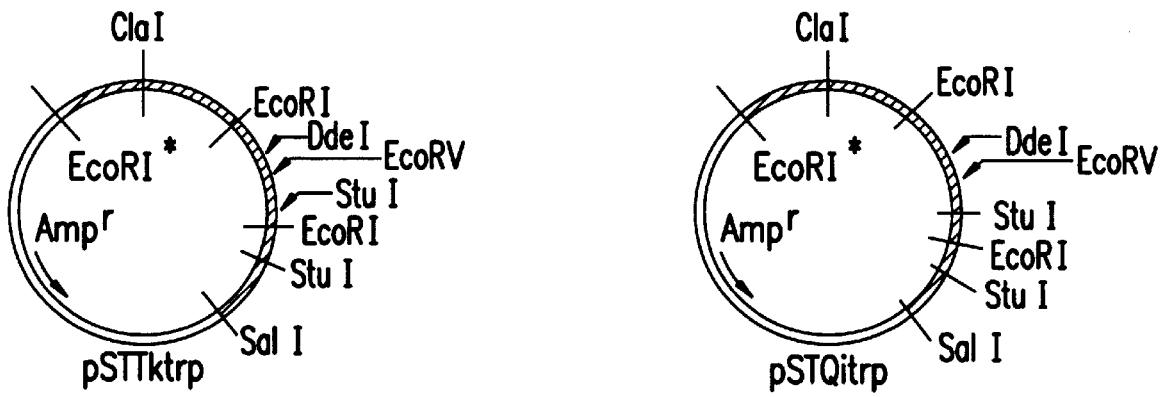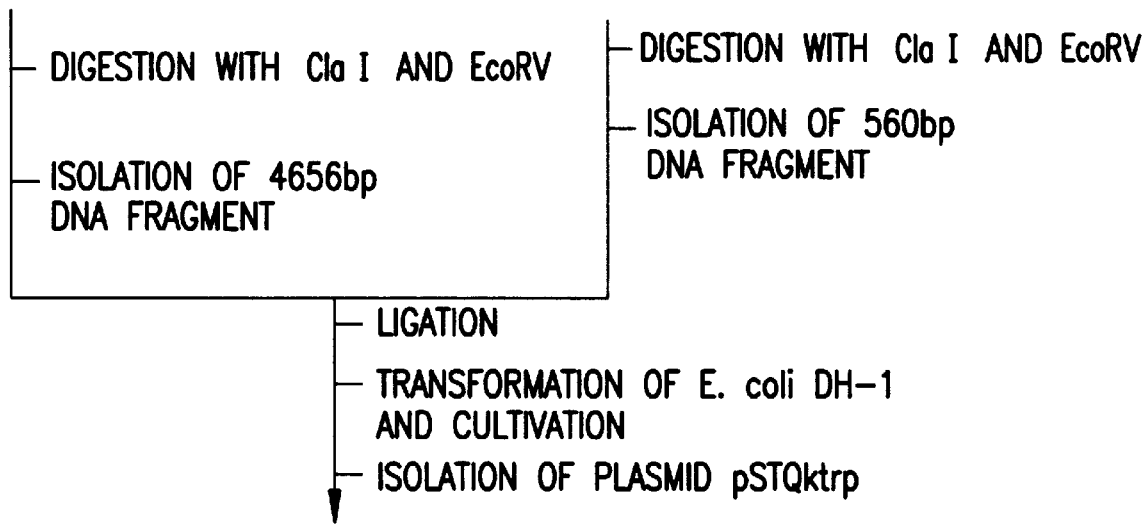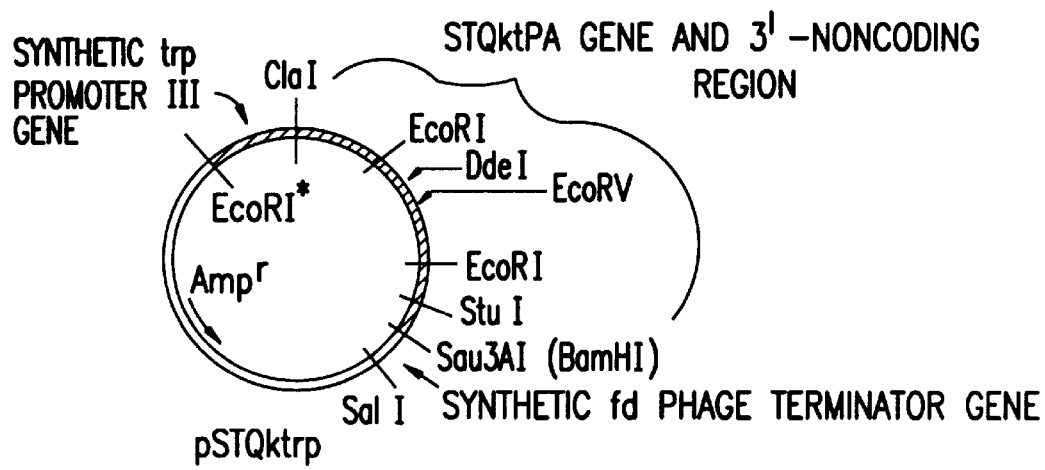
FIG.15

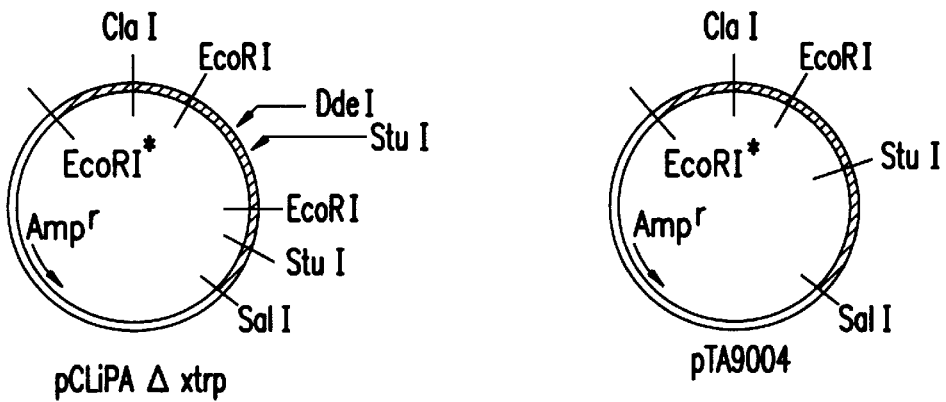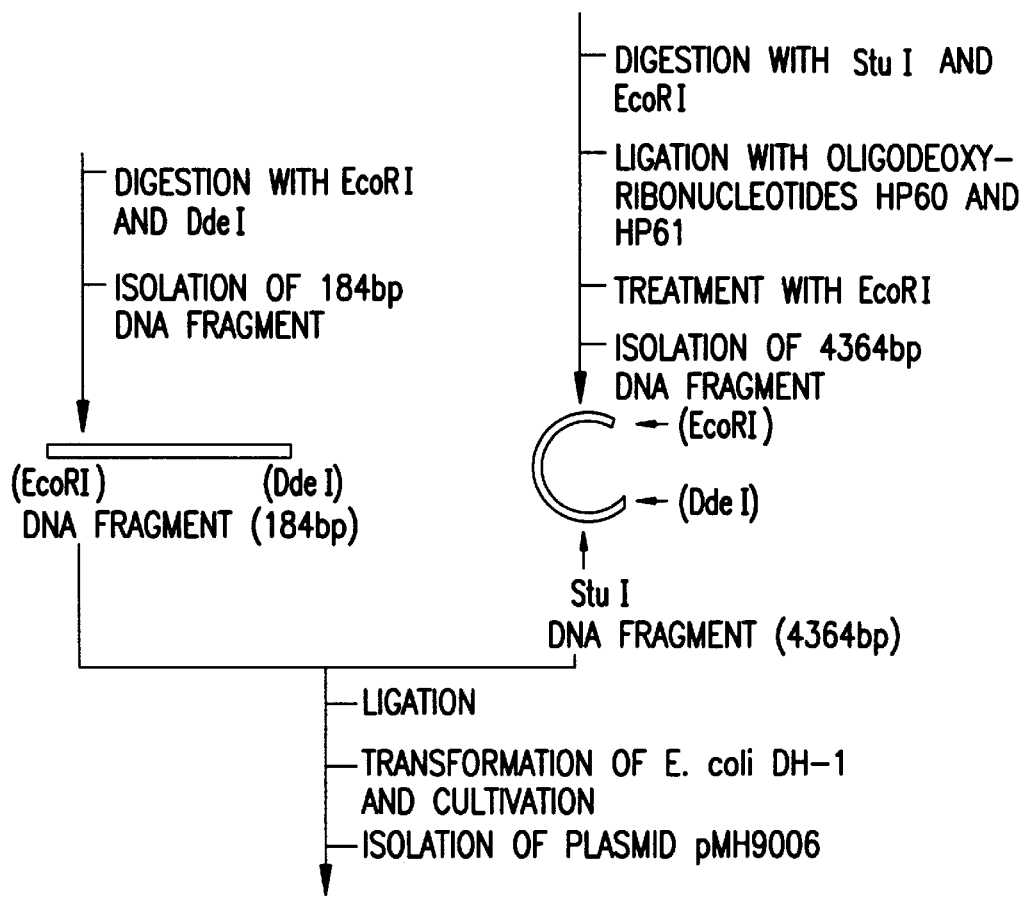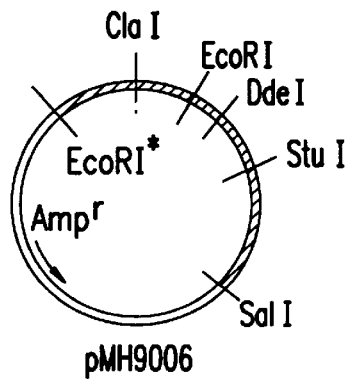
FIG.16

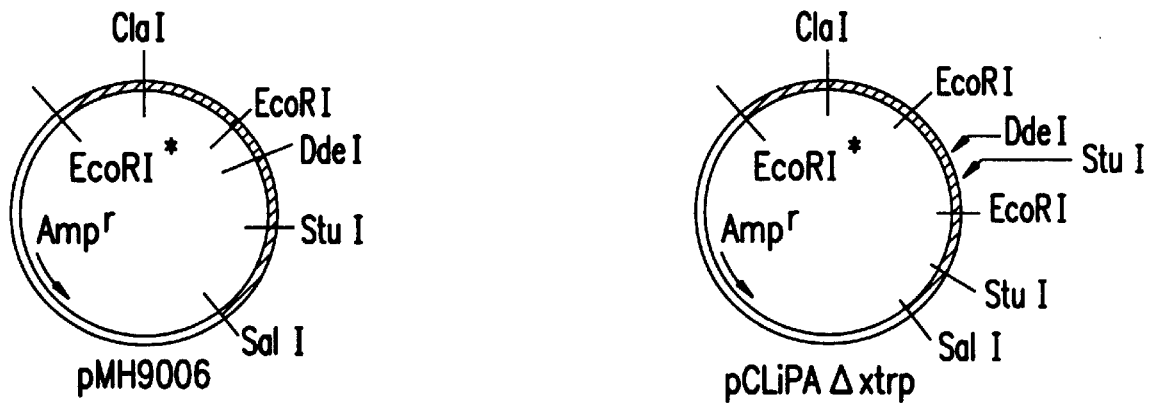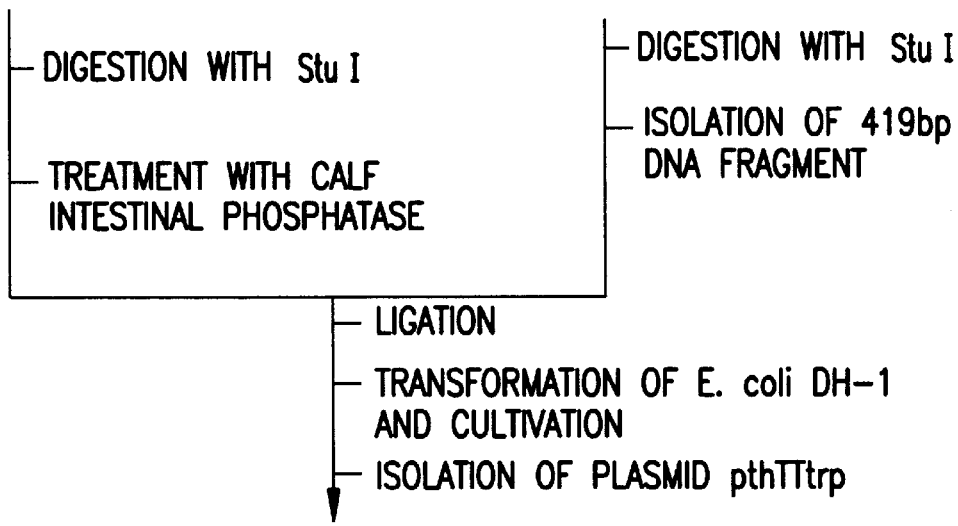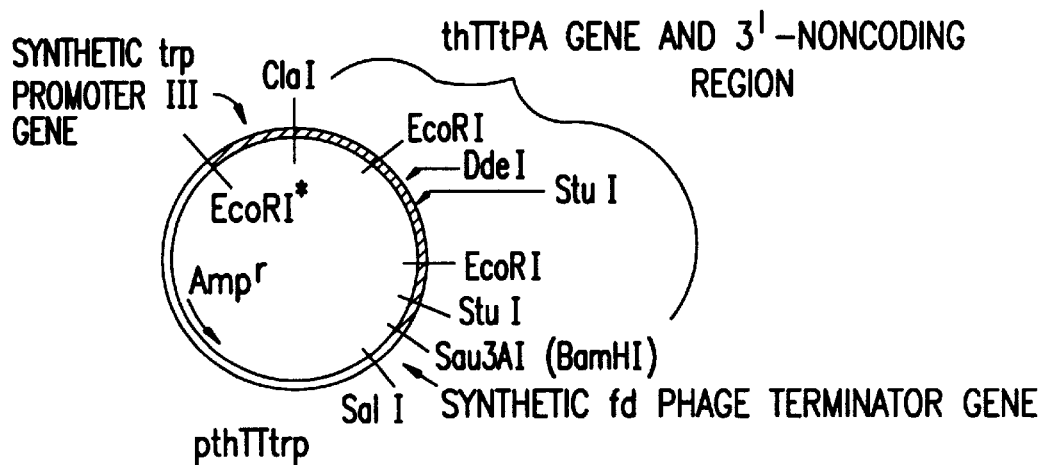
FIG.17

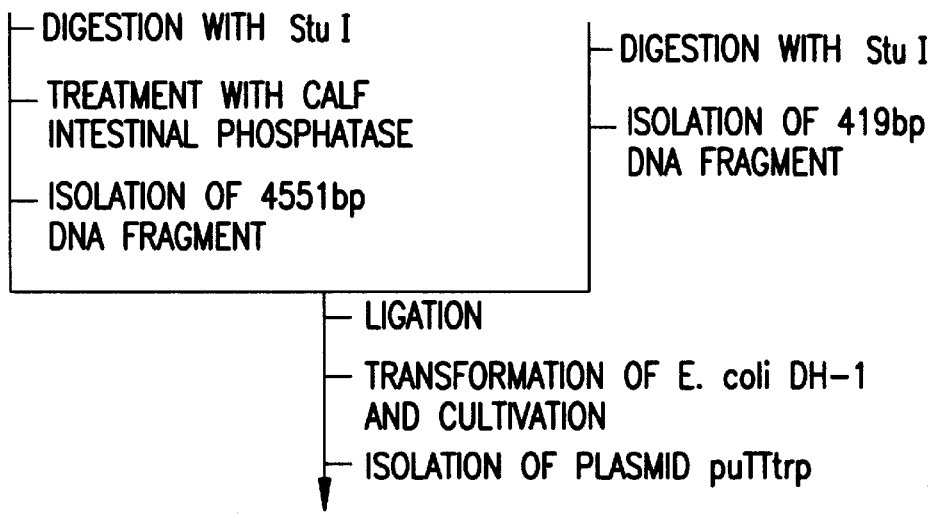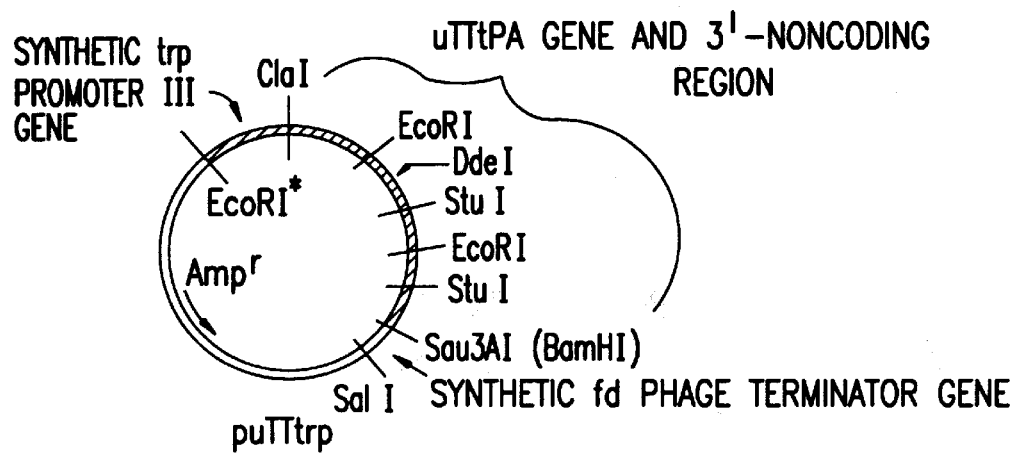
FIG.19

```
         10         20         30         40         50         60
5'- GTTAAGGGACGCTGTGAAGCAATCATGGATGCAATGAAGAGAGGGCTCTGCTGTGTGCTG
                     MetAspAlaMetLysArgGlyLeuCysCysValLeu 70         80         90        100        110        120
    CTGCTGTGTGGAGCAGTCTTCGTTTCGCCCAGCCAGGAAATCCATGCCCGATTCAGAAGA
    LeuLeuCysGlyAlaValPheValSerProSerGlnGluIleHisAlaArgPheArgArg 130        140        150        160        170        180
    GGAGCCAGATCTTACCAAGTGATCTGCAGAGATGAAAAAACGCAGATGATATACCAGCAA
    GlyAlaArgSerTyrGlnValIleCysArgAspGluLysThrGlnMetIleTyrGlnGln
    |→native tPA 190        200        210        220        230        240
    CATCAGTCATGGCTGCGCCCTGTGCTCAGAAGCAACCGGGTGGAATATTGCTGGTGCAAC
    HisGlnSerTrpLeuArgProValLeuArgSerAsnArgValGluTyrCysTrpCysAsn 250        260        270        280        290        300
    AGTGGCAGGGCACAGTGCCACTCAGTGCCTGTCAAAAGTTGCAGCGAGCCAAGGTGTTTC
    SerGlyArgAlaGlnCysHisSerValProValLysSerCysSerGluProArgCysPhe 310        320        330        340        350        360
    AACGGGGGCACCTGCCAGCAGGCCCTGTACTTCTCAGATTTCGTGTGCCAGTGCCCCGAA
    AsnGlyGlyThrCysGlnGlnAlaLeuTyrPheSerAspPheValCysGlnCysProGlu 370        380        390        400        410        420
    GGATTTGCTGGGAAGTGCTGTGAAATAGATACCAGGGCCACGTGCTACGAGGACCAGGGC
    GlyPheAlaGlyLysCysCysGluIleAspThrArgAlaThrCysTyrGluAspGlnGly 430        440        450        460        470        480
    ATCAGCTACAGGGGCACGTGGAGCACAGCGGAGAGTGGCGCCGAGTGCACCAACTGGAAC
    IleSerTyrArgGlyThrTrpSerThrAlaGluSerGlyAlaGluCysThrAsnTrpAsn 490        500        510        520        530        540
    AGCAGCGCGTTGGCCCAGAAGCCCTACAGCGGGCGGAGGCCAGACGCCATCAGGCTGGGC
    SerSerAlaLeuAlaGlnLysProTyrSerGlyArgArgProAspAlaIleArgLeuGly 550        560        570        580        590        600
    CTGGGGAACCACAACTACTGCAGAAACCCAGATCGAGACTCAAAGCCCTGGTGCTACGTC
    LeuGlyAsnHisAsnTyrCysArgAsnProAspArgAspSerLysProTrpCysTyrVal
```

FIG.21A

```
       610       620       630       640       650       660
TTTAAGGCGGGGAAGTACAGCTCAGAGTTCTGCAGCACCCCTGCCTGCTCTGAGGGAAAC
PheLysAlaGLyLysTyrSerSerGluPheCysSerThrProAlaCysSerGluGlyAsn 670       680       690       700       710       720
AGTGACTGCTACTTTGGGAATGGGTCAGCCTACCGTGGCACGCACAGCCTCACCGAGTCG
SerAspCysTyrPheGlyAsnGlySerAlaTyrArgGlyThrHisSerLeuThrGluSer 730       740       750       760       770       780
GGTGCCTCCTGCCTCCCGTGGAATTCCATGATCCTGATAGGCAAGGTTTACACAGCACAG
GlyAlaSerCysLeuProTrpAsnSerMetIleLeuIleGlyLysValTyrThrAlaGln 790       800       810       820       830       840
AACCCCAGTGCCCAGGCACTGGGCCTGGGCAAACATAATTACTGCCGGAATCCTGATGGG
AsnProSerAlaGlnAlaLeuGlyLeuGlyLysHisAsnTyrCysArgAsnProAspGly 850       860       870       880       890       900
GATGCCAAGCCCTGGTGCCACGTGCTGAAGAACCGCAGGCTGACGTGGGAGTACTGTGAT
AspAlaLysProTrpCysHisValLeuLysAsnArgArgLeuThrTrpGluTyrCysAsp 910       920       930       940       950       960
GTGCCCTCCTGCTCCACCTGCGGCCTGAGACAGTACAGCCAGCCTCAGTTTCGCATCAAA
ValProSerCysSerThrCysGlyLeuArgGlnTyrSerGlnProGlnPheArgIleLys 970       980       990      1000      1010      1020
GGAGGGCTCTTCGCCGACATCGCCTCCCACCCCTGGCAGGCTGCCATCTTTGCCAAGCAC
GlyGlyLeuPheAlaAspIleAlaSerHisProTrpGlnAlaAlaIlePheAlaLysHis 1030      1040      1050      1060      1070      1080
AGGAGGTCGCCCGGAGAGCGGTTCCTGTGCGGGGGCATACTCATCAGCTCCTGCTGGATT
ArgArgSerProGlyGluArgPheLeuCysGlyGlyIleLeuIleSerSerCysTrpIle 1090      1100      1110      1120      1130      1140
CTCTCTGCCGCCCACTGCTTCCAGGAGAGGTTTCCGCCCCACCACCTGACGGTGATCTTG
LeuSerAlaAlaHisCysPheGlnGluArgPheProProHisHisLeuThrValIleLeu 1150      1160      1170      1180      1190      1200
GGCAGAACATACCGGGTGGTCCCTGGCGAGGAGGAGCAGAAATTTGAAGTCGAAAAATAC
GlyArgThrTyrArgValValProGlyGluGluGluGlnLysPheGluValGluLysTyr 1210      1220      1230      1240      1250      1260
ATTGTCCATAAGGAATTCGATGATGACACTTACGACAATGACATTGCGCTGCTGCAGCTG
IleValHisLysGluPheAspAspAspThrTyrAspAsnAspIleAlaLeuLeuGlnLeu
```

FIG.21B

```
        1270       1280       1290       1300       1310       1320
AAATCGGATTCGTCCCGCTGTGCCCAGGAGAGCAGCGTGGTCCGCACTGTGTGCCTTCCC
LysSerAspSerSerArgCysAlaGlnGluSerSerValValArgThrValCysLeuPro 1330       1340       1350       1360       1370       1380
CCGGCGGACCTGCAGCTGCCGGACTGGACGGAGTGTGAGCTCTCCGGCTACGGCAAGCAT
ProAlaAspLeuGlnLeuProAspTrpThrGluCysGluLeuSerGlyTyrGlyLysHis 1390       1400       1410       1420       1430       1440
GAGGCCTTGTCTCCTTTCTATTCGGAGCGGCTGAAGGAGGCTCATGTCAGACTGTACCCA
GluAlaLeuSerProPheTyrSerGluArgLeuLysGluAlaHisValArgLeuTyrPro 1450       1460       1470       1480       1490       1500
TCCAGCCGCTGCACATCACAACATTTACTTAACAGAACAGTCACCGACAACATGCTGTGT
SerSerArgCysThrSerGlnHisLeuLeuAsnArgThrValThrAspAsnMetLueCys 1510       1520       1530       1540       1550       1560
GCTGGAGACACTCGGAGCGGCGGGCCCCAGGCAAACTTGCACGACGCCTGCCAGGGCGAT
AlaGlyAspThrArgSerGlyGlyProGlnAlaAsnLeuHisAspAlaCysGlnGlyAsp 1570       1580       1590       1600       1610       1620
TCGGGAGGCCCCCTGGTGTGTCTGAACGATGGCCGCATGACTTTGGTGGGCATCATCAGC
SerGlyGlyProLeuValCysLeuAsnAspGlyArgMetThrLeuValGlyIleIleSer 1630       1640       1650       1660       1670       1680
TGGGGCCTGGGCTGTGGACAGAAGGATGTCCCCGGGTGTGTACACAAAGGTTACCAACTAC
TrpGlyLeuGlyCysGlyGlnLysAspValProGlyValTyrThrLysValThrAsnTyr 1690       1700       1710       1720       1730       1740
CTAGACTGGATTCGTGACAACATGCGACCGTGACCAGGAACACCCGACTCCTCAAAAGCA
LeuAspTrpIleArgAspAsnMetArgPro***
                              ←|
        1750       1760       1770       1780       1790       1800
AATGAGATCCCGCCTCTTCTTCTTCAGAAGACACTGCAAAGGCGCAGTGCTTCTCTACAG 1810       1820       1830       1840       1850       1860
ACTTCTCCAGACCCACCACACCGCAGAAGCGGGACGAGACCCTACAGGAGAGGGAAGAGT 1870       1880       1890       1900       1910       1920
GCATTTTCCCAGATACTTCCCATTTTGGAAGTTTTCAGGACTTGGTCTGATTTCAGGATA 1930       1940       1950       1960       1970       1980
CTCTGTCAGATGGGAAGACATGAATGCACACTAGCCTCTCCAGGAATGCCTCCTCCCTGG
```

FIG.21C

```
           1990       2000       2010       2020       2030       2040
GCAGAAGTGGCCATGCCACCCTGTTTTCGCTAAAGCCCAACCTCCTGACCTGTCACCGTG 2050       2060       2070       2080       2090       2100
AGCAGCTTTGGAAACAGGACCACAAAAATGAAAGCATGTCTCAATAGTAAAAGAAACAAG

```
         10         20         30         40         50         60
5'- ATGTCTGAGGGAAACAGTGACTGCTACTTTGGGAATGGGTCAGCCTACCGTGGCACGCAG
    MetSerGluGlyAsnSerAspCysTyrPheGlyAsnGlySerAlaTyrArgGlyThrHis
      |→    TTKtPA
         70         80         90        100        110        120
    AGCCTCACCGAGTCGGGTGCCTCCTGCCTCCCGTGGAATTCCATGATCCTGATAGGCAAG
    SerLeuThrGluSerGlyAlaSerCysLeuProTrpAsnSerMetIleLeuIleGlyLys 130        140        150        160        170        180
    GTTTACACAGCACAGAACCCCAGTGCCCAGGCACTGGGCCTGGGCAAACATAATTACTGC
    ValTyrThrAlaGlnAsnProSerAlaGlnAlaLeuGlyLeuGlyLysHisAsnTyrCys 190        200        210        220        230        240
    CGGAATCCTGATGGGGATGCCAAGCCCTGGTGCCACGTGCTGAAGAACCGCAGGCTGACG
    ArgAsnProAspGlyAspAlaLysProTrpCysHisValLeuLysAsnArgArgLeuThr 250        260        270        280        290        300
    TGGGAGTACTGTGATGTGCCCTCCTGCTCCACCTGCGGCCTGAGACAGTACAGCCAGCCT
    TrpGluTyrCysAspValProSerCysSerThrCysGlyLeuArgGlnTyrSerGlnPro 310        320        330        340        350        360
    CAGTTTCGCATCAAAGGAGGGCTCTTCGCCGACATCGCCTCCCACCCCTGGCAGGCTGCC
    GlnPheArgIleLysGlyGlyLeuPheAlaAspIleAlaSerHisProTrpGlnAlaAla 370        380        390        400        410        420
    ATCTTTGCCAAGCACAGGAGGTCGCCCGGAGAGCGGTTCCTGTGCGGGGGCATACTCATC
    IlePheAlaLysHisArgArgSerProGlyGluArgPheLeuCysGlyGlyIleLeuIle 430        440        450        460        470        480
    AGCTCCTGCTGGATTCTCTCTGCCGCCCACTGCTTCCAGGAGAGGTTTCCGCCCCACCAC
    SerSerCysTrpIleLeuSerAlaAlaHisCysPheGlnGluArgPheProProHisHis 490        500        510        520        530        540
    CTGACGGTGATCTTGGGCAGAACATACCGGGTGGTCCCTGGCGAGGAGGAGCAGAAATTT
    LeuThrValIleLeuGlyArgThrTyrArgValValProGlyGluGluGluGlnLysPhe 550        560        570        580        590        600
    GAAGTCGAAAAATACATTGTCCATAAGGAATTCGATGATGACACTTACGACAATGACATT
    GluValGluLysTyrIleValHisLysGluPheAspAspAspThrTyrAspAsnAspIle 610        620        630        640        650        660
    GCGCTGCTGCAGCTGAAATCGGATTCGTCCCGCTGTGCCCAGGAGAGCAGCGTGGTCCGC
    AlaLeuLeuGlnLeuLysSerAspSerSerArgCysAlaGlnGluSerSerValValArg
```

FIG.29A

```
                 670       680       690       700       710       720
         ACTGTGTGCCTTCCCCCGGCGGACCTGCAGCTGCCGGACTGGACGGAGTGTGAGCTCTCC
         ThrValCysLeuProProAlaAspLeuGlnLeuProAspTrpThrGluCysGluLeuSer 730       740       750       760       770       780
         GGCTACGGCAAGCATGAGGCCTTGTCTCCTTTCTATTCGGAGCGGCTGAAGGAGGCTCAT
         GlyTyrGlyLysHisGluAlaLeuSerProPheTyrSerGluArgLeuLysGluAlaHis 790       800       810       820       830       840
         GTCAGACTGTACCCATCCAGCCGCTGCACATCACAACATTTACTTAACAGAACAGTCACC
         ValArgLeuTyrProSerSerArgCysThrSerGlnHisLeuLeuAsnArgThrValThr 850       860       870       880       890       900
         GACAACATGCTGTGTGCTGGAGACACTCGGAGCGGCGGGCCCCAGGCAAACTTGCACGAC
         AspAsnMetLeuCysAlaGlyAspThrArgSerGlyGlyProGlnAlaAsnLeuHisAsp 910       920       930       940       950       960
         GCCTGCCAGGGCGATTCGGGAGGCCCCCTGGTGTGTCTGAACGATGGCCGCATGACTTTG
         AlaCysGlnGlyAspSerGlyGlyProLeuValCysLeuAsnAspGlyArgMetThrLeu 970       980       990      1000      1010      1020
         GTGGGCATCATCAGCTGGGGCCTGGGCTGTGGACAGAAGGATGTCCCGGGTGTGTACACA
         ValGlyIleIleSerTrpGlyLeuGlyCysGlyGlnLysAspValProGlyValTyrThr 1030      1040      1050      1060      1070      1080
         AAGGTTACCAACTACCTAGACTGGATTCGTGACAACATGCGACCGTGA - 3'
         LysValThrAsnTyrLeuAspTrpIleArgAspAsnMetArgPro***
                                                        ←|
```

FIG.29B

```
          10         20         30         40         50         60
5'- ATGTCTGAGGGAAACAGTGACTGCTACTTTGGGAATGGGTCAGCCTACCGTGGCACGCAG
    MetSerGluGlyAsnSerAspCysTyrPheGlyAsnGlySerAlaTyrArgGlyThrHis
    |→   TTitPA
          70         80         90        100        110        120
    AGCCTCACCGAGTCGGGTGCCTCCTGCCTCCCGTGGAATTCCATGATCCTGATAGGCAAG
    SerLeuThrGluSerGlyAlaSerCysLeuProTrpAsnSerMetIleLeuIleGlyLys 130        140        150        160        170        180
    GTTTACACAGCACAGAACCCCAGTGCCCAGGCACTGGGCCTGGGCAAACATAATTACTGC
    ValTyrThrAlaGlnAsnProSerAlaGlnAlaLeuGlyLeuGlyLysHisAsnTyrCys 190        200        210        220        230        240
    CGGAATCCTGATGGGGATGCCAAGCCCTGGTGCCACGTGCTGAAGAACCGCAGGCTGACG
    ArgAsnProAspGlyAspAlaLysProTrpCysHisValLeuLysAsnArgArgLeuThr 250        260        270        280        290        300
    TGGGAGTACTGTGATGTGCCCTCCTGCTCCACCTGCGGCCTGAGACAGTACAGCCAGCCT
    TrpGluTyrCysAspValProSerCysSerThrCysGlyLeuArgGlnTyrSerGlnPro 310        320        330        340        350        360
    CAGTTTCGCATCAAAGGAGGGCTCTTCGCCGACATCGCCTCCCACCCCTGGCAGGCTGCC
    GlnPheArgIleLysGlyGlyLeuPheAlaAspIleAlaSerHisProTrpGlnAlaAla 370        380        390        400        410        420
    ATCTTTGCCAAGCACAGGAGGTCGCCCGGAGAGCGGTTCCTGTGCGGGGGCATACTCATC
    IlePheAlaLysHisArgArgSerProGlyGluArgPheLeuCysGlyGlyIleLeuIle 430        440        450        460        470        480
    AGCTCCTGCTGGATTCTCTCTGCCGCCCACTGCTTCCAGGAGAGGTTTCCGCCCCACCAC
    SerSerCysTrpIleLeuSerAlaAlaHisCysPheGlnGluArgPheProProHisHis 490        500        510        520        530        540
    CTGACGGTGATCTTGGGCAGAACATACCGGGTGGTCCCTGGCGAGGAGGAGCAGAAATTT
    LeuThrValIleLeuGlyArgThrTyrArgValValProGlyGluGluGluGlnLysPhe 550        560        570        580        590        600
    GAAGTCGAAAAATACATTGTCCATAAGGAATTCGATGATGACACTTACGACAATGACATT
    GluValGluLysTyrIleValHisLysGluPheAspAspAspThrTyrAspAsnAspIle 610        620        630        640        650        660
    GCGCTGCTGCAGCTGAAATCGGATTCGTCCCGCTGTGCCCAGGAGAGCAGCGTGGTCCGC
    AlaLeuLeuGlnLeuLysSerAspSerSerArgCysAlaGlnGluSerSerValValArg
```

FIG.30A

```
          670       680       690       700       710       720
ACTGTGTGCCTTCCCCCGGCGGACCTGCAGCTGCCGGACTGGACGGAGTGTGAGCTCTCC
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990      1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070      1080
AAGGTTACCAACTACCTAGACTGGATTCGTGACAACATGCGACCGTGA - 3'
LysValThrAsnTyrLeuAspTrpIleArgAspAsnMetArgPro***
                                                  ←|
```

FIG.30B

```
              10         20         30         40         50         60
5' - ATGTGTTATGAGGACCAGGGCATCAGCTACAGGGGCACGTGGAGCACAGCGGAGAGTGGC
     MetCysTyrGluAspGlnGlyIleSerTyrArgGlyThrTrpSerThrAlaGluSerGly
     |→ TQKtPA
              70         80         90        100        110        120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130        140        150        160        170        180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190        200        210        220        230        240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250        260        270        280        290        300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310        320        330        340        350        360
     ACGCACAGCCTCACCGAGTCGGGTGCCTCCTGCCTCCCGTGGAATTCCATGATCCTGATA
     ThrHisSerLeuTHrGluSerGlyAlaSerCysLeuProTrpAsnSerMetIleLeuIle 370        380        390        400        410        420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430        440        450        50        470        480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490        500        510        520        530        540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550        560        570        580        590        600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610        620        630        640        650        660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.31A

```
     670        680        690        700        710        720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730        740        750        760        770        780
CACCACCTGACGGTGATCTTGGGCAGAACATACCGGGTGGTCCCTGGCGAGGAGGAGCAG
HisHisLeuThrValIleLeuGlyArgThrTyrArgValValProGlyGluGluGluGln 790        800        810        820        830        840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850        860        870        880        890        900
GACATTGCGCTGCTGCAGCTGAAATCGGATTCGTCCCGCTGTGCCCAGGAGAGCAGCGTG
AspIleAlaLeuLeuGlnLeuLysSerAspSerSerArgCysAlaGlnGluSerSerVal 910        920        930        940        950        960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970        980        990       1000       1010       1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030       1040       1050       1060       1070       1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090       1100       1110       1120       1130       1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150       1160       1170       1180       1190       1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210       1220       1230       1240       1250       1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270       1280       1290       1300       1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
```

FIG.31B

```
                  10        20        30        40        50        60
5' - ATGTGTTATGAGGACCAGGGCATCAGCTACAGGGGCACGTGGAGCACAGCGGAGAGTGGC
     MetCysTyrGluAspGlnGlyIleSerTyrArgGlyThrTrpSerThrAlaGluSerGly
     |→ TQitPA
                  70        80        90       100       110       120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130       140       150       160       170       180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190       200       210       220       230       240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250       260       270       280       290       300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310       320       330       340       350       360
     ACGCACAGCCTCACCGAGTCGGGTGCCTCCTGCCTCCCGTGGAATTCCATGATCCTGATA
     ThrHisSerLeuTHrGluSerGlyAlaSerCysLeuProTrpAsnSerMetIleLeuIle 370       380       390       400       410       420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430       440       450       460       470       480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490       500       510       520       530       540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550       560       570       580       590       600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610       620       630       640       650       660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.32A

```
          670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuTHrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLueLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990      1000      1010      1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270      1280      1290      1300      1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
                                                      ←|
```

FIG.32B

```
              10         20         30         40         50         60
5' - ATGTCTGAGGGAAACAGTGACTGCTACTTTGGGAATGGGTCAGCCTACCGTGGCACGCAC
     MetSerGluGlyAsnSerAspCysTyrPheGLyAsnGlySerAlaTyrArgGlyThrHis
       |→ STTktPA
              70         80         90        100        110        120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130        140        150        160        170        180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190        200        210        220        230        240
     CGGAATCCTGATGGGGATGCCAAGCCCTGGTGCCACGTGCTGAAGAACCGCAGGCTGACG
     ArgAsnProAspGlyAspAlaLysProTrpCysHisValLeiLysAsnArgArgLeuThr 250        260        270        280        290        300
     TGGGAGTACTGTGATGTGCCCTCCTGCTCCACCTGCGGCCTGAGACAGTACAGCCAGCCA
     TrpGluTyrCysAspValProSerCysSerThrCysGlyLeuArgGlnTyrSerGlnPro 310        320        330        340        350        360
     CAGTTTGATATCAAAGGAGGCCTCTTCGCCGACATCGCCTCCCACCCCTGGCAGGCTGCC
     GlnPheAspIleLysGlyGlyLeuPheAlaAspIleAlaSerHisProTrpGlnAlaAla 370        380        390        400        410        420
     ATCTTTGCCAAGCACAGGAGGTCGCCCGGAGAGCGGTTCCTGTGCGGGGGCATACTCATC
     IlePheAlaLysHisArgArgSerProGlyGluArgPheLeuCysGlyGLyIleLeuIle 430        440        450        460        470        480
     AGCTCCTGCTGGATTCTCTCTGCCGCCCACTGCTTCCAGGAGAGGTTTCCGCCCCACCAC
     SerSerCysTrpIleLeuSerAlaAlaHisCysPheGlnGluArgPheProProHisHis 490        500        510        520        530        540
     CTGACGGTGATCTTGGGCAGAACATACCGGGTGGTCCCTGGCGAGGAGGAGCAGAAATTT
     LeuThrValIleLeuGlyArgThrTyrArgValValProGlyGluGluGluGlnLysPhe 550        560        570        580        590        600
     GAAGTCGAAAAATACATTGTCCATAAGGAATTCGATGATGACACTTACGACAATGACATT
     GluValGluLysTyrIleValHisLysGluPheAspAspAspThrTyrAspAsnAspIle 610        620        630        640        650        660
     GCGCTGCTGCAGCTGAAATCGGATTCGTCCCGCTGTGCCCAGGAGAGCAGCGTGGTCCGC
     AlaLeuLeuGlnLeuLysSerAspSerSerArgCysAlaGlnGluSerSerValValArg
```

FIG.33A

```
        670       680       690       700       710       720
ACTGTGTGCCTTCCCCCGGCGGACCTGCAGCTGCCGGACTGGACGGAGTGTGAGCTCTCT
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990       1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070
AAGGTTACCAACTACCTAGACTGGATTCGTGACAACATGCGACCGTGA - 3'
LysValThrAsnTyrLeuAspTrpIleArgAspAsnMetArgPro***
                                              ←|
```

FIG. 33B

```
        10         20         30         40         50         60
5' - ATGTGTTATGAGGACCAGGGGCATCAGCTACAGGGGCACGTGGAGCACAGCGGAGAGTGGC
     MetCysTyrGluAspGlnGlyIleSerTyrArgGlyThrTrpSerThrAlaGluSerGly
       |→ STQKtPA
        70         80         90        100        110        120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130        140        150        160        170        180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190        200        210        220        230        240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250        260        270        280        290        300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310        320        330        340        350        360
     ACGCACAGCCTCACCGAGTCGGGTGCCTCCTGCCTCCCGTGGAATTCCATGATCCTGATA
     ThrHisSerLeuThrGluSerGlyAlaSerCysLeuProTrpAsnSerMetIleLeuIle 370        380        390        400        410        420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430        440        450        460        470        480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490        500        510        520        530        540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550        560        570        580        590        600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610        620        630        640        650        660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.34A

```
        670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuThrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLeuLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990      1000      1010      1020
CTCTCCGGCTACGGCAAGCATGAGGCCTTGTCTCCTTTCTATTCGGAGCGGCTGAAGGAG
LeuSerGlyTyrGlyLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGluLeuGlyCysGlyGlnLysAspValProGlyVal 1270      1280      1290      1300      1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
                                                      ←|
```

FIG.34B

```
              10        20        30        40        50        60
5' - ATGTGTTATGAGGACCAGGGCATCAGCTACAGGGGCACGTGGAGCACAGCGGAGAGTGGC
     MetCysTyrGluAspGlnGlyIleSerTyrArgGlyThrTrpSerThrAlaGluSerGly
     |→ STQitPA
              70        80        90       100       110       120
     GCCGAGTGCACCAACTGGAACAGCAGCGCGTTGGCCCAGAAGCCCTACAGCGGGCGGAGG
     AlaGluCysThrAsnTrpAsnSerSerAlaLeuAlaGlnLysProTyrSerGlyArgArg 130       140       150       160       170       180
     CCAGACGCCATCAGGCTGGGCCTGGGGAACCACAACTACTGCAGAAACCCAGATCGAGAC
     ProAspAlaIleArgLeuGlyLeuGlyAsnHisAsnTyrCysArgAsnProAspArgAsp 190       200       210       220       230       240
     TCAAAGCCCTGGTGCTACGTCTTTAAGGCGGGGAAGTACAGCTCAGAGTTCTGCAGCACC
     SerLysProTrpCysTyrValPheLysAlaGlyLysTyrSerSerGluPheCysSerThr 250       260       270       280       290       300
     CCTGCCTGCTCTGAGGGAAACAGTGACTGCTACTTTGGGAATGGGTCAGCCTACCGTGGC
     ProAlaCysSerGluGlyAsnSerAspCysTyrPheGlyAsnGlySerAlaTyrArgGly 310       320       330       340       350       360
     ACGCACAGCCTCACCGAGTCGGGTGCCTCCTGCCTCCCGTGGAATTCCATGATCCTGATA
     ThrHisSerLeuThrGluSerGlyAlaSerCysLeuProTrpAsnSerMetIleLeuIle 370       380       390       400       410       420
     GGCAAGGTTTACACAGCACAGAACCCCAGTGCCCAGGCACTGGGCCTGGGCAAACATAAT
     GlyLysValTyrThrAlaGlnAsnProSerAlaGlnAlaLeuGlyLeuGlyLysHisAsn 430       440       450       460       470       480
     TACTGCCGGAATCCTGATGGGGATGCCAAGCCCTGGTGCCACGTGCTGAAGAACCGCAGG
     TyrCysArgAsnProAspGlyAspAlaLysProTrpCysHisValLeuLysAsnArgArg 490       500       510       520       530       540
     CTGACGTGGGAGTACTGTGATGTGCCCTCCTGCTCCACCTGCGGCCTGAGACAGTACAGC
     LeuThrTrpGluTyrCysAspValProSerCysSerThrCysGlyLeuArgGlnTyrSer 550       560       570       580       590       600
     CAGCCTCAGTTTCGCATCAAAGGAGGGCTCTTCGCCGACATCGCCTCCCACCCCTGGCAG
     GlnProGlnPheArgIleLysGlyGlyLeuPheAlaAspIleAlaSerHisProTrpGln 610       620       630       640       650       660
     GCTGCCATCTTTGCCAAGCACAGGAGGTCGCCCGGAGAGCGGTTCCTGTGCGGGGGCATA
     AlaAlaIlePheAlaLysHisArgArgSerProGlyGluArgPheLeuCysGlyGlyIle
```

FIG.35A

```
         670       680       690       700       710       720
CTCATCAGCTCCTGCTGGATTCTCTCTGCCGCCCACTGCTTCCAGGAGAGGTTTCCGCCC
LeuIleSerSerCysTrpIleLeuSerAlaAlaHisCysPheGlnGluArgPheProPro 730       740       750       760       770       780
CACCACCTGACGGTGATCTTGGGCAGAACATACCGGGTGGTCCCTGGCGAGGAGGAGCAG
HisHisLeuThrValIleLeuGlyArgThrTyrArgValValProGlyGluGluGluGln 790       800       810       820       830       840
AAATTTGAAGTCGAAAAATACATTGTCCATAAGGAATTCGATGATGACACTTACGACAAT
LysPheGluValGluLysTyrIleValHisLysGluPheAspAspAspThrTyrAspAsn 850       860       870       880       890       900
GACATTGCGCTGCTGCAGCTGAAATCGGATTCGTCCCGCTGTGCCCAGGAGAGCAGCGTG
AspIleAlaLeuLeuGlnLueLysSerAspSerSerArgCysAlaGlnGluSerSerVal 910       920       930       940       950       960
GTCCGCACTGTGTGCCTTCCCCCGGCGGACCTGCAGCTGCCGGACTGGACGGAGTGTGAG
ValArgThrValCysLeuProProAlaAspLeuGlnLeuProAspTrpThrGluCysGlu 970       980       990      1000      1010      1020
CTCTCCGGCTACGGCAAGCATGAGGCCTTGTCTCCTTTCTATTCGGAGCGGCTGAAGGAG
LeuSerGlyTyrGluLysHisGluAlaLeuSerProPheTyrSerGluArgLeuLysGlu 1030      1040      1050      1060      1070      1080
GCTCATGTCAGACTGTACCCATCCAGCCGCTGCACATCACAACATTTACTTAACAGAACA
AlaHisValArgLeuTyrProSerSerArgCysThrSerGlnHisLeuLeuAsnArgThr 1090      1100      1110      1120      1130      1140
GTCACCGACAACATGCTGTGTGCTGGAGACACTCGGAGCGGCGGGCCCCAGGCAAACTTG
ValThrAspAsnMetLeuCysAlaGlyAspThrArgSerGlyGlyProGlnAlaAsnLeu 1150      1160      1170      1180      1190      1200
CACGACGCCTGCCAGGGCGATTCGGGAGGCCCCCTGGTGTGTCTGAACGATGGCCGCATG
HisAspAlaCysGlnGlyAspSerGlyGlyProLeuValCysLeuAsnAspGlyArgMet 1210      1220      1230      1240      1250      1260
ACTTTGGTGGGCATCATCAGCTGGGGCCTGGGCTGTGGACAGAAGGATGTCCCGGGTGTG
ThrLeuValGlyIleIleSerTrpGlyLeuGlyCysGlyGlnLysAspValProGlyVal 1270      1280      1290      1300      1310
TACACAAAGGTTACCAACTACCTAGACTGGATTCGTGACAACATGCGACCGTGA - 3'
TyrThrLysValThrAsnTyrLeuAspTrpIleArgAspAsnMetArgPro***
```

FIG.35B

```
           10        20        30        40        50        60
5' - ATGTCTGAGGGAAACAGTGACTGCTACTTTGGGAATGGGTCAGCCTACCGTGGCACGCAC
     MetSerGluGlyAsnSerAspCysTyrPheGlyAsnGlySerAlaTyrArgGlyThrHis
     |→ UTTtPA
           70        80        90       100       110       120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130       140       150       160       170       180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190       200       210       220       230       240
     CGGAATCCTGATGGGGATGCCAAGCCCTGGTGCCACGTGCTGAAGAACCGCAGGCTGACG
     ArgAsnProAspGlyAspAlaLysProTrpCysHisValLeuLysAsnArgArgLeuThr 250       260       270       280       290       300
     TGGGAGTACTGTGATGTGCCCTCCTGCTCCACCTGCGGCCTGAGACAGACTCTGCGTCCG
     TrpGluTyrCysAspValProSerCysSerThrCysGlyLeuArgGlnThrLeuArgPro 310       320       330       340       350       360
     GGFTTCAAAATCAAAGGAGGCCTCTTCGCCGACATCGCCTCCCACCCCTGGCAGGCTGCC
     ArgPheLysIleLysGlyGlyLeuPheAlaAspIleAlaSerHisProTrpGlnAlaAla 370       380       390       400       410       420
     ATCTTTGCCAAGCACAGGAGGTCGCCCGGAGAGCGGTTCCTGTGCGGGGGCATACTCATC
     IlePheAlaLysHisArgArgSerProGlyGluArgPheLeuCysGlyGlyIleLeuIle 430       440       450       460       470       480
     AGCTCCTGCTGGATTCTCTCTGCCGCCCACTGCTTCCAGGAGAGGTTTCCGCCCCACCAC
     SerSerCysTrpIleLeuSerAlaAlaHisCysPheGlnGluArgPheProProHisHis 490       500       510       520       530       540
     CTGACGGTGATCTTGGGCAGAACATACCGGGTGGTCCCTGGCGAGGAGGAGCAGAAATTT
     LeuThrValIleLeuGlyArgThrTyrArgValValProGlyGluGluGluGlnLysPhe 550       560       570       580       590       600
     GAAGTCGAAAAATACATTGTCCATAAGGAATTCGATGATGACACTTACGACAATGACATT
     GluValGluLysTyrIleValHisLysGluPheAspAspAspThrTyrAspAsnAspIle 610       620       630       640       650       660
     GCGCTGCTGCAGCTGAAATCGGATTCGTCCCGCTGTGCCCAGGAGAGCAGCGTGGTCCGC
     AlaLeuLeuGlnLeuLysSerAspSerSerArgCysAlaGlnGluSerSerValValArg
```

FIG.36A

```
        670       680       690       700       710       720
ACTGTGTGCCTTCCCCCGGCGGACCTGCAGCTGCCGGACTGGACGGAGTGTGAGCTCTCT
ThrValCysLeuProProAlaAspLeuGlnLeuProAspTrpThrGluCysGluLeuSer 730       740       750       760       770       780
GGCTACGGCAAGCATGAGGCCTTGTCTCCTTTCTATTCGGAGCGGCTGAAGGAGGCTCAT
GlyTyrGlyLysHisGluAlaLeuSerProPheTyrSerGluArgLeuLysGluAlaHis 790       800       810       820       830       840
GTCAGACTGTACCCATCCAGCCGCTGCACATCACAACATTTACTTAACAGAACAGTCACC
ValArgLeuTyrProSerSerArgCysThrSerGlnHisLeuLeuAsnArgThrValThr 850       860       870       880       890       900
GACAACATGCTGTGTGCTGGAGACACTCGGAGCGGCGGGCCCCAGGCAAACTTGCACGAC
AspAsnMetLeuCysAlaGlyAspThrArgSerGlyGlyProGlnAlaAsnLeuHisAsp 910       920       930       940       950       960
GCCTGCCAGGGCGATTCGGGAGGCCCCCTGGTGTGTCTGAACGATGGCCGCATGACTTTG
AlaCysGlnGlyAspSerGlyGlyProLeuValCysLeuAsnAspGlyArgMetThrLeu 970       980       990      1000      1010      1020
GTGGGCATCATCAGCTGGGGCCTGGGCTGTGGACAGAAGGATGTCCCGGGTGTGTACACA
ValGlyIleIleSerTrpGlyLeuGlyCysGlyGlnLysAspValProGlyValTyrThr 1030      1040      1050      1060      1070
AAGGTTACCAACTACCTAGACTGGATTCGTGACAACATGCGACCGTGA - 3'
LysValThrAsnTyrLeuAspTrpIleArgAspAsnMetArgPro***
                                                  ←|
```

FIG.36B

```
              10         20         30         40         50         60
5' - ATGTCTGAGGGAAACAGTGACTGCTACTTTGGGAATGGGTCAGCCTACCGTGGCACGCAC
     MetSerGluGlyAsnSerAspCysTyrPheGLyAsnGlySerAlaTyrArgGlyThrHis
     |→ thTTtPA
              70         80         90        100        110        120
     AGCCTCACCGAGTCGGGTGCCTCCTGCCTCCCGTGGAATTCCATGATCCTGATAGGCAAG
     SerLeuThrGluSerGlyAlaSerCysLeuProTrpAsnSerMetIleLeuIleGlyLys 130        140        150        160        170        180
     GTTTACACAGCACAGAACCCCAGTGCCCAGGCACTGGGCCTGGGCAAACATAATTACTGC
     ValTyrThrAlaGlnAsnProSerAlaGlnAlaLeuGlyLeuGlyLysHisAsnTyrCys 190        200        210        220        230        240
     CGGAATCCTGATGGGGATGCCAAGCCCTGGTGCCACGTGCTGAAGAACCGCAGGCTGACG
     ArgAsnProAspGlyAspAlaLysProTrpCysHisValLeuLysAsnArgArgLeuThr 250        260        270        280        290        300
     TGGGAGTACTGTGATGTGCCCTCCTGCTCCACCTGCGGCCTGAGACAGTACAGCCAGCCA
     TrpGluTyrCysAspValProSerCysSerThrCysGlyLeuArgGlnTyrSerGlnPro 310        320        330        340        350        360
     ATTCCTAGATCTGGAGGCCTCTTCGCCGACATCGCCTCCCACCCCTGGCAGGCTGCCATC
     IleProArgSerGlyGlyLeuPheAlaAspIleAlaSerHisProTrpGlnAlaAlaIle 370        380        390        400        410        420
     TTTGCCAAGCACAGGAGGTCGCCCGGAGAGCGGTTCCTGTGCGGGGGGCATACTATCAGC
     PheAlaLysHisArgArgSerProGlyGluArgPheLeuCysGlyGlyIleLeuIleSer 430        440        450        460        470        480
     TCCTGCTGGATTCTCTCTGCCGCCCACTGCTTCCAGGAGAGGTTTCCGCCCCACCACCTG
     SerCysTrpIleLeuSerAlaAlaHisCysPheGlnGluArgPheProProHisHisLeu 490        500        510        520        530        540
     ACGGTGATCTTGGGCAGAACATACCGGGTGGTCCCTGGCGAGGAGGAGCAGAAATTTGAA
     ThrValIleLeuGlyArgThrTyrArgValValProGlyGluGluGluGlnLysPheGlu 550        560        570        580        590        600
     GTCGAAAAATACATTGTCCATAAGGAATTCGATGATGACACTTACGACAATGACATTGCG
     ValGluLysTyrIleValHisLysGluPheAspAspAspThrTyrAspAsnAspIleAla 610        620        630        640        650        660
     CTGCTGCAGCTGAAATCGGATTCGTCCCGCTGTGCCCAGGAGAGCAGCGTGGTCCGCACT
     LeuLeuGlnLeuLysSerAspSerSerArgCysAlaGlnGluLeuSerValValArgThr
```

FIG. 37A

```
         670       680       690       700       710       720
GTGTGCCTTCCCCCGGCGGACCTGCAGCTGCCGGACTGGACGGAGTGTGAGCTCTCCGGC
ValCysLeuProProAlaAspLeuGlnLeuProAspTrpThrGluCysGluLeuSerGly 730       740       750       760       770       780
TACGGCAAGCATGAGGCCTTGTCTCCTTTCTATTCGGAGCGGCTGAAGGAGGCTCATGTC
TyrGlyLysHisGluAlaLeuSerProPheTyrSerGluArgLeuLysGluAlaHisVal 790       800       810       820       830       840
AGACTGTACCATCCAGCCGCTGCACATCACAACARTTTACTTAACAGAACAGTCACCGAC
ArgLeuTyrProSerSerArgCysThrSerGlnHisLeuLeuAsnArgThrValThrAsp 850       860       870       880       890       900
AACATGCTGTGTGCTGGAGACACTCGGAGCGGCGGGCCCCAGGCAAACTTGCACGACGCC
AsnMetLeuCysAlaGlyAspThrArgSerGlyGlyProGlnAlaAsnLeuHisAspAla 910       920       930       940       950       960
TGCCAGGGCGATTCGGGAGGCCCCCTGGTGTGTCTGAACGATGGCCGCATGACTTTGGTG
CysGlnGlyAspSerGlyGlyProLeuValCysLeuAsnAspGlyArgMetThrLeuVal 970       980       990      1000      1010      1020
GGCATCATCAGCTGGGGCCTGGGCTGTGGACAGAAGGATGTCCCGGGTGTGTACACAAAG
GlyIleIleSerTrpGluLeuGlyCysGlyGlnLysAspValProGlyValTyrThrLys 1030      1040      1050      1060
GTTACCAACTACCTAGACTGGATTCGTGACAACATGCGACCGTGA - 3'
ValThrAsnTyrLeuAspTrpIleArgAspAsnMetArgPro***
                                            ←|
```

FIG.37B

```
            10        20        30        40        50        60
5'- ATGGATGCAATGAAGAGAGGGCTCTGCTGTGTGCTGCTGCTGTGTGGAGCAGTCTTCGTT
    MetAspAlaMetLysArgGlyLeuCysCysValLeuLeuLeuCysGlyAlaValPheVal 70        80        90       100       110       120
    TCGCCCAGCCAGGAAATCCATGCCCGATTCAGAAGAGGAGCCAGATCTTGCTACGAGGAC
    SerProSerGlnGluIleHisAlaArgPheArgArgGlyAlaArgSerCysTyrGluAsp
                                                |→ mTQktPA
           130       140       150       160       170       180
    CAGGGCATCAGCTACAGGGGCACGTGGAGCACAGCGGAGAGTGGCGCCGAGTGCACCAAC
    GlnGlyIleSerTyrArgGlyThrTrpSerThrAlaGluSerGlyAlaGluCysThrAsn 190       200       210       220       230       240
    TGGAACAGCAGCGCGTTGGCCCAGAAGCCCTACAGCGGGCGGAGGCCAGACGCCATCAGG
    TrpAsnSerSerAlaLeuAlaGlnLysProTyrSerGlyArgArgProAspAlaIleArg 250       260       270       280       290       300
    CTGGGCCTGGGGAACCACAACTACTGCAGAAACCCAGATCGAGACTCAAAGCCCTGGTGC
    LeuGlyLeuGlyAsnHisAsnTyrCysArgAsnProAspArgAspSerLysProTrpCys 310       320       330       340       350       360
    TACGTCTTTAAGGCGGGGAAGTACAGCTCAGAGTTCTGCAGCACCCCTGCCTGCTCTGAG
    TyrValPheLysAlaGlyLysTyrSerSerGluPheCysSerThrProAlaCysSerGlu 370       380       390       400       410       420
    GGAAACAGTGACTGCTACTTTGGGAATGGGTCAGCCTACCGTGGCACGCACAGCCTCACC
    GlyAsnSerAspCysTyrPheGlyAsnGlySerAlaTyrArgGlyThrHisSerLeuThr 430       440       450       460       470       480
    GAGTCGGGTGCCTCCTGCCTCCCGTGGAATTCCATGATCCTGATAGGCAAGGTTTACACA
    GluSerGlyAlaSerCysLeuProTrpAsnSerMetIleLeuIleGlyLysValTyrThr 490       500       510       520       530       540
    GCACAGAACCCCAGTGCCCAGGCACTGGGCCTGGGCAAACATAATTACTGCCGGAATCCT
    AlaGlnAsnProSerAlaGlnAlaLeuGlyLeuGlyLysHisAsnTyrCysArgAsnPro 550       560       570       580       590       600
    GATGGGGATGCCAAGCCCTGGTGCCACGTGCTGAAGAACCGCAGGCTGACGTGGGAGTAC
    AspGlyAspAlaLysProTrpCysHisValLeuLysAsnArgArgLeuThrTrpGluTyr 610       620       630       640       650       660
    TGTGATGTGCCCTCCTGCTCCACCTGCGGCCTGAGACAGTACAGCCAGCCTCAGTTTCGC
    CysAspValProSerCysSerThrCysGlyLeuArgGlnTyrSerGlnProGlnPheArg
```

FIG.38A

```
          670       680       690       700       710       720
ATCAAAGGAGGGCTCTTCGCCGACATCGCCTCCCACCCCTGGCAGGCTGCCATCTTTGCC
IleLysGlyGlyLeuPheAlaAspIleAlaSerHisProTrpGlnAlaAlaIlePheAla 730       740       750       760       770       780
AAGCACAGGAGGTCGCCCGGAGAGCGGTTCCTGTGCGGGGGCATACTCATCAGCTCCTGC
LysHisArgArgSerProGlyGluArgPheLeuCysGlyGlyIleLeuIleSerSerCys 790       800       810       820       830       840
TGGATTCTCTCTGCCGCCCACTGCTTCCAGGAGAGGTTTCCGCCCCACCACCTGACGGTG
TrpIleLeuSerAlaAlaHisCysPheGlnGluArgPheProProHisHisLeuThrVal 850       860       870       880       890       900
ATCTTGGGCAGAACATACCGGGTGGTCCCTGGCGAGGAGGAGCAGAAATTTGAAGTCGAA
IleLeuGlyArgThrTyrArgValValProGlyGluGluGluGlnLysPheGluValGlu 910       920       930       940       950       960
AAATACATTGTCCATAAGGAATTCGATGATGACACTTACGACAATGACATTGCGCTGCTG
LysTyrIleValHisLysGluPheAspAspAspThrTyrAspAsnAspIleAlaLeuLeu 970       980       990      1000      1010      1020
CAGCTGAAATCGGATTCGTCCCGCTGTGCCCAGGAGAGCAGCGTGGTCCGCACTGTGTGC
GlnLeuLysSerAspSerSerArgCysAlaGlnGluSerSerValValArgThrValCys 1030      1040      1050      1060      1070      1080
CTTCCCCCGGCGGACCTGCAGCTGCCGGACTGGACGGAGTGTGAGCTCTCCGGCTACGGC
LeuProProAlaAspLeuGlnLeuProAspTrpThrGluCysGluLeuSerGlyTyrGly 1090      1100      1110      1120      1130      1140
AAGCATGAGGCCTTGTCTCCTTTCTATTCGGAGCGGCTGAAGGAGGCTCATGTCAGACTG
LysHisGluAlaLeuSerProPheTyrSerGluArgLeuLysGluAlaHisValArgLeu 1150      1160      1170      1180      1190      1200
TACCCATCCAGCCGCTGCACATCACAACATTTACTTAACAGAACAGTCACCGACAACATG
TyrProSerSerArgCysThrSerGlnHisLeuLeuAsnArgThrValThrAspAsnMet 1210      1220      1230      1240      1250      1260
CTGTGTGCTGGAGACACTCGGAGCGGCGGGCCCCAGGCAAACTTGCACGACGCCTGCCAG
LeuCysAlaGlyAspThrArgSerGlyGlyProGlnAlaAsnLeuHisAspAlaCysGln 1270      1280      1290      1300      1310      1320
GGCGATTCTGGAGGCCCCCTGGTGTGTCTGAACGATGGCCGCATGACTTTGGTGGGCATC
GlyAspSerGlyGlyProLeuValCysLeuAsnAspGlyArgMetThrLeuValGlyIle
```

FIG.38B

```
          1330      1340      1350      1360      1370      1380
ATCAGCTGGGGCCTGGGCTGTGGACAGAAGGATGTCCCGGGTGTGTACACAAAGGTTACC
IleSerTrpGlyLeuGlyCysGlyGlnLysAspValProGlyValTyrThrLysValThr 1390      1400      1410      1420
AACTACCTAGACTGGATTCGTGACAACATGCGACCGTGA - 3'
AsnTyrLeuAspTrpIleArgAspAsnMetArgPro***
                                     ←|
```

FIG.38C

```
            10         20         30         40         50         60
5' - ATGGATGCAATGAAGAGAGGGCTCTGCTGTGTGCTGCTGCTGTGTGGAGCAGTCTTGCTT
     MetAspAlaMetLysArgGlyLeuCysCysValLeuLeuLeuCysGlyAlaValPheVal 70         80         90        100        110        120
     TCGCCCAGCCAGGAAATCCATGCCCGATTCAGAAGAGGAGCCAGATCTGAGGGAAACAGT
     SerProSerGlnGluIleHisAlaArgPheArgArgGlyAlaArgSerGluGlyAsnSer
                                                  |→ TTktPA
            130        140        150        160        170        180
     GACTGCTACTTTGGGAATGGGTCAGCCTACCGTGGCACGCACAGCCTCACCGAGTCGGGT
     AspCysTyrPheGlyAsnGlySerAlaTyrArgGlyThrHisSerLeuThrGluSerGly 190        200        210        220        230        240
     GCCTCCTGCCTCCCGTGGAATTCCATGATCCTGATAGGCAAGGTTTACACAGCACAGAAC
     AlaSerCysLeuProTrpAsnSerMetIleLeuIleGlyLysValTyrThrAlaGlnAsn 250        260        270        280        290        300
     CCCAGTGCCCAGGCACTGGGCCTGGGCAAACATAATTACTGCCGGAATCCTGATGGGGAT
     ProSerAlaGlnAlaLeuGlyLeuGlyLysHisAsnTyrCysArgAsnProAspGlyAsp 310        320        330        340        350        360
     GCCAAGCCCTGGTGCCACGTGCTGAAGAACCGCAGGCTGACGTGGGAGTACTGTGATGTG
     AlaLysProTrpCysHisValLeuLysAsnArgArgLeuThrTrpGluTyrCysAspVal 370        380        390        400        410        420
     CCCTCCTGCTCCACCTGCGGCCTGAGACAGTACAGCCAGCCTCAGTTTCGCATCAAAGGA
     ProSerCysSerThrCysGlyLeuArgGlnTyrSerGlnProGlnPheArgIleLysGly 430        440        450        460        470        480
     GGGCTCTTCGCCGACATCGCCTCCCACCCCTGGCAGGCTGCCATCTTTGCCAAGCACAGG
     GlyLeuPheAlaAspIleAlaSerHisProTrpGlnAlaAlaIlePheAlaLysHisArg 490        500        510        520        530        540
     AGGTCGCCCGGAGAGCGGTTCCTGTGCGGGGGCATACTCATCAGCTCCTGCTGGATTCTC
     ArgSerProGlyGluArgPheLeuCysGlyGlyIleLeuIleSerSerCysTrpIleLeu 550        560        570        580        590        600
     TCTGCCGCCCACTGCTTCCAGGAGAGGTTTCCGCCCCACCACCTGACGGTGATCTTGGGC
     SerAlaAlaHisCysPheGlnGluArgPheProProHisHisLeuThrValIleLeuGly 610        620        630        640        650        660
     AGAACATACCGGGTGGTCCCTGGCGAGGAGGAGCAGAAATTTGAAGTCGAAAAATACATT
     ArgThrTyrArgValValProGlyGluGluGluGlnLysPheGluValGluLysTyrIle
```

FIG.39A

```
          670       680       690       700       710       720
GTCCATAAGGAATTCGATGATGACACTTACGACAATGACATTGCGCTGCTGCAGCTGAAA
ValHisLysGluPheAspAspAspThrTyrAspAsnAspIleAlaLeuLeuGlnLeuLys 730       740       750       760       770       780
TCGGATTCGTCCCGCTGTGCCCAGGAGAGCAGCGTGGTCCGCACTGTGTGCCTTCCCCCG
SerAspSerSerArgCysAlaGlnGluSerSerValValArgThrValCysLeuProPro 790       800       810       820       830       840
GCGGACCTGCAGCTGCCGGACTGGACGGAGTGTGAGCTCTCCGGCTACGGCAAGCATGAG
AlaAspLeuGlnLeuProAspTrpThrGluCysGluLeuSerGlyTyrGlyLysHisGlu 850       860       870       880       890       900
GCCTTGTCTCCTTTCTATTCGGAGCGGCTGAAGGAGGCTCATGTCAGACTGTACCCATCC
AlaLeuSerProPheTyrSerGluArgLeuLysGluAlaHisValArgLeuTyrProSer 910       920       930       940       950       960
AGCCGCTGCACATCACAACATTTACTTAACAGAACAGTCACCGACAACATGCTGTGTGCT
SerArgCysThrSerGlnHisLeuLeuAsnArgThrValThrAspAsnMetLeuCysAla 970       980       990       1000      1010      1020
GGAGACACTCGGAGCGGCGGGCCCCAGGCAAACTTGCACGACGCCTGCCAGGGCGATTCG
GlyAspThrArgSerGlyGlyProGlnAlaAsnLeuHisAspAlaCysGlnGlyAspSer 1030      1040      1050      1060      1070      1080
GGAGGCCCCCTGGTGTGTCTGAACGATGGCCGCATGACTTTGGTGGGCATCATCAGCTGG
GlyGlyProLeuValCysLeuAsnAspGlyArgMetThrLeuValGlyIleIleSerTrp 1090      1100      1110      1120      1130      1140
GGCCTGGGCTGTGGACAGAAGGATGTCCCGGGTGTGTACACAAAGGTTACCAACTACCTA
GlyLeuGlyCysGlyGlnLysAspValProGlyValTyrThrLysValThrAsnTyrLeu 1150      1160      1170
GACTGGATTCGTGACAACATGCGACCGTGA - 3'
AspTrpIleArgAspAsnMetArgPro***
```

FIG.39B

```
              10        20        30        40        50        60
5' - ATGGATGCAATGAAGAGAGGGCTCTGCTGTGTGCTGCTGCTGTGTGGAGCAGTCTTGCTT
     MetAspAlaMetLysArgGlyLeuCysCysValLeuLeuLeuCysGlyAlaValPheVal 70        80        90       100       110       120
     TCGCCCAGCCAGGAAATCCATGCCCGATTCAGAAGAGGAGCCAGATCTGAGGGAAACAGT
     SerProSerGlnGluIleHisAlaArgPheArgArgGlyAlaArgSerGluGlyAsnSer
                                                |→ STTktPA
             130       140       150       160       170       180
     GACTGCTACTTTGGGAATGGGTCAGCCTACCGTGGCACGCACAGCCTCACCGAGTCGGGT
     AspCysTyrPheGlyAsnGlySerAlaTyrArgGlyThrHisSerLeuThrGluSerGly 190       200       210       220       230       240
     GCCTCCTGCCTCCCGTGGAATTCCATGATCCTGATAGGCAAGGTTTACACAGCACAGAAC
     AlaSerCysLeuProTrpAsnSerMetIleLeuIleGlyLysValTyrThrAlaGlnAsn 250       260       270       280       290       300
     CCCAGTGCCCAGGCACTGGGCCTGGGCAAACATAATTACTGCCGGAATCCTGATGGGGAT
     ProSerAlaGlnAlaLeuGlyLeuGlyLysHisAsnTyrCysArgAsnProAspGlyAsp 310       320       330       340       350       360
     GCCAAGCCCTGGTGCCACGTGCTGAAGAACCGGCAGGCTGACGTGGGAGTACTGTGATGTG
     AlaLysProTrpCysHisValLeuLysAsnArgArgLeuThrTrpGluTyrCysAspVal 370       380       390       400       410       420
     CCCTCCTGCTCCACCTGCGGCCTGAGACAGTACAGCCAGCCACAGTTTGATATCAAAGGA
     ProSerCysSerThrCysGlyLeuArgGlnTyrSerGlnProGlnPheAspIleLysGly 430       440       450       460       470       480
     GGCCTCTTCGCCGACATCGCCTCCCACCCCTGGCAGGCTGCCATCTTTGCCAAGCACAGG
     GlyLeuPheAlaAspIleAlaSerHisProTrpGlnAlaAlaIlePheAlaLysHisArg 490       500       510       520       530       540
     AGGTCGCCCGGAGAGCGGTTCCTGTGCGGGGGCATACTCATCAGCTCCTGCTGGATTCTC
     ArgSerProGlyGluArgPheLeuCysGlyGlyIleLeuIleSerSerCysTrpIleLeu 550       560       570       580       590       600
     TCTGCCGCCCACTGCTTCCAGGAGAGGTTTCCGCCCCACCACCTGACGGTGATCTTGGGC
     SerAlaAlaHisCysPheGlnGluArgPheProProHisHisLeuThrValIleLeuGly 610       620       630       640       650       660
     AGAACATACCGGGTGGTCCCTGGCGAGGAGGAGCAGAAATTTGAAGTCGAAAAATACATT
     ArgThrTyrArgValValProGlyGluGluGluGlnLysPheGluValGluLysTyrIle
```

FIG.40A

```
          670       680       690       700       710       720
GTCCATAAGGAATTCGATGATGACACTTACGACAATGACATTGCGCTGCTGCAGCTGAAA
ValHisLysGluPheAspAspAspThrTyrAspAsnAspIleAlaLeuLeuGlnLeuLys 730       740       750       760       770       780
TCGGATTCGTCCCGCTGTGCCCAGGAGAGCAGCGTGGTCCGCACTGTGTGCCTTCCCCCG
SerAspSerSerArgCysAlaGlnGluSerSerValValArgThrValCysLeuProPro 790       800       810       820       830       840
GCGGACCTGCAGCTGCCGGACTGGACGGAGTGTGAGCTCTCCGGCTACGGCAAGCATGAG
AlaAspLeuGlnLeuProAspTrpThrGluCysGluLeuSerGlyTyrGlyLysHisGlu 850       860       870       880       890       900
GCCTTGTCTCCTTTCTATTCGGAGCGGCTGAAGGAGGCTCATGTCAGACTGTACCCATCC
AlaLeuSerProPheTyrSerGluArgLeuLysGluAlaHisValArgLeuTyrProSer 910       920       930       940       950       960
AGCCGCTGCACATCACAACATTTACTTAACAGAACAGTCACCGACAACATGCTGTGTGCT
SerArgCysThrSerGlnHisLeuLeuAsnArgThrValThrAspAsnMetLeuCysAla 970       980       990      1000      1010      1020
GGAGACACTCGGAGCGGCGGGCCCCAGGCAAACTTGCACGACGCCTGCCAGGGCGATTCG
GlyAspThrArgSerGlyGlyProGlnAlaAsnLeuHisAspAlaCysGlnGlyAspSer 1030      1040      1050      1060      1070      1080
GGAGGCCCCCTGGTGTGTCTGAACGATGGCCGCATGACTTTGGTGGGCATCATCAGCTGG
GlyGLyProLeuValCysLeuAsnAspGlyArgMetThrLeuValGlyIleIleSerTrp 1090      1100      1110      1120      1130      1140
GGCCTGGGCTGTGGACAGAAGGATGTCCCGGGTGTGTACACAAAGGTTACCAACTACCTA
GlyLeuGlyCysGlyGlnLysAspValProGlyValTyrThrLysValThrAsnTyrLeu 1150      1160      1170
GACTGGATTCGTGACAACATGCGACCGTGA - 3'
AspTrpIleArgAspAsnMetArgPro***
                              ←|
```

FIG.40B

TISSUE PLASMINOGEN ACTIVATOR

This is a Division, of application Ser. No. 08/412,859 filed on Mar. 29, 1995, now U.S. Pat. No. 5,648,250, which is a continuation of application Ser. No. 08/238,796 filed on May 6, 1994, abandoned, which is a continuation of application Ser. No. 08/131,672 filed on Oct. 5, 1993, abandoned, which is a continuation of application Ser. No. 07/991,714 filed on Dec. 16, 1992, abandoned, which is a continuation of application Ser. No. 07/879,736 filed on May 6, 1992, abandoned, which is a continuation of application Ser. No. 07/711,410 filed on Jun. 5, 1991, abandoned, which is a continuation of application Ser. No. 07/227,149 filed on Aug. 2, 1988, abandoned.

This invention relates to a new tissue plasminogen activator. More particularly, it relates to a new tissue plasminogen activator which has strong activity for converting plasminogen into plasmin that degrades the fibrin network of blood clot to form soluble products and therefore is useful as a thrombolytic agent, to DNA sequence encoding amino acid sequence of it, to a process for producing it and pharmaceutical composition comprising it.

The whole amino acid sequence and structure of a native human "tissue plasminogen activator" (hereinafter referred to as "t-PA") and DNA sequence coding for it derived from a human melanoma cell (Bowes) have already been clarified by recombinant DNA technology [Cf. Nature 301, 214 (1983)].

However, the native t-PA obtained by expressing DNA encoding amino acid sequence of the native t-PA in *E. coli* can hardly be refolded and therefore only an extremely small quantity of the active t-PA can be recovered from the cultured cells of the *E. coli*.

From the results of various investigations, inventors of this invention succeeded in producing new t-PA which is well refolded, even in a form of the resultant product obtained from the *E. coli* cells to give an active t-PA, and display a longer half-life and has a stronger thrombolytic activity than the native t-PA.

The new t-PA of this invention may be represented by the following amino acid sequence (I) as its primary structure (SEQ ID NO:1).

```
                                    180                                          190
         R— Glu Gly Asn Ser Asp Cys Tyr Phe Gly Asn Gly Ser Ala Tyr Arg Gly Thr His Ser 200                                          210
         Leu Thr Glu Ser Gly Ala Ser Cys Leu Pro Trp Asn Ser Met Ile Leu Ile Gly Lys Val 220                                          230
         Tyr Thr Ala Gln Asn Pro Ser Ala Gln Ala Leu Gly Leu Gly Lys His Asn Tyr Cys Arg 240                                          250
         Asn Pro Asp Gly Asp Ala Lys Pro Trp Cys His Val Leu Lys Asn Arg Arg Leu Thr Trp 260                                          270
         Glu Tyr Cys Asp Val Pro Ser Cys Ser Thr Cys Gly Leu Arg Gln ——————— Y ———————

277          280                                      290
         ——————— X — Gly Gly Leu Phe Ala Asp Ile Ala Ser His Pro Trp Gln Ala Ala Ile 300                                          310
         Phe Ala Lys His Arg Arg Ser Pro Gly Glu Arg Phe Leu Cys Gly Gly Ile Leu Ile Ser 320                                          330
         Ser Cys Trp Ile Leu Ser Ala Ala His Cys Phe Gln Glu Arg Phe Pro Pro His His Leu 340                                          350
         Thr Val Ile Leu Gly Arg Thr Tyr Arg Val Val Pro Glu Glu Glu Glu Gln Lys Phe Gln 360                                          370
         Val Glu Lys Tyr Ile Val His Lys Glu Phe Asp Asp Asp Thr Tyr Asp Asn Asp Ile Ala 380                                          390
         Leu Leu Gln Leu Lys Ser Asp Ser Ser Arg Cys Ala Gln Glu Ser Ser Val Val Arg Thr 400                                          410
         Val Cys Leu Pro Pro Ala Asp Leu Gln Leu Pro Asp Trp Thr Glu Cys Glu Leu Ser Gly 420                                          430
         Tyr Gly Lys His Glu Ala Leu Ser Pro Phe Tyr Ser Glu Arg Leu Lys Glu Ala His Val 440                                          450
         Arg Leu Tyr Pro Ser Ser Arg Cys Thr Ser Gln His Leu Leu Asn Arg Thr Val Thr Asp 460                                          470
         Asn Met Leu Cys Ala Gly Asp Thr Arg Ser Gly Gly Pro Gln Ala Asn Leu His Asp Aal 480                                          490
         Cys Gln Gly Asp Ser Gly Gly Pro Leu Val Cys Leu Asn Asp Gly Arg Met Thr Leu Val 500                                          510
         Gly Ile Ile Ser Trp Gly Leu Gly Cys Gly Gln Lys Asp Val Pro Gly Val Tyr Thr Lys 520                   527
         Val Thr Asn Tyr Leu Asp Trp Ile Arg Asp Asn Met Arg Pro
```

-continued

```
                           92                                    100
    wherein R is Ser— or  Cys Tyr Glu Asp Gln Gly Ile  Ser  Tyr Arg Gly Thr Trp 110                                    120
Ser Thr Ala Glu Ser  Gly Ala Glu Cys Thr Asn Trp Asn Ser  Ser  Ala Leu Ala Gln Lys 130                                    140
Pro Tyr Ser Gly Arg  Arg Pro Asp Ala Ile  Arg Leu Gly Leu  Gly  Asn His Asn Tyr Cys 150                                    160
Arg Asn Pro Asp Arg  Asp Ser Lys Pro Trp Cys Tyr Val Phe  Lys  Ala Gly Lys Tyr Ser 170        174
Ser Glu Phe Cys Ser  Thr Pro Ala Cys Ser—
```

X is −Lys−, −Ile− or bond and (SEQ ID NO: 2)

Y is −TyrSerGlnProGlnPheArgIle− (SEQ ID NO: 3), −TyrSerGlnProGlnPheAspIle− (SEQ ID NO: 4),

−TyrSerGlnProIleProArgSer− (SEQ ID NO: 5) or −ThrLeuArgProArgPheLysIle− (SEQ ID NO: 6).

[The numbering of the amino acid sequences of the t-PA is according to that described in Nature 301, 217 (1983)]

In the above amino acid sequence, $Asn^{184}$, $Asn^{218}$ and $Asn^{448}$ may be glycosylated depending on the nature of host cellular environment in the process for the preparation thereof by recombinant DNA technology.

In this specification, the following code names are conveniently employed for the new t-PAs of this invention.

TTktPA

In the above amino acid sequence (I), R is Ser-, X is -Lys- and Y is -TyrSerGlnProGlnPheArgIle-(SEQ ID NO:3).

TTitPA

In the above amino acid sequence (I), R is Ser-, X is -Ile- and Y is -TyrSerGlnProGlnPheArgIle-(SEQ ID NO:3).

TQitPA

In the above amino acid sequence (I), R is the residues labelled $Cys^{92}$ to $Ser^{174}$- of the native tPA, X is -Ile- and Y is -TyrSerGlnProGlnPheArgIle-(SEQ ID NO:3).

TQktPA

In the above amino acid sequence (I), R is the residues labelled $Cys^{92}$ to $Ser^{74}$- of the native tPA, X is -Lys- and Y is -TyrSerGlnProGlnPheArgIle-(SEQ ID NO:3).

STTktPA

In the above amino acid sequence (I), R is Ser-, X is -Lys- and Y is -TyrSerGlnProGlnPheAspIle-(SEQ ID NO:4).

STQktPA

In the above amino acid sequence (I), R is the residues labelled $Cys^{92}$ $Ser^{174}$- of the native tPA, X is -Lys- and Y is -TyrSerGlnProGlnPheAspIle-(SEQ ID NO:4).

STQitPA

In the above amino acid sequence (I), R is the residues labelled $Cys^{92}$ to $Ser^{174}$- of the native tPA, X is -Ile- and Y is -TyrSerGlnProGlnPheAspIle-(SEQ ID NO:4).

thTTtPA

In the above amino acid sequence (I), R is Ser-, X is bond and Y is -TyrSerGlnProIleProArgSer-(SEQ ID NO:5)

uTTtPA

In the above amino acid sequence (I), R is Ser-, X is -Lys- and Y is -ThrLeuArgProArgPheLyslle-(SEQ ID NO:6)

The native t-PA is a single chain serine protease which is converted to a 2-chain form, heavy and light chains, linked by single disulfide bond with plasmin. The light chain (L) is a protease domain and therefore contains the active-site of the enzyme. The heavy chain (H) has a finger domain (F) (having homology to fibronectin), a growth factor domain (E) (homologous to epidermal growth factor) and two kringles (i.e. kringle 1 and kringle 2 domains; $K_1$ and $K_2$) having triple disulfide bonds. Accordingly, the native t-PA is composed of five functional domains F, E, $K_1$, $K_2$ and L [Cf. European Patent Application laid open No. 0196920 and Proc. Natl. Acad. Sci. USA 83 4670 (1986)].

Therefore, it is to be understood that this invention also provides (1) finger and growth factor domains lacking t-PA without glycosylation and (2) finger and growth factor domains lacking t-PA essentially free from other proteins of human and animal origin.

The above-defined t-PA includes t-PA essentially consisting of kringle 1 and kringle 2 domains of the heavy chain and the light chain of the native t-PA, and a t-PA prepared by deletion or substitution of the amino acid sequence of said t-PA (e.g. t-PA essentially consisting of kringle 2 domain of the heavy chain and the light chain of the native t-PA, the above-exemplified t-PAs in which $Lys^{277}$ is substituted with $Ile^{277}$, and/or $Arg^{275}$ is substituted with $Gly^{275}$, $Glu^{275}$, $Asp^{275}$, etc.).

The new t-PA of this invention can be prepared by recombinant DNA technology and polypeptide synthesis.

Namely, the new t-PA of this invention can be prepared by culturing a host cell transformed with an expression vector comprising DNA encoding an amino acid sequence of the new t-PA in a nutrient medium, and recovering the new t-PA from the cultured broth.

In the above process, particulars of which are explained in more detail as follows.

The host cell may include a microorganism [bacteria (e.g. *Escherichia coli, Bacillus subtilis*, etc.), yeast (e.g. *Saccharomyces cerevisiae*, etc.)], cultured human and animal cells (e.g. CHO cell, L929 cell, etc.) and cultured plant cells. Preferred examples of the microorganism may include bacteria, especially a strain belonging to the genus Escherichia (e.g. *E. coli* HB 101 ATCC 33694, *E. coli* HB 101-16 FERM BP-1872, *E. coli* 294 ATCC 31446, *E. coli* X 1776 ATCC 31537, etc.), yeast, animal cell lines (e.g. mouse L929 cell, Chinese hamster ovary (CHO) cell, etc.) and the like.

When the bacterium, especially *E. coli* is used as a host cell, the expression vector is usually comprising at least promoter-operator region, initiation codon, DNA encoding the amino acid sequence of the new t-PA, termination codon, terminator region and replicatable unit. When yeast or animal cell is used as host cell, the expression vector is preferably composed of at least promoter, initiation codon, DNA encoding the amino acid sequence of the signal peptide and the new t-PA and termination codon and it is possible that enhancer sequence, 5'- and 3'-noncoding region of the native t-PA, splicing junctions, polyadenylation site and replicatable unit are also inserted into the expression vector.

The promoter-operator region comprises promoter, operator and Shine-Dalgarno (SD) sequence (e.g. AAGG, etc.) Examples of the promoter-operator region may include conventionally employed promoter-operator region (e.g. lactose-operon, PL-promoter, trp-promoter, etc.) and the promoter for the expression of the new t-PA in mammalian cells may include HTLV-promoter, SV40 early or late-promoter, LTR-promoter, mouse metallothionein I (MMT)-promoter and vaccinia-promoter.

Preferred initiation codon may include methionine codon (ATG).

The DNA encoding signal peptide may include the DNA encoding signal peptide of t-PA.

The DNA encoding the amino acid sequence of the signal peptide or the new t-PA can be prepared in a conventional manner such as a partial or whole DNA synthesis using DNA synthesizer and/or treatment of the complete DNA sequence coding for native or mutant t-PA inserted in a suitable vector (e.g. pTPA21, pTPA25, pTPA102, p51H, pN53, pST112, etc.) obtainable from a transformant [e.g. $E.\ coli$ LE 392$\lambda^+$ (pTPA21), $E.\ coli$ JA 221 (pTPA 25) ATCC 39808, $E.\ coli$ JA 221 (pTPA 102) (Lys 277→Ile) ATCC 39811, $E.\ coli$ JM109 (p51H) FERM P-9774, $E.\ coli$ JM109(pN53) FERM P-9775, $E.\ coli$ DH-1(pST112) FERM BP-1966, etc.], or genome in a conventional manner (e.g. digestion with restriction enzyme, dephosphorylation with bacterial alkaline phosphatase, ligation using T4 DNA ligase).

The termination codon(s) may include conventionally employed termination codon (e.g. TAG, TGA, etc.).

The terminator region may contain-natural or synthetic terminator (e.g. synthetic fd phage terminator, etc.).

The replicatable unit is a DNA sequence capable of replicating the whole DNA sequence belonging thereto in the host cells and may include natural plasmid, artificially modified plasmid (e.g. DNA fragment prepared from natural plasmid) and synthetic plasmid and preferred examples of the plasmid may include plasmid pBR 322 or artificially modified thereof (DNA fragment obtained from a suitable restriction enzyme treatment of pBR 322) for $E.\ coli$, plasmid pRSVneo ATCC 37198, plasmid pSV2dhfr ATCC 37145 plasmid pdBPV-MMTneo ATCC 37224, plasmid pSV2neo ATCC 37149 for mammalian cell.

The enhancer sequence may include the enhancer sequence (72 bp) of SV40.

The polyadenylation site may include the polyadenylation site of SV40.

The splicing junction may include the splicing junction of SV40.

The promoter-operator region, initiation codon, DNA encoding the amino acid sequence of the new t-PA, termination codon(s) and terminator region can consecutively and circularly be linked with an adequate replicatable unit (plasmid) together, if desired using an adequate DNA fragment(s) (e.g. linker, other restriction site, etc.) in a conventional manner (e.g. digestion with restriction enzyme, phosphorylation using T4 polynucleotide kinase, ligation using T4 DNA-ligase) to give an expression vector. When mammalian cell line is used as a host cell, it is possible that enhancer sequence, promoter, 5'-noncoding region of the cDNA of the native t-PA, initiation codon, DNA encoding amino acid sequences of the signal peptide and the new t-PA, termination codon(s), 3'-noncoding region, splicing junctions and polyadenylation site are consecutively and circularly be linked with an adequate replicatable unit together in the above manner.

The expression vector can be inserted into a host cell. The insertion can be carried out in a conventional manner (e.g. transformation including transfection, microinjection, etc.) to give a transformant including transfectant.

For the production of the new t-PA in the process of this invention, thus obtained transformant comprising the expression vector is cultured in a nutrient medium.

The nutrient medium contains carbon source(s) (e.g. glucose, glycerine, mannitol, fructose, lactose, etc.) and inorganic or organic nitrogen source(s) (e.g. ammonium sulfate, ammonium chloride, hydrolysate of casein, yeast extract, polypeptone, bactotrypton, beef extracts, etc.). If desired, other nutritious sources [e.g. inorganic salts (e.g. sodium or potassium biphosphate, dipotassium hydrogen phosphate, magnesium chloride, magnesium sulfate, calcium chloride), vitamins (e.g. vitamin B1), antibiotics (e.g. ampicillin) etc.] may be added to the medium. For the culture of mammalian cell, Dulbecco's Modified Eagle's Minimum Essential Medium(DMEM) supplemented with fetal calf serum and an antibiotic is often used.

The culture of transformant may generally be carried out at pH 5.5–8.5 (preferably pH 7–7.5) and 18°–40° C. (preferable 25°–38° C.) for 5–50 hours.

When a bacterium such as $E.\ coli$ is used as a host cell, thus produced new t-PA generally exists in cells of the cultured transformant and the cells are collected by filtration or centrifugation, and cell wall and/or cell membrane thereof are destroyed in a conventional manner (e.g. treatment with super sonic waves and/or lysozyme, etc.) to give debris. From the debris, the new t-PA can be purified and isolated in a conventional manner as generally employed for the purification and isolation of natural or synthetic proteins [e.g. dissolution of protein with an appropriate solvent (e.g. 8M aqueous urea, 6M aqueous guanidium salts, etc.), dialysis, gel filtration, column chromatography, high performance liquid chromatography, etc.]. When the mammalian cell is used as a host cell, the produced new t-PA is generally exist in the culture solution. The culture filtrate (supernatant) is obtained by filtration or centrifugation of the cultured broth. From the culture filtrate, the new t-PA can be purified in a conventional manner as exemplified above.

It may be necessary to obtain the active t-PA from the cell debris of bacteria in the above case. For refolding of thus produced new t-PA, it is preferably employed a dialysis method which comprises, dialyzing a guanidine or urea solution of the new t-PA in the presence of reduced glutathione (GSH) and oxidized glutathione (GSSG) at the same concentration of glutathiones inside and outside of semipermeable membrane at 4°–40° C. for 2–60 hours. In this method, the concentration of the glutathiones is preferably more than 2 mM and the ratio of reduced glutathione and oxidized glutathione is preferably 10:1. Further, the glutathiones can be replaced with cysteine and cystine in this method. These method can be preferably used for refolding of all the t-PA including native t-PA produced by DNA recombinant technology.

The new t-PA of this invention is useful as a thrombolytic agent for the treatment of vascular diseases (e.g. myocardial infarction, stroke, heart attack, pulmonary embolism, deep vein thrombosis, peripheral arterial occlusion, etc.). The new t-PA of this invention in admixture with pharmaceutically acceptable carriers can be parenterally to mammals including human being in a form of a pharmaceutical composition such as infusion.

The pharmaceutically acceptable carriers may include various organic or inorganic carrier materials conventionally employed in the preparation of pharmaceutical composition comprising a peptide or protein (e.g. serum albumin etc.).

A dosage of the new t-PA of this invention is to be varied depending on various factors such as kind of diseases, weight and/or age of a patient, and further the kind of administration route.

The optimal dosage of the new t-PA of this invention is usually selected from a dose range of 0.1–10 mg/kg/day by injection or by infusion.

The total daily amount mentioned above may divisionally be given to the patient for several hours.

Mono(or di, or tri)mer (of oligonucleotides) can be prepared by, for examples the Hirose's method [Cf. Tanpakushitsu Kakusan Kohso 25, 255 (1980)] and coupling can be carried out, for examples on cellulose or polystyrene polymer by a phosphotriester method [Cf. Nucleic Acid Research, 9, 1691 (1981), Nucleic Acid Research 10, 1755 (1982)].

BRIEF DESCRIPTION OF THE DRAWINGS

Brief explanation of the accompanying drawings is as follows.

FIG. 1 shows construction and cloning of plasmid pHVBB.

FIG. 2 shows construction and cloning of plasmid pCLiPAxtrp.

FIG. 3 shows DNA sequence of BglII DNA fragment (1974 bp) (SEQ ID NO:38–39).

FIG. 4 shows construction and cloning of plasmid pCLiPAΔxtrp.

FIG. 5 shows construction and cloning of plasmid pTQiPAΔtrp.

FIG. 6 shows construction and cloning of plasmid pTA9004.

FIG. 7 shows construction and cloning of plasmid pTTkPAΔtrp.

FIG. 8 shows DNA sequence of EcoRI DNA fragment (472 bp) (SEQ ID NO:40–41) and

FIG. 9 shows construction and cloning of pTTiPAΔtrp.

FIG. 10 shows construction and cloning of plasmid pTQkPAΔtrp.

FIG. 12 shows construction and cloning of plasmid pST-Tktrp.

FIG. 14 shows construction and cloning of plasmid pST-Qitrp.

FIG. 15 shows construction and cloning of plasmid pSTQktrp.

FIG. 16 shows construction and cloning of plasmid pMH9006.

FIG. 17 shows construction and cloning of plasmid pthTTtrp.

FIG. 19 shows construction and cloning of plasmid puTTtrp.

FIG. 21 shows cDNA sequence of a native t-PA in pST112 (SEQ ID NO:42–43).

FIG. 29 shows DNA sequence of coding region in pTTkPAΔtrp (SEQ ID NO:44–45).

FIG. 30 shows DNA sequence of coding region in pTTiPAΔtrp (SEQ ID NO:46–47).

FIG. 31 shows DNA sequence of coding region in pTQkPAΔtrp (SEQ ID NO:48–49).

FIG. 32 shows DNA sequence of coding region in pTQiPAΔtrp (SEQ ID NO:50–51).

FIG. 33 shows DNA sequence of coding region in pST-Tktrp (SEQ ID NO:52–53).

FIG. 34 shows DNA sequence of coding region in pSTQktrp (SEQ ID NO:54–55).

FIG. 35 shows DNA sequence of coding region in pST-Qitrp (SEQ ID NO:56–57).

FIG. 36 shows DNA sequence of coding region in puTTtrp (SEQ ID NO:58–59).

FIG. 37 shows DNA sequence of coding region in pthTTtrp (SEQ ID NO:60–61).

FIG. 38 shows DNA sequence of coding region in pmTQk112 (SEQ ID NO:62–63).

FIG. 39 shows DNA sequence of coding region in pmTTk (SEQ ID NO:64–65).

FIG. 40 shows DNA sequence of coding region in pmSTTk (SEQ ID NO:66–67).

Figure 11:
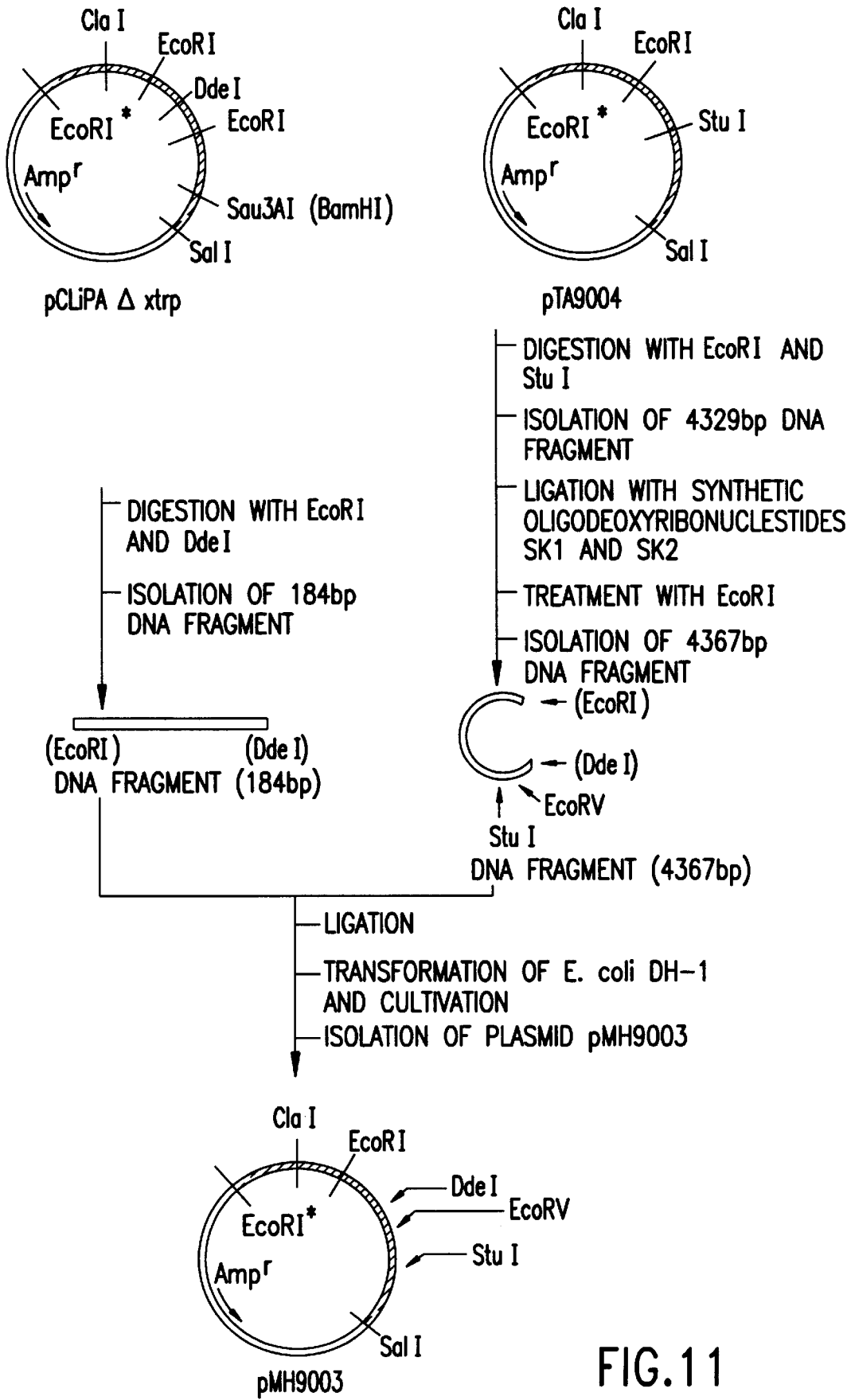
FIG. 11 shows construction and cloning of plasmid pMH9003.

The following Examples are give for the purpose of illustrating this invention, but not limited thereto.

In the Examples, all of the used enzymes (e.g. restriction enzyme, bacterial alkaline phosphatase, T4 DNA ligase) are commercially available and conditions of usage of the enzymes are obvious to the person skilled in the art, for examples, referring to a prescription attached to commercially sold enzymes.

EXAMPLE 1

(Synthesis of oligonucleotides)

The following oligonucleotides were prepared in a conventional manner described as mentioned above.

1) For pHVBB

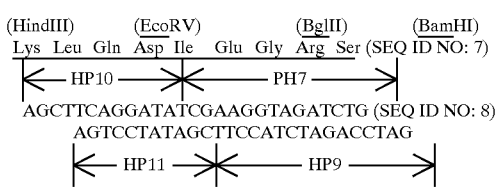

HP10; AG-CTT-CAG-GAT (SEQ ID NO:9)
HP7; ATC-GAA-GGT-AGA-TCT-G (SEQ ID NO:10)
HP11; C-GAT-ATC-CTG-A (SEQ ID NO:11)
HP9; GA-TCC-AGA-TCT-ACC-TT (SEQ ID NO:12)

2) For pTQiPAΔtrp and pTQkPAΔtrp

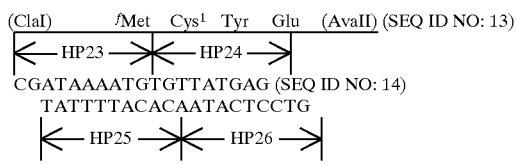

(ClaI)    /Met Cys¹ Tyr Glu   (AvaII) (SEQ ID NO: 13)
CGATAAAATGTGTTATGAG (SEQ ID NO: 14)
TATTTTACACAATACTCCTG

HP23; C-GAT-AAA-AT (SEQ ID NO:15)
HP24; G-TGT-TAT-GAG (SEQ ID NO:16)
EP25; ACA-CAT-TTT-AT (SEQ ID NO:17)
HP26; GTC-CTC-ATA (SEQ ID NO:18)

$Cys^1$ of TQitPA or TQktPA is corresponding to $Cys^{92}$ of the native t-PA reported in Nature 301, 214 (1983).

3) For pTTkPAΔtrp and pTTiPAΔtrp

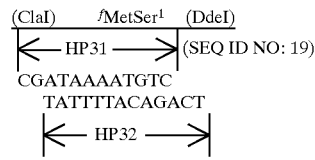

(ClaI)    /MetSer¹  (DdeI)
                         (SEQ ID NO: 19)
CGATAAAATGTC
TATTTTACAGACT

RP31; C-GAT-AAA-ATG-TC (SEQ ID NO:20)
RP32; TC-AGA-CAT-TTT-AT (SEQ ID NO:21)

$Ser^1$ of TTktPA or TTitPA is corresponding to $Ser^{174}$ of the native t-PA reported in Nature 301, 214 (1983).

EXAMPLE 2

(Construction and cloning of plasmid pMVMB) (as illustrated in FIG. 1)

Oligodeoxyribonucleotides HP7 and HP11 (0.2 nmole of each, see: Example 1-(1)) were phosphorylated in 20 μl of a ligation buffer (1 mM ATP, 50 mM tris-HCl (pH 7.6), 10 mM MgCl₂, 20 mM dithiothreitol, 1 mM spermidine, 50 μg/ml bovine serum albumin) with 2.5 units of T4 polynucleotide kinase (Takara Shuzo) at 37° C. for 1 hour. After heat inactivation of the enzyme, other oligodeoxyribonucleotides HP10 and HP9 (0.4 nmole of each), 1 μl of 20 mM ATP and 900 units of T4 DNA ligase (Takara Shuzo) were added to the reaction mixture. The resultant mixture was incubated at 15° C. for 30 minutes to give the crude 27 bp DNA fragment.

On the other hand, pCLaHtrp3t (an expression vector for α-hANP, the preparation of which is described in European Patent Application Laid open No. 0206769) was digested with BamHI and HindIII. The resulting 4137 bp DNA fragment was isolated by 0.8% agarose gel electrophoresis, and ligated to the crude 27 bp DNA fragment in the presence of T4 DNA ligase. The ligation mixture was used to transform *E. coli* DH-1 [Cf. Maniatis, T. et al., Molecular cloning p.505 (1982), Cold Spring Harbor Laboratory (New York)]. From one of the ampicillin resistant transformants, the desired plasmid pHVBB (4164 bp) was isolated and characterized by restriction endonuclease (BglII, EcoRV, PstI, HindIII and BamHI) digestion.

EXAMPLE 3

(Construction and cloning of plasmid pCLiPAxtrp) (as illustrated in FIG. 2)

pHVBB was digested with BqlII. The resulting 4164 linear DNA was incubated with bacterial alkaline phosphatase (Takara Shuzo) in 200 mM Tris-HCl (pH 8.0) at 37° C. for 1 hour to dephosphorylate the both 5' ends of the DNA. The resulting DNA was isolated by 5% polyacrylamide gel electrophoresis (PAGE).

On the other hand, pTPA 102 ($Lys^{277}$→Ile) [an expression vector for a mutant t-PA ($Lys^{277}$→Ile), a transformant comprising the same, *E. coli* JA 221 (pTPA 102) ($Lys^{277}$→Ile) ATCC 39811] was digested with BglII and the 1974 bp DNA fragment (DNA sequence of which is shown in FIG. 3) was isolated. The fragment was ligated to the 4164 bp BglII DNA fragment in the presence of T4 DNA ligase. After transformation of *E. coli* MM294 ATCC 33625, an ampicillin resistant transformant carrying the desired plasmid pCLiPAxtrp (6138 bp), into which the 1974 bp t-PA gene was inserted in a clockwise direction under the down stream of the peptide CLa gene, was obtained. pCLiPAxtrp was characterized by restriction endonuclease (PvuII, EcoRI and BglII) digestion.

EXAMPLE 4

(Construction and cloning of plasmid pCLiPAΔxtrp) (as illustrated in FIG. 4)

pCLiPAxtrp was digested with BamHI and SacI and the resultant 5388 bp DNA fragment was isolated. On the other hand, pCLiPAxtrp was digested with Sau3AI and SacI. The resultant 389 bp DNA fragment was ligated to the 5388 bp DNA fragment in the presence of T4 DNA ligase. The ligation mixture was used to transform *E. coli* DH-1. From one of the ampicillin resistant transformants, the desired plasmid pCLiPAΔxtrp (5777 bp) was isolated and was characterized by restriction endonuclease (ClaI, EcoRI, XhoI, NarI and SacI) digestion.

EXAMPLE 5

(Construction and cloning of plasmid pTQiPAΔtrp) (as illustrated in FIG. 5)

pTPA102 ($Lys^{277}$→Ile) as mentioned above was digested with AvaII and BbeI, an isoshizomer of NarI creating 4 nucleotide-long single-stranded cohesive terminal, and the resulting 50 bp DNA fragment encoding $Asp^{95}$-$Ala^{111}$ of the native t-PA was isolated. On the other hand, the synthetic 19 bp ClaI-AvaII DNA fragment was prepared from HP23, HP24, HP25 and HP26(see:Example 1) using T4 polynucleotide kinase and T4 DNA ligase. It was ligated to the 50 bp DNA fragment with T4 DNA ligase to construct the 69 bp ClaI-BbeI DNA fragment.

pCLiPAΔxtrp was linearized by BbeI partial digestion. The resultant 5777 bp DNA fragment was digested with ClaI and the 5149 bp DNA fragment was isolated. It was ligated to the 69 bp ClaI-BbeI DNA fragment in the presence of T4 DNA ligase. The ligation mixture was used to transform *E. coli* DH-1. From one of the ampicillin resistant transformants, the desired plasmid pTQiPAΔtrp (5218 bp) was obtained, which was characterized by restriction endonuclease digestion.

*E. coli* HB101-16 [HB101 (recA⁺, supE⁺, htpR16(am), tetʳ) FERM P-9502] was transformed with pTQiPAΔtrp to give a transformant, *E. coli* HB101-16 (pTQiPAΔtrp).

EXAMPLE 6

(Construction and cloning of plasmid pTA9004) (as illustrated in FIG. 6)

pCLiPAΔxtrp was digested with DdeI and EcoRI and the 91 bp DNA fragment encoding $Glu^{175}$-$Trp^{204}$ of the native t-PA was isolated. The resultant DNA was ligated to oligodeoxyribonucleotides HP31 and HP32(see:Example 1-(3)) using T4 polynucleotide kinase and T4 DNA ligase. The resultant 103 bp ClaI-EcoRI DNA fragment was ligated to the 4397 bp ClaI-EcoRI fragment of pCLiPAΔxtrp in the presence of T4 DNA ligase. The ligation mixture was used to transform E. coli DH-1. From one of the ampicillin resistant transformants, the desired plasmid pTA9004 (4500 bp) was obtained.

EXAMPLE 7

(Construction and cloning of plasmid pTTkPAΔtrp) (as illustrated in FIG. 7)

pTA9004 was digested with EcoRI and the resultant DNA fragment (4500 bp) was dephosphorylated with bacterial alkaline phosphatase. On the other hand, pTPA21 which comprises the complete cDNA sequence encoding the native t-PA and a portion of the 3'-noncoding region was digested with EcoRI and the 472 bp DNA fragment encoding $Asn^{205}$-$Lys^{361}$ of the native t-PA (DNA sequence of which is shown in FIG. 8) was isolated. The resultant DNA fragment was ligated to the dephosphorylated 4500 bp EcoRI DNA fragment in the presence of T4 DNA ligase. The ligation mixture was used to transform E. coli DH-1. From one of the ampicillin resistant transformants, the desired plasmid pTTkPAΔtrp (4972 bp) was isolated. E. coli HB 101-16 was transformed with pTTkPAΔtrp to give a transformant E. coli HB101-16 (pTTkPAΔtrp).

EXAMPLE 8

(Construction and cloning of plasmid pTTiPAΔtrp) (as illustrated in FIG. 9)

pTA9004 was digested with EcoRI and the resultant DNA was dephosphorylated with bacterial alkaline phosphatase. On the other hand, pTPA 102 ($Lys^{277}$→Ile) as mentioned above was digested with EcoRI and the 472 bp DNA fragment encoding $Asn^{205}$-$Lys^{361}$ of the mutant t-PA ($Lys^{277}$→Ile) was isolated. The resultant DNA fragment was ligated to the dephosphorylated 4500 bp EcoRI DNA fragment in the presence of T4 DNA ligase. The ligation mixture was used to transform E. coli DH-1. From one of the ampicillin resistant transformants, the desired plasmid pTTiPAΔtrp (4972 bp) was isolated. E. coli HB101-16 was transformed with pTTiPAΔtrp to give a transformant E. coli HB 101-16 (pTTiPAΔtrp).

EXAMPLE 9

(Expression and isolation)

A single colony of E. coli HB 101-16 (pTTkPAΔtrp) was inoculated into 5 ml of sterilized LA broth containing bactotrypton 10 g, yeast extract 5 g, NaCl 5 g, 50µg/ml ampicillin (pH 7.2–7.4) in a test tube and incubated at 37° C. for 8 hours under shaking condition. The cultured broth was added to 100 ml of sterilized fresh LA broth in a flask and incubated at 37° C. for 15 hours under shaking condition. A portion (20 ml) of the resultant broth was added to 400 ml of sterilized M9CA broth containing 25 µg/ml ampicillin, and the mixed broth was incubated at 37° C. When $A_{600}$ of the broth reached approximately 0.6, β-indoleacrylic acid was added to the broth in a final concentration of 10 µg/ml. The resultant broth was incubated at 37° C. for 3 hours, and centrifuged at 4° C., 8, 900×g for 10 minutes. The harvested cells were suspended in 100 ml of 10 mM Tris-HCl (pH 8.0) containing 5 mM EDTA, and treated with 50 mg of lysozyme at 4° C. for 1 hour. The resultant mixture was homogenized by a Biotron blender and centrifuged at 4° C., 8, 900×g for 30 minutes. The pellets were washed with 100 ml of 50% aqueous glycerol and dissolved in 800 ml of 10 mM Tris-HCl (pH 8.0) containing 8M urea. To the urea solution, 480 mg of GSH (Kojin) and 96 mg of GSSG (Kojin) were added. The resultant mixture was dialyzed twice against 16 liters of a buffer solution (pH 9.5) containing 20 mM acetic acid, 40 mM ammonia, 2 mM GSH and 0.2 mM GSSG at 4° C. for 15 hours. After centrifuging the mixture, the supernatant was assayed by the following fibrin plate assay. The fibrin plate assay (FPA) was carried out according to the method [Astrup T. and Müllertz S., Arch. Biochem. Biophys. 40 346–351 (1952)] with minor modification. A fibrin plate was prepared by mixing 5 ml of 1.2% human plasminogen-rich fibrinogen (Green-Cross) in 100 mM phosphate buffer (pH 7.2) with 5 ml of thrombin (Mochida, 50 units) in the same buffer, followed by allowing to stand at room temperature for 1 hour. The test solution or human native t-PA (WHO standard) (10 µl of each) were incubated at 37° C. for 18 hours. Using the human native t-PA as the standard, the activities of the samples were calculated from the areas of the lysis zones. From the result of assay, the t-PA activity of the supernatant containing TTkPA was $2.3 \times 10^5$ IU of the native t-PA/l.

EXAMPLE 10

(Expression and isolation)

A single colony of E. coli HB 101-16 (pTTiPAΔtrp) was cultured and TTitPA was isolated from the resultant cultured broth in the substantially the same manner as that described in Example 9. The t-PA activity of the resultant supernatant containing TTitPA was $2.0 \times 10^4$ IU of the native t-PA/l.

EXAMPLE 11

(Expression and isolation)

A single colony of E. coli HB 101-16 (pTQiPAΔtrp) was cultured and TQitPA was isolated from the resultant cultured broth in the substantially the same manner as that described in Example 9. The t-PA activity of the resultant supernatant containing TQitPA was $2.0 \times 10^4$ IU of the native t-PA/l.

EXAMPLE 12

(Purification of TTktPA)

All procedures were performed in cold room (at 4°–6° C.). The plasminogen activator, TTktPA in the supernatant renatured was isolated and purified as follows:

In the first step, the supernatant prepared from 20 liter of the cultured broth obtained in a similar manner to that described in Example 9 [TTktPA total activity: $3.4 \times 10^6$ IU of the native t-PA (WHO)] was loaded onto benzamidine Sepharose column [1.6 cm×3 cm: p-aminobenzamidine was linked covalently to CH Sepharose 4 B (Pharmacia) by the carbodiimide method described in the literature: Las Holmberg, et al., BBA, 445, 215–222 (1976)] equilibrated with 0.05M Tris-HCl (pH 8.0) containing 1M NaCl and 0.01% (v/v) Tween80 and then washed with the same buffer. The plasminogen activator was eluted with 0.05M Tris-HCl (pH 8.0) containing 1M arginine and 0.01% (v/v) Tween80.

In the next step, pooled active fractions were applied on IgG coupled Sepharose (FTP 1163) column (1.6 cm×3 cm)

[monoclonal anti t-PA antibody: FTP 1163 (Tsutomu Kaizu et al., Thrombosis Research, 40, 91–99 (1985) was coupled to CNBr activated Sepharose 4 B according to manufacture's instructions] equilibrated with 0.1M Tris-HCl (pH 8.0). The column was washed with 0.1M Tris-HCl (pH 8.0) containing 1M NaCl, 0.01% (v/v) Tween80 and Aprotinin (10 KIU/ml, Sigma). Elution was done with 0.1M glycine-HCl (pH 2.5) containing 0.5M NaCl, 0.01% Tween80 and Aprotinin (10 KIU/ml).

In the last step, pooled active fractions obtained from the IgG Sepharose (FTP1163) column were dialyzed against 1 liter of 0.01M phosphate buffer (pH 7.4) containing 1.6M KSCN and 0.01% (v/v) Tween80. The solution dialyzed was concentrated to about 2 ml by dialysis against solid polyethylene glycol 20,000. The concentrate obtained was gel-filtered on a Sephacryl S200HR (Pharmacia, 1.6 cm×90 cm) in 0.01M phosphate buffer (pH 7.4) containing 1.6M KSCN and 0.01% (v/v) Tween80. The pooled active fractions were concentrated to about 10 ml by dialysis against solid polyethylene glycol 20,000 and the concentrate was then dialyzed against 0.1M ammonium bicarbonate containing 0.15M NaCl and 0.01% (v/v) Tween80 to give dialyzate containing purified TTktPA (3.4 mg, $7.35 \times 10^5$ IU of the native t-PA (WHO)/mg·protein).

The TTktPA purified have following characteristics.
(i) Analytical SDS PAGE

A 15% polyacrylamide gel was prepared according to the method of Laemmli (U.K. Laemmli, Nature (London 227, 680–685 (1970)). The gel was stained with silver (H. M. Poehling, et al., Electrophoresis, 2, 141 (1981)).

TTktPA thus purified migrate on the SDS-PAGE as a single band at 35K Daltons under reducing condition and 32K Daltons under nonreducing condition, whereas material incubated with plasmin Sepharose (Per Wallin, et al., BBA, 719, 318–328 (1982)) yielded two bands at 30K Daltons (protease domain) and 13.5K Daltons (kringle domain) in the presence of reducing agent, and only one band at 32K Daltons in the absence of reducing agent.
(ii) HPLC TTktPA purified was applied to a (4.6 mm×75 mm) ultrapore RPSC column (Beckman, USA). Elution was performed with a linear gradient of acetonitrile (10–60% (v/v)) in 0.1% (v/v) trifluoroacetic acid at a flow rate of 1.0 ml/min over 30 minutes.

In this system, TTktPA was eluted as single major species at an acetonitrile concentration of approximately 36.5% (v/v).
(iii) N-terminal sequence analysis Purified single chain TTktPA was reduced and carboxymethylated, desalted on HPLC (Ultrapore RPSC column, concentrated by Speed Vac Concentrator (Savant) and analyzed using a gas phase sequencer, model 370A (Applied Biosystem). The N-terminal amino acid sequence of thus obtained TTktPA was as follows.

SerGluGlyAsn-(SEQ ID NO:27)

EXAMPLE 13

(Construction and cloning of plasmid pTQkPAΔtrp)
(as illustrated in FIG. 10)

The plasmid pTQiPAΔtrp was digested with EcoRI. The reaction mixture was dephosphorylated with bacterial alkaline phosphatase and the resultant 4744 bp DNA fragment was isolated. On the other hand, the plasmid pTPA 21 was digested with EcoRI and the resultant 472 bp DNA fragment was isolated. The 472 bp DNA fragment was ligated to the 4744 bp DNA fragment in the presence of T4 DNA ligase and the ligation mixture was used to transform E. coli DH-1. From one of the transformants resistant to ampicillin, the desired plasmid pTQkPAΔtrp was isolated and characterized by restriction mapping. E. coli HB101-16 was transformed with the plasmid pTQkPAΔtrp to give a transformant E. coli HB101-16 (pTQkPAΔtrp).

EXAMPLE 14

(Synthesis of oligonucleotides)

The following oligonucleotides were prepared in a conventional manner described as mentioned above.
1) Linkage sequence for pSTTktrp and pSTQktrp (SEQ ID NO:23–24)

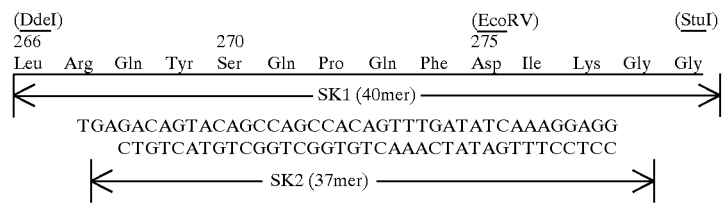

2) Linkage sequence for pSTQitrp (SEQ ID NO:25–26)

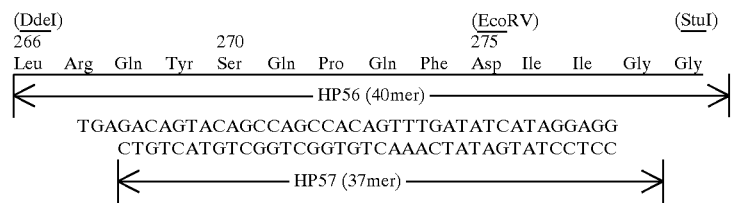

3) Linkage sequence for pthTTtrp (SEQ ID NO:27–28)

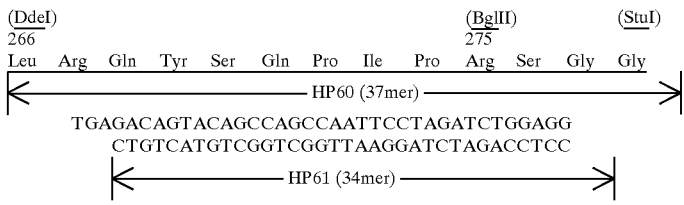

4) Linkage sequence for puTTtrp (SEQ ID NO:29–30)

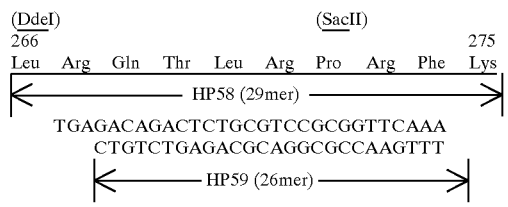

Numbers above the amino acids refer to the positions of the native t-PA reported by Pennica et al (Nature 301, 214–221, 1983).

EXAMPLE 15

(Construction and cloning of plasmid pMH9003) (as illustrated FIG. 11).

The plasmid pTA9004 was digested with EcoRI and StuI, and the resultant 4329 bp DNA fragment was isolated. The DNA fragment was ligated to the synthetic oligodeoxyribonucleotides SK1 and SK2 using T4 polynucleotide kinase and T4 DNA ligase. The reaction mixture was treated with EcoRI to reconstruct the cohesive end digested with EcoRI, and the resultant EcoRI-DdeI DNA fragment (4367 bp) was ligated to the 184 bp EcoRI-DdeI DNA fragment coding $Asn^{205}$-$Leu^{266}$ of the native t-PA which was obtained from the plasmid pCLiPAΔxtrp in the presence of T4 DNA ligase. The ligation mixture was used to transform E. coli DH-1. From one of the transformants resistant to ampicillin, the desired plasmid pMH9003 was isolated and characterized by restriction endonuclease digestion.

EXAMPLE 16

(Construction and cloning of plasmid pSTTktrp) (as illustrated in FIG. 12)

The plasmid pMH9003 was digested with StuI and the resulting DNA fragment (4551 bp) was dephosphorylated with calf intestinal phosphatase (Pharmacia AB). On the other hand, the plasmid pCLiPAΔxtrp was digested with StuI and the resultant 419 bp DNA fragment coding for Gly $^{279}$-$Ala^{419}$ of the native t-PA was isolated. The resultant DNA fragment was ligated to the 4551 bp StuI DNA fragment in the presence of T4 DNA ligase. The ligation mixture was used to transform E. coli DH-1. From one of the transformants resistant to ampicillin, the desired plasmid pSTTktrp was isolated and characterized by restriction endonuclease digestion. E. coli HB101-16 was transformed with the plasmid pSTTktrp to give a transformant, E. coli HB101-16 (pSTTktrp).

EXAMPLE 17

Figure 13:
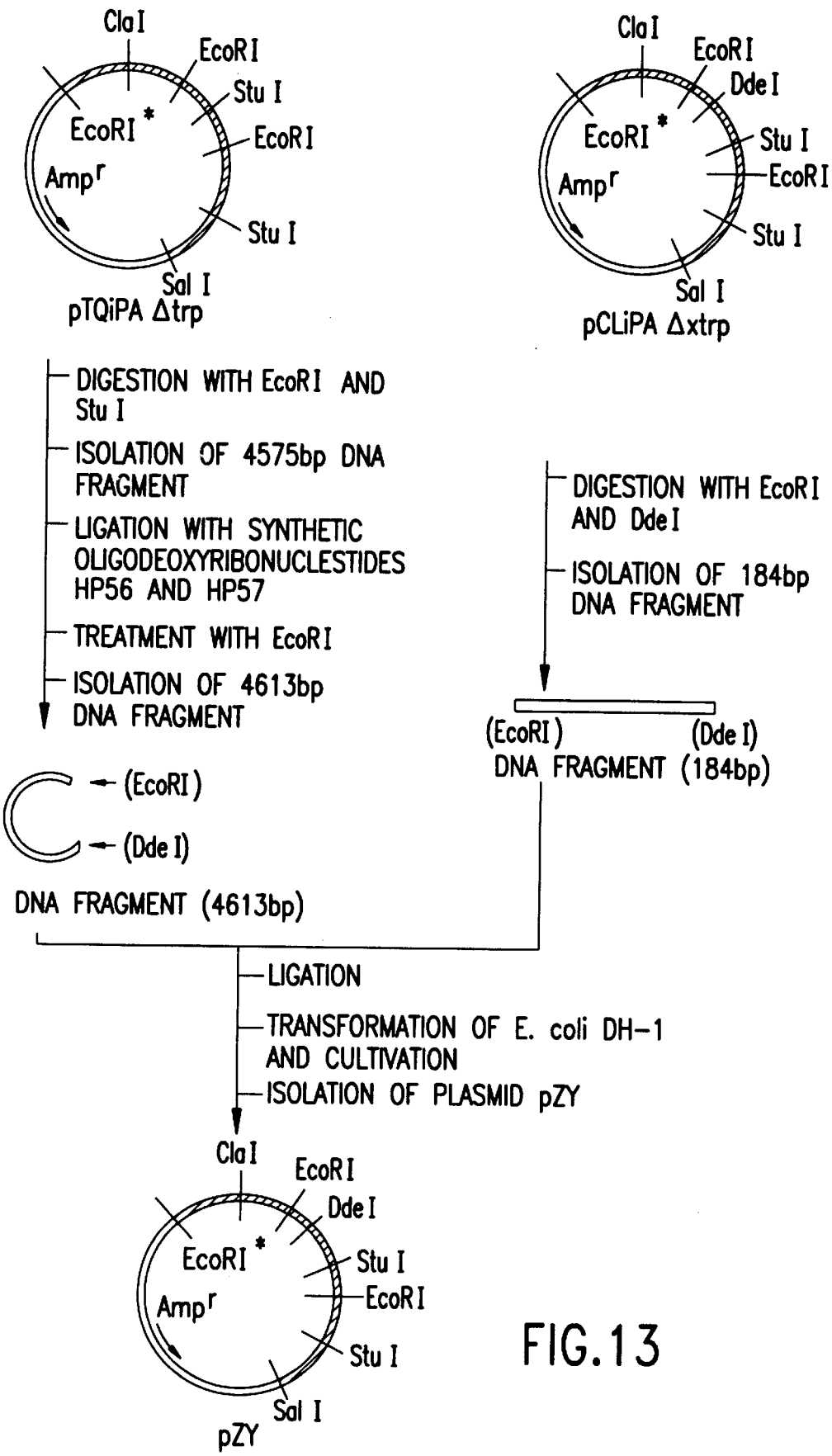
FIG. 13 shows construction and cloning of plasmid pZY.

(Construction and cloning of plasmid pZY) (as illustrated in FIG. 13)

The plasmid pTQiPAΔtrp was digested with EcoRI and StuI, and the resultant 4575 bp DNA fragment was isolated. The DNA fragment was ligated to the synthetic oligodeoxyribonucleotides HP56 and HP57 using T4 polynucleotide kinase and T4 DNA ligase. The reaction mixture was treated with EcoRI to reconstruct the cohesive end digested with EcoRI, and the resultant EcoRI-DdeI DNA fragment (4613 bp) was ligated to the 184 bp EcoRI-DdeI DNA coding for $Asn^{205}$-$Leu^{266}$ of the native t-PA which was prepared from the plasmid pCLiPAΔxtrp in the presence of T4 DNA ligase.

The ligation mixture was used to transform E. coli DH-1. From one of the transformants resistant to ampicillin, the desired plasmid pZY was isolated and characterized by restriction mapping.

EXAMPLE 18

(Construction and cloning of plasmid pSTQitrp) (as shown in FIG. 14)

The plasmid pZY was digested with StuI and the resulting DNA fragment (4797 bp) was dephosphorylated with calf intestinal phosphatase. On the other hand, the plasmid PCLiPAΔxtrp was digested with StuI and the resultant 419 bp DNA fragment coding for $Gly^{279}$-$Ala^{419}$ of the native t-PA was isolated. The 419 DNA fragment was ligated to the 4797 bp DNA fragment in the presence of T4 DNA ligase. The ligation mixture was used to transform E. coli DH-1. From one of the transformants resistant to ampicillin, the desired plasmid pSTQitrp was isolated and characterized by restriction mapping. E. coli HB101-16 was transformed with the plasmid pSTQitrp to give a transformant E. coli HB101-16 (pSTQitrp).

EXAMPLE 19

(Construction and cloning of plasmid pSTQktrp) (as illustrated in FIG. 15)

The plasmid pSTTktrp was digested with ClaI and EcoRV and the resultant 4656 bp DNA fragment was isolated. On the other hand, the plasmid pSTQitrp was digested with ClaI and EcoRV, and the 560 bp DNA fragment coding for $Cys^{1}$-$Asp^{184}$ of STQitPA was isolated. The resulting DNA fragment was ligated to the 4656 bp DNA fragment in the presence of T4 DNA ligase. The ligation mixture was used to transform E. coli DH-1.

From one of the transformants resistant to ampicillin, the desired plasmid pSTQktrp was isolated and characterized by restriction mapping. E. coli HB101-16 was transformed with pSTQktrp to give a. transformant HB101-16 (pSTQktrp).

EXAMPLE 20

(Construction and cloning of plasmid pME9006) (as illustrated in FIG. 16)

The plasmid pTA9004 was digested with StuI and EcoRI, and the resultant 4329 bp DNA fragment was isolated. The DNA fragment was ligated to synthetic oligodeoxyribonucleotides HP60 and HP61 using T4 polynucleotide kinase and T4 DNA ligase. The ligation mixture was digested with EcoRI to regenerate the cohesive end digested with EcoRI, and the resultant EcoRI-DdeI DNA fragment (4364 bp) was ligated to the 184 bp EcoRI-DdeI DNA fragment coding for $Asn^{205}$-$Leu^{266}$ of the native t-PA which was prepared from the plasmid pCLiPAΔxtrp. The ligation mixture was used to transform *E. coli* DH-1. From one of the transformants resistant to ampicillin, the desired plasmid pMH9006 was isolated and characterized by restriction mapping.

EXAMPLE 21

(Construction and cloning of pthTTtrp) (as illustrated in FIG. 17)

The plasmid pMH9006 was digested with StuI and the resultant linearized DNA fragment (4548 bp) was dephosphorylated with calf intestinal phosphatase. On the other hand, the plasmid pCLiPAΔxtrp was digested with StuI and the 419 bp DNA fragment encoding $Gly^{279}$-$Ala^{419}$ of the native t-PA was isolated. The resultant DNA fragment was ligated to the 4548 bp DNA fragment in the presence of T4 DNA ligase. The ligation mixture was used to transform *E. coli* DH-1.

From one of the transformants resistant to ampicillin, the desired plasmid pthTTtrp was isolated and characterized by restriction mapping. *E. coli* HB101-16 was transformed with the plasmid pthTTtrp to give an transformant *E. coli* HB101-16 (pthTTtrp)

EXAMPLE 22

Figure 18:
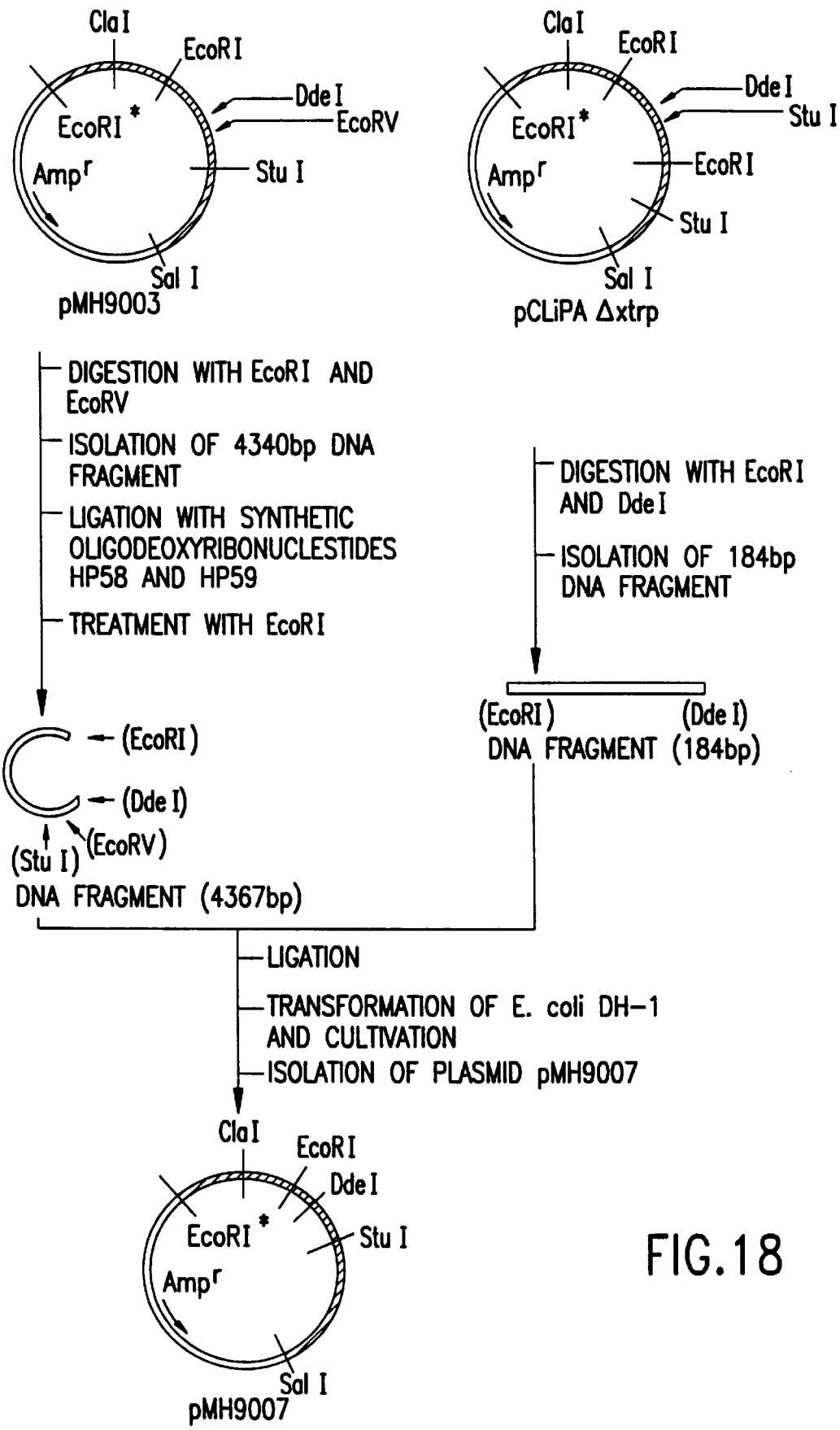
FIG. 18 shows construction and cloning of plasmid pMH9007.

(Construction and cloning of plasmid pMH9007) (as illustrated in FIG. 18)

The plasmid pMH9003 was digested with EcoRI and EcoRV, and the 4340 bp DNA fragment was isolated. The resultant DNA fragment was ligated to the synthetic oligodeoxyribonucleotides HP58 and HP59 by using T4 polynucleotide kinase and T4 DNA ligase. The ligation mixture was treated with EcoRI to regenerate the cohesive terminal digested with EcoRI.

The resultant DNA fragment (4367 bp) was ligated to the 184 bp EcoRI-DdeI DNA fragment obtained from the plasmid pCLiPAΔxtrp in the presence of T4DNA ligase. The ligation mixture was used to transform *E. coli* DH-1.

From one of the transformants resistant to ampicillin, the desired plasmid pMH9007 was isolated and characterized by restriction mapping.

EXAMPLE 23

(Construction and cloning of plasmid pTTtrp) (as illustrated in FIG. 19)

The plasmid pMH9007 was digested with StuI and the resultant linearized DNA fragment (4551 bp) was dephosphorylated with calf intestinal phosphatase. On the other hand, the plasmid pCLiPAΔxtrp was digested with StuI and the resultant 419bp DNA fragment was isolated. The 419 bp DNA fragment was ligated with the 4551 bp DNA fragment in the presence of T4 DNA ligase. The ligation mixture was used to transform *E. coli* DH-1.

From one of the transformants resistance to ampicillin, the desired plasmid puTTtrp was isolated and characterized by restriction mapping. *E. coli* HB101-16 was transformed with the plasmid puTTtrp to give a transformant *E. coli* HB101-16 (puTTtrp).

EXAMPLE 24

(Expression and isolation)

*E. coli* HB101-16 (pTQkPAΔtrp) was cultured and TQk-tPA was isolated from the resultant cultured broth in substantially the same manner as described in Example 9. The t-PA activity of the resultant supernatant containing TQktPA was $7.7 \times 10^4$ IU of the native t-PA/l.

EXAMPLE 25

(Expression and isolation)

*E. coli* HB101-16 (pSTTktrp), *E. coli* HB101-16 (pSTQktrp), *E. coli* HB101-16(pSTQitrp), *E. coli* HB101-16 (pthTTtrp) and *E. coli* HB101-16 (puTTtrp) were used for the expression of new t-PAs. Cultivation of the bacteria was carried out in substantially the same manner as that described in Example 9. The cell pellets obtained from the resultant cultured broth (200 ml) were suspended in 20 ml of 10 mM phosphate buffered saline (pH 8.0) and sonicated at 4° C. for 1 minute. After centrifugation at 15,000 rpm for 20 minutes at 4° C., the resultant pellets were suspended in 20ml of Triton X-100 solution (0.5% Triton X-100, 8% sucrose, 50 mM EDTA, 10 mM Tris.HCl, pH 8.0) and sonicated at 4° C. for 1 minute. The suspension was centrifuged at 15,000 rpm for 20 minute. The resultant pellets were washed with 20 ml of 50% aqueous glycerol and 20 ml of ice-cold ethanol, successively, and dissolved in 20 ml of 8M urea solution containing 8M urea, 20 mM acetic acid, 40 mM ammonium hydroxide, 0.4 mM cysteine and 0.04 mM cystine, pH9.5) by sonication.

After centrifugation at 15,000 rpm for 20 minutes, the supernatant was diluted to A280=0.1 (absorbance at 280 nm) with the 8M urea solution. The resultant solution was dialysed against 10 times volume of aqueous solution containing 20 mM acetic acid, 40 mM ammonium hydroxide, 0.4 mM cysteine and 0.04 mM cystine (pH 9.5) at room temperature for 15 hours. In the above procedure, each of the dialysates containing the new t-PAs, STTktPA, STQktPA, STQitPA, thTTtPA or uTTtPA was obtained from the cultured broth of *E. coli* HB101-16 (pSTTktrp), *E. coli* HB101-16 (pSTQktrp), *E. coli* HB101-16 (pSTQitrp), *E. coli* HB101-16 (pthTTtrp) or *E. coli* HB 101-16 (puTTtrp), respectively. Each of the resultant dialysates was subjected to the fibrin plate assay as described in Example 9, respectively. The results are shown in the following table.

| New t-PA contained in the dialysate | Activity (IU of the native t-PA/l) |
|---|---|
| STTktPA | $1.1 \times 10^5$ |
| STQktPA | $2.3 \times 10^4$ |
| STQitPA | $2.3 \times 10^4$ |
| thTTtPA | $3.7 \times 10^4$ |
| uTTtPA | not detected *) |

*)uTTtPA may be a proenzyme like pro-urokinase. Although it was inactive by fibrin plate assay, it was produced in a ratio of 29 μg/l of the cultured broth as analysed by enzyme immunoassay.

EXAMPLE 26

(Determination of molecular weights of new tPAs)

Molecular weights of the new t-PAs as produced in the above Examples were determined by SDS-PAGE analysis using marker proteins(94,000, 67,000, 45,000, 30,000, 14,400 daltons). The results are shown in the following table.

Molecular weights of the new t-PAs as produced in the above Examples were determined by SDS-PAGE analysis using marker proteins(94,000, 67,000, 45,000, 30,000, 14,400 daltons). The results are shown in the following table.

| The new t-PAs | molecular weight (dalton) |
|---|---|
| TTktPA | approximately 38,000 |
| TTitPA | approximately 38,000 |
| TQitPA | approximately 45,000 |
| TQktPA | approximately 45,000 |
| STTktPA | approximately 38,000 |
| STQktPA | approximately 45,000 |
| STQitPA | approximately 45,000 |
| thTTtPA | approximately 38,000 |
| uTTtPA | approximately 38,000 |

EXAMPLE 27

(Identification of DNA sequence)

Expression vectors were characterized and identified by restriction mapping followed by partial DNA sequencing by the dideoxyribonucleotide chain termination method [Smith, A. J. H. Meth. Enzym. 65, 560–580 (1980)] applied to double strand DNA.

The plasmid pTTkPAΔtrp (2 μg in 16 μl of 10 mM Tris.HCl (pH 7.4)–1 mM EDTA) was treated with 2 mM EDTA (2 μl) and 2N NaOH (2 μl) at room temperature for 5 minutes. To the resultant mixture, 5M ammonium acetate (8 μl) and EtOH (100 μl) was added. The mixture was cooled at −80° C. for 30 minutes and centrifuged at 12,000 rpm for 5 minutes. After discarding the supernatant, precipitates were washed with ice-cold 70% aqueous EtOH and dried in vacuo to give the denatured plasmid.

The plasmid was annealed with a synthetic oligodeoxyribonucleotide primer (5'-ATATTCTGAAATGAGCTGT, (SEQ ID NO:31) corresponding to −55~−37th position of the tryptophan promoter, 5 ng) in 40 mM Tris.HCl (pH 7.5)-20 mM MgCl$_2$-50 mM NaCl at 65° C. for 15 minutes followed by gently cooling to room temperature in 30 minutes. The sequencing reaction was performed with T7 polymerase (Sequenase, United States Biochemical Corp) and -$^{35}$S-dATP (Amersham) according to Tabor, S and Richardson, C.C.,Proc. Natl. Acad. Sci. U.S.A. 84, 4767–4771 (1987). The determined sequence (approximately 150 bases from the primer i.e. 35 bases in the tryptophan promoter and 115 bases in the N-terminal coding sequence of TTktPA) was identical with that as expected.

The DNA sequence of pTQkPAΔtrp was performed in a similar manner as described above.

The DNA sequences of pSTTkPAtrp, pthTTtrp and puTTtrp were performed in a similar manner as above except for using a synthetic oligodeoxyribonucleotide (5'-CTCCGGGCGACCTCCTGTG, (SEQ ID NO:32) complementary to the DNA sequence for His$^{297}$-Gly$^{302}$ of native tPA).

EXAMPLE 28

(Identification of amino acid sequence)

Purified STTktPA which was purified from the dialysate comprising STTktPA obtained in Example 25 by the similar purification method described in Example 12, was dissolved in 8M urea-50 mM Tris.HCl (pH 8.0)-1.5% β-mercaptoethanol, and treated with monoiodoacetic acid for carboxymethylation of SH group in Cys residues. The resultant carboxymethylated STTktPA was purified by preparative HPLC using COSMOSIL 5C$_4$-300 (4.6 mmφ×50 mm, Nakarai Tesque), and sequenced by a gas-phase sequencer 470A (Applied Biosystems Inc). The N-terminal sequence of the sample was Ser-Glu-Gly-Asn-Ser-Asp-Cys-Tyr-Phe-Gly-Asn-Gly-Ser-Ala-Tyr (SEQ ID NO:33) which was identical with the sequence as expected.

EXAMPLE 29

Figure 20:
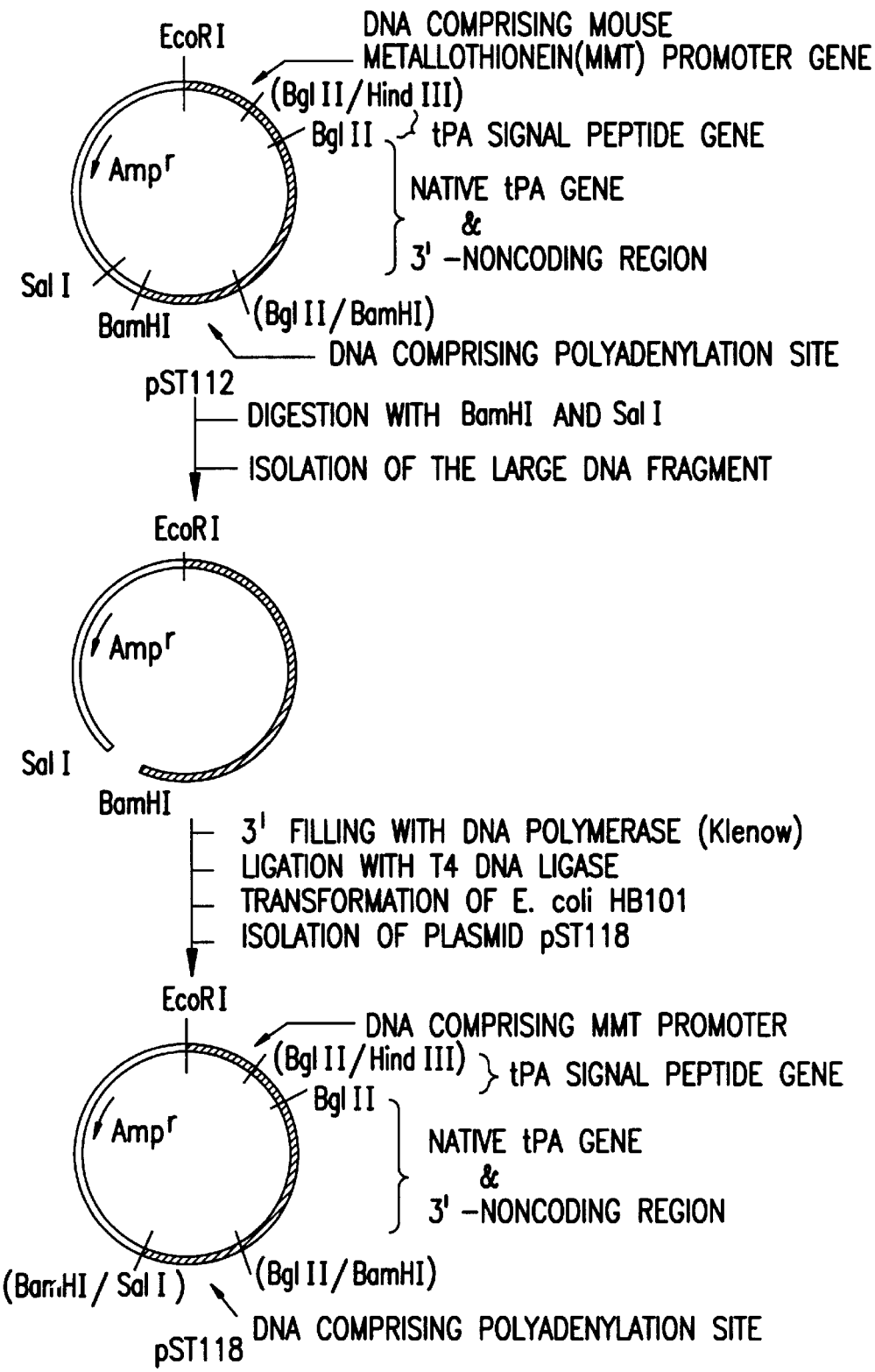
FIG. 20 shows construction and cloning of plasmid pST118.

(Construction and cloning of pST118) (as illustrated in FIG. 20)

The plasmid pST112 [an expression vector for a native t-PA which can be isolated from a transformant comprising the same, E. coli DH-1 FERM BP-1966, the complete cDNA sequence of a native t-PA in pST 112 is illustrated in FIG. 21] was digested with BamHI and SalI.

The large DNA was isolated and blunted with DNA polymerase I (Klenow fragment). The resultant DNA fragment was self-ligated with T4 DNA ligase. The ligation mixture was used to transform E. coli HB11. From one of ampicillin resistant transformants, the objective plasmid pST118 was obtained and characterized by restriction mapping.

EXAMPLE 30

Figure 22:
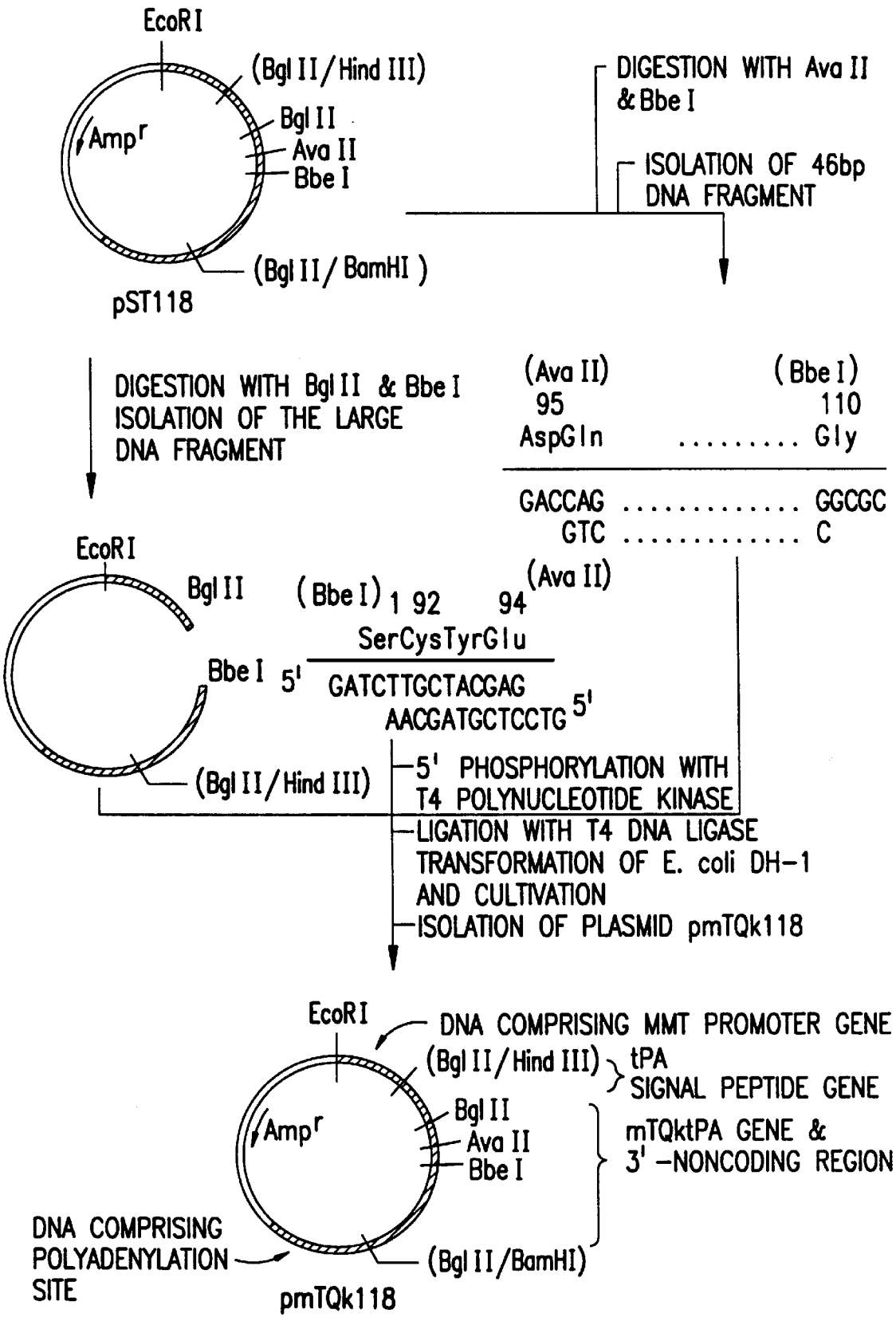
FIG. 22 shows construction and cloning of plasmid pmTQk118
Figure 23:
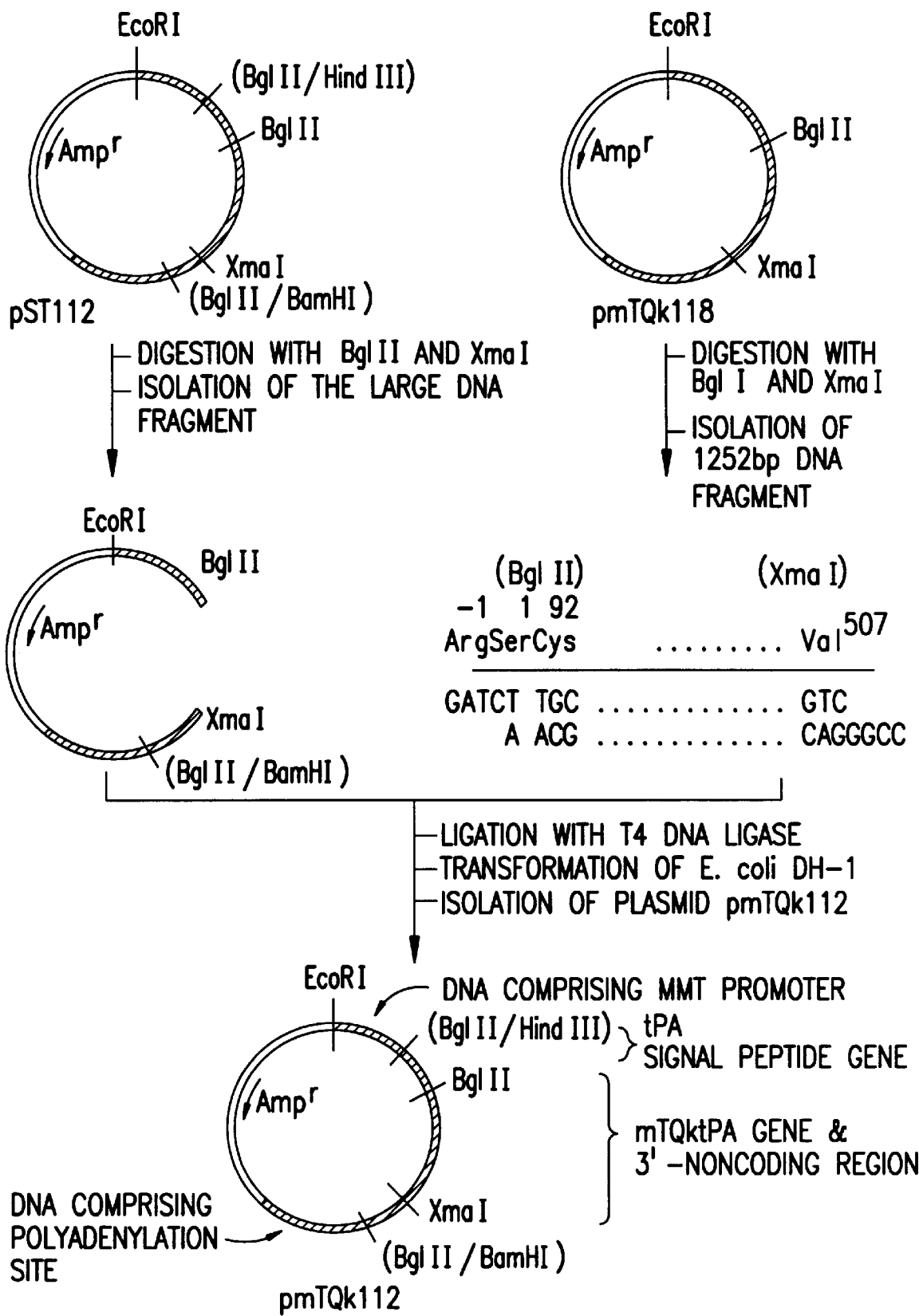
FIG. 23 shows construction and cloning of plasmid pmTQk112.

(Construction and cloning of pmTQk112) (as illustrated in FIG. 22 and 23)

The plasmid pST118 was digested with BglII and BbeI. The large DNA fragment was isolated and ligated to synthetic BglII-AvaII DNAs (5'-GATCTTGCTACGAG (SEQ ID NO:34) and 5'-GTCCTCGTAGCAA (SEQ ID NO:35), each oligomer was phosphorylated with T4 polynucleotide kinase (Takara Suzo)) coding for Arg$^{-1}$ Ser$^{-1}$ Cys$^{92}$ Tyr Glu, and Ava II-BbeI DNA coding for Asp$^{95}$-Gly$^{110}$ of the native tPA from pST118 with T4 DNA ligase (Takara Suzo).

The ligation mixture was used to transform E. coli DH-1. From one of the ampicillin resistant transformants, the objective plasmid pmTQk118 was isolated and characterized by restriction mapping.

On the other hand, the plasmid pST112 was digested with BglII and XmaI. The large DNA fragment was isolated and ligated to 1253 bp BglII-XmaI DNA coding for Arg$^{-1}$-Val$^{507}$ from pmTQk118 with T4 DNA ligase to give pmTQk112, an expression vector for mTQktPA in mammalian cell.

EXAMPLE 31

Figure 24:
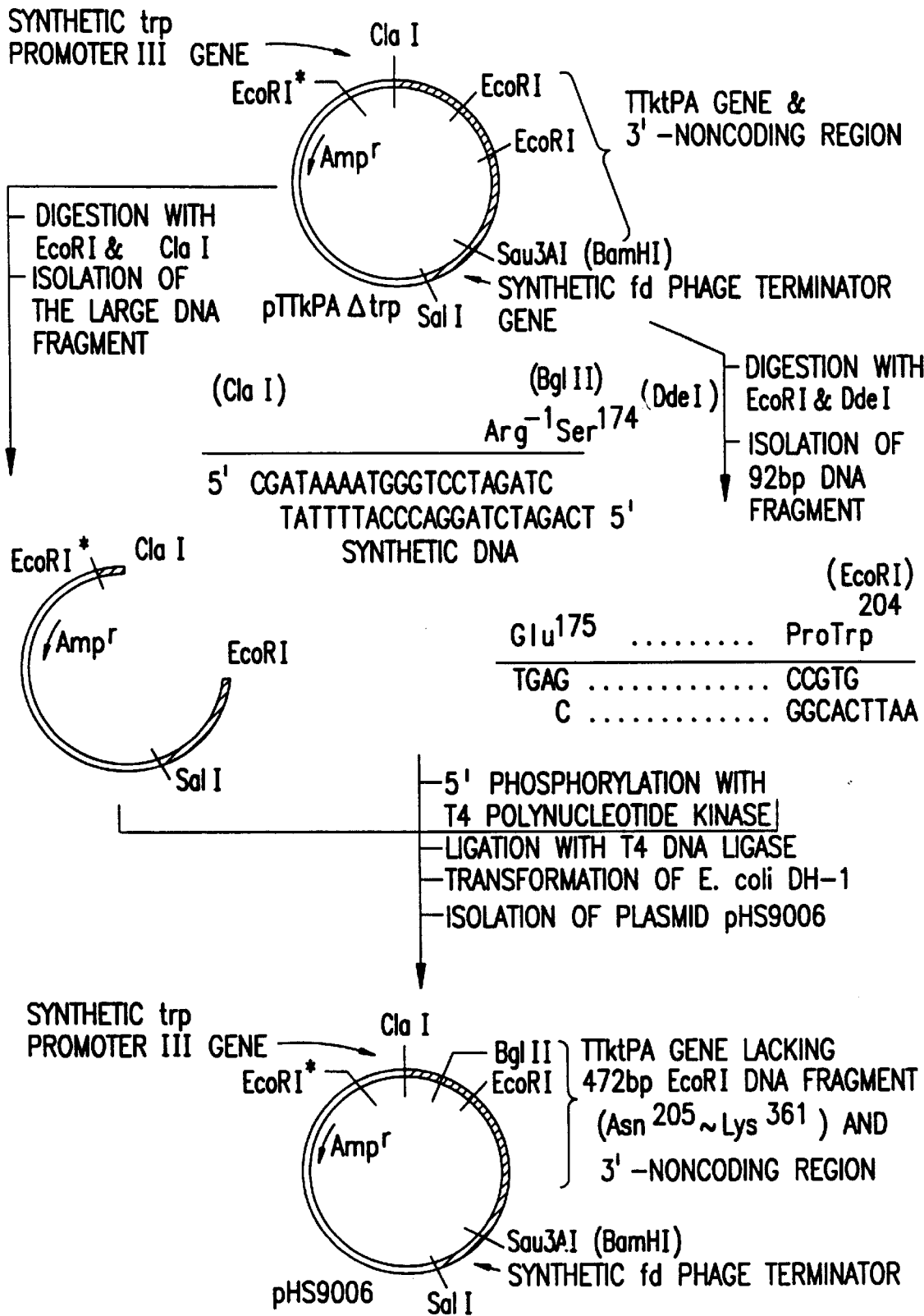
FIG. 24 shows construction and cloning of plasmid pHS9006.
Figure 25:
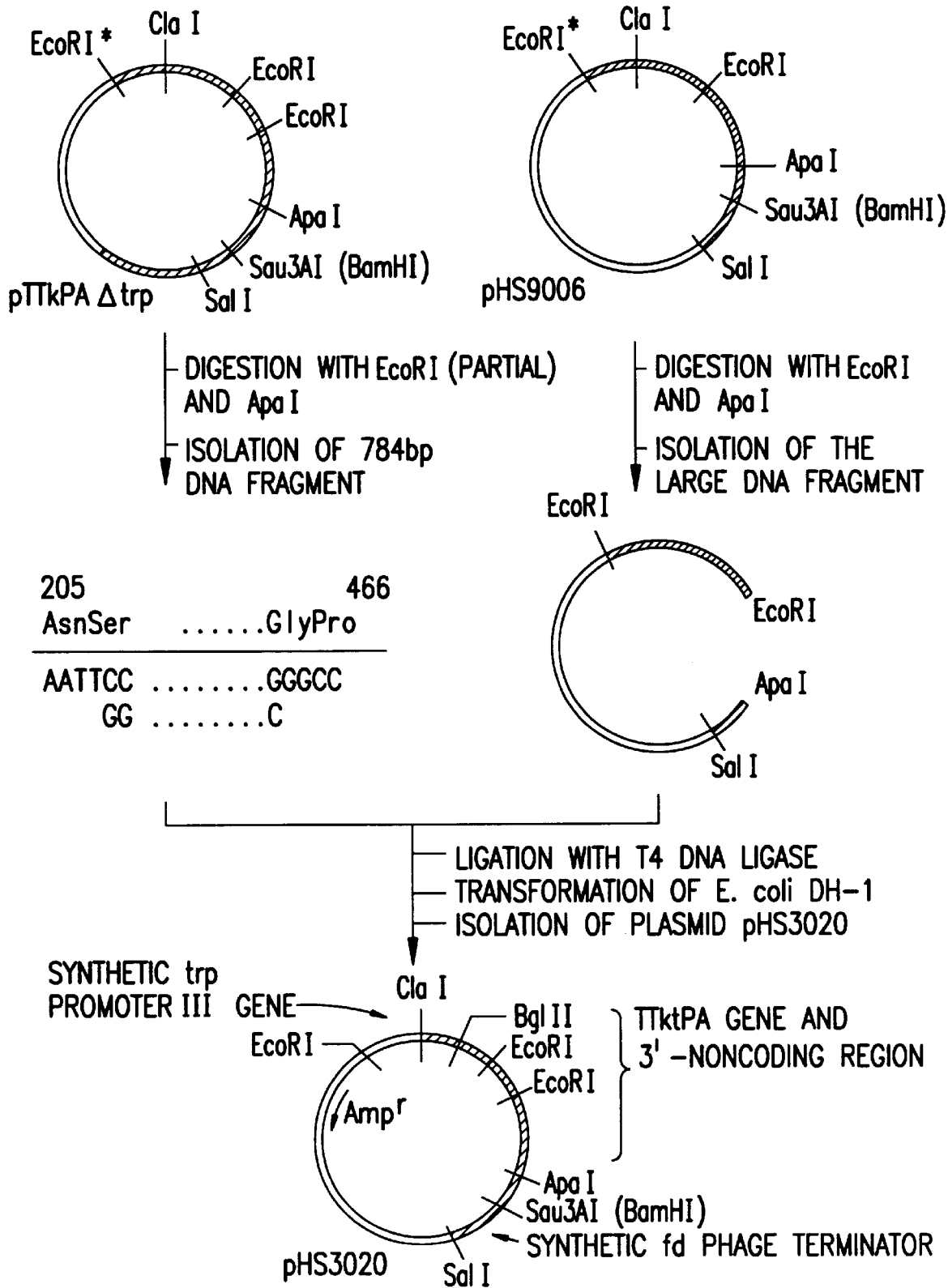
FIG. 25 shows construction and cloning of plasmid pHS3020.
Figure 26:
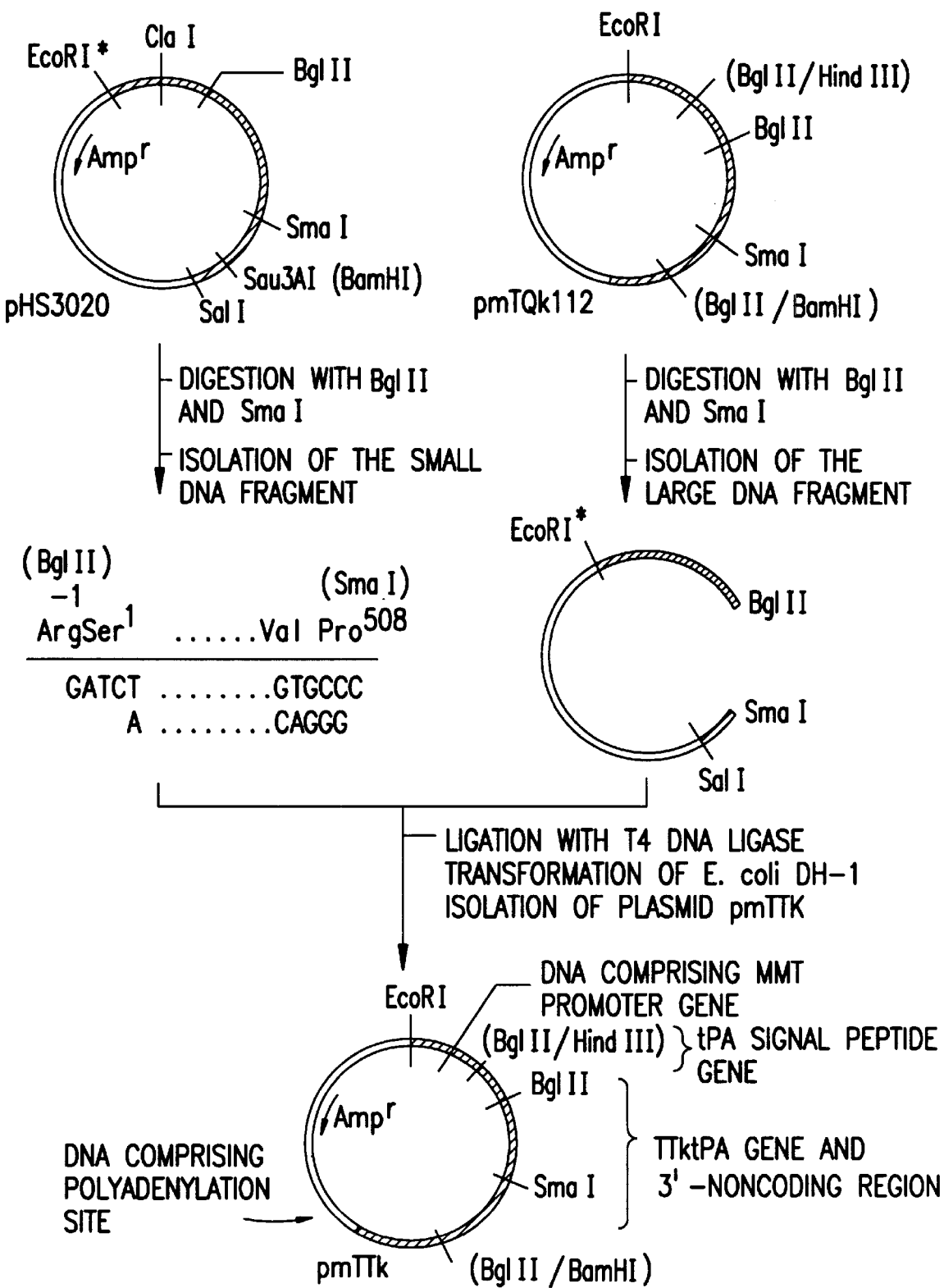
FIG. 26 shows construction and cloning of plasmid pmTTk.

(Construction and cloning of pmTTk) (as illustrated in FIG. 24, 25 and 26)

pTTkPAΔtrp was digested with ClaI and EcoRI completely. The large DNA fragment was isolated and ligated to ClaI-DdeI synthetic DNAs (5'-CGATAAAATGGGTCCTAGATC (SEQ ID NO:36) and 5'-TCAGATCTAGGACCCATTTTAT, (SEQ ID NO:37) each DNA was phosphorylated with T4 polynucleotide kinase) including BglII restriction site and 9 bp DdeI-EcoRI DNA coding for Glu$^{175}$-Trp$^{204}$ from pTTkPAΔtrp with T4 DNA ligase to give pHS9006. pTTkPAΔtrp was digested with EcoRI (partial) and ApaI. The 781 bp DNA fragment was isolated and ligated to 4.1 kbp EcoRI-ApaI DNA fragment from pHS9006 to give pHS3020 coding for Arg$^{-1}$ plus Ser$^{174}$-Pro$^{527}$.

pHS3020 was digested with BglII and SmaI. The small DNA fragment coding for Arg$^{-1}$ plus Ser$^{174}$-Pro$^{508}$ was isolated and ligated to the BglII-SmaI large DNA fragment from pmTQk112 to give pmTTk, an expression vector for TTktPA in mammalian cell.

EXAMPLE 32

Figure 27:
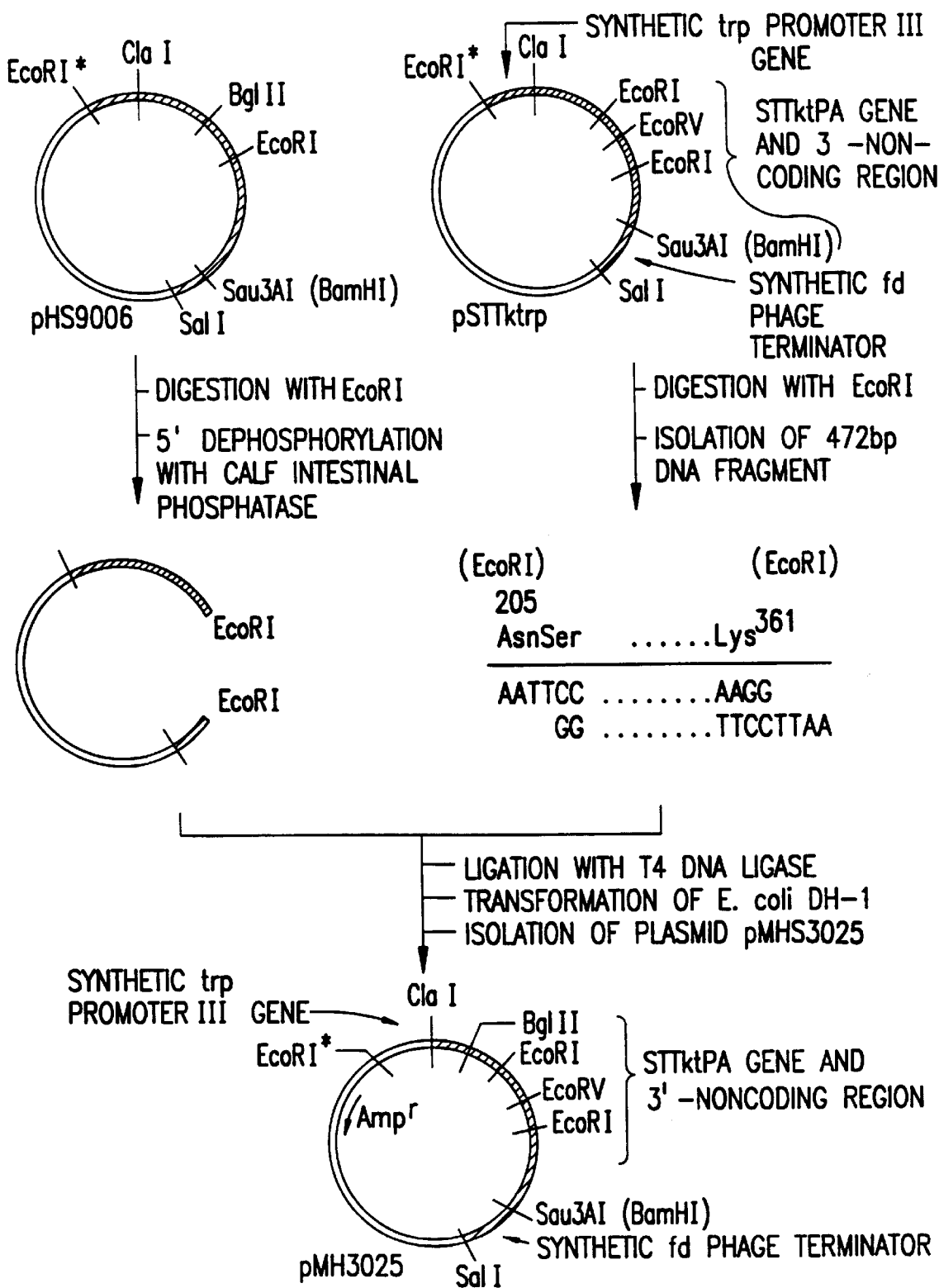
FIG. 27 shows construction and cloning of plasmid pMH3025.
Figure 28:
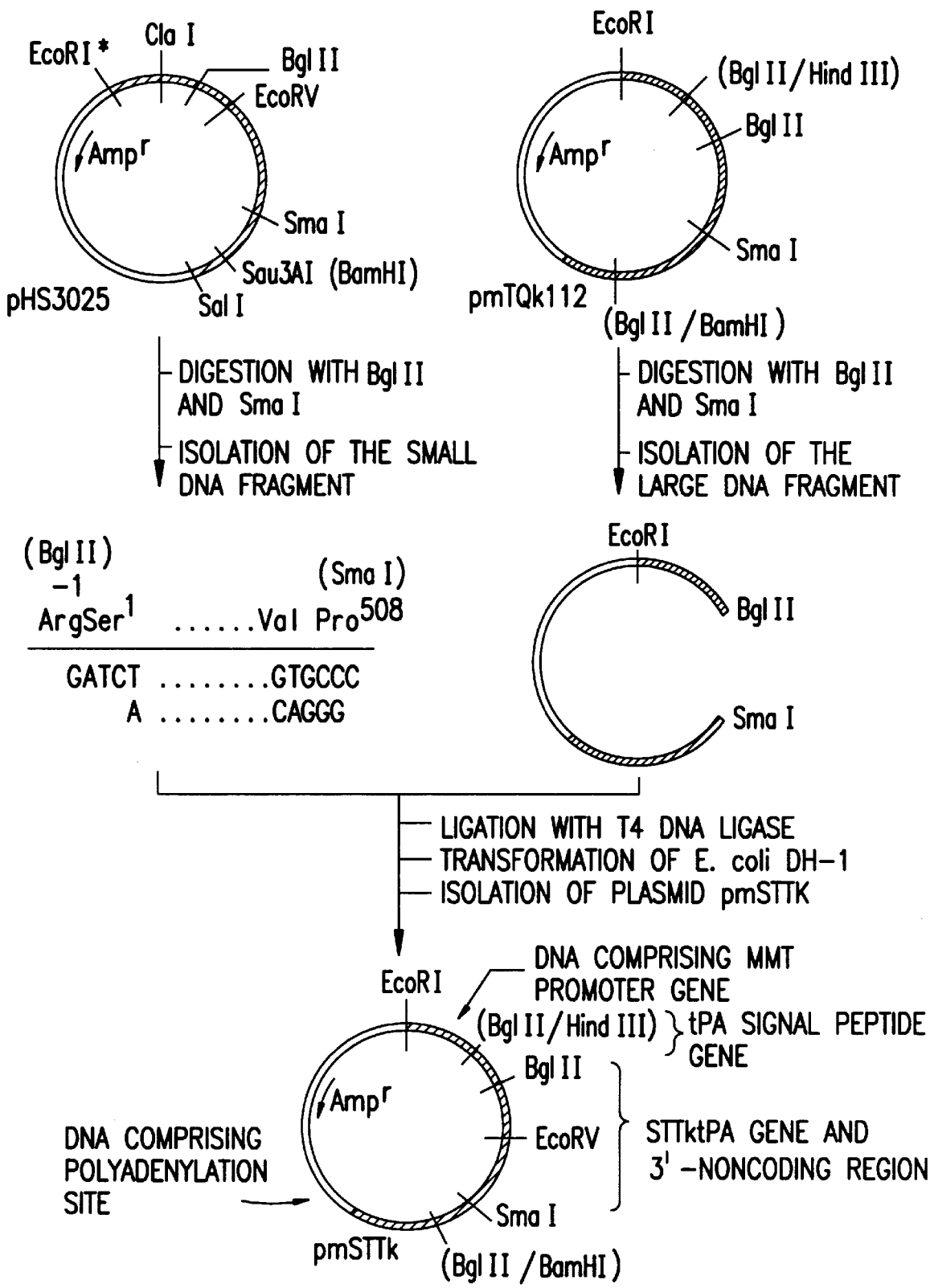
FIG. 28 shows construction and cloning of plasmid pmSTTk.

(Construction and cloning of pmSTTk) (as illustrated in FIG. 27 and 28)

pHS9006 was digested with EcoRI. The large DNA fragment was isolated, dephosphorylated with calf intestinal phosphatase (Pharmacia) and ligated to the 472 bp EcoRI DNA coding for Asn$^{205}$ Asp$^{275}$-Lys$^{361}$ from pSTTkΔtrp to give pMH3025. pMH3025 was digested with BglII and SmaI. The small DNA fragment was isolated and ligated to the large fragment BglII-SmaI DNA from pmTQk112 to give pmSTTk, an expression vector for STTktPA in mammalian cell.

EXAMPLE 33

(Expression)
Construction of L-929 Transformants
A. Preparation of the Cells
A culture of L-929 cell line was used in this example. L-929 cells can be generated from ATCC #CCL-1, and were maintained in DMEM containing kanamycin and 10% (vol/vol) fetal calf serum at 37° C. in 5% $CO_2$. These cells were plated in a cell density of $5 \times 10^5$ per 10 cm petri dish on the day before transformation, and provided 50–60% confluency on the day transformation. The media was changed three hours before the transformation. Two 10 cm petri dishes of cells were used to each transformation.
B. Preparation of the DNA solution
Plasmid DNA was introduced into L-929 cells using a calcium phosphate technique in a similar manner to that described in Gorman, DNA Cloning II, 143 (1985), IRL press.
Thirty μg of the expression plasmid (pmTQk112, pmTTk or pmSTTk) plus 3 μg of plasmid pSV2neo ATCC No. 37149 was added to 186 μl of 2M $CaCl_2$ and 1.3 ml of water. 1.5 ml of the DNA solution was then added dropwise to 1.5 ml of 2xHBS (1.63% NaCl, 1.19% Hepes, 0.04% $Na_2HPO_4$ pH 7.12) under bubbling. The mixture was allowed to stand 30 minutes at room temperature before it was added to the cells.
C. Transfection of the cells
The 0.6 ml of the DNA solution was added to a 10 cm petri dish of L-929 cells with gentle agitation and incubated at 37° C. for 18 hours in a $CO_2$ incubator. The cells were washed twice with DMEM. Complete fresh growth media containing 10% FCS was then added, and the cells were incubated at 37° C. for 24 hours in a $CO_2$ incubator. The cells were trypsinized and subcultured 1:10 into selective medium composed of DMEM containing 300 μg/ml geneticin (G418) and 10% FCS.

Cells which express the phosphotransferase (neo$^r$ gene product) can survive in the selective media and form colonies. Medium was changed every 3–4 days and colonies were isolated after 12–14 days. G418 resistant colonies were picked up by mild trypsinization in small cylinders, grown to mass cultures and tested for the secretion of mutant t-PA. The cells were grown in 1.7 cm diameter muti-well plate dishes with 3 ml of the medium to a total of about $3 \times 10^5$ cells. Medium was removed and washed with PBS. Cells-were cultured in 1 ml of inducible culture media composed of DMEM containing 0.04 mM $ZnSO_4$, 1 mM sodium butylate and 2% FCS at 37° C. for 24 hours and activity of mutant t-PA in the medium was confirmed an indirect spectrophotometric assay using the chromogenic agent S2251 [Cf. Thrombosis Research 31, 427 (1983)].

E. coli DH-1 was transformed with the plasmid, pmTQk112, pmTTk or pmSTTk for the purpose of the deposit in a conventional manner.

The following microorganisms shown in the above Examples have been deposited with one of the INTERNATIONAL DEPOSITORY AUTHORITY ON THE BUDAPEST TREATY, Fermentation Research Institute, Agency of Industrial Science and Technology residing at 1–3, Higashi 1 chome, Tsukuba-shi, Ibaraki-ken305, Japan since Jul. 30, Oct. 13 and Nov. 5, 1987 and July, 1988, and were assigned the following deposit numbers, respectively.

| Microorganisms | Deposit number |
| --- | --- |
| Escherichia coli HB101-16 | FERM BP-1872 |
| Escherichia coli HB101-16 (pTTkPAΔtrp) | FERM BP-1871 |
| Escherichia coli HB101-16 (pTTiPAΔtrp) | FERM BP-1869 |
| Escherichia coli HB101-16 (PTQiPAΔtrp) | FERM BP-1870 |
| Escherichia coli HB101-16 (pTQkPAΔtrp) | FERM BP-1521 |
| Escherichia coli HB101-16 (pSTTktrp) | FERM BP-1517 |
| Escherichia coli HB101-16 (pSTQitrp) | FERM BP-1516 |
| Escherichia coli HB101-16 (pSTQktrp) | FERM BP-1518 |
| Escherichia coli HB101-16 (pthTTtrp) | FERM BP-1562 |
| Escherichia coli HB101-16 (puTTtrp) | FERM BP-1519 |
| Escherichia coli DH-1(pST112) | FERM BP-1966 |
| Escherichia coli DH-1(pmTQk112) | FERM BP-1965 |
| Escherichia coli DH-1(pmTTk) | FERM BP-1967 |
| Escherichia coli DH-1(pmSTTk) | FERM BP-1964 |

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
( A ) LENGTH: 347 amino acids
( B ) TYPE: amino acid
( C ) STRANDEDNESS: single (D) TOPOLOGY: linear (ii) MOLECULE TYPE: protein (xi) SEQUENCE DESCRIPTION: SEQ ID NO:1:

| Xaa | Glu | Gly | Asn | Ser | Asp | Cys | Tyr | Phe | Gly | Asn | Gly | Ser | Ala | Tyr | Arg |
| 1 | | | | 5 | | | | | 10 | | | | | 15 | |

| Gly | Thr | His | Ser | Leu | Thr | Glu | Ser | Gly | Ala | Ser | Cys | Leu | Pro | Trp | Asn |
| | | | 20 | | | | 25 | | | | | | 30 | | |

| Ser | Met | Ile | Leu | Ile | Gly | Lys | Val | Tyr | Thr | Ala | Gln | Asn | Pro | Ser | Ala |
| | | 35 | | | | | 40 | | | | | 45 | | | |

| Gln | Ala | Leu | Gly | Leu | Gly | Lys | His | Asn | Tyr | Cys | Arg | Asn | Pro | Asp | Gly |
| | 50 | | | | | 55 | | | | | 60 | | | | |

| Asp | Ala | Lys | Pro | Trp | Cys | His | Val | Leu | Lys | Asn | Arg | Arg | Leu | Thr | Trp |
| 65 | | | | | 70 | | | | | 75 | | | | | 80 |

| Glu | Tyr | Cys | Asp | Val | Pro | Ser | Cys | Ser | Thr | Cys | Gly | Leu | Arg | Gln | Xaa |
| | | | | 85 | | | | | 90 | | | | | 95 | |

| Xaa | Gly | Gly | Leu | Phe | Ala | Asp | Ile | Ala | Ser | His | Pro | Trp | Gln | Ala | Ala |
| | | | 100 | | | | | 105 | | | | | 110 | | |

| Ile | Phe | Ala | Lys | His | Arg | Arg | Ser | Pro | Gly | Glu | Arg | Phe | Leu | Cys | Gly |
| | | 115 | | | | | 120 | | | | | 125 | | | |

| Gly | Ile | Leu | Ile | Ser | Ser | Cys | Trp | Ile | Leu | Ser | Ala | Ala | His | Cys | Phe |
| | | 130 | | | | | 135 | | | | | 140 | | | |

| Gln | Glu | Arg | Phe | Pro | Pro | His | His | Leu | Thr | Val | Ile | Leu | Gly | Arg | Thr |
| 145 | | | | | 150 | | | | | 155 | | | | | 160 |

| Tyr | Arg | Val | Val | Pro | Glu | Glu | Glu | Glu | Gln | Lys | Phe | Glu | Val | Glu | Lys |
| | | | | 165 | | | | | 170 | | | | | 175 | |

| Tyr | Ile | Val | His | Lys | Glu | Phe | Asp | Asp | Thr | Tyr | Asp | Asn | Asp | Ile |
| | | | 180 | | | | | 185 | | | | | 190 | | |

| Ala | Leu | Leu | Gln | Leu | Lys | Ser | Asp | Ser | Ser | Arg | Cys | Ala | Gln | Glu | Ser |
| | | 195 | | | | | 200 | | | | | 205 | | | |

| Ser | Val | Val | Arg | Thr | Val | Cys | Leu | Pro | Pro | Ala | Asp | Leu | Gln | Leu | Pro |
| | 210 | | | | | 215 | | | | | 220 | | | | |

| Asp | Trp | Thr | Glu | Cys | Glu | Leu | Ser | Gly | Tyr | Gly | Lys | His | Glu | Ala | Leu |
| 225 | | | | | 230 | | | | | 235 | | | | | 240 |

| Ser | Pro | Phe | Tyr | Ser | Glu | Arg | Leu | Lys | Glu | Ala | His | Val | Arg | Leu | Tyr |
| | | | | 245 | | | | | 250 | | | | | 255 | |

| Pro | Ser | Ser | Arg | Cys | Thr | Ser | Gln | His | Leu | Leu | Asn | Arg | Thr | Val | Thr |
| | | | 260 | | | | | 265 | | | | | 270 | | |

| Asp | Asn | Met | Leu | Cys | Ala | Gly | Asp | Thr | Arg | Ser | Gly | Gly | Pro | Gln | Ala |
| | | | 275 | | | | | 280 | | | | | 285 | | |

| Asn | Leu | His | Asp | Ala | Cys | Gln | Gly | Asp | Ser | Gly | Gly | Pro | Leu | Val | Cys |
| | | | 290 | | | | | 295 | | | | | 300 | | |

| Leu | Asn | Asp | Gly | Arg | Met | Thr | Leu | Val | Gly | Ile | Ile | Ser | Trp | Gly | Leu |
| 305 | | | | | 310 | | | | | 315 | | | | | 320 |

| Gly | Cys | Gly | Gln | Lys | Asp | Val | Pro | Gly | Val | Tyr | Thr | Lys | Val | Thr | Asn |
| | | | | 325 | | | | | 330 | | | | | 335 | |

| Tyr | Leu | Asp | Trp | Ile | Arg | Asp | Asn | Met | Arg | Pro |
| | | | | 340 | | | | | 345 | |

(2) INFORMATION FOR SEQ ID NO:2:

(i) SEQUENCE CHARACTERISTICS:
(A) LENGTH: 83 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:2:

| Cys | Tyr | Glu | Asp | Gln | Gly | Ile | Ser | Tyr | Arg | Gly | Thr | Trp | Ser | Thr | Ala |
|---|---|---|---|---|---|---|---|---|---|---|---|---|---|---|---|
| 1 | | | | 5 | | | | | 10 | | | | | 15 | |
| Glu | Ser | Gly | Ala | Glu | Cys | Thr | Asn | Trp | Asn | Ser | Ser | Ala | Leu | Ala | Gln |
| | | | 20 | | | | 25 | | | | | | 30 | | |
| Lys | Pro | Tyr | Ser | Gly | Arg | Arg | Pro | Asp | Ala | Ile | Arg | Leu | Gly | Leu | Gly |
| | | 35 | | | | | 40 | | | | | 45 | | | |
| Asn | His | Asn | Tyr | Cys | Arg | Asn | Pro | Asp | Arg | Asp | Ser | Lys | Pro | Trp | Cys |
| | 50 | | | | | 55 | | | | | 60 | | | | |
| Tyr | Val | Phe | Lys | Ala | Gly | Lys | Tyr | Ser | Ser | Glu | Phe | Cys | Ser | Thr | Pro |
| 65 | | | | | 70 | | | | | 75 | | | | | 80 |
| Ala | Cys | Ser | | | | | | | | | | | | | |

( 2 ) INFORMATION FOR SEQ ID NO:3:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

| Tyr | Ser | Gln | Pro | Gln | Phe | Arg | Ile |
|---|---|---|---|---|---|---|---|
| 1 | | | | 5 | | | |

( 2 ) INFORMATION FOR SEQ ID NO:4:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

| Tyr | Ser | Gln | Pro | Gln | Phe | Asp | Ile |
|---|---|---|---|---|---|---|---|
| 1 | | | | 5 | | | |

( 2 ) INFORMATION FOR SEQ ID NO:5:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

| Tyr | Ser | Gln | Pro | Ile | Pro | Arg | Ser |
|---|---|---|---|---|---|---|---|
| 1 | | | | 5 | | | |

( 2 ) INFORMATION FOR SEQ ID NO:6:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Thr Leu Arg Pro Arg Phe Lys Ile
1               5

( 2 ) INFORMATION FOR SEQ ID NO:7:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:7:

Lys Leu Gln Asp Ile Glu Gly Arg Ser
1               5

( 2 ) INFORMATION FOR SEQ ID NO:8:

( i ) SEQUENCE CHARACTERISTICS:
      ( A ) LENGTH: 27 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:8:

AGCTTCAGGA TATCGAAGGT AGATCTG                27

( 2 ) INFORMATION FOR SEQ ID NO:9:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:9:

AGCTTCAGGA T                                 11

( 2 ) INFORMATION FOR SEQ ID NO:10:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: other nucleic acid
      ( A ) DESCRIPTION: /desc = "SYNTHETIC OLIGONUCLEOTIDE"

( x i ) SEQUENCE DESCRIPTION: SEQ ID NO:10:

ATCGAAGGTA GATCTG                            16

( 2 ) INFORMATION FOR SEQ ID NO:11:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: other nucleic acid ( A ) DESCRIPTION: /desc = "SYNTHETIC OLIGONUCLEOTIDE"

( x i ) SEQUENCE DESCRIPTION: SEQ ID NO:11:

CGATATCCTG A  11

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:12:

GATCCAGATC TACCTT  16

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Met Cys Tyr Glu
    1

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:14:

CGATAAAATG TGTTATGAG  19

( 2 ) INFORMATION FOR SEQ ID NO:15:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:15:

CGATAAAAT  9

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "SYNTHETIC OLIGONUCLEOTIDE"

( x i ) SEQUENCE DESCRIPTION: SEQ ID NO:16:

GTGTTATGAG                                                                                                       10

( 2 ) INFORMATION FOR SEQ ID NO:17:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:17:

ACACATTTTA T                                                                                                     11

( 2 ) INFORMATION FOR SEQ ID NO:18:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:18:

GTCCTCATA                                                                                                         9

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:19:

CGATAAAATG TC                                                                                                    12

( 2 ) INFORMATION FOR SEQ ID NO:20:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:20:

CGATAAAATG TC                                                                                                    12

( 2 ) INFORMATION FOR SEQ ID NO:21:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "SYNTHETIC OLIGONUCLEOTIDE"

( x i ) SEQUENCE DESCRIPTION: SEQ ID NO:21:

TCAGACATTT TAT 13

( 2 ) INFORMATION FOR SEQ ID NO:22:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Ser Glu Gly Asn
1

( 2 ) INFORMATION FOR SEQ ID NO:23:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Leu Arg Gln Tyr Ser Gln Pro Gln Phe Asp Ile Lys Gly Gly
1               5                   10

( 2 ) INFORMATION FOR SEQ ID NO:24:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:24:

TGAGACAGTA CAGCCAGCCA CAGTTTGATA TCAAAGGAGG 40

( 2 ) INFORMATION FOR SEQ ID NO:25:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Leu Arg Gln Tyr Ser Gln Pro Gln Phe Asp Ile Ile Gly Gly
1               5                   10

( 2 ) INFORMATION FOR SEQ ID NO:26:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: other nucleic acid ( A ) DESCRIPTION: /desc = "SYNTHETIC OLIGONUCLEOTIDE"

( x i ) SEQUENCE DESCRIPTION: SEQ ID NO:26:

TGAGACAGTA CAGCCAGCCA CAGTTTGATA TCATAGGAGG 40

( 2 ) INFORMATION FOR SEQ ID NO:27:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Leu Arg Gln Tyr Ser Gln Pro Ile Pro Arg Ser Gly Gly
1               5                   10

( 2 ) INFORMATION FOR SEQ ID NO:28:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:28:

TGAGACAGTA CAGCCAGCCA ATTCCTAGAT CTGGAGG 37

( 2 ) INFORMATION FOR SEQ ID NO:29:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

Leu Arg Gln Thr Leu Arg Pro Arg Phe Lys
1               5                   10

( 2 ) INFORMATION FOR SEQ ID NO:30:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:30:

TGAGACAGAC TCTGCGTCCG CGGTTCAAA 29

( 2 ) INFORMATION FOR SEQ ID NO:31:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "SYNTHETIC OLIGONUCLEOTIDE"

( x i ) SEQUENCE DESCRIPTION: SEQ ID NO:31:

ATATTCTGAA ATGAGCTGT 19

( 2 ) INFORMATION FOR SEQ ID NO:32:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:32:

CTCCGGGCGA CCTCCTGTG 19

( 2 ) INFORMATION FOR SEQ ID NO:33:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Ser Glu Gly Asn Ser Asp Cys Tyr Phe Gly Asn Gly Ser Ala Tyr
1               5                   10                  15

( 2 ) INFORMATION FOR SEQ ID NO:34:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:34:

GATCTTGCTA CGAG 14

( 2 ) INFORMATION FOR SEQ ID NO:35:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:35:

GTCCTCGTAG CAA 13

( 2 ) INFORMATION FOR SEQ ID NO:36:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc = "SYNTHETIC OLIGONUCLEOTIDE"

( x i ) SEQUENCE DESCRIPTION: SEQ ID NO:36:

CGATAAAATG GGTCCTAGAT C        21

( 2 ) INFORMATION FOR SEQ ID NO:37:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC OLIGONUCLEOTIDE"

( x i ) SEQUENCE DESCRIPTION: SEQ ID NO:37:

TCAGATCTAG GACCCATTTT AT        22

( 2 ) INFORMATION FOR SEQ ID NO:38:

( i ) SEQUENCE CHARACTERISTICS:
        ( A ) LENGTH: 1974 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 3..1583

( x i ) SEQUENCE DESCRIPTION: SEQ ID NO:38:

```
GA  TCT  TAC  CAA  GTG  ATC  TGC  AGA  GAT  GAA  AAA  ACG  CAG  ATG  ATA  TAC        47
    Ser  Tyr  Gln  Val  Ile  Cys  Arg  Asp  Glu  Lys  Thr  Gln  Met  Ile  Tyr
     1              5                        10                         15

CAG  CAA  CAT  CAG  TCA  TGG  CTG  CGC  CCT  GTG  CTC  AGA  AGC  AAC  CGG  GTG        95
Gln  Gln  His  Gln  Ser  Trp  Leu  Arg  Pro  Val  Leu  Arg  Ser  Asn  Arg  Val
               20                        25                        30

GAA  TAT  TGC  TGG  TGC  AAC  AGT  GGC  AGG  GCA  CAG  TGC  CAC  TCA  GTG  CCT       143
Glu  Tyr  Cys  Trp  Cys  Asn  Ser  Gly  Arg  Ala  Gln  Cys  His  Ser  Val  Pro
          35                        40                        45

GTC  AAA  AGT  TGC  AGC  GAG  CCA  AGG  TGT  TTC  AAC  GGG  GGC  ACC  TGC  CAG       191
Val  Lys  Ser  Cys  Ser  Glu  Pro  Arg  Cys  Phe  Asn  Gly  Gly  Thr  Cys  Gln
     50                        55                        60

CAG  GCC  CTG  TAC  TTC  TCA  GAT  TTC  GTG  TGC  CAG  TGC  CCC  GAA  GGA  TTT       239
Gln  Ala  Leu  Tyr  Phe  Ser  Asp  Phe  Val  Cys  Gln  Cys  Pro  Glu  Gly  Phe
65                        70                        75

GCT  GGG  AAG  TGC  TGT  GAA  ATA  GAT  ACC  AGG  GCC  ACG  TGC  TAC  GAG  GAC       287
Ala  Gly  Lys  Cys  Cys  Glu  Ile  Asp  Thr  Arg  Ala  Thr  Cys  Tyr  Glu  Asp
80                        85                        90                         95

CAG  GGC  ATC  AGC  TAC  AGG  GGC  ACG  TGG  AGC  ACA  GCG  GAG  AGT  GGC  GCC       335
Gln  Gly  Ile  Ser  Tyr  Arg  Gly  Thr  Trp  Ser  Thr  Ala  Glu  Ser  Gly  Ala
                    100                       105                       110

GAG  TGC  ACC  AAC  TGG  AAC  AGC  AGC  GCG  TTG  GCC  CAG  AAG  CCC  TAC  AGC       383
Glu  Cys  Thr  Asn  Trp  Asn  Ser  Ser  Ala  Leu  Ala  Gln  Lys  Pro  Tyr  Ser
                    115                       120                       125

GGG  CGG  AGG  CCA  GAC  GCC  ATC  AGG  CTG  GGC  CTG  GGG  AAC  CAC  AAC  TAC       431
Gly  Arg  Arg  Pro  Asp  Ala  Ile  Arg  Leu  Gly  Leu  Gly  Asn  His  Asn  Tyr
               130                       135                       140

TGC  AGA  AAC  CCA  GAT  CGA  GAC  TCA  AAG  CCC  TGG  TGC  TAC  GTC  TTT  AAG       479
Cys  Arg  Asn  Pro  Asp  Arg  Asp  Ser  Lys  Pro  Trp  Cys  Tyr  Val  Phe  Lys
          145                       150                       155

GCG  GGG  AAG  TAC  AGC  TCA  GAG  TTC  TGC  AGC  ACC  CCT  GCC  TGC  TCT  GAG       527
```

```
                Ala  Gly  Lys  Tyr  Ser  Ser  Glu  Phe  Cys  Ser  Thr  Pro  Ala  Cys  Ser  Glu
                160                 165                 170                 175

GGA  AAC  AGT  GAC  TGC  TAC  TTT  GGG  AAT  GGG  TCA  GCC  TAC  CGT  GGC  ACG                    575
Gly  Asn  Ser  Asp  Cys  Tyr  Phe  Gly  Asn  Gly  Ser  Ala  Tyr  Arg  Gly  Thr
               180                 185                                190

CAC  AGC  CTC  ACC  GAG  TCG  GGT  GCC  TCC  TGC  CTC  CCG  TGG  AAT  TCC  ATG                    623
His  Ser  Leu  Thr  Glu  Ser  Gly  Ala  Ser  Cys  Leu  Pro  Trp  Asn  Ser  Met
               195                 200                      205

ATC  CTG  ATA  GGC  AAG  GTT  TAC  ACA  GCA  CAG  AAC  CCC  AGT  GCC  CAG  GCA                    671
Ile  Leu  Ile  Gly  Lys  Val  Tyr  Thr  Ala  Gln  Asn  Pro  Ser  Ala  Gln  Ala
               210                 215                      220

CTG  GGC  CTG  GGC  AAA  CAT  AAT  TAC  TGC  CGG  AAT  CCT  GAT  GGG  GAT  GCC                    719
Leu  Gly  Leu  Gly  Lys  His  Asn  Tyr  Cys  Arg  Asn  Pro  Asp  Gly  Asp  Ala
               225                 230                      235

AAG  CCC  TGG  TGC  CAC  GTG  CTG  AAG  AAC  CGC  AGG  CTG  ACG  TGG  GAG  TAC                    767
Lys  Pro  Trp  Cys  His  Val  Leu  Lys  Asn  Arg  Arg  Leu  Thr  Trp  Glu  Tyr
240                           245                 250                      255

TGT  GAT  GTG  CCC  TCC  TGC  TCC  ACC  TGC  GGC  CTG  AGA  CAG  TAC  AGC  CAG                    815
Cys  Asp  Val  Pro  Ser  Cys  Ser  Thr  Cys  Gly  Leu  Arg  Gln  Tyr  Ser  Gln
                    260                 265                           270

CCT  CAG  TTT  CGC  ATA  ATA  GGA  GGC  CTC  TTC  GCC  GAC  ATC  GCC  TCC  CAC                    863
Pro  Gln  Phe  Arg  Ile  Ile  Gly  Gly  Leu  Phe  Ala  Asp  Ile  Ala  Ser  His
               275                 280                      285

CCC  TGG  CAG  GCT  GCC  ATC  TTT  GCC  AAG  CAC  AGG  AGG  TCG  CCC  GGA  GAG                    911
Pro  Trp  Gln  Ala  Ala  Ile  Phe  Ala  Lys  His  Arg  Arg  Ser  Pro  Gly  Glu
               290                 295                      300

CGG  TTC  CTG  TGC  GGG  GGC  ATA  CTC  ATC  AGC  TCC  TGC  TGG  ATT  CTC  TCT                    959
Arg  Phe  Leu  Cys  Gly  Gly  Ile  Leu  Ile  Ser  Ser  Cys  Trp  Ile  Leu  Ser
     305                      310                           315

GCC  GCC  CAC  TGC  TTC  CAG  GAG  AGG  TTT  CCG  CCC  CAC  CAC  CTG  ACG  GTG                    1007
Ala  Ala  His  Cys  Phe  Gln  Glu  Arg  Phe  Pro  Pro  His  His  Leu  Thr  Val
320                           325                 330                      335

ATC  TTG  GGC  AGA  ACA  TAC  CGG  GTG  GTC  CCT  GGC  GAG  GAG  GAG  CAG  AAA                    1055
Ile  Leu  Gly  Arg  Thr  Tyr  Arg  Val  Val  Pro  Gly  Glu  Glu  Glu  Gln  Lys
                         340                 345                           350

TTT  GAA  GTC  GAA  AAA  TAC  ATT  GTC  CAT  AAG  GAA  TTC  GAT  GAT  GAC  ACT                    1103
Phe  Glu  Val  Glu  Lys  Tyr  Ile  Val  His  Lys  Glu  Phe  Asp  Asp  Asp  Thr
                    355                 360                           365

TAC  GAC  AAT  GAC  ATT  GCG  CTG  CTG  CAG  CTG  AAA  TCG  GAT  TCG  TCC  CGC                    1151
Tyr  Asp  Asn  Asp  Ile  Ala  Leu  Leu  Gln  Leu  Lys  Ser  Asp  Ser  Ser  Arg
               370                 375                      380

TGT  GCC  CAG  GAG  AGC  AGC  GTG  GTC  CGC  ACT  GTG  TGC  CTT  CCC  CCG  GCG                    1199
Cys  Ala  Gln  Glu  Ser  Ser  Val  Val  Arg  Thr  Val  Cys  Leu  Pro  Pro  Ala
     385                      390                           395

GAC  CTG  CAG  CTG  CCG  GAC  TGG  ACG  GAG  TGT  GAG  CTC  TCC  GGC  TAC  GGC                    1247
Asp  Leu  Gln  Leu  Pro  Asp  Trp  Thr  Glu  Cys  Glu  Leu  Ser  Gly  Tyr  Gly
400                      405                      410                      415

AAG  CAT  GAG  GCC  TTG  TCT  CCT  TTC  TAT  TCG  GAG  CGG  CTG  AAG  GAG  GCT                    1295
Lys  His  Glu  Ala  Leu  Ser  Pro  Phe  Tyr  Ser  Glu  Arg  Leu  Lys  Glu  Ala
                         420                 425                           430

CAT  GTC  AGA  CTG  TAC  CCA  TCC  AGC  CGC  TGC  ACA  TCA  CAA  CAT  TTA  CTT                    1343
His  Val  Arg  Leu  Tyr  Pro  Ser  Ser  Arg  Cys  Thr  Ser  Gln  His  Leu  Leu
               435                 440                      445

AAC  AGA  ACA  GTC  ACC  GAC  AAC  ATG  CTG  TGT  GCT  GGA  GAC  ACT  CGG  AGC                    1391
Asn  Arg  Thr  Val  Thr  Asp  Asn  Met  Leu  Cys  Ala  Gly  Asp  Thr  Arg  Ser
          450                 455                           460

GGC  GGG  CCC  CAG  GCA  AAC  TTG  CAC  GAC  GCC  TGC  CAG  GGC  GAT  TCG  GGA                    1439
Gly  Gly  Pro  Gln  Ala  Asn  Leu  His  Asp  Ala  Cys  Gln  Gly  Asp  Ser  Gly
     465                 470                      475

GGC  CCC  CTG  GTG  TGT  CTG  AAC  GAT  GGC  CGC  ATG  ACT  TTG  GTG  GGC  ATC                    1487
```

```
Gly  Pro  Leu  Val  Cys  Leu  Asn  Asp  Gly  Arg  Met  Thr  Leu  Val  Gly  Ile
480                      485                 490                      495

ATC  AGC  TGG  GGC  CTG  GGC  TGT  GGA  CAG  AAG  GAT  GTC  CCG  GGT  GTG  TAC        1535
Ile  Ser  Trp  Gly  Leu  Gly  Cys  Gly  Gln  Lys  Asp  Val  Pro  Gly  Val  Tyr
                    500                      505                      510

ACA  AAG  GTT  ACC  AAC  TAC  CTA  GAC  TGG  ATT  CGT  GAC  AAC  ATG  CGA  CCG        1583
Thr  Lys  Val  Thr  Asn  Tyr  Leu  Asp  Trp  Ile  Arg  Asp  Asn  Met  Arg  Pro
                    515                      520                      525

TGACCAGGAA  CACCCGACTC  CTCAAAAGCA  AATGAGATCC  CGCCTCTTCT  TCTTCAGAAG              1643

ACACTGCAAA  GGCGCAGTGC  TTCTCTACAG  ACTTCTCCAG  ACCCACCACA  CCGCAGAAGC              1703

GGGACGAGAC  CCTACAGGAG  AGGGAAGAGT  GCATTTTCCC  AGATACTTCC  CATTTTGGAA              1763

GTTTTCAGGA  CTTGGTCTGA  TTTCAGGATA  CTCTGTCAGA  TGGGAAGACA  TGAATGCACA              1823

CTAGCCTCTC  CAGGAATGCC  TCCTCCCTGG  GCAGAAGTGG  CCATGCCACC  CTGTTTTCGC              1883

TAAAGCCCAA  CCTCCTGACC  TGTCACCGTG  AGCAGCTTTG  GAAACAGGAC  CACAAAAATG              1943

AAAGCATGTC  TCAATAGTAA  AAGAAACAAG  A                                               1974
```

( 2 ) INFORMATION FOR SEQ ID NO:39:

( i ) SEQUENCE CHARACTERISTICS:
        ( A ) LENGTH: 527 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

```
Ser  Tyr  Gln  Val  Ile  Cys  Arg  Asp  Glu  Lys  Thr  Gln  Met  Ile  Tyr  Gln
1                   5                   10                      15

Gln  His  Gln  Ser  Trp  Leu  Arg  Pro  Val  Leu  Arg  Ser  Asn  Arg  Val  Glu
               20                  25                      30

Tyr  Cys  Trp  Cys  Asn  Ser  Gly  Arg  Ala  Gln  Cys  His  Ser  Val  Pro  Val
          35                  40                      45

Lys  Ser  Cys  Ser  Glu  Pro  Arg  Cys  Phe  Asn  Gly  Thr  Cys  Gln  Gln
     50                  55                  60

Ala  Leu  Tyr  Phe  Ser  Asp  Phe  Val  Cys  Gln  Cys  Pro  Glu  Gly  Phe  Ala
65                       70                  75                           80

Gly  Lys  Cys  Cys  Glu  Ile  Asp  Thr  Arg  Ala  Thr  Cys  Tyr  Glu  Asp  Gln
                    85                       90                      95

Gly  Ile  Ser  Tyr  Arg  Gly  Thr  Trp  Ser  Thr  Ala  Glu  Ser  Gly  Ala  Glu
                    100                      105                     110

Cys  Thr  Asn  Trp  Asn  Ser  Ser  Ala  Leu  Ala  Gln  Lys  Pro  Tyr  Ser  Gly
               115                      120                     125

Arg  Arg  Pro  Asp  Ala  Ile  Arg  Leu  Gly  Leu  Gly  Asn  His  Asn  Tyr  Cys
     130                      135                     140

Arg  Asn  Pro  Asp  Arg  Asp  Ser  Lys  Pro  Trp  Cys  Tyr  Val  Phe  Lys  Ala
145                      150                     155                          160

Gly  Lys  Tyr  Ser  Ser  Glu  Phe  Cys  Ser  Thr  Pro  Ala  Cys  Ser  Glu  Gly
                    165                     170                     175

Asn  Ser  Asp  Cys  Tyr  Phe  Gly  Asn  Gly  Ser  Ala  Tyr  Arg  Gly  Thr  His
               180                      185                     190

Ser  Leu  Thr  Glu  Ser  Gly  Ala  Ser  Cys  Leu  Pro  Trp  Asn  Ser  Met  Ile
          195                      200                     205

Leu  Ile  Gly  Lys  Val  Tyr  Thr  Ala  Gln  Asn  Pro  Ser  Ala  Gln  Ala  Leu
     210                      215                     220

Gly  Leu  Gly  Lys  His  Asn  Tyr  Cys  Arg  Asn  Pro  Asp  Gly  Asp  Ala  Lys
```

|       |       |       |       | 225   |       |       |       |       | 230   |       |       |       |       | 235   |       |       |       |       | 240   |
|-------|-------|-------|-------|-------|-------|-------|-------|-------|-------|-------|-------|-------|-------|-------|-------|-------|-------|-------|-------|
| Pro   | Trp   | Cys   | His   | Val   | Leu   | Lys   | Asn   | Arg   | Arg   | Leu   | Thr   | Trp   | Glu   | Tyr   | Cys   |
|       |       |       |       |       | 245   |       |       |       |       | 250   |       |       |       |       | 255   |
| Asp   | Val   | Pro   | Ser   | Cys   | Ser   | Thr   | Cys   | Gly   | Leu   | Arg   | Gln   | Tyr   | Ser   | Gln   | Pro   |
|       |       |       | 260   |       |       |       |       | 265   |       |       |       |       | 270   |       |       |
| Gln   | Phe   | Arg   | Ile   | Ile   | Gly   | Gly   | Leu   | Phe   | Ala   | Asp   | Ile   | Ala   | Ser   | His   | Pro   |
|       |       | 275   |       |       |       |       |       | 280   |       |       |       |       | 285   |       |       |
| Trp   | Gln   | Ala   | Ala   | Ile   | Phe   | Ala   | Lys   | His   | Arg   | Arg   | Ser   | Pro   | Gly   | Glu   | Arg   |
|       |       | 290   |       |       |       |       | 295   |       |       |       |       | 300   |       |       |       |
| Phe   | Leu   | Cys   | Gly   | Gly   | Ile   | Leu   | Ile   | Ser   | Ser   | Cys   | Trp   | Ile   | Leu   | Ser   | Ala   |
| 305   |       |       |       |       |       | 310   |       |       |       |       | 315   |       |       |       | 320   |
| Ala   | His   | Cys   | Phe   | Gln   | Glu   | Arg   | Phe   | Pro   | Pro   | His   | His   | Leu   | Thr   | Val   | Ile   |
|       |       |       |       | 325   |       |       |       |       | 330   |       |       |       |       | 335   |       |
| Leu   | Gly   | Arg   | Thr   | Tyr   | Arg   | Val   | Val   | Pro   | Gly   | Glu   | Glu   | Glu   | Gln   | Lys   | Phe   |
|       |       |       | 340   |       |       |       |       | 345   |       |       |       |       | 350   |       |       |
| Glu   | Val   | Glu   | Lys   | Tyr   | Ile   | Val   | His   | Lys   | Glu   | Phe   | Asp   | Asp   | Asp   | Thr   | Tyr   |
|       |       | 355   |       |       |       |       | 360   |       |       |       |       | 365   |       |       |       |
| Asp   | Asn   | Asp   | Ile   | Ala   | Leu   | Leu   | Gln   | Leu   | Lys   | Ser   | Asp   | Ser   | Ser   | Arg   | Cys   |
|       | 370   |       |       |       |       | 375   |       |       |       |       | 380   |       |       |       |       |
| Ala   | Gln   | Glu   | Ser   | Ser   | Val   | Val   | Arg   | Thr   | Val   | Cys   | Leu   | Pro   | Pro   | Ala   | Asp   |
| 385   |       |       |       |       | 390   |       |       |       |       | 395   |       |       |       |       | 400   |
| Leu   | Gln   | Leu   | Pro   | Asp   | Trp   | Thr   | Glu   | Cys   | Glu   | Leu   | Ser   | Gly   | Tyr   | Gly   | Lys   |
|       |       |       |       | 405   |       |       |       |       | 410   |       |       |       |       | 415   |       |
| His   | Glu   | Ala   | Leu   | Ser   | Pro   | Phe   | Tyr   | Ser   | Glu   | Arg   | Leu   | Lys   | Glu   | Ala   | His   |
|       |       |       | 420   |       |       |       |       | 425   |       |       |       |       | 430   |       |       |
| Val   | Arg   | Leu   | Tyr   | Pro   | Ser   | Ser   | Arg   | Cys   | Thr   | Ser   | Gln   | His   | Leu   | Leu   | Asn   |
|       |       | 435   |       |       |       |       | 440   |       |       |       |       | 445   |       |       |       |
| Arg   | Thr   | Val   | Thr   | Asp   | Asn   | Met   | Leu   | Cys   | Ala   | Gly   | Asp   | Thr   | Arg   | Ser   | Gly   |
|       | 450   |       |       |       |       | 455   |       |       |       |       | 460   |       |       |       |       |
| Gly   | Pro   | Gln   | Ala   | Asn   | Leu   | His   | Asp   | Ala   | Cys   | Gln   | Gly   | Asp   | Ser   | Gly   | Gly   |
| 465   |       |       |       |       | 470   |       |       |       |       | 475   |       |       |       |       | 480   |
| Pro   | Leu   | Val   | Cys   | Leu   | Asn   | Asp   | Gly   | Arg   | Met   | Thr   | Leu   | Val   | Gly   | Ile   | Ile   |
|       |       |       |       | 485   |       |       |       |       | 490   |       |       |       |       | 495   |       |
| Ser   | Trp   | Gly   | Leu   | Gly   | Cys   | Gly   | Gln   | Lys   | Asp   | Val   | Pro   | Gly   | Val   | Tyr   | Thr   |
|       |       |       | 500   |       |       |       |       | 505   |       |       |       |       | 510   |       |       |
| Lys   | Val   | Thr   | Asn   | Tyr   | Leu   | Asp   | Trp   | Ile   | Arg   | Asp   | Asn   | Met   | Arg   | Pro   |       |
|       |       | 515   |       |       |       |       | 520   |       |       |       |       | 525   |       |       |       |

( 2 ) INFORMATION FOR SEQ ID NO:40:

( i ) SEQUENCE CHARACTERISTICS:
        ( A ) LENGTH: 472 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..471

( x i ) SEQUENCE DESCRIPTION: SEQ ID NO:40:

| AAT | TCC | ATG | ATC | CTG | ATA | GGC | AAG | GTT | TAC | ACA | GCA | CAG | AAC | CCC | AGT | 48 |
|-----|-----|-----|-----|-----|-----|-----|-----|-----|-----|-----|-----|-----|-----|-----|-----|----|
| Asn | Ser | Met | Ile | Leu | Ile | Gly | Lys | Val | Tyr | Thr | Ala | Gln | Asn | Pro | Ser |    |
| 1   |     |     |     | 5   |     |     |     |     | 10  |     |     |     |     | 15  |     |    |

| GCC | CAG | GCA | CTG | GGC | CTG | GGC | AAA | CAT | AAT | TAC | TGC | CGG | AAT | CCT | GAT | 96 |
|-----|-----|-----|-----|-----|-----|-----|-----|-----|-----|-----|-----|-----|-----|-----|-----|----|
| Ala | Gln | Ala | Leu | Gly | Leu | Gly | Lys | His | Asn | Tyr | Cys | Arg | Asn | Pro | Asp |    |
|     |     | 20  |     |     |     |     | 25  |     |     |     |     | 30  |     |     |     |    |

| | | | | | | | | | | | | | | | | |
|---|---|---|---|---|---|---|---|---|---|---|---|---|---|---|---|---|
| GGG | GAT | GCC | AAG | CCC | TGG | TGC | CAC | GTG | CTG | AAG | AAC | CGC | AGG | CTG | ACG | 144 |
| Gly | Asp | Ala | Lys | Pro | Trp | Cys | His | Val | Leu | Lys | Asn | Arg | Arg | Leu | Thr | |
| | | 35 | | | | | 40 | | | | | 45 | | | | |
| TGG | GAG | TAC | TGT | GAT | GTG | CCC | TCC | TGC | TCC | ACC | TGC | GGC | CTG | AGA | CAG | 192 |
| Trp | Glu | Tyr | Cys | Asp | Val | Pro | Ser | Cys | Ser | Thr | Cys | Gly | Leu | Arg | Gln | |
| | 50 | | | | | 55 | | | | | 60 | | | | | |
| TAC | AGC | CAG | CCT | CAG | TTT | CGC | ATC | AAA | GGA | GGG | CTC | TTC | GCC | GAC | ATC | 240 |
| Tyr | Ser | Gln | Pro | Gln | Phe | Arg | Ile | Lys | Gly | Gly | Leu | Phe | Ala | Asp | Ile | |
| 65 | | | | | 70 | | | | | 75 | | | | | 80 | |
| GCC | TCC | CAC | CCC | TGG | CAG | GCT | GCC | ATC | TTT | GCC | AAG | CAC | AGG | AGG | TCG | 288 |
| Ala | Ser | His | Pro | Trp | Gln | Ala | Ala | Ile | Phe | Ala | Lys | His | Arg | Arg | Ser | |
| | | | | 85 | | | | | 90 | | | | | 95 | | |
| CCC | GGA | GAG | CGG | TTC | CTG | TGC | GGG | GGC | ATA | CTC | ATC | AGC | TCC | TGC | TGG | 336 |
| Pro | Gly | Glu | Arg | Phe | Leu | Cys | Gly | Gly | Ile | Leu | Ile | Ser | Ser | Cys | Trp | |
| | | | 100 | | | | | 105 | | | | | 110 | | | |
| ATT | CTC | TCT | GCC | GCC | CAC | TGC | TTC | CAG | GAG | AGG | TTT | CCG | CCC | CAC | CAC | 384 |
| Ile | Leu | Ser | Ala | Ala | His | Cys | Phe | Gln | Glu | Arg | Phe | Pro | Pro | His | His | |
| | | 115 | | | | | 120 | | | | | 125 | | | | |
| CTG | ACG | GTG | ATC | TTG | GGC | AGA | ACA | TAC | CGG | GTG | GTC | CCT | GGC | GAG | GAG | 432 |
| Leu | Thr | Val | Ile | Leu | Gly | Arg | Thr | Tyr | Arg | Val | Val | Pro | Gly | Glu | Glu | |
| | 130 | | | | | 135 | | | | | 140 | | | | | |
| GAG | CAG | AAA | TTT | GAA | GTC | GAA | AAA | TAC | ATT | GTC | CAT | AAG | G | | | 472 |
| Glu | Gln | Lys | Phe | Glu | Val | Glu | Lys | Tyr | Ile | Val | His | Lys | | | | |
| 145 | | | | | 150 | | | | | 155 | | | | | | |

( 2 ) INFORMATION FOR SEQ ID NO:41:

( i ) SEQUENCE CHARACTERISTICS:
( A ) LENGTH: 157 amino acids
( B ) TYPE: amino acid
( D ) TOPOLOGY: linear ( i i ) MOLECULE TYPE: protein ( x i ) SEQUENCE DESCRIPTION: SEQ ID NO:41:

| | | | | | | | | | | | | | | |
|---|---|---|---|---|---|---|---|---|---|---|---|---|---|---|
| Asn | Ser | Met | Ile | Leu | Ile | Gly | Lys | Val | Tyr | Thr | Ala | Gln | Asn | Pro | Ser |
| 1 | | | | 5 | | | | | 10 | | | | | 15 | |
| Ala | Gln | Ala | Leu | Gly | Leu | Gly | Lys | His | Asn | Tyr | Cys | Arg | Asn | Pro | Asp |
| | | | 20 | | | | | 25 | | | | | 30 | | |
| Gly | Asp | Ala | Lys | Pro | Trp | Cys | His | Val | Leu | Lys | Asn | Arg | Arg | Leu | Thr |
| | | 35 | | | | | 40 | | | | | 45 | | | |
| Trp | Glu | Tyr | Cys | Asp | Val | Pro | Ser | Cys | Ser | Thr | Cys | Gly | Leu | Arg | Gln |
| | 50 | | | | | 55 | | | | | 60 | | | | |
| Tyr | Ser | Gln | Pro | Gln | Phe | Arg | Ile | Lys | Gly | Gly | Leu | Phe | Ala | Asp | Ile |
| 65 | | | | | 70 | | | | | 75 | | | | | 80 |
| Ala | Ser | His | Pro | Trp | Gln | Ala | Ala | Ile | Phe | Ala | Lys | His | Arg | Arg | Ser |
| | | | | 85 | | | | | 90 | | | | | 95 | |
| Pro | Gly | Glu | Arg | Phe | Leu | Cys | Gly | Gly | Ile | Leu | Ile | Ser | Ser | Cys | Trp |
| | | | 100 | | | | | 105 | | | | | 110 | | |
| Ile | Leu | Ser | Ala | Ala | His | Cys | Phe | Gln | Glu | Arg | Phe | Pro | Pro | His | His |
| | | 115 | | | | | 120 | | | | | 125 | | | |
| Leu | Thr | Val | Ile | Leu | Gly | Arg | Thr | Tyr | Arg | Val | Val | Pro | Gly | Glu | Glu |
| | 130 | | | | | 135 | | | | | 140 | | | | |
| Glu | Gln | Lys | Phe | Glu | Val | Glu | Lys | Tyr | Ile | Val | His | Lys | | | |
| 145 | | | | | 150 | | | | | 155 | | | | | |

( 2 ) INFORMATION FOR SEQ ID NO:42:

( i ) SEQUENCE CHARACTERISTICS:
( A ) LENGTH: 2101 base pairs (B) TYPE: nucleic acid
(C) STRANDEDNESS: double
(D) TOPOLOGY: circular (ii) MOLECULE TYPE: DNA (genomic)

(ix) FEATURE:
    (A) NAME/KEY: CDS
    (B) LOCATION: 25..1710

(xi) SEQUENCE DESCRIPTION: SEQ ID NO:42:

```
GTTAAGGGAC GCTGTGAAGC AATC ATG GAT GCA ATG AAG AGA GGG CTC TGC         51
                              Met Asp Ala Met Lys Arg Gly Leu Cys
                               1               5

TGT GTG CTG GGA GCC AGA TCT TAC CAA GTG ATC TGC AGA GAT GAA AAA        99
Cys Val Leu Gly Ala Arg Ser Tyr Gln Val Ile Cys Arg Asp Glu Lys
 10              15                  20                  25

ACG CAG ATG ATA TAC CAG CAA GGA GCC AGA TCT TAC CAA GTG ATC TGC       147
Thr Gln Met Ile Tyr Gln Gln Gly Ala Arg Ser Tyr Gln Val Ile Cys
             30                  35                  40

AGA GAT GAA AAA ACG CAG ATG ATA TAC CAG CAA CAT CAG TCA TGG CTG       195
Arg Asp Glu Lys Thr Gln Met Ile Tyr Gln Gln His Gln Ser Trp Leu
                 45                  50                  55

CGC CCT GTG CTC AGA AGC AAC CGG GTG GAA TAT TGC TGG TGC AAC AGT       243
Arg Pro Val Leu Arg Ser Asn Arg Val Glu Tyr Cys Trp Cys Asn Ser
             60                  65                  70

GGC AGG GCA CAG TGC CAC TCA GTG CCT GTC AAA AGT TGC AGC GAG CCA       291
Gly Arg Ala Gln Cys His Ser Val Pro Val Lys Ser Cys Ser Glu Pro
 75                  80                  85

AGG TGT TTC AAC GGG GGC ACC TGC CAG CAG GCC CTG TAC TTC TCA GAT       339
Arg Cys Phe Asn Gly Gly Thr Cys Gln Gln Ala Leu Tyr Phe Ser Asp
 90              95                 100                 105

TTC GTG TGC CAG TGC CCC GAA GGA TTT GCT GGG AAG TGC TGT GAA ATA       387
Phe Val Cys Gln Cys Pro Glu Gly Phe Ala Gly Lys Cys Cys Glu Ile
             110                 115                 120

GAT ACC AGG GCC ACG TGC TAC GAG GAC CAG GGC ATC AGC TAC AGG GGC       435
Asp Thr Arg Ala Thr Cys Tyr Glu Asp Gln Gly Ile Ser Tyr Arg Gly
                 125                 130                 135

ACG TGG AGC ACA GCG GAG AGT GGC GCC GAG TGC ACC AAC TGG AAC AGC       483
Thr Trp Ser Thr Ala Glu Ser Gly Ala Glu Cys Thr Asn Trp Asn Ser
             140                 145                 150

AGC GCG TTG GCC CAG AAG CCC TAC AGC GGG CGG AGG CCA GAC GCC ATC       531
Ser Ala Leu Ala Gln Lys Pro Tyr Ser Gly Arg Arg Pro Asp Ala Ile
 155                 160                 165

AGG CTG GGC CTG GGG AAC CAC AAC TAC TGC AGA AAC CCA GAT CGA GAC       579
Arg Leu Gly Leu Gly Asn His Asn Tyr Cys Arg Asn Pro Asp Arg Asp
170              175                 180                 185

TCA AAG CCC TGG TGC TAC GTC TTT AAG GCG GGG AAG TAC AGC TCA GAG       627
Ser Lys Pro Trp Cys Tyr Val Phe Lys Ala Gly Lys Tyr Ser Ser Glu
             190                 195                 200

TTC TGC AGC ACC CCT GCC TGT TCT GAG GGA AAC AGT GAC TGC TAC TTT       675
Phe Cys Ser Thr Pro Ala Cys Ser Glu Gly Asn Ser Asp Cys Tyr Phe
             205                 210                 215

GGG AAT GGG TCA GCC TAC CGT GGC ACG CAC AGC CTC ACC GAG TCG GGT       723
Gly Asn Gly Ser Ala Tyr Arg Gly Thr His Ser Leu Thr Glu Ser Gly
         220                 225                 230

GCC TCC TGC CTC CCG TGG AAT TCC ATG ATC CTG ATA GGC AAG GTT TAC       771
Ala Ser Cys Leu Pro Trp Asn Ser Met Ile Leu Ile Gly Lys Val Tyr
 235                 240                 245

ACA GCA CAG AAC CCC AGT GCC CAG GCA CTG GGC CTG GGC AAA CAT AAT       819
Thr Ala Gln Asn Pro Ser Ala Gln Ala Leu Gly Leu Gly Lys His Asn
250                 255                 260                 265
```

-continued

| | | | | | | | | | | | | | | | | |
|---|---|---|---|---|---|---|---|---|---|---|---|---|---|---|---|---|
| TAC | TGC | CGG | AAT | CCT | GAT | GGG | GAT | GCC | AAG | CCC | TGG | TGC | CAC | GTG | CTG | 867 |
| Tyr | Cys | Arg | Asn | Pro 270 | Asp | Gly | Asp | Ala | Lys 275 | Pro | Trp | Cys | His | Val 280 | Leu | |
| AAG | AAC | CGC | AGG | CTG | ACG | TGG | GAG | TAC | TGT | GAT | GTG | CCC | TCC | TGC | TCC | 915 |
| Lys | Asn | Arg | Arg 285 | Leu | Thr | Trp | Glu | Tyr 290 | Cys | Asp | Val | Pro | Ser 295 | Cys | Ser | |
| ACC | TGC | GGC | CTG | AGA | CAG | TAC | AGC | CAG | CCT | CAG | TTT | CGC | ATC | AAA | GGA | 963 |
| Thr | Cys | Gly 300 | Leu | Arg | Gln | Tyr | Ser 305 | Gln | Pro | Gln | Phe | Arg 310 | Ile | Lys | Gly | |
| GGG | CTC | TTC | GCC | GAC | ATC | GCC | TCC | CAC | CCC | TGG | CAG | GCT | GCC | ATC | TTT | 1011 |
| Gly | Leu 315 | Phe | Ala | Asp | Ile | Ala 320 | Ser | His | Pro | Trp | Gln 325 | Ala | Ala | Ile | Phe | |
| GCC | AAG | CAC | AGG | AGG | TCG | CCC | GGA | GAG | CGG | TTC | CTG | TGC | GGG | GGC | ATA | 1059 |
| Ala 330 | Lys | His | Arg | Arg 335 | Ser | Pro | Gly | Glu | Arg 340 | Phe | Leu | Cys | Gly | Gly | Ile 345 | |
| CTC | ATC | AGC | TCC | TGC | TGG | ATT | CTC | TCT | GCC | GCC | CAC | TGC | TTC | CAG | GAG | 1107 |
| Leu | Ile | Ser | Ser | Cys 350 | Trp | Ile | Leu | Ser | Ala 355 | Ala | His | Cys | Phe | Gln 360 | Glu | |
| AGG | TTT | CCG | CCC | CAC | CAC | CTG | ACG | GTG | ATC | TTG | GGC | AGA | ACA | TAC | CGG | 1155 |
| Arg | Phe | Pro | Pro 365 | His | His | Leu | Thr | Val 370 | Ile | Leu | Gly | Arg | Thr 375 | Tyr | Arg | |
| GTG | GTC | CCT | GGC | GAG | GAG | GAG | CAG | AAA | TTT | GAA | GTC | GAA | AAA | TAC | ATT | 1203 |
| Val | Val | Pro 380 | Gly | Glu | Glu | Glu | Gln 385 | Lys | Phe | Glu | Val | Glu 390 | Lys | Tyr | Ile | |
| GTC | CAT | AAG | GAA | TTC | GAT | GAT | GAC | ACT | TAC | GAC | AAT | GAC | ATT | GCG | CTG | 1251 |
| Val | His | Lys 395 | Glu | Phe | Asp | Asp | Asp 400 | Thr | Tyr | Asp | Asn | Asp 405 | Ile | Ala | Leu | |
| CTG | CAG | CTG | AAA | TCG | GAT | TCG | TCC | CGC | TGT | GCC | CAG | GAG | AGC | AGC | GTG | 1299 |
| Leu 410 | Gln | Leu | Lys | Ser | Asp 415 | Ser | Ser | Arg | Cys | Ala 420 | Gln | Glu | Ser | Ser | Val 425 | |
| GTC | CGC | ACT | GTG | TGC | CTT | CCC | CCG | GCG | GAC | CTG | CAG | CTG | CCG | GAC | TGG | 1347 |
| Val | Arg | Thr | Val | Cys 430 | Leu | Pro | Pro | Ala | Asp 435 | Leu | Gln | Leu | Pro | Asp 440 | Trp | |
| ACG | GAG | TGT | GAG | CTC | TCC | GGC | TAC | GGC | AAG | CAT | GAG | GCC | TTG | TCT | CCT | 1395 |
| Thr | Glu | Cys | Glu 445 | Leu | Ser | Gly | Tyr | Gly 450 | Lys | His | Glu | Ala | Leu 455 | Ser | Pro | |
| TTC | TAT | TCG | GAG | CGG | CTG | AAG | GAG | GCT | CAT | GTC | AGA | CTG | TAC | CCA | TCC | 1443 |
| Phe | Tyr | Ser 460 | Glu | Arg | Leu | Lys | Glu 465 | Ala | His | Val | Arg | Leu 470 | Tyr | Pro | Ser | |
| AGC | CGC | TGC | ACA | TCA | CAA | CAT | TTA | CTT | AAC | AGA | ACA | GTC | ACC | GAC | AAC | 1491 |
| Ser | Arg 475 | Cys | Thr | Ser | Gln | His 480 | Leu | Leu | Asn | Arg | Thr 485 | Val | Thr | Asp | Asn | |
| ATG | CTG | TGT | GCT | GGA | GAC | ACT | CGG | AGC | GGC | GGG | CCC | CAG | GCA | AAC | TTG | 1539 |
| Met 490 | Leu | Cys | Ala | Gly | Asp 495 | Thr | Arg | Ser | Gly | Gly 500 | Pro | Gln | Ala | Asn | Leu 505 | |
| CAC | GAC | GCC | TGC | CAG | GGC | GAT | TCG | GGA | GGC | CCC | CTG | GTG | TGT | CTG | AAC | 1587 |
| His | Asp | Ala | Cys | Gln 510 | Gly | Asp | Ser | Gly | Gly 515 | Pro | Leu | Val | Cys | Leu 520 | Asn | |
| GAT | GGC | CGC | ATG | ACT | TTG | GTG | GGC | ATC | ATC | AGC | TGG | GGC | CTG | GGC | TGT | 1635 |
| Asp | Gly | Arg | Met | Thr 525 | Leu | Val | Gly | Ile | Ile 530 | Ser | Trp | Gly | Leu | Gly 535 | Cys | |
| GGA | CAG | AAG | GAT | GTC | CCG | GGT | GTG | TAC | ACA | AAG | GTT | ACC | AAC | TAC | CTA | 1683 |
| Gly | Gln | Lys | Asp 540 | Val | Pro | Gly | Val | Tyr 545 | Thr | Lys | Val | Thr | Asn 550 | Tyr | Leu | |
| GAC | TGG | ATT | CGT | GAC | AAC | ATG | CGA | CCG | TGACCAGGAA | CACCCGACTC | | | | | | 1730 |
| Asp | Trp | Ile | Arg | Asp 555 | Asn | Met | Arg 560 | Pro | | | | | | | | |

CTCAAAAGCA AATGAGATCC CGCCTCTTCT TCTTCAGAAG ACACTGCAAA GGCGCAGTGC 1790

TTCTCTACAG ACTTCTCCAG ACCCACCACA CCGCAGAAGC GGGACGAGAC CCTACAGGAG 1850

```
AGGGAAGAGT  GCATTTTCCC  AGATACTTCC  CATTTTGGAA  GTTTTCAGGA  CTTGGTCTGA    1910

TTTCAGGATA  CTCTGTCAGA  TGGGAAGACA  TGAATGCACA  CTAGCCTCTC  CAGGAATGCC    1970

TCCTCCCTGG  GCAGAAGTGG  CCATGCCACC  CTGTTTTCGC  TAAAGCCCAA  CCTCCTGACC    2030

TGTCACCGTG  AGCAGCTTTG  GAAACAGGAC  CACAAAAATG  AAAGCATGTC  TCAATAGTAA    2090

AAGAAACAAG  A                                                             2101
```

( 2 ) INFORMATION FOR SEQ ID NO:43:

( i ) SEQUENCE CHARACTERISTICS:
        ( A ) LENGTH: 562 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

```
Met Asp Ala Met Lys Arg Gly Leu Cys Cys Val Leu Gly Ala Arg Ser
 1               5                  10                  15

Tyr Gln Val Ile Cys Arg Asp Glu Lys Thr Gln Met Ile Tyr Gln Gln
             20                  25                  30

Gly Ala Arg Ser Tyr Gln Val Ile Cys Arg Asp Glu Lys Thr Gln Met
         35                  40                  45

Ile Tyr Gln Gln His Gln Ser Trp Leu Arg Pro Val Leu Arg Ser Asn
     50                  55                  60

Arg Val Glu Tyr Cys Trp Cys Asn Ser Gly Arg Ala Gln Cys His Ser
 65                  70                  75                  80

Val Pro Val Lys Ser Cys Ser Glu Pro Arg Cys Phe Asn Gly Gly Thr
                 85                  90                  95

Cys Gln Gln Ala Leu Tyr Phe Ser Asp Phe Val Cys Gln Cys Pro Glu
             100                 105                 110

Gly Phe Ala Gly Lys Cys Cys Glu Ile Asp Thr Arg Ala Thr Cys Tyr
         115                 120                 125

Glu Asp Gln Gly Ile Ser Tyr Arg Gly Thr Trp Ser Thr Ala Glu Ser
     130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                 165                 170                 175

Asn Tyr Cys Arg Asn Pro Asp Arg Asp Ser Lys Pro Trp Cys Tyr Val
             180                 185                 190

Phe Lys Ala Gly Lys Tyr Ser Ser Glu Phe Cys Ser Thr Pro Ala Cys
         195                 200                 205

Ser Glu Gly Asn Ser Asp Cys Tyr Phe Gly Asn Gly Ser Ala Tyr Arg
     210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                 245                 250                 255

Gln Ala Leu Gly Leu Gly Lys His Asn Tyr Cys Arg Asn Pro Asp Gly
             260                 265                 270

Asp Ala Lys Pro Trp Cys His Val Leu Lys Asn Arg Arg Leu Thr Trp
         275                 280                 285

Glu Tyr Cys Asp Val Pro Ser Cys Ser Thr Cys Gly Leu Arg Gln Tyr
     290                 295                 300

Ser Gln Pro Gln Phe Arg Ile Lys Gly Gly Leu Phe Ala Asp Ile Ala
```

|  | 305 |  |  |  | 310 |  |  |  | 315 |  |  |  | 320 |
|---|---|---|---|---|---|---|---|---|---|---|---|---|---|

Ser His Pro Trp Gln Ala Ala Ile Phe Ala Lys His Arg Arg Ser Pro
                    325                     330                     335

Gly Glu Arg Phe Leu Cys Gly Gly Ile Leu Ile Ser Ser Cys Trp Ile
                340                     345                     350

Leu Ser Ala Ala His Cys Phe Gln Glu Arg Phe Pro Pro His His Leu
                355                     360                     365

Thr Val Ile Leu Gly Arg Thr Tyr Arg Val Val Pro Gly Glu Glu Glu
            370                     375                     380

Gln Lys Phe Glu Val Glu Lys Tyr Ile Val His Lys Glu Phe Asp Asp
385                     390                     395                     400

Asp Thr Tyr Asp Asn Asp Ile Ala Leu Leu Gln Leu Lys Ser Asp Ser
                        405                     410                     415

Ser Arg Cys Ala Gln Glu Ser Ser Val Val Arg Thr Val Cys Leu Pro
                420                     425                     430

Pro Ala Asp Leu Gln Leu Pro Asp Trp Thr Glu Cys Glu Leu Ser Gly
                435                     440                     445

Tyr Gly Lys His Glu Ala Leu Ser Pro Phe Tyr Ser Glu Arg Leu Lys
            450                     455                     460

Glu Ala His Val Arg Leu Tyr Pro Ser Ser Arg Cys Thr Ser Gln His
465                     470                     475                     480

Leu Leu Asn Arg Thr Val Thr Asp Asn Met Leu Cys Ala Gly Asp Thr
                        485                     490                     495

Arg Ser Gly Gly Pro Gln Ala Asn Leu His Asp Ala Cys Gln Gly Asp
                500                     505                     510

Ser Gly Gly Pro Leu Val Cys Leu Asn Asp Gly Arg Met Thr Leu Val
            515                     520                     525

Gly Ile Ile Ser Trp Gly Leu Gly Cys Gly Gln Lys Asp Val Pro Gly
530                     535                     540

Val Tyr Thr Lys Val Thr Asn Tyr Leu Asp Trp Ile Arg Asp Asn Met
545                     550                     555                     560

Arg Pro ( 2 ) INFORMATION FOR SEQ ID NO:44:

( i ) SEQUENCE CHARACTERISTICS:
        ( A ) LENGTH: 1068 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1065

( x i ) SEQUENCE DESCRIPTION: SEQ ID NO:44:

ATG TCT GAG GGA AAC AGT GAC TGC TAC TTT GGG AAT GGG TCA GCC TAC         48
Met Ser Glu Gly Asn Ser Asp Cys Tyr Phe Gly Asn Gly Ser Ala Tyr
 1               5                  10                  15

CGT GGC ACG CAC AGC CTC ACC GAG TCG GGT GCC TCC TGC CTC CCG TGG         96
Arg Gly Thr His Ser Leu Thr Glu Ser Gly Ala Ser Cys Leu Pro Trp
                20                  25                  30

AAT TCC ATG ATC CTG ATA GGC AAG GTT TAC ACA GCA CAG AAC CCC AGT        144
Asn Ser Met Ile Leu Ile Gly Lys Val Tyr Thr Ala Gln Asn Pro Ser
            35                  40                  45

GCC CAG GCA CTG GGC CTG GGC AAA CAT AAT TAC TGC CGG AAT CCT GAT        192
Ala Gln Ala Leu Gly Leu Gly Lys His Asn Tyr Cys Arg Asn Pro Asp

```
            50                           55                          60
GGG  GAT  GCC  AAG  CCC  TGG  TGC  CAC  GTG  CTG  AAG  AAC  CGC  AGG  CTG  ACG        240
Gly  Asp  Ala  Lys  Pro  Trp  Cys  His  Val  Leu  Lys  Asn  Arg  Arg  Leu  Thr
65             70                       75                            80

TGG  GAG  TAC  TGT  GAT  GTG  CCC  TCC  TGC  TCC  ACC  TGC  GGC  CTG  AGA  CAG        288
Trp  Glu  Tyr  Cys  Asp  Val  Pro  Ser  Cys  Ser  Thr  Cys  Gly  Leu  Arg  Gln
                    85                        90                      95

TAC  AGC  CAG  CCT  CAG  TTT  CGC  ATC  AAA  GGA  GGG  CTC  TTC  GCC  GAC  ATC        336
Tyr  Ser  Gln  Pro  Gln  Phe  Arg  Ile  Lys  Gly  Gly  Leu  Phe  Ala  Asp  Ile
               100                      105                 110

GCC  TCC  CAC  CCC  TGG  CAG  GCT  GCC  ATC  TTT  GCC  AAG  CAC  AGG  AGG  TCG        384
Ala  Ser  His  Pro  Trp  Gln  Ala  Ala  Ile  Phe  Ala  Lys  His  Arg  Arg  Ser
               115                      120                 125

CCC  GGA  GAG  CGG  TTC  CTG  TGC  GGG  GGC  ATA  CTC  ATC  AGC  TCC  TGC  TGG        432
Pro  Gly  Glu  Arg  Phe  Leu  Cys  Gly  Gly  Ile  Leu  Ile  Ser  Ser  Cys  Trp
130                           135                           140

ATT  CTC  TCT  GCC  GCC  CAC  TGC  TTC  CAG  GAG  AGG  TTT  CCG  CCC  CAC  CAC        480
Ile  Leu  Ser  Ala  Ala  His  Cys  Phe  Gln  Glu  Arg  Phe  Pro  Pro  His  His
145                      150                      155                      160

CTG  ACG  GTG  ATC  TTG  GGC  AGA  ACA  TAC  CGG  GTG  GTC  CCT  GGC  GAG  GAG        528
Leu  Thr  Val  Ile  Leu  Gly  Arg  Thr  Tyr  Arg  Val  Val  Pro  Gly  Glu  Glu
                    165                      170                      175

GAG  CAG  AAA  TTT  GAA  GTC  GAA  AAA  TAC  ATT  GTC  CAT  AAG  GAA  TTC  GAT        576
Glu  Gln  Lys  Phe  Glu  Val  Glu  Lys  Tyr  Ile  Val  His  Lys  Glu  Phe  Asp
               180                      185                      190

GAT  GAC  ACT  TAC  GAC  AAT  GAC  ATT  GCG  CTG  CTG  CAG  CTG  AAA  TCG  GAT        624
Asp  Asp  Thr  Tyr  Asp  Asn  Asp  Ile  Ala  Leu  Leu  Gln  Leu  Lys  Ser  Asp
               195                      200                      205

TCG  TCC  CGC  TGT  GCC  CAG  GAG  AGC  AGC  GTG  GTC  CGC  ACT  GTG  TGC  CTT        672
Ser  Ser  Arg  Cys  Ala  Gln  Glu  Ser  Ser  Val  Val  Arg  Thr  Val  Cys  Leu
210                           215                           220

CCC  CCG  GCG  GAC  CTG  CAG  CTG  CCG  GAC  TGG  ACG  GAG  TGT  GAG  CTC  TCC        720
Pro  Pro  Ala  Asp  Leu  Gln  Leu  Pro  Asp  Trp  Thr  Glu  Cys  Glu  Leu  Ser
225                      230                      235                      240

GGC  TAC  GGC  AAG  CAT  GAG  GCC  TTG  TCT  CCT  TTC  TAT  TCG  GAG  CGG  CTG        768
Gly  Tyr  Gly  Lys  His  Glu  Ala  Leu  Ser  Pro  Phe  Tyr  Ser  Glu  Arg  Leu
                    245                      250                      255

AAG  GAG  GCT  CAT  GTC  AGA  CTG  TAC  CCA  TCC  AGC  CGC  TGC  ACA  TCA  CAA        816
Lys  Glu  Ala  His  Val  Arg  Leu  Tyr  Pro  Ser  Ser  Arg  Cys  Thr  Ser  Gln
               260                      265                      270

CAT  TTA  CTT  AAC  AGA  ACA  GTC  ACC  GAC  AAC  ATG  CTG  TGT  GCT  GGA  GAC        864
His  Leu  Leu  Asn  Arg  Thr  Val  Thr  Asp  Asn  Met  Leu  Cys  Ala  Gly  Asp
               275                      280                      285

ACT  CGG  AGC  GGC  GGG  CCC  CAG  GCA  AAC  TTG  CAC  GAC  GCC  TGC  CAG  GGC        912
Thr  Arg  Ser  Gly  Gly  Pro  Gln  Ala  Asn  Leu  His  Asp  Ala  Cys  Gln  Gly
     290                      295                      300

GAT  TCG  GGA  GGC  CCC  CTG  GTG  TGT  CTG  AAC  GAT  GGC  CGC  ATG  ACT  TTG        960
Asp  Ser  Gly  Gly  Pro  Leu  Val  Cys  Leu  Asn  Asp  Gly  Arg  Met  Thr  Leu
305                      310                      315                      320

GTG  GGC  ATC  ATC  AGC  TGG  GGC  CTG  GGC  TGT  GGA  CAG  AAG  GAT  GTC  CCG       1008
Val  Gly  Ile  Ile  Ser  Trp  Gly  Leu  Gly  Cys  Gly  Gln  Lys  Asp  Val  Pro
                    325                      330                      335

GGT  GTG  TAC  ACA  AAG  GTT  ACC  AAC  TAC  CTA  GAC  TGG  ATT  CGT  GAC  AAC       1056
Gly  Val  Tyr  Thr  Lys  Val  Thr  Asn  Tyr  Leu  Asp  Trp  Ile  Arg  Asp  Asn
               340                      345                      350

ATG  CGA  CCG  TGA                                                                   1068
Met  Arg  Pro
               355
```

( 2 ) INFORMATION FOR SEQ ID NO:45:

( i ) SEQUENCE CHARACTERISTICS:
 ( A ) LENGTH: 355 amino acids
 ( B ) TYPE: amino acid
 ( D ) TOPOLOGY: linear ( i i ) MOLECULE TYPE: protein ( x i ) SEQUENCE DESCRIPTION: SEQ ID NO:45:

| Met | Ser | Glu | Gly | Asn | Ser | Asp | Cys | Tyr | Phe | Gly | Asn | Gly | Ser | Ala | Tyr |
| 1 | | | | 5 | | | | | 10 | | | | | 15 | |
| Arg | Gly | Thr | His | Ser | Leu | Thr | Glu | Ser | Gly | Ala | Ser | Cys | Leu | Pro | Trp |
| | | | 20 | | | | | 25 | | | | | 30 | | |
| Asn | Ser | Met | Ile | Leu | Ile | Gly | Lys | Val | Tyr | Thr | Ala | Gln | Asn | Pro | Ser |
| | | | 35 | | | | 40 | | | | | 45 | | | |
| Ala | Gln | Ala | Leu | Gly | Leu | Gly | Lys | His | Asn | Tyr | Cys | Arg | Asn | Pro | Asp |
| | | 50 | | | | 55 | | | | | 60 | | | | |
| Gly | Asp | Ala | Lys | Pro | Trp | Cys | His | Val | Leu | Lys | Asn | Arg | Arg | Leu | Thr |
| 65 | | | | | 70 | | | | | 75 | | | | | 80 |
| Trp | Glu | Tyr | Cys | Asp | Val | Pro | Ser | Cys | Ser | Thr | Cys | Gly | Leu | Arg | Gln |
| | | | | 85 | | | | | 90 | | | | | 95 | |
| Tyr | Ser | Gln | Pro | Gln | Phe | Arg | Ile | Lys | Gly | Gly | Leu | Phe | Ala | Asp | Ile |
| | | | 100 | | | | | 105 | | | | | 110 | | |
| Ala | Ser | His | Pro | Trp | Gln | Ala | Ala | Ile | Phe | Ala | Lys | His | Arg | Arg | Ser |
| | | 115 | | | | | 120 | | | | | 125 | | | |
| Pro | Gly | Glu | Arg | Phe | Leu | Cys | Gly | Gly | Ile | Leu | Ile | Ser | Ser | Cys | Trp |
| | 130 | | | | | 135 | | | | | 140 | | | | |
| Ile | Leu | Ser | Ala | Ala | His | Cys | Phe | Gln | Glu | Arg | Phe | Pro | Pro | His | His |
| 145 | | | | | 150 | | | | | 155 | | | | | 160 |
| Leu | Thr | Val | Ile | Leu | Gly | Arg | Thr | Tyr | Arg | Val | Val | Pro | Gly | Glu | Glu |
| | | | | 165 | | | | | 170 | | | | | 175 | |
| Glu | Gln | Lys | Phe | Glu | Val | Glu | Lys | Tyr | Ile | Val | His | Lys | Glu | Phe | Asp |
| | | | 180 | | | | | 185 | | | | | 190 | | |
| Asp | Asp | Thr | Tyr | Asp | Asn | Asp | Ile | Ala | Leu | Leu | Gln | Leu | Lys | Ser | Asp |
| | | 195 | | | | | 200 | | | | | 205 | | | |
| Ser | Ser | Arg | Cys | Ala | Gln | Glu | Ser | Ser | Val | Val | Arg | Thr | Val | Cys | Leu |
| | 210 | | | | | 215 | | | | | 220 | | | | |
| Pro | Pro | Ala | Asp | Leu | Gln | Leu | Pro | Asp | Trp | Thr | Glu | Cys | Glu | Leu | Ser |
| 225 | | | | | 230 | | | | | 235 | | | | | 240 |
| Gly | Tyr | Gly | Lys | His | Glu | Ala | Leu | Ser | Pro | Phe | Tyr | Ser | Glu | Arg | Leu |
| | | | | 245 | | | | | 250 | | | | | 255 | |
| Lys | Glu | Ala | His | Val | Arg | Leu | Tyr | Pro | Ser | Ser | Arg | Cys | Thr | Ser | Gln |
| | | | 260 | | | | | 265 | | | | | 270 | | |
| His | Leu | Leu | Asn | Arg | Thr | Val | Thr | Asp | Asn | Met | Leu | Cys | Ala | Gly | Asp |
| | | 275 | | | | | 280 | | | | | 285 | | | |
| Thr | Arg | Ser | Gly | Gly | Pro | Gln | Ala | Asn | Leu | His | Asp | Ala | Cys | Gln | Gly |
| | 290 | | | | | 295 | | | | | 300 | | | | |
| Asp | Ser | Gly | Gly | Pro | Leu | Val | Cys | Leu | Asn | Asp | Gly | Arg | Met | Thr | Leu |
| 305 | | | | | 310 | | | | | 315 | | | | | 320 |
| Val | Gly | Ile | Ile | Ser | Trp | Gly | Leu | Gly | Cys | Gly | Gln | Lys | Asp | Val | Pro |
| | | | | 325 | | | | | 330 | | | | | 335 | |
| Gly | Val | Tyr | Thr | Lys | Val | Thr | Asn | Tyr | Leu | Asp | Trp | Ile | Arg | Asp | Asn |
| | | | 340 | | | | | 345 | | | | | 350 | | |
| Met | Arg | Pro | | | | | | | | | | | | | |
| | | 355 | | | | | | | | | | | | | |

( 2 ) INFORMATION FOR SEQ ID NO:46:

( i ) SEQUENCE CHARACTERISTICS:
        ( A ) LENGTH: 1068 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1065

( x i ) SEQUENCE DESCRIPTION: SEQ ID NO:46:

```
ATG TCT GAG GGA AAC AGT GAC TGC TAC TTT GGG AAT GGG TCA GCC TAC        48
Met Ser Glu Gly Asn Ser Asp Cys Tyr Phe Gly Asn Gly Ser Ala Tyr
 1               5                  10                  15

CGT GGC ACG CAC AGC CTC ACC GAG TCG GGT GCC TCC TGC CTC CCG TGG        96
Arg Gly Thr His Ser Leu Thr Glu Ser Gly Ala Ser Cys Leu Pro Trp
             20                  25                  30

AAT TCC ATG ATC CTG ATA GGC AAG GTT TAC ACA GCA CAG AAC CCC AGT       144
Asn Ser Met Ile Leu Ile Gly Lys Val Tyr Thr Ala Gln Asn Pro Ser
         35                  40                  45

GCC CAG GCA CTG GGC CTG GGC AAA CAT AAT TAC TGC CGG AAT CCT GAT       192
Ala Gln Ala Leu Gly Leu Gly Lys His Asn Tyr Cys Arg Asn Pro Asp
     50                  55                  60

GGG GAT GCC AAG CCC TGG TGC CAC GTG CTG AAG AAC CGC AGG CTG ACG       240
Gly Asp Ala Lys Pro Trp Cys His Val Leu Lys Asn Arg Arg Leu Thr
 65                  70                  75                  80

TGG GAG TAC TGT GAT GTG CCC TCC TGC TCC ACC TGC GGC CTG AGA CAG       288
Trp Glu Tyr Cys Asp Val Pro Ser Cys Ser Thr Cys Gly Leu Arg Gln
             85                  90                  95

TAC AGC CAG CCT CAG TTT CGC ATC ATA GGA GGC CTC TTC GCC GAC ATC       336
Tyr Ser Gln Pro Gln Phe Arg Ile Ile Gly Gly Leu Phe Ala Asp Ile
            100                 105                 110

GCC TCC CAC CCC TGG CAG GCT GCC ATC TTT GCC AAG CAC AGG AGG TCG       384
Ala Ser His Pro Trp Gln Ala Ala Ile Phe Ala Lys His Arg Arg Ser
            115                 120                 125

CCC GGA GAG CGG TTC CTG TGC GGG GGC ATA CTC ATC AGC TCC TGC TGG       432
Pro Gly Glu Arg Phe Leu Cys Gly Gly Ile Leu Ile Ser Ser Cys Trp
    130                 135                 140

ATT CTC TCT GCC GCC CAC TGC TTC CAG GAG AGG TTT CCG CCC CAC CAC       480
Ile Leu Ser Ala Ala His Cys Phe Gln Glu Arg Phe Pro Pro His His
145                 150                 155                 160

CTG ACG GTG ATC TTG GGC AGA ACA TAC CGG GTG GTC CCT GGC GAG GAG       528
Leu Thr Val Ile Leu Gly Arg Thr Tyr Arg Val Val Pro Gly Glu Glu
                165                 170                 175

GAG CAG AAA TTT GAA GTC GAA AAA TAC ATT GTC CAT AAG GAA TTC GAT       576
Glu Gln Lys Phe Glu Val Glu Lys Tyr Ile Val His Lys Glu Phe Asp
            180                 185                 190

GAT GAC ACT TAC GAC AAT GAC ATT GCG CTG CTG CAG CTG AAA TCG GAT       624
Asp Asp Thr Tyr Asp Asn Asp Ile Ala Leu Leu Gln Leu Lys Ser Asp
        195                 200                 205

TCG TCC CGC TGT GCC CAG GAG AGC AGC GTG GTC CGC ACT GTG TGC CTT       672
Ser Ser Arg Cys Ala Gln Glu Ser Ser Val Val Arg Thr Val Cys Leu
    210                 215                 220

CCC CCG GCG GAC CTG CAG CTG CCG GAC TGG ACG GAG TGT GAG CTC TCC       720
Pro Pro Ala Asp Leu Gln Leu Pro Asp Trp Thr Glu Cys Glu Leu Ser
225                 230                 235                 240

GGC TAC GGC AAG CAT GAG GCC TTG TCT CCT TTC TAT TCG GAG CGG CTG       768
Gly Tyr Gly Lys His Glu Ala Leu Ser Pro Phe Tyr Ser Glu Arg Leu
                245                 250                 255
```

| | | | | | | | | | | | | | | | | |
|---|---|---|---|---|---|---|---|---|---|---|---|---|---|---|---|---|
| AAG | GAG | GCT | CAT | GTC | AGA | CTG | TAC | CCA | TCC | AGC | CGC | TGC | ACA | TCA | CAA | 816 |
| Lys | Glu | Ala | His 260 | Val | Arg | Leu | Tyr | Pro 265 | Ser | Ser | Arg | Cys | Thr 270 | Ser | Gln | |
| CAT | TTA | CTT | AAC | AGA | ACA | GTC | ACC | GAC | AAC | ATG | CTG | TGT | GCT | GGA | GAC | 864 |
| His | Leu | Leu 275 | Asn | Arg | Thr | Val | Asp 280 | Asn | Met | Leu | Cys 285 | Ala | Gly | Asp | | |
| ACT | CGG | AGC | GGC | GGG | CCC | CAG | GCA | AAC | TTG | CAC | GAC | GCC | TGC | CAG | GGC | 912 |
| Thr | Arg 290 | Ser | Gly | Gly | Pro | Gln 295 | Ala | Asn | Leu | His | Asp 300 | Ala | Cys | Gln | Gly | |
| GAT | TCG | GGA | GGC | CCC | CTG | GTG | TGT | CTG | AAC | GAT | GGC | CGC | ATG | ACT | TTG | 960 |
| Asp 305 | Ser | Gly | Gly | Pro | Leu 310 | Val | Cys | Leu | Asn | Asp 315 | Gly | Arg | Met | Thr | Leu 320 | |
| GTG | GGC | ATC | ATC | AGC | TGG | GGC | CTG | GGC | TGT | GGA | CAG | AAG | GAT | GTC | CCG | 1008 |
| Val | Gly | Ile | Ile | Ser 325 | Trp | Gly | Leu | Gly | Cys 330 | Gly | Gln | Lys | Asp | Val 335 | Pro | |
| GGT | GTG | TAC | ACA | AAG | GTT | ACC | AAC | TAC | CTA | GAC | TGG | ATT | CGT | GAC | AAC | 1056 |
| Gly | Val | Tyr | Thr 340 | Lys | Val | Thr | Asn | Tyr 345 | Leu | Asp | Trp | Ile | Arg 350 | Asp | Asn | |
| ATG | CGA | CCG | TGA | | | | | | | | | | | | | 1068 |
| Met | Arg | Pro 355 | | | | | | | | | | | | | | |

(2) INFORMATION FOR SEQ ID NO:47:

(i) SEQUENCE CHARACTERISTICS:
        (A) LENGTH: 355 amino acids
        (B) TYPE: amino acid
        (D) TOPOLOGY: linear (ii) MOLECULE TYPE: protein (xi) SEQUENCE DESCRIPTION: SEQ ID NO:47:

| | | | | | | | | | | | | | | |
|---|---|---|---|---|---|---|---|---|---|---|---|---|---|---|
| Met 1 | Ser | Glu | Gly | Asn 5 | Ser | Asp | Cys | Tyr | Phe 10 | Gly | Asn | Gly | Ser | Ala 15 | Tyr |
| Arg | Gly | Thr | His 20 | Ser | Leu | Thr | Glu | Ser 25 | Gly | Ala | Ser | Cys | Leu 30 | Pro | Trp |
| Asn | Ser | Met 35 | Ile | Leu | Ile | Gly | Lys 40 | Val | Tyr | Thr | Ala | Gln 45 | Asn | Pro | Ser |
| Ala | Gln 50 | Ala | Leu | Gly | Leu | Gly 55 | Lys | His | Asn | Tyr | Cys 60 | Arg | Asn | Pro | Asp |
| Gly 65 | Asp | Ala | Lys | Pro | Trp 70 | Cys | His | Val | Leu | Lys 75 | Asn | Arg | Arg | Leu | Thr 80 |
| Trp | Glu | Tyr | Cys | Asp 85 | Val | Pro | Ser | Cys | Ser 90 | Thr | Cys | Gly | Leu | Arg 95 | Gln |
| Tyr | Ser | Gln | Pro 100 | Gln | Phe | Arg | Ile | Ile 105 | Gly | Gly | Leu | Phe | Ala 110 | Asp | Ile |
| Ala | Ser | His 115 | Pro | Trp | Gln | Ala | Ala 120 | Ile | Phe | Ala | Lys | His 125 | Arg | Arg | Ser |
| Pro | Gly 130 | Glu | Arg | Phe | Leu | Cys 135 | Gly | Gly | Ile | Leu | Ile 140 | Ser | Ser | Cys | Trp |
| Ile 145 | Leu | Ser | Ala | Ala | His 150 | Cys | Phe | Gln | Glu | Arg 155 | Phe | Pro | Pro | His | His 160 |
| Leu | Thr | Val | Ile | Leu 165 | Gly | Arg | Thr | Tyr | Arg 170 | Val | Val | Pro | Gly | Glu 175 | Glu |
| Glu | Gln | Lys | Phe 180 | Glu | Val | Glu | Lys | Tyr 185 | Ile | Val | His | Lys | Glu 190 | Phe | Asp |
| Asp | Asp | Thr | Tyr 195 | Asp | Asn | Asp | Ile | Ala 200 | Leu | Leu | Gln | Leu | Lys 205 | Ser | Asp |
| Ser | Ser | Arg | Cys | Ala | Gln | Glu | Ser | Ser | Val | Val | Arg | Thr | Val | Cys | Leu |

```
                210                          215                          220
Pro   Pro   Ala   Asp   Leu   Gln   Leu   Pro   Asp   Trp   Thr   Glu   Cys   Glu   Leu   Ser
225                     230                          235                          240

Gly   Tyr   Gly   Lys   His   Glu   Ala   Leu   Ser   Pro   Phe   Tyr   Ser   Glu   Arg   Leu
                  245                          250                          255

Lys   Glu   Ala   His   Val   Arg   Leu   Tyr   Pro   Ser   Ser   Arg   Cys   Thr   Ser   Gln
                  260                          265                          270

His   Leu   Leu   Asn   Arg   Thr   Val   Thr   Asp   Asn   Met   Leu   Cys   Ala   Gly   Asp
                  275                          280                          285

Thr   Arg   Ser   Gly   Gly   Pro   Gln   Ala   Asn   Leu   His   Asp   Ala   Cys   Gln   Gly
            290                          295                          300

Asp   Ser   Gly   Gly   Pro   Leu   Val   Cys   Leu   Asn   Asp   Gly   Arg   Met   Thr   Leu
305                           310                          315                          320

Val   Gly   Ile   Ile   Ser   Trp   Gly   Leu   Gly   Cys   Gly   Gln   Lys   Asp   Val   Pro
                        325                          330                          335

Gly   Val   Tyr   Thr   Lys   Val   Thr   Asn   Tyr   Leu   Asp   Trp   Ile   Arg   Asp   Asn
                  340                          345                          350

Met   Arg   Pro
            355
```

( 2 ) INFORMATION FOR SEQ ID NO:48:

( i ) SEQUENCE CHARACTERISTICS:
        ( A ) LENGTH: 1314 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1311

( x i ) SEQUENCE DESCRIPTION: SEQ ID NO:48:

```
ATG   TGT   TAT   GAG   GAC   CAG   GGC   ATC   AGC   TAC   AGG   GGC   ACG   TGG   AGC   ACA         48
Met   Cys   Tyr   Glu   Asp   Gln   Gly   Ile   Ser   Tyr   Arg   Gly   Thr   Trp   Ser   Thr
 1                      5                          10                            15

GCG   GAG   AGT   GGC   GCC   GAG   TGC   ACC   AAC   TGG   AAC   AGC   AGC   GCG   TTG   GCC         96
Ala   Glu   Ser   Gly   Ala   Glu   Cys   Thr   Asn   Trp   Asn   Ser   Ser   Ala   Leu   Ala
                  20                          25                            30

CAG   AAG   CCC   TAC   AGC   GGG   CGG   AGG   CCA   GAC   GCC   ATC   AGG   CTG   GGC   CTG        144
Gln   Lys   Pro   Tyr   Ser   Gly   Arg   Arg   Pro   Asp   Ala   Ile   Arg   Leu   Gly   Leu
            35                          40                            45

GGG   AAC   CAC   AAC   TAC   TGC   AGA   AAC   CCA   GAT   CGA   GAC   TCA   AAG   CCC   TGG        192
Gly   Asn   His   Asn   Tyr   Cys   Arg   Asn   Pro   Asp   Arg   Asp   Ser   Lys   Pro   Trp
      50                          55                            60

TGC   TAC   GTC   TTT   AAG   GCG   GGG   AAG   TAC   AGC   TCA   GAG   TTC   TGC   AGC   ACC        240
Cys   Tyr   Val   Phe   Lys   Ala   Gly   Lys   Tyr   Ser   Ser   Glu   Phe   Cys   Ser   Thr
65                            70                            75                            80

CCT   GCC   TGC   TCT   GAG   GGA   AAC   AGT   GAC   TGC   TAC   TTT   GGG   AAT   GGG   TCA        288
Pro   Ala   Cys   Ser   Glu   Gly   Asn   Ser   Asp   Cys   Tyr   Phe   Gly   Asn   Gly   Ser
                        85                            90                            95

GCC   TAC   CGT   GGC   ACG   CAC   AGC   CTC   ACC   GAG   TCG   GGT   GCC   TCC   TGC   CTC        336
Ala   Tyr   Arg   Gly   Thr   His   Ser   Leu   Thr   Glu   Ser   Gly   Ala   Ser   Cys   Leu
                  100                         105                           110

CCG   TGG   AAT   TCC   ATG   ATC   CTG   ATA   GGC   AAG   GTT   TAC   ACA   GCA   CAG   AAC        384
Pro   Trp   Asn   Ser   Met   Ile   Leu   Ile   Gly   Lys   Val   Tyr   Thr   Ala   Gln   Asn
            115                         120                           125

CCC   AGT   GCC   CAG   GCA   CTG   GGC   CTG   GGC   AAA   CAT   AAT   TAC   TGC   CGG   AAT        432
Pro   Ser   Ala   Gln   Ala   Leu   Gly   Leu   Gly   Lys   His   Asn   Tyr   Cys   Arg   Asn
```

```
                    130                           135                             140
CCT  GAT  GGG  GAT  GCC  AAG  CCC  TGG  TGC  CAC  GTG  CTG  AAG  AAC  CGC  AGG        480
Pro  Asp  Gly  Asp  Ala  Lys  Pro  Trp  Cys  His  Val  Leu  Lys  Asn  Arg  Arg
145                      150                      155                      160

CTG  ACG  TGG  GAG  TAC  TGT  GAT  GTG  CCC  TCC  TGC  TCC  ACC  TGC  GGC  CTG        528
Leu  Thr  Trp  Glu  Tyr  Cys  Asp  Val  Pro  Ser  Cys  Ser  Thr  Cys  Gly  Leu
                    165                      170                      175

AGA  CAG  TAC  AGC  CAG  CCT  CAG  TTT  CGC  ATC  AAA  GGA  GGG  CTC  TTC  GCC        576
Arg  Gln  Tyr  Ser  Gln  Pro  Gln  Phe  Arg  Ile  Lys  Gly  Gly  Leu  Phe  Ala
               180                      185                      190

GAC  ATC  GCC  TCC  CAC  CCC  TGG  CAG  GCT  GCC  ATC  TTT  GCC  AAG  CAC  AGG        624
Asp  Ile  Ala  Ser  His  Pro  Trp  Gln  Ala  Ala  Ile  Phe  Ala  Lys  His  Arg
          195                      200                      205

AGG  TCG  CCC  GGA  GAG  CGG  TTC  CTG  TGC  GGG  GGC  ATA  CTC  ATC  AGC  TCC        672
Arg  Ser  Pro  Gly  Glu  Arg  Phe  Leu  Cys  Gly  Gly  Ile  Leu  Ile  Ser  Ser
     210                      215                      220

TGC  TGG  ATT  CTC  TCT  GCC  GCC  CAC  TGC  TTC  CAG  GAG  AGG  TTT  CCG  CCC        720
Cys  Trp  Ile  Leu  Ser  Ala  Ala  His  Cys  Phe  Gln  Glu  Arg  Phe  Pro  Pro
225                      230                      235                      240

CAC  CAC  CTG  ACG  GTG  ATC  TTG  GGC  AGA  ACA  TAC  CGG  GTG  GTC  CCT  GGC        768
His  His  Leu  Thr  Val  Ile  Leu  Gly  Arg  Thr  Tyr  Arg  Val  Val  Pro  Gly
                    245                      250                      255

GAG  GAG  GAG  CAG  AAA  TTT  GAA  GTC  GAA  AAA  TAC  ATT  GTC  CAT  AAG  GAA        816
Glu  Glu  Glu  Gln  Lys  Phe  Glu  Val  Glu  Lys  Tyr  Ile  Val  His  Lys  Glu
               260                      265                      270

TTC  GAT  GAT  GAC  ACT  TAC  GAC  AAT  GAC  ATT  GCG  CTG  CTG  CAG  CTG  AAA        864
Phe  Asp  Asp  Asp  Thr  Tyr  Asp  Asn  Asp  Ile  Ala  Leu  Leu  Gln  Leu  Lys
          275                      280                      285

TCG  GAT  TCG  TCC  CGC  TGT  GCC  CAG  GAG  AGC  AGC  GTG  GTC  CGC  ACT  GTG        912
Ser  Asp  Ser  Ser  Arg  Cys  Ala  Gln  Glu  Ser  Ser  Val  Val  Arg  Thr  Val
     290                      295                      300

TGC  CTT  CCC  CCG  GCG  GAC  CTG  CAG  CTG  CCG  GAC  TGG  ACG  GAG  TGT  GAG        960
Cys  Leu  Pro  Pro  Ala  Asp  Leu  Gln  Leu  Pro  Asp  Trp  Thr  Glu  Cys  Glu
305                      310                      315                      320

CTC  TCC  GGC  TAC  GGC  AAG  CAT  GAG  GCC  TTG  TCT  CCT  TTC  TAT  TCG  GAG       1008
Leu  Ser  Gly  Tyr  Gly  Lys  His  Glu  Ala  Leu  Ser  Pro  Phe  Tyr  Ser  Glu
                    325                      330                      335

CGG  CTG  AAG  GAG  GCT  CAT  GTC  AGA  CTG  TAC  CCA  TCC  AGC  CGC  TGC  ACA       1056
Arg  Leu  Lys  Glu  Ala  His  Val  Arg  Leu  Tyr  Pro  Ser  Ser  Arg  Cys  Thr
               340                      345                      350

TCA  CAA  CAT  TTA  CTT  AAC  AGA  ACA  GTC  ACC  GAC  AAC  ATG  CTG  TGT  GCT       1104
Ser  Gln  His  Leu  Leu  Asn  Arg  Thr  Val  Thr  Asp  Asn  Met  Leu  Cys  Ala
          355                      360                      365

GGA  GAC  ACT  CGG  AGC  GGC  GGG  CCC  CAG  GCA  AAC  TTG  CAC  GAC  GCC  TGC       1152
Gly  Asp  Thr  Arg  Ser  Gly  Gly  Pro  Gln  Ala  Asn  Leu  His  Asp  Ala  Cys
     370                      375                      380

CAG  GGC  GAT  TCG  GGA  GGC  CCC  CTG  GTG  TGT  CTG  AAC  GAT  GGC  CGC  ATC       1200
Gln  Gly  Asp  Ser  Gly  Gly  Pro  Leu  Val  Cys  Leu  Asn  Asp  Gly  Arg  Ile
385                      390                      395                      400

ACT  TTG  GTG  GGC  ATC  ATC  AGC  TGG  GGC  CTG  GGC  TGT  GGA  CAG  AAG  GAT       1248
Thr  Leu  Val  Gly  Ile  Ile  Ser  Trp  Gly  Leu  Gly  Cys  Gly  Gln  Lys  Asp
                    405                      410                      415

GTC  CCG  GGT  GTG  TAC  ACA  AAG  GTT  ACC  AAC  TAC  CTA  GAC  TGG  ATT  CGT       1296
Val  Pro  Gly  Val  Tyr  Thr  Lys  Val  Thr  Asn  Tyr  Leu  Asp  Trp  Ile  Arg
               420                      425                      430

GAC  AAC  ATG  CGA  CCG  TGA                                                         1314
Asp  Asn  Met  Arg  Pro
                435
```

( 2 ) INFORMATION FOR SEQ ID NO:49:

(i) SEQUENCE CHARACTERISTICS:
  (A) LENGTH: 437 amino acids
  (B) TYPE: amino acid
  (D) TOPOLOGY: linear (ii) MOLECULE TYPE: protein (xi) SEQUENCE DESCRIPTION: SEQ ID NO:49:

| Met 1 | Cys | Tyr | Glu | Asp 5 | Gln | Gly | Ile | Ser | Tyr 10 | Arg | Gly | Thr | Trp | Ser 15 | Thr |
|---|---|---|---|---|---|---|---|---|---|---|---|---|---|---|---|
| Ala | Glu | Ser | Gly 20 | Ala | Glu | Cys | Thr | Asn 25 | Trp | Asn | Ser | Ser | Ala 30 | Leu | Ala |
| Gln | Lys | Pro 35 | Tyr | Ser | Gly | Arg | Arg 40 | Pro | Asp | Ala | Ile | Arg 45 | Leu | Gly | Leu |
| Gly | Asn 50 | His | Asn | Tyr | Cys | Arg 55 | Asn | Pro | Asp | Arg | Asp 60 | Ser | Lys | Pro | Trp |
| Cys 65 | Tyr | Val | Phe | Lys | Ala 70 | Gly | Lys | Tyr | Ser | Ser 75 | Glu | Phe | Cys | Ser | Thr 80 |
| Pro | Ala | Cys | Ser | Glu 85 | Gly | Asn | Ser | Asp | Cys 90 | Tyr | Phe | Gly | Asn | Gly 95 | Ser |
| Ala | Tyr | Arg | Gly 100 | Thr | His | Ser | Leu | Thr 105 | Glu | Ser | Gly | Ala | Ser 110 | Cys | Leu |
| Pro | Trp | Asn 115 | Ser | Met | Ile | Leu | Ile 120 | Gly | Lys | Val | Tyr | Thr 125 | Ala | Gln | Asn |
| Pro | Ser 130 | Ala | Gln | Ala | Leu | Gly 135 | Leu | Gly | Lys | His | Asn 140 | Tyr | Cys | Arg | Asn |
| Pro 145 | Asp | Gly | Asp | Ala | Lys 150 | Pro | Trp | Cys | His | Val 155 | Leu | Lys | Asn | Arg | Arg 160 |
| Leu | Thr | Trp | Glu | Tyr 165 | Cys | Asp | Val | Pro | Ser 170 | Cys | Ser | Thr | Cys 175 | Gly | Leu |
| Arg | Gln | Tyr | Ser 180 | Gln | Pro | Gln | Phe | Arg 185 | Ile | Lys | Gly | Gly | Leu 190 | Phe | Ala |
| Asp | Ile | Ala 195 | Ser | His | Pro | Trp | Gln 200 | Ala | Ala | Ile | Phe | Ala 205 | Lys | His | Arg |
| Arg | Ser 210 | Pro | Gly | Glu | Arg | Phe 215 | Leu | Cys | Gly | Gly | Ile 220 | Leu | Ile | Ser | Ser |
| Cys 225 | Trp | Ile | Leu | Ser | Ala 230 | Ala | His | Cys | Phe | Gln 235 | Glu | Arg | Phe | Pro | Pro 240 |
| His | His | Leu | Thr | Val 245 | Ile | Leu | Gly | Arg | Thr 250 | Tyr | Arg | Val | Val | Pro 255 | Gly |
| Glu | Glu | Glu | Gln 260 | Lys | Phe | Glu | Val | Glu 265 | Lys | Tyr | Ile | Val | His 270 | Lys | Glu |
| Phe | Asp | Asp 275 | Asp | Thr | Tyr | Asp | Asn 280 | Asp | Ile | Ala | Leu | Leu 285 | Gln | Leu | Lys |
| Ser | Asp 290 | Ser | Ser | Arg | Cys | Ala 295 | Gln | Glu | Ser | Ser | Val 300 | Val | Arg | Thr | Val |
| Cys 305 | Leu | Pro | Pro | Ala | Asp 310 | Leu | Gln | Leu | Pro | Asp 315 | Trp | Thr | Glu | Cys | Glu 320 |
| Leu | Ser | Gly | Tyr | Gly 325 | Lys | His | Glu | Ala | Leu 330 | Ser | Pro | Phe | Tyr | Ser 335 | Glu |
| Arg | Leu | Lys | Glu 340 | Ala | His | Val | Arg | Leu 345 | Tyr | Pro | Ser | Ser | Arg 350 | Cys | Thr |
| Ser | Gln | His 355 | Leu | Leu | Asn | Arg | Thr 360 | Val | Thr | Asp | Asn | Met 365 | Leu | Cys | Ala |
| Gly | Asp | Thr | Arg | Ser | Gly | Gly | Pro | Gln | Ala | Asn | Leu | His | Asp | Ala | Cys |

-continued

```
                    370                              375                              380
Gln  Gly  Asp  Ser  Gly  Gly  Pro  Leu  Val  Cys  Leu  Asn  Asp  Gly  Arg  Ile
385                      390                          395                          400

Thr  Leu  Val  Gly  Ile  Ile  Ser  Trp  Gly  Leu  Gly  Cys  Gly  Gln  Lys  Asp
                    405                              410                          415

Val  Pro  Gly  Val  Tyr  Thr  Lys  Val  Thr  Asn  Tyr  Leu  Asp  Trp  Ile  Arg
                    420                              425                      430

Asp  Asn  Met  Arg  Pro
               435
```

( 2 ) INFORMATION FOR SEQ ID NO:50:

( i ) SEQUENCE CHARACTERISTICS:
        ( A ) LENGTH: 1314 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1311

( x i ) SEQUENCE DESCRIPTION: SEQ ID NO:50:

```
ATG  TGT  TAT  GAG  GAC  CAG  GGC  ATC  AGC  TAC  AGG  GGC  ACG  TGG  AGC  ACA         48
Met  Cys  Tyr  Glu  Asp  Gln  Gly  Ile  Ser  Tyr  Arg  Gly  Thr  Trp  Ser  Thr
 1                   5                        10                       15

GCG  GAG  AGT  GGC  GCC  GAG  TGC  ACC  AAC  TGG  AAC  AGC  AGC  GCG  TTG  GCC         96
Ala  Glu  Ser  Gly  Ala  Glu  Cys  Thr  Asn  Trp  Asn  Ser  Ser  Ala  Leu  Ala
                20                            25                       30

CAG  AAG  CCC  TAC  AGC  GGG  CGG  AGG  CCA  GAC  GCC  ATC  AGG  CTG  GGC  CTG        144
Gln  Lys  Pro  Tyr  Ser  Gly  Arg  Arg  Pro  Asp  Ala  Ile  Arg  Leu  Gly  Leu
           35                       40                       45

GGG  AAC  CAC  AAC  TAC  TGC  AGA  AAC  CCA  GAT  CGA  GAC  TCA  AAG  CCC  TGG        192
Gly  Asn  His  Asn  Tyr  Cys  Arg  Asn  Pro  Asp  Arg  Asp  Ser  Lys  Pro  Trp
      50                       55                       60

TGC  TAC  GTC  TTT  AAG  GCG  GGG  AAG  TAC  AGC  TCA  GAG  TTC  TGC  AGC  ACC        240
Cys  Tyr  Val  Phe  Lys  Ala  Gly  Lys  Tyr  Ser  Ser  Glu  Phe  Cys  Ser  Thr
 65                      70                       75                       80

CCT  GCC  TGC  TCT  GAG  GGA  AAC  AGT  GAC  TGC  TAC  TTT  GGG  AAT  GGG  TCA        288
Pro  Ala  Cys  Ser  Glu  Gly  Asn  Ser  Asp  Cys  Tyr  Phe  Gly  Asn  Gly  Ser
                     85                            90                       95

GCC  TAC  CGT  GGC  ACG  CAC  AGC  CTC  ACC  GAG  TCG  GGT  GCC  TCC  TGC  CTC        336
Ala  Tyr  Arg  Gly  Thr  His  Ser  Leu  Thr  Glu  Ser  Gly  Ala  Ser  Cys  Leu
               100                           105                      110

CCG  TGG  AAT  TCC  ATG  ATC  CTG  ATA  GGC  AAG  GTT  TAC  ACA  GCA  CAG  AAC        384
Pro  Trp  Asn  Ser  Met  Ile  Leu  Ile  Gly  Lys  Val  Tyr  Thr  Ala  Gln  Asn
          115                           120                      125

CCC  AGT  GCC  CAG  GCA  CTG  GGC  CTG  GGC  AAA  CAT  AAT  TAC  TGC  CGG  AAT        432
Pro  Ser  Ala  Gln  Ala  Leu  Gly  Leu  Gly  Lys  His  Asn  Tyr  Cys  Arg  Asn
         130                           135                      140

CCT  GAT  GGG  GAT  GCC  AAG  CCC  TGG  TGC  CAC  GTG  CTG  AAG  AAC  CGC  AGG        480
Pro  Asp  Gly  Asp  Ala  Lys  Pro  Trp  Cys  His  Val  Leu  Lys  Asn  Arg  Arg
145                      150                           155                      160

CTG  ACG  TGG  GAG  TAC  TGT  GAT  GTG  CCC  TCC  TGC  TCC  ACC  TGC  GGC  CTG        528
Leu  Thr  Trp  Glu  Tyr  Cys  Asp  Val  Pro  Ser  Cys  Ser  Thr  Cys  Gly  Leu
                    165                           170                      175

AGA  CAG  TAC  AGC  CAG  CCT  CAG  TTT  CGC  ATC  ATA  GGA  GGC  CTC  TTC  GCC        576
Arg  Gln  Tyr  Ser  Gln  Pro  Gln  Phe  Arg  Ile  Ile  Gly  Gly  Leu  Phe  Ala
               180                           185                      190

GAC  ATC  GCC  TCC  CAC  CCC  TGG  CAG  GCT  GCC  ATC  TTT  GCC  AAG  CAC  AGG        624
```

```
                Asp  Ile  Ala  Ser  His  Pro  Trp  Gln  Ala  Ala  Ile  Phe  Ala  Lys  His  Arg
                          195                      200                     205

AGG  TCG  CCC  GGA  GAG  CGG  TTC  CTG  TGC  GGG  GGC  ATA  CTC  ATC  AGC  TCC              672
Arg  Ser  Pro  Gly  Glu  Arg  Phe  Leu  Cys  Gly  Gly  Ile  Leu  Ile  Ser  Ser
     210                      215                     220

TGC  TGG  ATT  CTC  TCT  GCC  GCC  CAC  TGC  TTC  CAG  GAG  AGG  TTT  CCG  CCC              720
Cys  Trp  Ile  Leu  Ser  Ala  Ala  His  Cys  Phe  Gln  Glu  Arg  Phe  Pro  Pro
225                      230                      235                     240

CAC  CAC  CTG  ACG  GTG  ATC  TTG  GGC  AGA  ACA  TAC  CGG  GTG  GTC  CCT  GGC              768
His  His  Leu  Thr  Val  Ile  Leu  Gly  Arg  Thr  Tyr  Arg  Val  Val  Pro  Gly
               245                      250                     255

GAG  GAG  GAG  CAG  AAA  TTT  GAA  GTC  GAA  AAA  TAC  ATT  GTC  CAT  AAG  GAA              816
Glu  Glu  Glu  Gln  Lys  Phe  Glu  Val  Glu  Lys  Tyr  Ile  Val  His  Lys  Glu
               260                      265                     270

TTC  GAT  GAT  GAC  ACT  TAC  GAC  AAT  GAC  ATT  GCG  CTG  CTG  CAG  CTG  AAA              864
Phe  Asp  Asp  Asp  Thr  Tyr  Asp  Asn  Asp  Ile  Ala  Leu  Leu  Gln  Leu  Lys
          275                      280                     285

TCG  GAT  TCG  TCC  CGC  TGT  GCC  CAG  GAG  AGC  AGC  GTG  GTC  CGC  ACT  GTG              912
Ser  Asp  Ser  Ser  Arg  Cys  Ala  Gln  Glu  Ser  Ser  Val  Val  Arg  Thr  Val
          290                      295                     300

TGC  CTT  CCC  CCG  GCG  GAC  CTG  CAG  CTG  CCG  GAC  TGG  ACG  GAG  TGT  GAG              960
Cys  Leu  Pro  Pro  Ala  Asp  Leu  Gln  Leu  Pro  Asp  Trp  Thr  Glu  Cys  Glu
305                      310                      315                     320

CTC  TCC  GGC  TAC  GGC  AAG  CAT  GAG  GCC  TTG  TCT  CCT  TTC  TAT  TCG  GAG             1008
Leu  Ser  Gly  Tyr  Gly  Lys  His  Glu  Ala  Leu  Ser  Pro  Phe  Tyr  Ser  Glu
               325                      330                     335

CGG  CTG  AAG  GAG  GCT  CAT  GTC  AGA  CTG  TAC  CCA  TCC  AGC  CGC  TGC  ACA             1056
Arg  Leu  Lys  Glu  Ala  His  Val  Arg  Leu  Tyr  Pro  Ser  Ser  Arg  Cys  Thr
               340                      345                     350

TCA  CAA  CAT  TTA  CTT  AAC  AGA  ACA  GTC  ACC  GAC  AAC  ATG  CTG  TGT  GCT             1104
Ser  Gln  His  Leu  Leu  Asn  Arg  Thr  Val  Thr  Asp  Asn  Met  Leu  Cys  Ala
          355                      360                     365

GGA  GAC  ACT  CGG  AGC  GGC  GGG  CCC  CAG  GCA  AAC  TTG  CAC  GAC  GCC  TGC             1152
Gly  Asp  Thr  Arg  Ser  Gly  Gly  Pro  Gln  Ala  Asn  Leu  His  Asp  Ala  Cys
     370                      375                     380

CAG  GGC  GAT  TCG  GGA  GGC  CCC  CTG  GTG  TGT  CTG  AAC  GAT  GGC  CGC  ATG             1200
Gln  Gly  Asp  Ser  Gly  Gly  Pro  Leu  Val  Cys  Leu  Asn  Asp  Gly  Arg  Met
385                      390                      395                     400

ACT  TTG  GTG  GGC  ATC  ATC  AGC  TGG  GGC  CTG  GGC  TGT  GGA  CAG  AAG  GAT             1248
Thr  Leu  Val  Gly  Ile  Ile  Ser  Trp  Gly  Leu  Gly  Cys  Gly  Gln  Lys  Asp
               405                      410                     415

GTC  CCG  GGT  GTG  TAC  ACA  AAG  GTT  ACC  AAC  TAC  CTA  GAC  TGG  ATT  CGT             1296
Val  Pro  Gly  Val  Tyr  Thr  Lys  Val  Thr  Asn  Tyr  Leu  Asp  Trp  Ile  Arg
               420                      425                     430

GAC  AAC  ATG  CGA  CCG  TGA                                                               1314
Asp  Asn  Met  Arg  Pro
               435
```

( 2 ) INFORMATION FOR SEQ ID NO:51:

( i ) SEQUENCE CHARACTERISTICS:
        ( A ) LENGTH: 437 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Met  Cys  Tyr  Glu  Asp  Gln  Gly  Ile  Ser  Tyr  Arg  Gly  Thr  Trp  Ser  Thr
1                   5                        10                      15

Ala  Glu  Ser  Gly  Ala  Glu  Cys  Thr  Asn  Trp  Asn  Ser  Ser  Ala  Leu  Ala
               20                      25                      30
```

Gln Lys Pro Tyr Ser Gly Arg Arg Pro Asp Ala Ile Arg Leu Gly Leu
         35                  40                 45

Gly Asn His Asn Tyr Cys Arg Asn Pro Asp Arg Asp Ser Lys Pro Trp
         50                  55                 60

Cys Tyr Val Phe Lys Ala Gly Lys Tyr Ser Ser Glu Phe Cys Ser Thr
 65              70                  75                      80

Pro Ala Cys Ser Gly Asn Ser Asp Cys Tyr Phe Gly Asn Gly Ser
                 85                  90                  95

Ala Tyr Arg Gly Thr His Ser Leu Thr Glu Ser Gly Ala Ser Cys Leu
             100             105             110

Pro Trp Asn Ser Met Ile Leu Ile Gly Lys Val Tyr Thr Ala Gln Asn
         115             120             125

Pro Ser Ala Gln Ala Leu Gly Leu Gly Lys His Asn Tyr Cys Arg Asn
         130             135             140

Pro Asp Gly Asp Ala Lys Pro Trp Cys His Val Leu Lys Asn Arg Arg
145                 150             155                     160

Leu Thr Trp Glu Tyr Cys Asp Val Pro Ser Cys Ser Thr Cys Gly Leu
                 165             170             175

Arg Gln Tyr Ser Gln Pro Gln Phe Arg Ile Ile Gly Gly Leu Phe Ala
             180             185             190

Asp Ile Ala Ser His Pro Trp Gln Ala Ala Ile Phe Ala Lys His Arg
         195             200             205

Arg Ser Pro Gly Glu Arg Phe Leu Cys Gly Gly Ile Leu Ile Ser Ser
     210             215             220

Cys Trp Ile Leu Ser Ala Ala His Cys Phe Gln Glu Arg Phe Pro Pro
225                 230             235                     240

His His Leu Thr Val Ile Leu Gly Arg Thr Tyr Arg Val Val Pro Gly
                 245             250             255

Glu Glu Glu Gln Lys Phe Glu Val Glu Lys Tyr Ile Val His Lys Glu
             260             265             270

Phe Asp Asp Asp Thr Tyr Asp Asn Asp Ile Ala Leu Leu Gln Leu Lys
         275             280             285

Ser Asp Ser Ser Arg Cys Ala Gln Glu Ser Ser Val Val Arg Thr Val
     290             295             300

Cys Leu Pro Pro Ala Asp Leu Gln Leu Pro Asp Trp Thr Glu Cys Glu
305                 310             315                     320

Leu Ser Gly Tyr Gly Lys His Glu Ala Leu Ser Pro Phe Tyr Ser Glu
                 325             330             335

Arg Leu Lys Glu Ala His Val Arg Leu Tyr Pro Ser Ser Arg Cys Thr
             340             345             350

Ser Gln His Leu Leu Asn Arg Thr Val Thr Asp Asn Met Leu Cys Ala
         355             360             365

Gly Asp Thr Arg Ser Gly Gly Pro Gln Ala Asn Leu His Asp Ala Cys
         370             375             380

Gln Gly Asp Ser Gly Gly Pro Leu Val Cys Leu Asn Asp Gly Arg Met
385                 390             395                     400

Thr Leu Val Gly Ile Ile Ser Trp Gly Leu Gly Cys Gly Gln Lys Asp
                 405             410             415

Val Pro Gly Val Tyr Thr Lys Val Thr Asn Tyr Leu Asp Trp Ile Arg
             420             425             430

Asp Asn Met Arg Pro
             435

( 2 ) INFORMATION FOR SEQ ID NO:52:

( i ) SEQUENCE CHARACTERISTICS:
        ( A ) LENGTH: 1068 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1065

( x i ) SEQUENCE DESCRIPTION: SEQ ID NO:52:

```
ATG  TCT  GAG  GGA  AAC  AGT  GAC  TGC  TAC  TTT  GGG  AAT  GGG  TCA  GCC  TAC        48
Met  Ser  Glu  Gly  Asn  Ser  Asp  Cys  Tyr  Phe  Gly  Asn  Gly  Ser  Ala  Tyr
 1              5                        10                       15

CGT  GGC  ACG  CAC  AGC  CTC  ACC  GAG  TCG  GGT  GCC  TCC  TGC  CTC  CCG  TGG        96
Arg  Gly  Thr  His  Ser  Leu  Thr  Glu  Ser  Gly  Ala  Ser  Cys  Leu  Pro  Trp
             20                       25                       30

AAT  TCC  ATG  ATC  CTG  ATA  GGC  AAG  GTT  TAC  ACA  GCA  CAG  AAC  CCC  AGT       144
Asn  Ser  Met  Ile  Leu  Ile  Gly  Lys  Val  Tyr  Thr  Ala  Gln  Asn  Pro  Ser
         35                       40                       45

GCC  CAG  GCA  CTG  GGC  CTG  GGC  AAA  CAT  AAT  TAC  TGC  CGG  AAT  CCT  GAT       192
Ala  Gln  Ala  Leu  Gly  Leu  Gly  Lys  His  Asn  Tyr  Cys  Arg  Asn  Pro  Asp
     50                       55                       60

GGG  GAT  GCC  AAG  CCC  TGG  TGC  CAC  GTG  CTG  AAG  AAC  CGC  AGG  CTG  ACG       240
Gly  Asp  Ala  Lys  Pro  Trp  Cys  His  Val  Leu  Lys  Asn  Arg  Arg  Leu  Thr
 65                       70                       75                       80

TGG  GAG  TAC  TGT  GAT  GTG  CCC  TCC  TGC  TCC  ACC  TGC  GGC  CTG  AGA  CAG       288
Trp  Glu  Tyr  Cys  Asp  Val  Pro  Ser  Cys  Ser  Thr  Cys  Gly  Leu  Arg  Gln
                      85                       90                       95

TAC  AGC  CAG  CCA  CAG  TTT  GAT  ATC  AAA  GGA  GGC  CTC  TTC  GCC  GAC  ATC       336
Tyr  Ser  Gln  Pro  Gln  Phe  Asp  Ile  Lys  Gly  Gly  Leu  Phe  Ala  Asp  Ile
              100                      105                      110

GCC  TCC  CAC  CCC  TGG  CAG  GCT  GCC  ATC  TTT  GCC  AAG  CAC  AGG  AGG  TCG       384
Ala  Ser  His  Pro  Trp  Gln  Ala  Ala  Ile  Phe  Ala  Lys  His  Arg  Arg  Ser
              115                      120                      125

CCC  GGA  GAG  CGG  TTC  CTG  TGC  GGG  GGC  ATA  CTC  ATC  AGC  TCC  TGC  TGG       432
Pro  Gly  Glu  Arg  Phe  Leu  Cys  Gly  Gly  Ile  Leu  Ile  Ser  Ser  Cys  Trp
      130                      135                      140

ATT  CTC  TCT  GCC  GCC  CAC  TGC  TTC  CAG  GAG  AGG  TTT  CCG  CCC  CAC  CAC       480
Ile  Leu  Ser  Ala  Ala  His  Cys  Phe  Gln  Glu  Arg  Phe  Pro  Pro  His  His
145                      150                      155                      160

CTG  ACG  GTG  ATC  TTG  GGC  AGA  ACA  TAC  CGG  GTG  GTC  CCT  GGC  GAG  GAG       528
Leu  Thr  Val  Ile  Leu  Gly  Arg  Thr  Tyr  Arg  Val  Val  Pro  Gly  Glu  Glu
                     165                      170                      175

GAG  CAG  AAA  TTT  GAA  GTC  GAA  AAA  TAC  ATT  GTC  CAT  AAG  GAA  TTC  GAT       576
Glu  Gln  Lys  Phe  Glu  Val  Glu  Lys  Tyr  Ile  Val  His  Lys  Glu  Phe  Asp
               180                      185                      190

GAT  GAC  ACT  TAC  GAC  AAT  GAC  ATT  GCG  CTG  CTG  CAG  CTG  AAA  TCG  GAT       624
Asp  Asp  Thr  Tyr  Asp  Asn  Asp  Ile  Ala  Leu  Leu  Gln  Leu  Lys  Ser  Asp
          195                      200                      205

TCG  TCC  CGC  TGT  GCC  CAG  GAG  AGC  AGC  GTG  GTC  CGC  ACT  GTG  TGC  CTT       672
Ser  Ser  Arg  Cys  Ala  Gln  Glu  Ser  Ser  Val  Val  Arg  Thr  Val  Cys  Leu
     210                      215                      220

CCC  CCG  GCG  GAC  CTG  CAG  CTG  CCG  GAC  TGG  ACG  GAG  TGT  GAG  CTC  TCC       720
Pro  Pro  Ala  Asp  Leu  Gln  Leu  Pro  Asp  Trp  Thr  Glu  Cys  Glu  Leu  Ser
225                      230                      235                      240

GGC  TAC  GGC  AAG  CAT  GAG  GCC  TTG  TCT  CCT  TTC  TAT  TCG  GAG  CGG  CTG       768
Gly  Tyr  Gly  Lys  His  Glu  Ala  Leu  Ser  Pro  Phe  Tyr  Ser  Glu  Arg  Leu
                     245                      250                      255
```

| | | | | | | | | | | | | | | | | |
|---|---|---|---|---|---|---|---|---|---|---|---|---|---|---|---|---|
|AAG|GAG|GCT|CAT|GTC|AGA|CTG|TAC|CCA|TCC|AGC|CGC|TGC|ACA|TCA|CAA|816|
|Lys|Glu|Ala|His|Val|Arg|Leu|Tyr|Pro|Ser|Ser|Arg|Cys|Thr|Ser|Gln| |
| | | |260| | | |265| | | | |270| | | | |
|CAT|TTA|CTT|AAC|AGA|ACA|GTC|ACC|GAC|AAC|ATG|CTG|TGT|GCT|GGA|GAC|864|
|His|Leu|Leu|Asn|Arg|Thr|Val|Thr|Asp|Asn|Met|Leu|Cys|Ala|Gly|Asp| |
| | |275| | | |280| | | | |285| | | | | |
|ACT|CGG|AGC|GGC|GGG|CCC|CAG|GCA|AAC|TTG|CAC|GAC|GCC|TGC|CAG|GGC|912|
|Thr|Arg|Ser|Gly|Gly|Pro|Gln|Ala|Asn|Leu|His|Asp|Ala|Cys|Gln|Gly| |
| |290| | | |295| | | | |300| | | | | | |
|GAT|TCG|GGA|GGC|CCC|CTG|GTG|TGT|CTG|AAC|GAT|GGC|CGC|ATG|ACT|TTG|960|
|Asp|Ser|Gly|Gly|Pro|Leu|Val|Cys|Leu|Asn|Asp|Gly|Arg|Met|Thr|Leu| |
|305| | | | |310| | | | |315| | | | |320| |
|GTG|GGC|ATC|ATC|AGC|TGG|GGC|CTG|GGC|TGT|GGA|CAG|AAG|GAT|GTC|CCG|1008|
|Val|Gly|Ile|Ile|Ser|Trp|Gly|Leu|Gly|Cys|Gly|Gln|Lys|Asp|Val|Pro| |
| | | | |325| | | | |330| | | | |335| | |
|GGT|GTG|TAC|ACA|AAG|GTT|ACC|AAC|TAC|CTA|GAC|TGG|ATT|CGT|GAC|AAC|1056|
|Gly|Val|Tyr|Thr|Lys|Val|Thr|Asn|Tyr|Leu|Asp|Trp|Ile|Arg|Asp|Asn| |
| | | |340| | | |345| | | | |350| | | | |
|ATG|CGA|CCG|TGA| | | | | | | | | | | | |1068|
|Met|Arg|Pro| | | | | | | | | | | | | | |
| | |355| | | | | | | | | | | | | | |

( 2 ) INFORMATION FOR SEQ ID NO:53:

( i ) SEQUENCE CHARACTERISTICS:
    ( A ) LENGTH: 355 amino acids
    ( B ) TYPE: amino acid
    ( D ) TOPOLOGY: linear ( i i ) MOLECULE TYPE: protein ( x i ) SEQUENCE DESCRIPTION: SEQ ID NO:53:

| | | | | | | | | | | | | | | |
|---|---|---|---|---|---|---|---|---|---|---|---|---|---|---|
|Met|Ser|Glu|Gly|Asn|Ser|Asp|Cys|Tyr|Phe|Gly|Asn|Gly|Ser|Ala|Tyr|
|1| | | |5| | | |10| | | | |15| |
|Arg|Gly|Thr|His|Ser|Leu|Thr|Glu|Ser|Gly|Ala|Ser|Cys|Leu|Pro|Trp|
| | | |20| | | |25| | | | |30| | |
|Asn|Ser|Met|Ile|Leu|Ile|Gly|Lys|Val|Tyr|Thr|Ala|Gln|Asn|Pro|Ser|
| | |35| | | |40| | | | |45| | | |
|Ala|Gln|Ala|Leu|Gly|Leu|Gly|Lys|His|Asn|Tyr|Cys|Arg|Asn|Pro|Asp|
| |50| | | |55| | | | |60| | | | |
|Gly|Asp|Ala|Lys|Pro|Trp|Cys|His|Val|Leu|Lys|Asn|Arg|Arg|Leu|Thr|
|65| | | |70| | | | |75| | | | |80|
|Trp|Glu|Tyr|Cys|Asp|Val|Pro|Ser|Cys|Ser|Thr|Cys|Gly|Leu|Arg|Gln|
| | | |85| | | | |90| | | | |95| |
|Tyr|Ser|Gln|Pro|Gln|Phe|Asp|Ile|Lys|Gly|Gly|Leu|Phe|Ala|Asp|Ile|
| | | |100| | | |105| | | | |110| | |
|Ala|Ser|His|Pro|Trp|Gln|Ala|Ala|Ile|Phe|Ala|Lys|His|Arg|Arg|Ser|
| | |115| | | |120| | | | |125| | | |
|Pro|Gly|Glu|Arg|Phe|Leu|Cys|Gly|Gly|Ile|Leu|Ile|Ser|Ser|Cys|Trp|
| |130| | | |135| | | | |140| | | | |
|Ile|Leu|Ser|Ala|Ala|His|Cys|Phe|Gln|Glu|Arg|Phe|Pro|Pro|His|His|
|145| | | |150| | | | |155| | | | |160|
|Leu|Thr|Val|Ile|Leu|Gly|Arg|Thr|Tyr|Arg|Val|Val|Pro|Gly|Glu|Glu|
| | | |165| | | |170| | | | |175| | |
|Glu|Gln|Lys|Phe|Glu|Val|Glu|Lys|Tyr|Ile|Val|His|Lys|Glu|Phe|Asp|
| | |180| | | |185| | | | |190| | | |
|Asp|Asp|Thr|Tyr|Asp|Asn|Asp|Ile|Ala|Leu|Leu|Gln|Leu|Lys|Ser|Asp|
| | |195| | | |200| | | | |205| | | |
|Ser|Ser|Arg|Cys|Ala|Gln|Glu|Ser|Ser|Val|Val|Arg|Thr|Val|Cys|Leu|

|     |     |     |     | 210 |     |     |     |     | 215 |     |     |     |     | 220 |     |
| --- | --- | --- | --- | --- | --- | --- | --- | --- | --- | --- | --- | --- | --- | --- | --- |
| Pro 225 | Pro | Ala | Asp | Leu | Gln 230 | Leu | Pro | Asp | Trp | Thr 235 | Glu | Cys | Glu | Leu | Ser 240 |
| Gly | Tyr | Gly | Lys | His 245 | Glu | Ala | Leu | Ser | Pro 250 | Phe | Tyr | Ser | Glu | Arg 255 | Leu |
| Lys | Glu | Ala | His | Val 260 | Arg | Leu | Tyr | Pro 265 | Ser | Ser | Arg | Cys 270 | Thr | Ser | Gln |
| His | Leu | Leu 275 | Asn | Arg | Thr | Val | Thr 280 | Asp | Asn | Met | Leu | Cys 285 | Ala | Gly | Asp |
| Thr | Arg 290 | Ser | Gly | Gly | Pro | Gln 295 | Ala | Asn | Leu | His | Asp 300 | Ala | Cys | Gln | Gly |
| Asp 305 | Ser | Gly | Gly | Pro | Leu 310 | Val | Cys | Leu | Asn | Asp 315 | Gly | Arg | Met | Thr | Leu 320 |
| Val | Gly | Ile | Ile | Ser 325 | Trp | Gly | Leu | Gly | Cys 330 | Gly | Gln | Lys | Asp | Val 335 | Pro |
| Gly | Val | Tyr | Thr 340 | Lys | Val | Thr | Asn | Leu 345 | Asp | Trp | Ile | Arg 350 | Asp | Asn |     |
| Met | Arg | Pro 355 |     |     |     |     |     |     |     |     |     |     |     |     |     |

( 2 ) INFORMATION FOR SEQ ID NO:54:

( i ) SEQUENCE CHARACTERISTICS:
      ( A ) LENGTH: 1314 base pairs
      ( B ) TYPE: nucleic acid
      ( C ) STRANDEDNESS: double
      ( D ) TOPOLOGY: circular ( i i ) MOLECULE TYPE: DNA (genomic)

( i x ) FEATURE:
      ( A ) NAME/KEY: CDS
      ( B ) LOCATION: 1..1311

( x i ) SEQUENCE DESCRIPTION: SEQ ID NO:54:

| ATG | TGT | TAT | GAG | GAC | CAG | GGC | ATC | AGC | TAC | AGG | GGC | ACG | TGG | AGC | ACA | 48 |
| --- | --- | --- | --- | --- | --- | --- | --- | --- | --- | --- | --- | --- | --- | --- | --- | --- |
| Met 1 | Cys | Tyr | Glu | Asp 5 | Gln | Gly | Ile | Ser | Tyr 10 | Arg | Gly | Thr | Trp | Ser 15 | Thr |  |
| GCG | GAG | AGT | GGC | GCC | GAG | TGC | ACC | AAC | TGG | AAC | AGC | AGC | GCG | TTG | GCC | 96 |
| Ala | Glu | Ser | Gly 20 | Ala | Glu | Cys | Thr | Asn 25 | Trp | Asn | Ser | Ser | Ala 30 | Leu | Ala |  |
| CAG | AAG | CCC | TAC | AGC | GGG | CGG | AGG | CCA | GAC | GCC | ATC | AGG | CTG | GGC | CTG | 144 |
| Gln | Lys | Pro 35 | Tyr | Ser | Gly | Arg | Arg 40 | Pro | Asp | Ala | Ile | Arg 45 | Leu | Gly | Leu |  |
| GGG | AAC | CAC | AAC | TAC | TGC | AGA | AAC | CCA | GAT | CGA | GAC | TCA | AAG | CCC | TGG | 192 |
| Gly | Asn 50 | His | Asn | Tyr | Cys | Arg 55 | Asn | Pro | Asp | Arg | Asp 60 | Ser | Lys | Pro | Trp |  |
| TGC | TAC | GTC | TTT | AAG | GCG | GGG | AAG | TAC | AGC | TCA | GAG | TTC | TGC | AGC | ACC | 240 |
| Cys 65 | Tyr | Val | Phe | Lys | Ala 70 | Gly | Lys | Tyr | Ser | Ser 75 | Glu | Phe | Cys | Ser | Thr 80 |  |
| CCT | GCC | TGC | TCT | GAG | GGA | AAC | AGT | GAC | TGC | TAC | TTT | GGG | AAT | GGG | TCA | 288 |
| Pro | Ala | Cys | Ser | Glu 85 | Gly | Asn | Ser | Asp | Cys 90 | Tyr | Phe | Gly | Asn | Gly 95 | Ser |  |
| GCC | TAC | CGT | GGC | ACG | CAC | AGC | CTC | ACC | GAG | TCG | GGT | GCC | TCC | TGC | CTC | 336 |
| Ala | Tyr | Arg | Gly 100 | Thr | His | Ser | Leu | Thr 105 | Glu | Ser | Gly | Ala | Ser 110 | Cys | Leu |  |
| CCG | TGG | AAT | TCC | ATG | ATC | CTG | ATA | GGC | AAG | GTT | TAC | ACA | GCA | CAG | AAC | 384 |
| Pro | Trp | Asn 115 | Ser | Met | Ile | Leu | Ile 120 | Gly | Lys | Val | Tyr | Thr 125 | Ala | Gln | Asn |  |
| CCC | AGT | GCC | CAG | GCA | CTG | GGC | CTG | GGC | AAA | CAT | AAT | TAC | TGC | CGG | AAT | 432 |
| Pro | Ser | Ala | Gln | Ala | Leu | Gly | Leu | Gly | Lys | His | Asn | Tyr | Cys | Arg | Asn |  |

```
                    130                           135                              140
CCT  GAT  GGG  GAT  GCC  AAG  CCC  TGG  TGC  CAC  GTG  CTG  AAG  AAC  CGC  AGG        480
Pro  Asp  Gly  Asp  Ala  Lys  Pro  Trp  Cys  His  Val  Leu  Lys  Asn  Arg  Arg
145                 150                           155                              160

CTG  ACG  TGG  GAG  TAC  TGT  GAT  GTG  CCC  TCC  TGC  TCC  ACC  TGC  GGC  CTG        528
Leu  Thr  Trp  Glu  Tyr  Cys  Asp  Val  Pro  Ser  Cys  Ser  Thr  Cys  Gly  Leu
                    165                           170                              175

AGA  CAG  TAC  AGC  CAG  CCA  CAG  TTT  GAT  ATC  AAA  GGA  GGC  CTC  TTC  GCC        576
Arg  Gln  Tyr  Ser  Gln  Pro  Gln  Phe  Asp  Ile  Lys  Gly  Gly  Leu  Phe  Ala
               180                           185                              190

GAC  ATC  GCC  TCC  CAC  CCC  TGG  CAG  GCT  GCC  ATC  TTT  GCC  AAG  CAC  AGG        624
Asp  Ile  Ala  Ser  His  Pro  Trp  Gln  Ala  Ala  Ile  Phe  Ala  Lys  His  Arg
               195                           200                              205

AGG  TCG  CCC  GGA  GAG  CGG  TTC  CTG  TGC  GGG  GGC  ATA  CTC  ATC  AGC  TCC        672
Arg  Ser  Pro  Gly  Glu  Arg  Phe  Leu  Cys  Gly  Gly  Ile  Leu  Ile  Ser  Ser
     210                           215                              220

TGC  TGG  ATT  CTC  TCT  GCC  GCC  CAC  TGC  TTC  CAG  GAG  AGG  TTT  CCG  CCC        720
Cys  Trp  Ile  Leu  Ser  Ala  Ala  His  Cys  Phe  Gln  Glu  Arg  Phe  Pro  Pro
225                           230                           235                    240

CAC  CAC  CTG  ACG  GTG  ATC  TTG  GGC  AGA  ACA  TAC  CGG  GTG  GTC  CCT  GGC        768
His  His  Leu  Thr  Val  Ile  Leu  Gly  Arg  Thr  Tyr  Arg  Val  Val  Pro  Gly
                         245                           250                         255

GAG  GAG  GAG  CAG  AAA  TTT  GAA  GTC  GAA  AAA  TAC  ATT  GTC  CAT  AAG  GAA        816
Glu  Glu  Glu  Gln  Lys  Phe  Glu  Val  Glu  Lys  Tyr  Ile  Val  His  Lys  Glu
                    260                           265                              270

TTC  GAT  GAT  GAC  ACT  TAC  GAC  AAT  GAC  ATT  GCG  CTG  CTG  CAG  CTG  AAA        864
Phe  Asp  Asp  Asp  Thr  Tyr  Asp  Asn  Asp  Ile  Ala  Leu  Leu  Gln  Leu  Lys
               275                           280                              285

TCG  GAT  TCG  TCC  CGC  TGT  GCC  CAG  GAG  AGC  AGC  GTG  GTC  CGC  ACT  GTG        912
Ser  Asp  Ser  Ser  Arg  Cys  Ala  Gln  Glu  Ser  Ser  Val  Val  Arg  Thr  Val
     290                           295                           300

TGC  CTT  CCC  CCG  GCG  GAC  CTG  CAG  CTG  CCG  GAC  TGG  ACG  GAG  TGT  GAG        960
Cys  Leu  Pro  Pro  Ala  Asp  Leu  Gln  Leu  Pro  Asp  Trp  Thr  Glu  Cys  Glu
305                           310                           315                    320

CTC  TCC  GGC  TAC  GGC  AAG  CAT  GAG  GCC  TTG  TCT  CCT  TTC  TAT  TCG  GAG       1008
Leu  Ser  Gly  Tyr  Gly  Lys  His  Glu  Ala  Leu  Ser  Pro  Phe  Tyr  Ser  Glu
                         325                           330                         335

CGG  CTG  AAG  GAG  GCT  CAT  GTC  AGA  CTG  TAC  CCA  TCC  AGC  CGC  TGC  ACA       1056
Arg  Leu  Lys  Glu  Ala  His  Val  Arg  Leu  Tyr  Pro  Ser  Ser  Arg  Cys  Thr
                    340                           345                              350

TCA  CAA  CAT  TTA  CTT  AAC  AGA  ACA  GTC  ACC  GAC  AAC  ATG  CTG  TGT  GCT       1104
Ser  Gln  His  Leu  Leu  Asn  Arg  Thr  Val  Thr  Asp  Asn  Met  Leu  Cys  Ala
               355                           360                              365

GGA  GAC  ACT  CGG  AGC  GGC  GGG  CCC  CAG  GCA  AAC  TTG  CAC  GAC  GCC  TGC       1152
Gly  Asp  Thr  Arg  Ser  Gly  Gly  Pro  Gln  Ala  Asn  Leu  His  Asp  Ala  Cys
     370                           375                              380

CAG  GGC  GAT  TCG  GGA  GGC  CCC  CTG  GTG  TGT  CTG  AAC  GAT  GGC  CGC  ATG       1200
Gln  Gly  Asp  Ser  Gly  Gly  Pro  Leu  Val  Cys  Leu  Asn  Asp  Gly  Arg  Met
385                           390                           395                    400

ACT  TTG  GTG  GGC  ATC  ATC  AGC  TGG  GGC  CTG  GGC  TGT  GGA  CAG  AAG  GAT       1248
Thr  Leu  Val  Gly  Ile  Ile  Ser  Trp  Gly  Leu  Gly  Cys  Gly  Gln  Lys  Asp
                         405                           410                         415

GTC  CCG  GGT  GTG  TAC  ACA  AAG  GTT  ACC  AAC  TAC  CTA  GAC  TGG  ATT  CGT       1296
Val  Pro  Gly  Val  Tyr  Thr  Lys  Val  Thr  Asn  Tyr  Leu  Asp  Trp  Ile  Arg
                    420                           425                              430

GAC  AAC  ATG  CGA  CCG  TGA                                                         1314
Asp  Asn  Met  Arg  Pro
               435
```

( 2 ) INFORMATION FOR SEQ ID NO:55:

( i ) SEQUENCE CHARACTERISTICS:
  ( A ) LENGTH: 437 amino acids
  ( B ) TYPE: amino acid
  ( D ) TOPOLOGY: linear ( i i ) MOLECULE TYPE: protein ( x i ) SEQUENCE DESCRIPTION: SEQ ID NO:55:

| Met | Cys | Tyr | Glu | Asp | Gln | Gly | Ile | Ser | Tyr | Arg | Gly | Thr | Trp | Ser | Thr |
|---|---|---|---|---|---|---|---|---|---|---|---|---|---|---|---|
| 1 | | | | 5 | | | | | 10 | | | | | 15 | |
| Ala | Glu | Ser | Gly | Ala | Glu | Cys | Thr | Asn | Trp | Asn | Ser | Ser | Ala | Leu | Ala |
| | | | 20 | | | | 25 | | | | | 30 | | | |
| Gln | Lys | Pro | Tyr | Ser | Gly | Arg | Arg | Pro | Asp | Ala | Ile | Arg | Leu | Gly | Leu |
| | | 35 | | | | | 40 | | | | | 45 | | | |
| Gly | Asn | His | Asn | Tyr | Cys | Arg | Asn | Pro | Asp | Arg | Asp | Ser | Lys | Pro | Trp |
| | | 50 | | | | | 55 | | | | 60 | | | | |
| Cys | Tyr | Val | Phe | Lys | Ala | Gly | Lys | Tyr | Ser | Ser | Glu | Phe | Cys | Ser | Thr |
| 65 | | | | | 70 | | | | 75 | | | | | | 80 |
| Pro | Ala | Cys | Ser | Glu | Gly | Asn | Ser | Asp | Cys | Tyr | Phe | Gly | Asn | Gly | Ser |
| | | | | 85 | | | | | 90 | | | | | 95 | |
| Ala | Tyr | Arg | Gly | Thr | His | Ser | Leu | Thr | Glu | Ser | Gly | Ala | Ser | Cys | Leu |
| | | | | 100 | | | | 105 | | | | | 110 | | |
| Pro | Trp | Asn | Ser | Met | Ile | Leu | Ile | Gly | Lys | Val | Tyr | Thr | Ala | Gln | Asn |
| | | | 115 | | | | 120 | | | | | 125 | | | |
| Pro | Ser | Ala | Gln | Ala | Leu | Gly | Leu | Gly | Lys | His | Asn | Tyr | Cys | Arg | Asn |
| | 130 | | | | | 135 | | | | | 140 | | | | |
| Pro | Asp | Gly | Asp | Ala | Lys | Pro | Trp | Cys | His | Val | Leu | Lys | Asn | Arg | Arg |
| 145 | | | | | 150 | | | | 155 | | | | | | 160 |
| Leu | Thr | Trp | Glu | Tyr | Cys | Asp | Val | Pro | Ser | Cys | Ser | Thr | Cys | Gly | Leu |
| | | | | 165 | | | | 170 | | | | | | 175 | |
| Arg | Gln | Tyr | Ser | Gln | Pro | Gln | Phe | Asp | Ile | Lys | Gly | Gly | Leu | Phe | Ala |
| | | | 180 | | | | 185 | | | | | 190 | | | |
| Asp | Ile | Ala | Ser | His | Pro | Trp | Gln | Ala | Ala | Ile | Phe | Ala | Lys | His | Arg |
| | | 195 | | | | | 200 | | | | | 205 | | | |
| Arg | Ser | Pro | Gly | Glu | Arg | Phe | Leu | Cys | Gly | Gly | Ile | Leu | Ile | Ser | Ser |
| | 210 | | | | | 215 | | | | | 220 | | | | |
| Cys | Trp | Ile | Leu | Ser | Ala | Ala | His | Cys | Phe | Gln | Glu | Arg | Phe | Pro | Pro |
| 225 | | | | | 230 | | | | 235 | | | | | | 240 |
| His | His | Leu | Thr | Val | Ile | Leu | Gly | Arg | Thr | Tyr | Arg | Val | Val | Pro | Gly |
| | | | | 245 | | | | 250 | | | | | 255 | | |
| Glu | Glu | Glu | Gln | Lys | Phe | Glu | Val | Glu | Lys | Tyr | Ile | Val | His | Lys | Glu |
| | | | 260 | | | | 265 | | | | | 270 | | | |
| Phe | Asp | Asp | Asp | Thr | Tyr | Asp | Asn | Asp | Ile | Ala | Leu | Leu | Gln | Leu | Lys |
| | | 275 | | | | 280 | | | | | 285 | | | | |
| Ser | Asp | Ser | Ser | Arg | Cys | Ala | Gln | Glu | Ser | Ser | Val | Val | Arg | Thr | Val |
| | 290 | | | | | 295 | | | | | 300 | | | | |
| Cys | Leu | Pro | Pro | Ala | Asp | Leu | Gln | Leu | Pro | Asp | Trp | Thr | Glu | Cys | Glu |
| 305 | | | | | 310 | | | | 315 | | | | | | 320 |
| Leu | Ser | Gly | Tyr | Gly | Lys | His | Glu | Ala | Leu | Ser | Pro | Phe | Tyr | Ser | Glu |
| | | | | 325 | | | | 330 | | | | | 335 | | |
| Arg | Leu | Lys | Glu | Ala | His | Val | Arg | Leu | Tyr | Pro | Ser | Ser | Arg | Cys | Thr |
| | | | 340 | | | | 345 | | | | | 350 | | | |
| Ser | Gln | His | Leu | Leu | Asn | Arg | Thr | Val | Thr | Asp | Asn | Met | Leu | Cys | Ala |
| | | 355 | | | | 360 | | | | | 365 | | | | |
| Gly | Asp | Thr | Arg | Ser | Gly | Gly | Pro | Gln | Ala | Asn | Leu | His | Asp | Ala | Cys |

```
            370                         375                         380
Gln  Gly  Asp  Ser  Gly  Gly  Pro  Leu  Val  Cys  Leu  Asn  Asp  Gly  Arg  Met
385                      390                      395                      400

Thr  Leu  Val  Gly  Ile  Ile  Ser  Trp  Gly  Leu  Gly  Cys  Gly  Gln  Lys  Asp
                    405                      410                      415

Val  Pro  Gly  Val  Tyr  Thr  Lys  Val  Thr  Asn  Tyr  Leu  Asp  Trp  Ile  Arg
               420                      425                      430

Asp  Asn  Met  Arg  Pro
               435
```

( 2 ) INFORMATION FOR SEQ ID NO:56:

( i ) SEQUENCE CHARACTERISTICS:
        ( A ) LENGTH: 1314 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1311

( x i ) SEQUENCE DESCRIPTION: SEQ ID NO:56:

```
ATG  TGT  TAT  GAG  GAC  CAG  GGC  ATC  AGC  TAC  AGG  GGC  ACG  TGG  AGC  ACA     48
Met  Cys  Tyr  Glu  Asp  Gln  Gly  Ile  Ser  Tyr  Arg  Gly  Thr  Trp  Ser  Thr
 1                    5                        10                       15

GCG  GAG  AGT  GGC  GCC  GAG  TGC  ACC  AAC  TGG  AAC  AGC  AGC  GCG  TTG  GCC     96
Ala  Glu  Ser  Gly  Ala  Glu  Cys  Thr  Asn  Trp  Asn  Ser  Ser  Ala  Leu  Ala
                20                       25                       30

CAG  AAG  CCC  TAC  AGC  GGG  CGG  AGG  CCA  GAC  GCC  ATC  AGG  CTG  GGC  CTG    144
Gln  Lys  Pro  Tyr  Ser  Gly  Arg  Arg  Pro  Asp  Ala  Ile  Arg  Leu  Gly  Leu
           35                       40                       45

GGG  AAC  CAC  AAC  TAC  TGC  AGA  AAC  CCA  GAT  CGA  GAC  TCA  AAG  CCC  TGG    192
Gly  Asn  His  Asn  Tyr  Cys  Arg  Asn  Pro  Asp  Arg  Asp  Ser  Lys  Pro  Trp
      50                       55                       60

TGC  TAC  GTC  TTT  AAG  GCG  GGG  AAG  TAC  AGC  TCA  GAG  TTC  TGC  AGC  ACC    240
Cys  Tyr  Val  Phe  Lys  Ala  Gly  Lys  Tyr  Ser  Ser  Glu  Phe  Cys  Ser  Thr
 65                       70                       75                       80

CCT  GCC  TGC  TCT  GAG  GGA  AAC  AGT  GAC  TGC  TAC  TTT  GGG  AAT  GGG  TCA    288
Pro  Ala  Cys  Ser  Glu  Gly  Asn  Ser  Asp  Cys  Tyr  Phe  Gly  Asn  Gly  Ser
                85                       90                       95

GCC  TAC  CGT  GGC  ACG  CAC  AGC  CTC  ACC  GAG  TCG  GGT  GCC  TCC  TGC  CTC    336
Ala  Tyr  Arg  Gly  Thr  His  Ser  Leu  Thr  Glu  Ser  Gly  Ala  Ser  Cys  Leu
               100                      105                      110

CCG  TGG  AAT  TCC  ATG  ATC  CTG  ATA  GGC  AAG  GTT  TAC  ACA  GCA  CAG  AAC    384
Pro  Trp  Asn  Ser  Met  Ile  Leu  Ile  Gly  Lys  Val  Tyr  Thr  Ala  Gln  Asn
          115                      120                      125

CCC  AGT  GCC  CAG  GCA  CTG  GGC  CTG  GGC  AAA  CAT  AAT  TAC  TGC  CGG  AAT    432
Pro  Ser  Ala  Gln  Ala  Leu  Gly  Leu  Gly  Lys  His  Asn  Tyr  Cys  Arg  Asn
          130                      135                      140

CCT  GAT  GGG  GAT  GCC  AAG  CCC  TGG  TGC  CAC  GTG  CTG  AAG  AAC  CGC  AGG    480
Pro  Asp  Gly  Asp  Ala  Lys  Pro  Trp  Cys  His  Val  Leu  Lys  Asn  Arg  Arg
145                      150                      155                      160

CTG  ACG  TGG  GAG  TAC  TGT  GAT  GTG  CCC  TCC  TGC  TCC  ACC  TGC  GGC  CTG    528
Leu  Thr  Trp  Glu  Tyr  Cys  Asp  Val  Pro  Ser  Cys  Ser  Thr  Cys  Gly  Leu
                    165                      170                      175

AGA  CAG  TAC  AGC  CAG  CCA  CAG  TTT  GAT  ATC  ATA  GGA  GGC  CTC  TTC  GCC    576
Arg  Gln  Tyr  Ser  Gln  Pro  Gln  Phe  Asp  Ile  Ile  Gly  Gly  Leu  Phe  Ala
               180                      185                      190

GAC  ATC  GCC  TCC  CAC  CCC  TGG  CAG  GCT  GCC  ATC  TTT  GCC  AAG  CAC  AGG    624
```

| Asp | Ile | Ala | Ser | His | Pro | Trp | Gln | Ala | Ala | Ile | Phe | Ala | Lys | His | Arg | |
|---|---|---|---|---|---|---|---|---|---|---|---|---|---|---|---|---|
|   | 195 |   |   |   |   | 200 |   |   |   |   |   | 205 |   |   |   |   |

| AGG | TCG | CCC | GGA | GAG | CGG | TTC | CTG | TGC | GGG | GGC | ATA | CTC | ATC | AGC | TCC | 672 |
|---|---|---|---|---|---|---|---|---|---|---|---|---|---|---|---|---|
| Arg | Ser | Pro | Gly | Glu | Arg | Phe | Leu | Cys | Gly | Gly | Ile | Leu | Ile | Ser | Ser |   |
|   | 210 |   |   |   |   | 215 |   |   |   |   | 220 |   |   |   |   |   |

| TGC | TGG | ATT | CTC | TCT | GCC | GCC | CAC | TGC | TTC | CAG | GAG | AGG | TTT | CCG | CCC | 720 |
|---|---|---|---|---|---|---|---|---|---|---|---|---|---|---|---|---|
| Cys | Trp | Ile | Leu | Ser | Ala | Ala | His | Cys | Phe | Gln | Glu | Arg | Phe | Pro | Pro |   |
| 225 |   |   |   |   | 230 |   |   |   |   | 235 |   |   |   |   | 240 |   |

| CAC | CAC | CTG | ACG | GTG | ATC | TTG | GGC | AGA | ACA | TAC | CGG | GTG | GTC | CCT | GGC | 768 |
|---|---|---|---|---|---|---|---|---|---|---|---|---|---|---|---|---|
| His | His | Leu | Thr | Val | Ile | Leu | Gly | Arg | Thr | Tyr | Arg | Val | Val | Pro | Gly |   |
|   |   |   |   | 245 |   |   |   |   | 250 |   |   |   |   | 255 |   |   |

| GAG | GAG | GAG | CAG | AAA | TTT | GAA | GTC | GAA | AAA | TAC | ATT | GTC | CAT | AAG | GAA | 816 |
|---|---|---|---|---|---|---|---|---|---|---|---|---|---|---|---|---|
| Glu | Glu | Glu | Gln | Lys | Phe | Glu | Val | Glu | Lys | Tyr | Ile | Val | His | Lys | Glu |   |
|   |   |   | 260 |   |   |   |   | 265 |   |   |   |   | 270 |   |   |   |

| TTC | GAT | GAT | GAC | ACT | TAC | GAC | AAT | GAC | ATT | GCG | CTG | CTG | CAG | CTG | AAA | 864 |
|---|---|---|---|---|---|---|---|---|---|---|---|---|---|---|---|---|
| Phe | Asp | Asp | Asp | Thr | Tyr | Asp | Asn | Asp | Ile | Ala | Leu | Leu | Gln | Leu | Lys |   |
|   |   | 275 |   |   |   |   | 280 |   |   |   |   | 285 |   |   |   |   |

| TCG | GAT | TCG | TCC | CGC | TGT | GCC | CAG | GAG | AGC | AGC | GTG | GTC | CGC | ACT | GTG | 912 |
|---|---|---|---|---|---|---|---|---|---|---|---|---|---|---|---|---|
| Ser | Asp | Ser | Ser | Arg | Cys | Ala | Gln | Glu | Ser | Ser | Val | Val | Arg | Thr | Val |   |
|   | 290 |   |   |   |   | 295 |   |   |   |   | 300 |   |   |   |   |   |

| TGC | CTT | CCC | CCG | GCG | GAC | CTG | CAG | CTG | CCC | GAC | TGG | ACG | GAG | TGT | GAG | 960 |
|---|---|---|---|---|---|---|---|---|---|---|---|---|---|---|---|---|
| Cys | Leu | Pro | Pro | Ala | Asp | Leu | Gln | Leu | Pro | Asp | Trp | Thr | Glu | Cys | Glu |   |
| 305 |   |   |   |   | 310 |   |   |   |   | 315 |   |   |   |   | 320 |   |

| CTC | TCC | GGC | TAC | GGC | AAG | CAT | GAG | GCC | TTG | TCT | CCT | TTC | TAT | TCG | GAG | 1008 |
|---|---|---|---|---|---|---|---|---|---|---|---|---|---|---|---|---|
| Leu | Ser | Gly | Tyr | Gly | Lys | His | Glu | Ala | Leu | Ser | Pro | Phe | Tyr | Ser | Glu |   |
|   |   |   |   | 325 |   |   |   |   | 330 |   |   |   |   | 335 |   |   |

| CGG | CTG | AAG | GAG | GCT | CAT | GTC | AGA | CTG | TAC | CCA | TCC | AGC | CGC | TGC | ACA | 1056 |
|---|---|---|---|---|---|---|---|---|---|---|---|---|---|---|---|---|
| Arg | Leu | Lys | Glu | Ala | His | Val | Arg | Leu | Tyr | Pro | Ser | Ser | Arg | Cys | Thr |   |
|   |   |   | 340 |   |   |   |   | 345 |   |   |   |   | 350 |   |   |   |

| TCA | CAA | CAT | TTA | CTT | AAC | AGA | ACA | GTC | ACC | GAC | AAC | ATG | CTG | TGT | GCT | 1104 |
|---|---|---|---|---|---|---|---|---|---|---|---|---|---|---|---|---|
| Ser | Gln | His | Leu | Leu | Asn | Arg | Thr | Val | Thr | Asp | Asn | Met | Leu | Cys | Ala |   |
|   |   | 355 |   |   |   |   | 360 |   |   |   |   | 365 |   |   |   |   |

| GGA | GAC | ACT | CGG | AGC | GGC | GGG | CCC | CAG | GCA | AAC | TTG | CAC | GAC | GCC | TGC | 1152 |
|---|---|---|---|---|---|---|---|---|---|---|---|---|---|---|---|---|
| Gly | Asp | Thr | Arg | Ser | Gly | Gly | Pro | Gln | Ala | Asn | Leu | His | Asp | Ala | Cys |   |
|   | 370 |   |   |   |   | 375 |   |   |   |   | 380 |   |   |   |   |   |

| CAG | GGC | GAT | TCG | GGA | GGC | CCC | CTG | GTG | TGT | CTG | AAC | GAT | GGC | CGC | ATG | 1200 |
|---|---|---|---|---|---|---|---|---|---|---|---|---|---|---|---|---|
| Gln | Gly | Asp | Ser | Gly | Gly | Pro | Leu | Val | Cys | Leu | Asn | Asp | Gly | Arg | Met |   |
| 385 |   |   |   |   | 390 |   |   |   |   | 395 |   |   |   |   | 400 |   |

| ACT | TTG | GTG | GGC | ATC | ATC | AGC | TGG | GGC | CTG | GGC | TGT | GGA | CAG | AAG | GAT | 1248 |
|---|---|---|---|---|---|---|---|---|---|---|---|---|---|---|---|---|
| Thr | Leu | Val | Gly | Ile | Ile | Ser | Trp | Gly | Leu | Gly | Cys | Gly | Gln | Lys | Asp |   |
|   |   |   |   | 405 |   |   |   |   | 410 |   |   |   |   | 415 |   |   |

| GTC | CCG | GGT | GTG | TAC | ACA | AAG | GTT | ACC | AAC | TAC | CTA | GAC | TGG | ATT | CGT | 1296 |
|---|---|---|---|---|---|---|---|---|---|---|---|---|---|---|---|---|
| Val | Pro | Gly | Val | Tyr | Thr | Lys | Val | Thr | Asn | Tyr | Leu | Asp | Trp | Ile | Arg |   |
|   |   |   | 420 |   |   |   |   | 425 |   |   |   |   | 430 |   |   |   |

| GAC | AAC | ATG | CGA | CCG | TGA |  |  |  |  |  |  |  |  |  |  | 1314 |
|---|---|---|---|---|---|---|---|---|---|---|---|---|---|---|---|---|
| Asp | Asn | Met | Arg | Pro |   |   |   |   |   |   |   |   |   |   |   |   |
|   |   | 435 |   |   |   |   |   |   |   |   |   |   |   |   |   |   |

( 2 ) INFORMATION FOR SEQ ID NO:57:

( i ) SEQUENCE CHARACTERISTICS:
        ( A ) LENGTH: 437 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

| Met | Cys | Tyr | Glu | Asp | Gln | Gly | Ile | Ser | Tyr | Arg | Gly | Thr | Trp | Ser | Thr |
|---|---|---|---|---|---|---|---|---|---|---|---|---|---|---|---|
| 1 |   |   |   | 5 |   |   |   |   | 10 |   |   |   |   | 15 |   |

| Ala | Glu | Ser | Gly | Ala | Glu | Cys | Thr | Asn | Trp | Asn | Ser | Ser | Ala | Leu | Ala |
|---|---|---|---|---|---|---|---|---|---|---|---|---|---|---|---|
|   |   |   | 20 |   |   |   |   | 25 |   |   |   |   | 30 |   |   |

```
Gln Lys Pro Tyr Ser Gly Arg Arg Pro Asp Ala Ile Arg Leu Gly Leu
         35                  40                 45
Gly Asn His Asn Tyr Cys Arg Asn Pro Asp Arg Asp Ser Lys Pro Trp
         50                  55                 60
Cys Tyr Val Phe Lys Ala Gly Lys Tyr Ser Ser Glu Phe Cys Ser Thr
 65                  70                  75                  80
Pro Ala Cys Ser Glu Gly Asn Ser Asp Cys Tyr Phe Gly Asn Gly Ser
                 85                  90                      95
Ala Tyr Arg Gly Thr His Ser Leu Thr Glu Ser Gly Ala Ser Cys Leu
                100             105                 110
Pro Trp Asn Ser Met Ile Leu Ile Gly Lys Val Tyr Thr Ala Gln Asn
             115             120             125
Pro Ser Ala Gln Ala Leu Gly Leu Gly Lys His Asn Tyr Cys Arg Asn
         130             135             140
Pro Asp Gly Asp Ala Lys Pro Trp Cys His Val Leu Lys Asn Arg Arg
145                 150             155                 160
Leu Thr Trp Glu Tyr Cys Asp Val Pro Ser Cys Ser Thr Cys Gly Leu
                165             170             175
Arg Gln Tyr Ser Gln Pro Gln Phe Asp Ile Ile Gly Gly Leu Phe Ala
             180             185             190
Asp Ile Ala Ser His Pro Trp Gln Ala Ala Ile Phe Ala Lys His Arg
         195             200             205
Arg Ser Pro Gly Glu Arg Phe Leu Cys Gly Gly Ile Leu Ile Ser Ser
    210             215             220
Cys Trp Ile Leu Ser Ala Ala His Cys Phe Gln Glu Arg Phe Pro Pro
225             230             235                 240
His His Leu Thr Val Ile Leu Gly Arg Thr Tyr Arg Val Val Pro Gly
                245             250             255
Glu Glu Glu Gln Lys Phe Glu Val Glu Lys Tyr Ile Val His Lys Glu
             260             265             270
Phe Asp Asp Asp Thr Tyr Asp Asn Asp Ile Ala Leu Leu Gln Leu Lys
         275             280             285
Ser Asp Ser Ser Arg Cys Ala Gln Glu Ser Ser Val Val Arg Thr Val
    290             295             300
Cys Leu Pro Pro Ala Asp Leu Gln Leu Pro Asp Trp Thr Glu Cys Glu
305             310             315                 320
Leu Ser Gly Tyr Gly Lys His Glu Ala Leu Ser Pro Phe Tyr Ser Glu
                325             330             335
Arg Leu Lys Glu Ala His Val Arg Leu Tyr Pro Ser Ser Arg Cys Thr
             340             345             350
Ser Gln His Leu Leu Asn Arg Thr Val Thr Asp Asn Met Leu Cys Ala
         355             360             365
Gly Asp Thr Arg Ser Gly Gly Pro Gln Ala Asn Leu His Asp Ala Cys
         370             375             380
Gln Gly Asp Ser Gly Gly Pro Leu Val Cys Leu Asn Asp Gly Arg Met
385                 390             395                 400
Thr Leu Val Gly Ile Ile Ser Trp Gly Leu Gly Cys Gly Gln Lys Asp
                405             410             415
Val Pro Gly Val Tyr Thr Lys Val Thr Asn Tyr Leu Asp Trp Ile Arg
             420             425             430
Asp Asn Met Arg Pro
             435
```

( 2 ) INFORMATION FOR SEQ ID NO:58:

( i ) SEQUENCE CHARACTERISTICS:
    ( A ) LENGTH: 1068 base pairs
    ( B ) TYPE: nucleic acid
    ( C ) STRANDEDNESS: double
    ( D ) TOPOLOGY: circular ( i i ) MOLECULE TYPE: DNA (genomic)

( i x ) FEATURE:
    ( A ) NAME/KEY: CDS
    ( B ) LOCATION: 1..1065

( x i ) SEQUENCE DESCRIPTION: SEQ ID NO:58:

```
ATG TCT GAG GGA AAC AGT GAC TGC TAC TTT GGG AAT GGG TCA GCC TAC       48
Met Ser Glu Gly Asn Ser Asp Cys Tyr Phe Gly Asn Gly Ser Ala Tyr
  1               5                   10                  15

CGT GGC ACG CAC AGC CTC ACC GAG TCG GGT GCC TCC TGC CTC CCG TGG       96
Arg Gly Thr His Ser Leu Thr Glu Ser Gly Ala Ser Cys Leu Pro Trp
             20                  25                  30

AAT TCC ATG ATC CTG ATA GGC AAG GTT TAC ACA GCA CAG AAC CCC AGT      144
Asn Ser Met Ile Leu Ile Gly Lys Val Tyr Thr Ala Gln Asn Pro Ser
         35                  40                  45

GCC CAG GCA CTG GGC CTG GGC AAA CAT AAT TAC TGC CGG AAT CCT GAT      192
Ala Gln Ala Leu Gly Leu Gly Lys His Asn Tyr Cys Arg Asn Pro Asp
     50                  55                  60

GGG GAT GCC AAG CCC TGG TGC CAC GTG CTG AAG AAC CGC AGG CTG ACG      240
Gly Asp Ala Lys Pro Trp Cys His Val Leu Lys Asn Arg Arg Leu Thr
 65                  70                  75                  80

TGG GAG TAC TGT GAT GTG CCC TCC TGC TCC ACC TGC GGC CTG AGA CAG      288
Trp Glu Tyr Cys Asp Val Pro Ser Cys Ser Thr Cys Gly Leu Arg Gln
                 85                  90                  95

ACT CTG CGT CCG CGG TTC AAA ATC AAA GGA GGC CTC TTC GCC GAC ATC      336
Thr Leu Arg Pro Arg Phe Lys Ile Lys Gly Gly Leu Phe Ala Asp Ile
            100                 105                 110

GCC TCC CAC CCC TGG CAG GCT GCC ATT TTT GCC AAG CAC AGG AGG TCG      384
Ala Ser His Pro Trp Gln Ala Ala Ile Phe Ala Lys His Arg Arg Ser
        115                 120                 125

CCC GGA GAG CGG TTC CTG TGC GGG GGC ATA CTC ATC AGC TCC TGC TGG      432
Pro Gly Glu Arg Phe Leu Cys Gly Gly Ile Leu Ile Ser Ser Cys Trp
    130                 135                 140

ATT CTC TCT GCC GCC CAC TGC TTC CAG GAG AGG TTT CCG CCC CAC CAC      480
Ile Leu Ser Ala Ala His Cys Phe Gln Glu Arg Phe Pro Pro His His
145                 150                 155                 160

CTG ACG GTG ATC TTG GGC AGA ACA TAC CGG GTG GTC CCT GGC GAG GAG      528
Leu Thr Val Ile Leu Gly Arg Thr Tyr Arg Val Val Pro Gly Glu Glu
                165                 170                 175

GAG CAG AAA TTT GAA GTC GAA AAA TAC ATT GTC CAT AAG GAA TTC GAT      576
Glu Gln Lys Phe Glu Val Glu Lys Tyr Ile Val His Lys Glu Phe Asp
            180                 185                 190

GAT GAC ACT TAC GAC AAT GAC ATT GCG CTG CTG CAG CTG AAA TCG GAT      624
Asp Asp Thr Tyr Asp Asn Asp Ile Ala Leu Leu Gln Leu Lys Ser Asp
        195                 200                 205

TCG TCC CGC TGT GCC CAG GAG AGC AGC GTG GTC CGC ACT GTG TGC CTT      672
Ser Ser Arg Cys Ala Gln Glu Ser Ser Val Val Arg Thr Val Cys Leu
    210                 215                 220

CCC CCG GCG GAC CTG CAG CTG CCG GAC TGG ACG GAG TGT GAG CTC TCC      720
Pro Pro Ala Asp Leu Gln Leu Pro Asp Trp Thr Glu Cys Glu Leu Ser
225                 230                 235                 240

GGC TAC GGC AAG CAT GAG GCC TTG TCT CCT TTC TAT TCG GAG CGG CTG      768
Gly Tyr Gly Lys His Glu Ala Leu Ser Pro Phe Tyr Ser Glu Arg Leu
                245                 250                 255
```

| | | | | | | | | | | | | | | | | |
|---|---|---|---|---|---|---|---|---|---|---|---|---|---|---|---|---|
| AAG | GAG | GCT | CAT | GTC | AGA | CTG | TAC | CCA | TCC | AGC | CGC | TGC | ACA | TCA | CAA | 816 |
| Lys | Glu | Ala | His 260 | Val | Arg | Leu | Tyr | Pro 265 | Ser | Ser | Arg | Cys | Thr 270 | Ser | Gln | |
| CAT | TTA | CTT | AAC | AGA | ACA | GTC | ACC | GAC | AAC | ATG | CTG | TGT | GCT | GGA | GAC | 864 |
| His | Leu | Leu 275 | Asn | Arg | Thr | Val | Thr 280 | Asp | Asn | Met | Leu | Cys 285 | Ala | Gly | Asp | |
| ACT | CGG | AGC | GGC | GGG | CCC | CAG | GCA | AAC | TTG | CAC | GAC | GCC | TGC | CAG | GGC | 912 |
| Thr | Arg 290 | Ser | Gly | Gly | Pro | Gln 295 | Ala | Asn | Leu | His | Asp 300 | Ala | Cys | Gln | Gly | |
| GAT | TCG | GGA | GGC | CCC | CTG | GTG | TGT | CTG | AAC | GAT | GGC | CGC | ATG | ACT | TTG | 960 |
| Asp 305 | Ser | Gly | Gly | Pro | Leu 310 | Val | Cys | Leu | Asn | Asp 315 | Gly | Arg | Met | Thr | Leu 320 | |
| GTG | GGC | ATC | ATC | AGC | TGG | GGC | CTG | GGC | TGT | GGA | CAG | AAG | GAT | GTC | CCG | 1008 |
| Val | Gly | Ile | Ile | Ser 325 | Trp | Gly | Leu | Gly | Cys 330 | Gly | Gln | Lys | Asp | Val 335 | Pro | |
| GGT | GTG | TAC | ACA | AAG | GTT | ACC | AAC | TAC | CTA | GAC | TGG | ATT | CGT | GAC | AAC | 1056 |
| Gly | Val | Tyr | Thr 340 | Lys | Val | Thr | Asn | Tyr 345 | Leu | Asp | Trp | Ile | Arg 350 | Asp | Asn | |
| ATG | CGA | CCG | TGA | | | | | | | | | | | | | 1068 |
| Met | Arg | Pro 355 | | | | | | | | | | | | | | |

( 2 ) INFORMATION FOR SEQ ID NO:59:

( i ) SEQUENCE CHARACTERISTICS:
        ( A ) LENGTH: 355 amino acids
        ( B ) TYPE: amino acid
        ( D ) TOPOLOGY: linear ( i i ) MOLECULE TYPE: protein ( x i ) SEQUENCE DESCRIPTION: SEQ ID NO:59:

| | | | | | | | | | | | | | | |
|---|---|---|---|---|---|---|---|---|---|---|---|---|---|---|
| Met 1 | Ser | Glu | Gly | Asn 5 | Ser | Asp | Cys | Tyr | Phe 10 | Gly | Asn | Gly | Ser | Ala 15 | Tyr |
| Arg | Gly | Thr | His 20 | Ser | Leu | Thr | Glu | Ser 25 | Gly | Ala | Ser | Cys | Leu 30 | Pro | Trp |
| Asn | Ser | Met 35 | Ile | Leu | Ile | Gly | Lys 40 | Val | Tyr | Thr | Ala | Gln 45 | Asn | Pro | Ser |
| Ala | Gln 50 | Ala | Leu | Gly | Leu | Gly 55 | Lys | His | Asn | Tyr | Cys 60 | Arg | Asn | Pro | Asp |
| Gly 65 | Asp | Ala | Lys | Pro | Trp 70 | Cys | His | Val | Leu | Lys 75 | Asn | Arg | Arg | Leu | Thr 80 |
| Trp | Glu | Tyr | Cys | Asp 85 | Val | Pro | Ser | Cys | Ser 90 | Thr | Cys | Gly | Leu | Arg 95 | Gln |
| Thr | Leu | Arg | Pro 100 | Arg | Phe | Lys | Ile | Lys 105 | Gly | Gly | Leu | Phe | Ala 110 | Asp | Ile |
| Ala | Ser | His 115 | Pro | Trp | Gln | Ala | Ala 120 | Ile | Phe | Ala | Lys | His 125 | Arg | Arg | Ser |
| Pro | Gly 130 | Glu | Arg | Phe | Leu | Cys 135 | Gly | Gly | Ile | Leu | Ile 140 | Ser | Ser | Cys | Trp |
| Ile 145 | Leu | Ser | Ala | Ala | His 150 | Cys | Phe | Gln | Glu | Arg 155 | Phe | Pro | Pro | His | His 160 |
| Leu | Thr | Val | Ile | Leu 165 | Gly | Arg | Thr | Tyr | Arg 170 | Val | Val | Pro | Gly | Glu 175 | Glu |
| Glu | Gln | Lys | Phe 180 | Glu | Val | Glu | Lys | Tyr 185 | Ile | Val | His | Lys | Glu 190 | Phe | Asp |
| Asp | Asp | Thr 195 | Tyr | Asp | Asn | Asp | Ile 200 | Ala | Leu | Leu | Gln | Leu 205 | Lys | Ser | Asp |
| Ser | Ser | Arg | Cys | Ala | Gln | Glu | Ser | Ser | Val | Val | Arg | Thr | Val | Cys | Leu |

```
                    210                        215                         220

Pro   Pro   Ala   Asp   Leu   Gln   Leu   Pro   Asp   Trp   Thr   Glu   Cys   Glu   Leu   Ser
225                     230                           235                              240

Gly   Tyr   Gly   Lys   His   Glu   Ala   Leu   Ser   Pro   Phe   Tyr   Ser   Glu   Arg   Leu
                  245                           250                           255

Lys   Glu   Ala   His   Val   Arg   Leu   Tyr   Pro   Ser   Ser   Arg   Cys   Thr   Ser   Gln
                  260                     265                                 270

His   Leu   Leu   Asn   Arg   Thr   Val   Thr   Asp   Asn   Met   Leu   Cys   Ala   Gly   Asp
            275                     280                           285

Thr   Arg   Ser   Gly   Gly   Pro   Gln   Ala   Asn   Leu   His   Asp   Ala   Cys   Gln   Gly
      290                     295                           300

Asp   Ser   Gly   Gly   Pro   Leu   Val   Cys   Leu   Asn   Asp   Gly   Arg   Met   Thr   Leu
305                           310                     315                              320

Val   Gly   Ile   Ile   Ser   Trp   Gly   Leu   Gly   Cys   Gly   Gln   Lys   Asp   Val   Pro
                        325                           330                     335

Gly   Val   Tyr   Thr   Lys   Val   Thr   Asn   Tyr   Leu   Asp   Trp   Ile   Arg   Asp   Asn
                  340                     345                                 350

Met   Arg   Pro
            355
```

( 2 ) INFORMATION FOR SEQ ID NO:60:

( i ) SEQUENCE CHARACTERISTICS:
        ( A ) LENGTH: 1065 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1062

( x i ) SEQUENCE DESCRIPTION: SEQ ID NO:60:

```
ATG   TCT   GAG   GGA   AAC   AGT   GAC   TGC   TAC   TTT   GGG   AAT   GGG   TCA   GCC   TAC     48
Met   Ser   Glu   Gly   Asn   Ser   Asp   Cys   Tyr   Phe   Gly   Asn   Gly   Ser   Ala   Tyr
 1                      5                           10                          15

CGT   GGC   ACG   CAC   AGC   CTC   ACC   GAG   TCG   GGT   GCC   TCC   TGC   CTC   CCG   TGG     96
Arg   Gly   Thr   His   Ser   Leu   Thr   Glu   Ser   Gly   Ala   Ser   Cys   Leu   Pro   Trp
                  20                          25                          30

AAT   TCC   ATG   ATC   CTG   ATA   GGC   AAG   GTT   TAC   ACA   GCA   CAG   AAC   CCC   AGT    144
Asn   Ser   Met   Ile   Leu   Ile   Gly   Lys   Val   Tyr   Thr   Ala   Gln   Asn   Pro   Ser
            35                          40                          45

GCC   CAG   GCA   CTG   GGC   CTG   GGC   AAA   CAT   AAT   TAC   TGC   CGG   AAT   CCT   GAT    192
Ala   Gln   Ala   Leu   Gly   Leu   Gly   Lys   His   Asn   Tyr   Cys   Arg   Asn   Pro   Asp
      50                          55                          60

GGG   GAT   GCC   AAG   CCC   TGG   TGC   CAC   GTG   CTG   AAG   AAC   CGC   AGG   CTG   ACG    240
Gly   Asp   Ala   Lys   Pro   Trp   Cys   His   Val   Leu   Lys   Asn   Arg   Arg   Leu   Thr
65                          70                          75                          80

TGG   GAG   TAC   TGT   GAT   GTG   CCC   TCC   TGC   TCC   ACC   TGC   GGC   CTG   AGA   CAG    288
Trp   Glu   Tyr   Cys   Asp   Val   Pro   Ser   Cys   Ser   Thr   Cys   Gly   Leu   Arg   Gln
                        85                          90                          95

TAC   AGC   CAG   CCA   ATT   CCT   AGA   TCT   GGA   GGC   CTC   TTC   GCC   GAC   ATC   GCC    336
Tyr   Ser   Gln   Pro   Ile   Pro   Arg   Ser   Gly   Gly   Leu   Phe   Ala   Asp   Ile   Ala
                  100                         105                         110

TCC   CAC   CCC   TGG   CAG   GCT   GCC   ATC   TTT   GCC   AAG   CAC   AGG   AGG   TCG   CCC    384
Ser   His   Pro   Trp   Gln   Ala   Ala   Ile   Phe   Ala   Lys   His   Arg   Arg   Ser   Pro
            115                         120                         125

GGA   GAG   CGG   TTC   CTG   TGC   GGG   GGC   ATA   CTC   ATC   AGC   TCC   TGC   TGG   ATT    432
Gly   Glu   Arg   Phe   Leu   Cys   Gly   Gly   Ile   Leu   Ile   Ser   Ser   Cys   Trp   Ile
```

```
                     130                               135                               140
CTC   TCT   GCC   GCC   CAC   TGC   TTC   CAG   GAG   AGG   TTT   CCG   CCC   CAC   CAC   CTG         480
Leu   Ser   Ala   Ala   His   Cys   Phe   Gln   Glu   Arg   Phe   Pro   Pro   His   His   Leu
145                     150                                 155                                 160

ACG   GTG   ATC   TTG   GGC   AGA   ACA   TAC   CGG   GTG   GTC   CCT   GGC   GAG   GAG   GAG         528
Thr   Val   Ile   Leu   Gly   Arg   Thr   Tyr   Arg   Val   Val   Pro   Gly   Glu   Glu   Glu
                        165                                 170                           175

CAG   AAA   TTT   GAA   GTC   GAA   AAA   TAC   ATT   GTC   CAT   AAG   GAA   TTC   GAT   GAT         576
Gln   Lys   Phe   Glu   Val   Glu   Lys   Tyr   Ile   Val   His   Lys   Glu   Phe   Asp   Asp
                  180                                 185                           190

GAC   ACT   TAC   GAC   AAT   GAC   ATT   GCG   CTG   CTG   CAG   CTG   AAA   TCG   GAT   TCG         624
Asp   Thr   Tyr   Asp   Asn   Asp   Ile   Ala   Leu   Leu   Gln   Leu   Lys   Ser   Asp   Ser
            195                           200                           205

TCC   CGC   TGT   GCC   CAG   GAG   AGC   AGC   GTG   GTC   CGC   ACT   GTG   TGC   CTT   CCC         672
Ser   Arg   Cys   Ala   Gln   Glu   Ser   Ser   Val   Val   Arg   Thr   Val   Cys   Leu   Pro
210                                 215                                 220

CCG   GCG   GAC   CTG   CAG   CTG   CCG   GAC   TGG   ACG   GAG   TGT   GAG   CTC   TCC   GGC         720
Pro   Ala   Asp   Leu   Gln   Leu   Pro   Asp   Trp   Thr   Glu   Cys   Glu   Leu   Ser   Gly
225                                 230                                 235                     240

TAC   GGC   AAG   CAT   GAG   GCC   TTG   TCT   CCT   TTC   TAT   TCG   GAG   CGG   CTG   AAG         768
Tyr   Gly   Lys   His   Glu   Ala   Leu   Ser   Pro   Phe   Tyr   Ser   Glu   Arg   Leu   Lys
                        245                                 250                           255

GAG   GCT   CAT   GTC   AGA   CTG   TAC   CCA   TCC   AGC   CGC   TGC   ACA   TCA   CAA   CAT         816
Glu   Ala   His   Val   Arg   Leu   Tyr   Pro   Ser   Ser   Arg   Cys   Thr   Ser   Gln   His
                  260                                 265                           270

TTA   CTT   AAC   AGA   ACA   GTC   ACC   GAC   AAC   ATG   CTG   TGT   GCT   GGA   GAC   ACT         864
Leu   Leu   Asn   Arg   Thr   Val   Thr   Asp   Asn   Met   Leu   Cys   Ala   Gly   Asp   Thr
            275                           280                           285

CGG   AGC   GGC   GGG   CCC   CAG   GCA   AAC   TTG   CAC   GAC   GCC   TGC   CAG   GGC   GAT         912
Arg   Ser   Gly   Gly   Pro   Gln   Ala   Asn   Leu   His   Asp   Ala   Cys   Gln   Gly   Asp
290                                 295                                 300

TCG   GGA   GGC   CCC   CTG   GTG   TGT   CTG   AAC   GAT   GGC   CGC   ATG   ACT   TTG   GTG         960
Ser   Gly   Gly   Pro   Leu   Val   Cys   Leu   Asn   Asp   Gly   Arg   Met   Thr   Leu   Val
305                                 310                                 315                     320

GGC   ATC   ATC   AGC   TGG   GGC   CTG   GGC   TGT   GGA   CAG   AAG   GAT   GTC   CCG   GGT        1008
Gly   Ile   Ile   Ser   Trp   Gly   Leu   Gly   Cys   Gly   Gln   Lys   Asp   Val   Pro   Gly
                        325                                 330                           335

GTG   TAC   ACA   AAG   GTT   ACC   AAC   TAC   CTA   GAC   TGG   ATT   CGT   GAC   AAC   ATG        1056
Val   Tyr   Thr   Lys   Val   Thr   Asn   Tyr   Leu   Asp   Trp   Ile   Arg   Asp   Asn   Met
                  340                                 345                           350

CGA   CCG   TGA                                                                                    1065
Arg   Pro
```

( 2 ) INFORMATION FOR SEQ ID NO:61:

( i ) SEQUENCE CHARACTERISTICS:
          ( A ) LENGTH: 354 amino acids
          ( B ) TYPE: amino acid
          ( D ) TOPOLOGY: linear ( i i ) MOLECULE TYPE: protein ( x i ) SEQUENCE DESCRIPTION: SEQ ID NO:61:

```
Met   Ser   Glu   Gly   Asn   Ser   Asp   Cys   Tyr   Phe   Gly   Asn   Gly   Ser   Ala   Tyr
1                       5                             10                              15

Arg   Gly   Thr   His   Ser   Leu   Thr   Glu   Ser   Gly   Ala   Ser   Cys   Leu   Pro   Trp
                  20                          25                          30

Asn   Ser   Met   Ile   Leu   Ile   Gly   Lys   Val   Tyr   Thr   Ala   Gln   Asn   Pro   Ser
                  35                          40                          45

Ala   Gln   Ala   Leu   Gly   Leu   Gly   Lys   His   Asn   Tyr   Cys   Arg   Asn   Pro   Asp
            50                          55                          60
```

```
Gly  Asp  Ala  Lys  Pro  Trp  Cys  His  Val  Leu  Lys  Asn  Arg  Arg  Leu  Thr
 65                  70                  75                            80

Trp  Glu  Tyr  Cys  Asp  Val  Pro  Ser  Cys  Ser  Thr  Cys  Gly  Leu  Arg  Gln
                85                       90                       95

Tyr  Ser  Gln  Pro  Ile  Pro  Arg  Ser  Gly  Gly  Leu  Phe  Ala  Asp  Ile  Ala
               100                      105                      110

Ser  His  Pro  Trp  Gln  Ala  Ala  Ile  Phe  Ala  Lys  His  Arg  Arg  Ser  Pro
          115                      120                      125

Gly  Glu  Arg  Phe  Leu  Cys  Gly  Gly  Ile  Leu  Ile  Ser  Ser  Cys  Trp  Ile
     130                      135                      140

Leu  Ser  Ala  Ala  His  Cys  Phe  Gln  Glu  Arg  Phe  Pro  Pro  His  His  Leu
145                      150                      155                      160

Thr  Val  Ile  Leu  Gly  Arg  Thr  Tyr  Arg  Val  Val  Pro  Gly  Glu  Glu  Glu
               165                      170                           175

Gln  Lys  Phe  Glu  Val  Glu  Lys  Tyr  Ile  Val  His  Lys  Glu  Phe  Asp  Asp
               180                      185                      190

Asp  Thr  Tyr  Asp  Asn  Asp  Ile  Ala  Leu  Leu  Gln  Leu  Lys  Ser  Asp  Ser
          195                      200                      205

Ser  Arg  Cys  Ala  Gln  Glu  Ser  Ser  Val  Val  Arg  Thr  Val  Cys  Leu  Pro
     210                      215                      220

Pro  Ala  Asp  Leu  Gln  Leu  Pro  Asp  Trp  Thr  Glu  Cys  Glu  Leu  Ser  Gly
225                      230                      235                      240

Tyr  Gly  Lys  His  Glu  Ala  Leu  Ser  Pro  Phe  Tyr  Ser  Glu  Arg  Leu  Lys
               245                      250                      255

Glu  Ala  His  Val  Arg  Leu  Tyr  Pro  Ser  Ser  Arg  Cys  Thr  Ser  Gln  His
                260                      265                      270

Leu  Leu  Asn  Arg  Thr  Val  Thr  Asp  Asn  Met  Leu  Cys  Ala  Gly  Asp  Thr
          275                      280                      285

Arg  Ser  Gly  Gly  Pro  Gln  Ala  Asn  Leu  His  Asp  Ala  Cys  Gln  Gly  Asp
     290                      295                      300

Ser  Gly  Gly  Pro  Leu  Val  Cys  Leu  Asn  Asp  Gly  Arg  Met  Thr  Leu  Val
305                      310                      315                      320

Gly  Ile  Ile  Ser  Trp  Gly  Leu  Gly  Cys  Gly  Gln  Lys  Asp  Val  Pro  Gly
                325                      330                      335

Val  Tyr  Thr  Lys  Val  Thr  Asn  Tyr  Leu  Asp  Trp  Ile  Arg  Asp  Asn  Met
               340                      345                      350

Arg  Pro
```

( 2 ) INFORMATION FOR SEQ ID NO:62:

( i ) SEQUENCE CHARACTERISTICS:
        ( A ) LENGTH: 1419 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1416

( x i ) SEQUENCE DESCRIPTION: SEQ ID NO:62:

```
ATG  GAT  GCA  ATG  AAG  AGA  GGG  CTC  TGC  TGT  GTG  CTG  CTG  CTG  TGT  GGA    48
Met  Asp  Ala  Met  Lys  Arg  Gly  Leu  Cys  Cys  Val  Leu  Leu  Leu  Cys  Gly
 1                   5                   10                       15

CCA  GTC  TTC  GTT  TCG  CCC  AGC  CAG  GAA  ATC  CAT  GCC  CGA  TTC  AGA  AGA    96
Pro  Val  Phe  Val  Ser  Pro  Ser  Gln  Glu  Ile  His  Ala  Arg  Phe  Arg  Arg
```

-continued

|     |     |     | 20  |     |     |     |     | 25  |     |     |     |     | 30  |     |     |      |
|-----|-----|-----|-----|-----|-----|-----|-----|-----|-----|-----|-----|-----|-----|-----|-----|------|
| GGA | GCC | AGA | TCT | TGC | TAC | GAG | GAC | CAG | GGC | ATC | AGC | TAC | AGG | GGC | ACG | 144  |
| Gly | Ala | Arg | Ser | Cys | Tyr | Glu | Asp | Gln | Gly | Ile | Ser | Tyr | Arg | Gly | Thr |      |
|     |     | 35  |     |     |     | 40  |     |     |     |     |     | 45  |     |     |     |      |

| TGG | ACC | ACA | GCG | GAG | AGT | GGC | GCC | GAG | TGC | ACC | AAC | TGG | AAC | AGC | AGC | 192 |
| Trp | Thr | Thr | Ala | Glu | Ser | Gly | Ala | Glu | Cys | Thr | Asn | Trp | Asn | Ser | Ser |     |
|     | 50  |     |     |     |     | 55  |     |     |     |     |     | 60  |     |     |     |     |

| GCG | TTG | GCC | CAG | AAG | CCC | TAC | AGC | GGG | CGG | AGG | CCA | GAC | CCC | ATC | AGG | 240 |
| Ala | Leu | Ala | Gln | Lys | Pro | Tyr | Ser | Gly | Arg | Arg | Pro | Asp | Pro | Ile | Arg |     |
| 65  |     |     |     |     | 70  |     |     |     |     | 75  |     |     |     |     | 80  |     |

| CTG | GGC | CTG | GGG | AAC | CAC | AAC | TAC | TGC | AGA | AAC | CCA | GAT | CGA | GAC | TCA | 288 |
| Leu | Gly | Leu | Gly | Asn | His | Asn | Tyr | Cys | Arg | Asn | Pro | Asp | Arg | Asp | Ser |     |
|     |     |     |     |     | 85  |     |     |     | 90  |     |     |     |     | 95  |     |     |

| AAG | CCC | TGG | TGC | TAC | GTC | TTT | AAG | GCG | GGG | AAG | TAC | AGC | TCA | GAG | TTC | 336 |
| Lys | Pro | Trp | Cys | Tyr | Val | Phe | Lys | Ala | Gly | Lys | Tyr | Ser | Ser | Glu | Phe |     |
|     |     |     | 100 |     |     |     |     | 105 |     |     |     |     | 110 |     |     |     |

| TGC | AGC | ACC | CCT | GCC | TGC | TCT | GAG | GGA | AAC | AGT | GAC | TGC | TAC | TTT | GGG | 384 |
| Cys | Ser | Thr | Pro | Ala | Cys | Ser | Glu | Gly | Asn | Ser | Asp | Cys | Tyr | Phe | Gly |     |
|     |     | 115 |     |     |     |     | 120 |     |     |     |     | 125 |     |     |     |     |

| AAT | GGG | TCA | GCC | TAC | CGT | GGC | ACG | CAC | AGC | CTC | ACC | GAG | TCG | GGT | GCC | 432 |
| Asn | Gly | Ser | Ala | Tyr | Arg | Gly | Thr | His | Ser | Leu | Thr | Glu | Ser | Gly | Ala |     |
|     |     | 130 |     |     |     | 135 |     |     |     |     | 140 |     |     |     |     |     |

| TCC | TGC | CTC | CCG | TGG | AAT | TCC | ATG | ATC | CTG | ATA | GGC | AAG | GTT | TAC | ACA | 480 |
| Ser | Cys | Leu | Pro | Trp | Asn | Ser | Met | Ile | Leu | Ile | Gly | Lys | Val | Tyr | Thr |     |
| 145 |     |     |     |     | 150 |     |     |     |     | 155 |     |     |     |     | 160 |     |

| GCA | CAG | AAC | CCC | AGT | GCC | CAG | GCA | CTG | GGC | CTG | GGC | AAA | CAT | AAT | TAC | 528 |
| Ala | Gln | Asn | Pro | Ser | Ala | Gln | Ala | Leu | Gly | Leu | Gly | Lys | His | Asn | Tyr |     |
|     |     |     |     | 165 |     |     |     |     | 170 |     |     |     |     | 175 |     |     |

| TGC | CGG | AAT | CCT | GAT | GGG | GAT | GCC | AAG | CCC | TGG | TGC | CAC | GTG | CTG | AAG | 576 |
| Cys | Arg | Asn | Pro | Asp | Gly | Asp | Ala | Lys | Pro | Trp | Cys | His | Val | Leu | Lys |     |
|     |     |     | 180 |     |     |     |     | 185 |     |     |     |     | 190 |     |     |     |

| AAC | CGC | AGG | CTG | ACG | TGG | GAG | TAC | TGT | GAT | GTG | CCC | TCC | TGC | TCC | ACC | 624 |
| Asn | Arg | Arg | Leu | Thr | Trp | Glu | Tyr | Cys | Asp | Val | Pro | Ser | Cys | Ser | Thr |     |
|     |     | 195 |     |     |     |     | 200 |     |     |     |     | 205 |     |     |     |     |

| TGC | GGC | CTG | AGA | CAG | TAC | AGC | CAG | CCT | CAG | TTT | CGC | ATC | AAA | GGA | GGG | 672 |
| Cys | Gly | Leu | Arg | Gln | Tyr | Ser | Gln | Pro | Gln | Phe | Arg | Ile | Lys | Gly | Gly |     |
|     | 210 |     |     |     |     | 215 |     |     |     |     | 220 |     |     |     |     |     |

| CTC | TTC | GCC | GAC | ATC | GCC | TCC | CAC | CCC | TGG | CAG | GCT | GCC | ATC | TTT | GCC | 720 |
| Leu | Phe | Ala | Asp | Ile | Ala | Ser | His | Pro | Trp | Gln | Ala | Ala | Ile | Phe | Ala |     |
| 225 |     |     |     |     | 230 |     |     |     |     | 235 |     |     |     |     | 240 |     |

| AAG | CAC | AGG | AGG | TCG | CCC | GGA | GAG | CGG | TTC | CTG | TGC | GGG | GGC | ATA | CTC | 768 |
| Lys | His | Arg | Arg | Ser | Pro | Gly | Glu | Arg | Phe | Leu | Cys | Gly | Gly | Ile | Leu |     |
|     |     |     |     | 245 |     |     |     |     | 250 |     |     |     |     | 255 |     |     |

| ATC | AGC | TCC | TGC | TGG | ATT | CTC | TCT | GCC | GCC | CAC | TGC | TTC | CAG | GAG | AGG | 816 |
| Ile | Ser | Ser | Cys | Trp | Ile | Leu | Ser | Ala | Ala | His | Cys | Phe | Gln | Glu | Arg |     |
|     |     |     | 260 |     |     |     |     | 265 |     |     |     |     | 270 |     |     |     |

| TTT | CCG | CCC | CAC | CAC | CTG | ACG | GTG | ATC | TTG | GGC | AGA | ACA | TAC | CGG | GTG | 864 |
| Phe | Pro | Pro | His | His | Leu | Thr | Val | Ile | Leu | Gly | Arg | Thr | Tyr | Arg | Val |     |
|     |     | 275 |     |     |     |     | 280 |     |     |     |     | 285 |     |     |     |     |

| GTC | CCT | GGC | GAG | GAG | GAG | CAG | AAA | TTT | GAA | GTC | GAA | AAA | TAC | ATT | GTC | 912 |
| Val | Pro | Gly | Glu | Glu | Glu | Gln | Lys | Phe | Glu | Val | Glu | Lys | Tyr | Ile | Val |     |
|     | 290 |     |     |     |     | 295 |     |     |     |     | 300 |     |     |     |     |     |

| CAT | AAG | GAA | TTC | GAT | GAT | GAC | ACT | TAC | GAC | AAT | GAC | ATT | GCG | CTG | CTG | 960 |
| His | Lys | Glu | Phe | Asp | Asp | Asp | Thr | Tyr | Asp | Asn | Asp | Ile | Ala | Leu | Leu |     |
| 305 |     |     |     |     | 310 |     |     |     |     | 315 |     |     |     |     | 320 |     |

| CAG | CTG | AAA | TCG | GAT | TCG | TCC | CGC | TGT | GCC | CAG | GAG | AGC | AGC | GTG | GTC | 1008 |
| Gln | Leu | Lys | Ser | Asp | Ser | Ser | Arg | Cys | Ala | Gln | Glu | Ser | Ser | Val | Val |     |
|     |     |     |     | 325 |     |     |     |     | 330 |     |     |     |     | 335 |     |     |

| CGC | ACT | GTG | TGC | CTT | CCC | CCG | GCG | GAC | CTG | CAG | CTG | CCG | GAC | TGG | ACG | 1056 |
| Arg | Thr | Val | Cys | Leu | Pro | Pro | Ala | Asp | Leu | Gln | Leu | Pro | Asp | Trp | Thr |     |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 340 |     |     |     |     | 345 |     |     |     |     |     | 350 |     |      |
| GAG | TGT | GAG | CTC | TCC | GGC | TAC | GGC | AAG | CAT | GAG | GCC | TTG | TCT | CCT | TTC | 1104 |
| Glu | Cys | Glu | Leu | Ser | Gly | Tyr | Gly | Lys | His | Glu | Ala | Leu | Ser | Pro | Phe |      |
|     |     | 355 |     |     |     |     | 360 |     |     |     |     | 365 |     |     |     |      |
| TAT | TCG | GAG | CGG | CTG | AAG | GAG | GCT | CAT | GTC | AGA | CTG | TAC | CCA | TCC | AGC | 1152 |
| Tyr | Ser | Glu | Arg | Leu | Lys | Glu | Ala | His | Val | Arg | Leu | Tyr | Pro | Ser | Ser |      |
|     |     | 370 |     |     |     |     | 375 |     |     |     |     | 380 |     |     |     |      |
| CGC | TGC | ACA | TCA | CAA | CAT | TTA | CTT | AAC | AGA | ACA | GTC | ACC | GAC | AAC | ATG | 1200 |
| Arg | Cys | Thr | Ser | Gln | His | Leu | Leu | Asn | Arg | Thr | Val | Thr | Asp | Asn | Met |      |
| 385 |     |     |     |     | 390 |     |     |     |     | 395 |     |     |     |     | 400 |      |
| CTG | TGT | GCT | GGA | GAC | ACT | CGG | AGC | GGC | GGG | CCC | CAG | GCA | AAC | TTG | CAC | 1248 |
| Leu | Cys | Ala | Gly | Asp | Thr | Arg | Ser | Gly | Gly | Pro | Gln | Ala | Asn | Leu | His |      |
|     |     |     |     | 405 |     |     |     |     | 410 |     |     |     |     | 415 |     |      |
| GAC | GCC | TGC | CAG | GGC | GAT | TCG | GGA | GGC | CCC | CTG | GTG | TGT | CTG | AAC | GAT | 1296 |
| Asp | Ala | Cys | Gln | Gly | Asp | Ser | Gly | Gly | Pro | Leu | Val | Cys | Leu | Asn | Asp |      |
|     |     |     | 420 |     |     |     |     | 425 |     |     |     |     | 430 |     |     |      |
| GGC | CGC | ATG | ACT | TTG | GTG | GGC | ATC | ATC | AGC | TGG | GGC | CTG | GGC | TGT | GGA | 1344 |
| Gly | Arg | Met | Thr | Leu | Val | Gly | Ile | Ile | Ser | Trp | Gly | Leu | Gly | Cys | Gly |      |
|     |     | 435 |     |     |     |     |     | 440 |     |     |     |     | 445 |     |     |      |
| CAG | AAG | GAT | GTC | CCG | GGT | GTG | TAC | ACA | AAG | GTT | ACC | AAC | TAC | CTA | GAC | 1392 |
| Gln | Lys | Asp | Val | Pro | Gly | Val | Tyr | Thr | Lys | Val | Thr | Asn | Tyr | Leu | Asp |      |
|     | 450 |     |     |     |     | 455 |     |     |     |     | 460 |     |     |     |     |      |
| TGG | ATT | CGT | GAC | AAC | ATG | CGA | CCG | TGA |     |     |     |     |     |     |     | 1419 |
| Trp | Ile | Arg | Asp | Asn | Met | Arg | Pro |     |     |     |     |     |     |     |     |      |
| 465 |     |     |     |     | 470 |     |     |     |     |     |     |     |     |     |     |      |

( 2 ) INFORMATION FOR SEQ ID NO:63:

( i ) SEQUENCE CHARACTERISTICS:
        ( A ) LENGTH: 472 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

| Met | Asp | Ala | Met | Lys | Arg | Gly | Leu | Cys | Cys | Val | Leu | Leu | Leu | Cys | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Pro | Val | Phe | Val | Ser | Pro | Ser | Gln | Glu | Ile | His | Ala | Arg | Phe | Arg | Arg |
|     |     |     | 20  |     |     |     |     | 25  |     |     |     |     | 30  |     |     |
| Gly | Ala | Arg | Ser | Cys | Tyr | Glu | Asp | Gln | Gly | Ile | Ser | Tyr | Arg | Gly | Thr |
|     |     | 35  |     |     |     |     | 40  |     |     |     |     | 45  |     |     |     |
| Trp | Thr | Thr | Ala | Glu | Ser | Gly | Ala | Glu | Cys | Thr | Asn | Trp | Asn | Ser | Ser |
|     | 50  |     |     |     |     | 55  |     |     |     |     | 60  |     |     |     |     |
| Ala | Leu | Ala | Gln | Lys | Pro | Tyr | Ser | Gly | Arg | Arg | Pro | Asp | Pro | Ile | Arg |
| 65  |     |     |     |     | 70  |     |     |     |     | 75  |     |     |     |     | 80  |
| Leu | Gly | Leu | Gly | Asn | His | Asn | Tyr | Cys | Arg | Asn | Pro | Asp | Arg | Asp | Ser |
|     |     |     |     | 85  |     |     |     |     | 90  |     |     |     |     | 95  |     |
| Lys | Pro | Trp | Cys | Tyr | Val | Phe | Lys | Ala | Gly | Lys | Tyr | Ser | Ser | Glu | Phe |
|     |     |     | 100 |     |     |     |     | 105 |     |     |     |     | 110 |     |     |
| Cys | Ser | Thr | Pro | Ala | Cys | Ser | Glu | Gly | Asn | Ser | Asp | Cys | Tyr | Phe | Gly |
|     |     | 115 |     |     |     |     | 120 |     |     |     |     | 125 |     |     |     |
| Asn | Gly | Ser | Ala | Tyr | Arg | Gly | Thr | His | Ser | Leu | Thr | Glu | Ser | Gly | Ala |
|     | 130 |     |     |     |     | 135 |     |     |     |     | 140 |     |     |     |     |
| Ser | Cys | Leu | Pro | Trp | Asn | Ser | Met | Ile | Leu | Ile | Gly | Lys | Val | Tyr | Thr |
| 145 |     |     |     |     | 150 |     |     |     |     | 155 |     |     |     |     | 160 |
| Ala | Gln | Asn | Pro | Ser | Ala | Gln | Ala | Leu | Gly | Leu | Gly | Lys | His | Asn | Tyr |
|     |     |     |     | 165 |     |     |     |     | 170 |     |     |     |     | 175 |     |
| Cys | Arg | Asn | Pro | Asp | Gly | Asp | Ala | Lys | Pro | Trp | Cys | His | Val | Leu | Lys |

180                              185                              190

Asn  Arg  Arg  Leu  Thr  Trp  Glu  Tyr  Cys  Asp  Val  Pro  Ser  Cys  Ser  Thr
          195                      200                      205

Cys  Gly  Leu  Arg  Gln  Tyr  Ser  Gln  Pro  Gln  Phe  Arg  Ile  Lys  Gly  Gly
     210                      215                           220

Leu  Phe  Ala  Asp  Ile  Ala  Ser  His  Pro  Trp  Gln  Ala  Ala  Ile  Phe  Ala
225                      230                      235                           240

Lys  His  Arg  Arg  Ser  Pro  Gly  Glu  Arg  Phe  Leu  Cys  Gly  Gly  Ile  Leu
               245                           250                           255

Ile  Ser  Ser  Cys  Trp  Ile  Leu  Ser  Ala  Ala  His  Cys  Phe  Gln  Glu  Arg
               260                      265                      270

Phe  Pro  Pro  His  His  Leu  Thr  Val  Ile  Leu  Gly  Arg  Thr  Tyr  Arg  Val
          275                      280                      285

Val  Pro  Gly  Glu  Glu  Glu  Gln  Lys  Phe  Glu  Val  Glu  Lys  Tyr  Ile  Val
     290                      295                      300

His  Lys  Glu  Phe  Asp  Asp  Thr  Tyr  Asp  Asn  Asp  Ile  Ala  Leu  Leu
305                      310                      315                           320

Gln  Leu  Lys  Ser  Asp  Ser  Ser  Arg  Cys  Ala  Gln  Glu  Ser  Ser  Val  Val
               325                      330                           335

Arg  Thr  Val  Cys  Leu  Pro  Pro  Ala  Asp  Leu  Gln  Leu  Pro  Asp  Trp  Thr
               340                      345                      350

Glu  Cys  Glu  Leu  Ser  Gly  Tyr  Gly  Lys  His  Glu  Ala  Leu  Ser  Pro  Phe
          355                      360                      365

Tyr  Ser  Glu  Arg  Leu  Lys  Glu  Ala  His  Val  Arg  Leu  Tyr  Pro  Ser  Ser
     370                      375                      380

Arg  Cys  Thr  Ser  Gln  His  Leu  Leu  Asn  Arg  Thr  Val  Thr  Asp  Asn  Met
385                      390                      395                           400

Leu  Cys  Ala  Gly  Asp  Thr  Arg  Ser  Gly  Gly  Pro  Gln  Ala  Asn  Leu  His
               405                      410                           415

Asp  Ala  Cys  Gln  Gly  Asp  Ser  Gly  Gly  Pro  Leu  Val  Cys  Leu  Asn  Asp
               420                      425                           430

Gly  Arg  Met  Thr  Leu  Val  Gly  Ile  Ile  Ser  Trp  Gly  Leu  Gly  Cys  Gly
          435                      440                      445

Gln  Lys  Asp  Val  Pro  Gly  Val  Tyr  Thr  Lys  Val  Thr  Asn  Tyr  Leu  Asp
     450                      455                      460

Trp  Ile  Arg  Asp  Asn  Met  Arg  Pro
465                      470

( 2 ) INFORMATION FOR SEQ ID NO:64:

( i ) SEQUENCE CHARACTERISTICS:
        ( A ) LENGTH: 1170 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1167

( x i ) SEQUENCE DESCRIPTION: SEQ ID NO:64:

ATG  GAT  GCA  ATG  AAG  AGA  GGG  CTC  TGC  TGT  GTG  CTG  CTG  CTG  TGT  GGA         48
Met  Asp  Ala  Met  Lys  Arg  Gly  Leu  Cys  Cys  Val  Leu  Leu  Leu  Cys  Gly
1                   5                        10                       15

GCA  CTC  TTC  GTT  TCG  CCC  AGC  CAG  GAA  ATC  CAT  GCC  CGA  TTC  AGA  AGA         96
Ala  Leu  Phe  Val  Ser  Pro  Ser  Gln  Glu  Ile  His  Ala  Arg  Phe  Arg  Arg
               20                       25                            30

| | | | | | | | | | | | | | | | | |
|---|---|---|---|---|---|---|---|---|---|---|---|---|---|---|---|---|
| GGA | GCC | AGA | TCT | GAG | GGA | AAC | AGT | GAC | TGC | TAC | TTT | GGG | AAT | GGG | TCA | 144 |
| Gly | Ala | Arg | Ser | Glu | Gly | Asn | Ser | Asp | Cys | Tyr | Phe | Gly | Asn | Gly | Ser | |
| | | 35 | | | | | 40 | | | | | 45 | | | | |
| GCC | TAC | CGT | GGC | ACG | CAC | AGC | CTC | ACC | GAG | TCG | GGT | GCC | TCC | TGC | CTC | 192 |
| Ala | Tyr | Arg | Gly | Thr | His | Ser | Leu | Thr | Glu | Ser | Gly | Ala | Ser | Cys | Leu | |
| | 50 | | | | | 55 | | | | | 60 | | | | | |
| CCG | TGG | AAT | TCC | ATG | ATC | CTG | ATA | GGC | AAG | GTT | TAC | ACA | GCA | CAG | AAC | 240 |
| Pro | Trp | Asn | Ser | Met | Ile | Leu | Ile | Gly | Lys | Val | Tyr | Thr | Ala | Gln | Asn | |
| 65 | | | | | 70 | | | | | 75 | | | | | 80 | |
| CCC | AGT | GCC | CAG | GCA | CTG | GGC | CTG | GGC | AAA | CAT | AAT | TAC | TGC | CGG | AAT | 288 |
| Pro | Ser | Ala | Gln | Ala | Leu | Gly | Leu | Gly | Lys | His | Asn | Tyr | Cys | Arg | Asn | |
| | | | | 85 | | | | | 90 | | | | | 95 | | |
| CCT | GAT | GGG | GAT | GCC | AAG | CCC | TGG | TGC | CAC | GTG | CTG | AAG | AAC | CGC | AGG | 336 |
| Pro | Asp | Gly | Asp | Ala | Lys | Pro | Trp | Cys | His | Val | Leu | Lys | Asn | Arg | Arg | |
| | | | 100 | | | | | 105 | | | | | 110 | | | |
| CTG | ACG | TGG | GAG | TAC | TGT | GAT | GTG | CCC | TCC | TGC | TCC | ACC | TGC | GGC | CTG | 384 |
| Leu | Thr | Trp | Glu | Tyr | Cys | Asp | Val | Pro | Ser | Cys | Ser | Thr | Cys | Gly | Leu | |
| | | | 115 | | | | | 120 | | | | | 125 | | | |
| AGA | CAG | TAC | AGC | CAG | CCT | CAG | TTT | CGC | ATC | AAA | GGA | GGG | CTC | TTC | GCC | 432 |
| Arg | Gln | Tyr | Ser | Gln | Pro | Gln | Phe | Arg | Ile | Lys | Gly | Gly | Leu | Phe | Ala | |
| | 130 | | | | | 135 | | | | | 140 | | | | | |
| GAC | ATC | GCC | TCC | CAC | CCC | TGG | CAG | GCT | CCC | ATC | TTT | GCC | AAG | CAC | AGG | 480 |
| Asp | Ile | Ala | Ser | His | Pro | Trp | Gln | Ala | Pro | Ile | Phe | Ala | Lys | His | Arg | |
| 145 | | | | | 150 | | | | | 155 | | | | | 160 | |
| AGG | TCG | CCC | GGA | GAG | CGG | TTC | CTG | TGC | GGG | GGC | ATA | CTC | ATC | AGC | TCC | 528 |
| Arg | Ser | Pro | Gly | Glu | Arg | Phe | Leu | Cys | Gly | Gly | Ile | Leu | Ile | Ser | Ser | |
| | | | | 165 | | | | | 170 | | | | | 175 | | |
| TGC | TGG | ATT | CTC | TCT | GCC | GCC | CAC | TGC | TTC | CAG | GAG | AGG | TTT | CCG | CCC | 576 |
| Cys | Trp | Ile | Leu | Ser | Ala | Ala | His | Cys | Phe | Gln | Glu | Arg | Phe | Pro | Pro | |
| | | | 180 | | | | | 185 | | | | | 190 | | | |
| CAC | CAC | CTG | ACG | GTG | ATC | TTG | GGC | AGA | ACA | TAC | CGG | GTG | GTC | CCT | GGC | 624 |
| His | His | Leu | Thr | Val | Ile | Leu | Gly | Arg | Thr | Tyr | Arg | Val | Val | Pro | Gly | |
| | | 195 | | | | | 200 | | | | | 205 | | | | |
| GAG | GAG | GAG | CAG | AAA | TTT | GAA | GTC | GAA | AAA | TAC | ATT | GTC | CAT | AAG | GAA | 672 |
| Glu | Glu | Glu | Gln | Lys | Phe | Glu | Val | Glu | Lys | Tyr | Ile | Val | His | Lys | Glu | |
| | 210 | | | | | 215 | | | | | 220 | | | | | |
| TTC | GAT | GAT | GAC | ACT | TAC | GAC | AAT | GAC | ATT | GCG | CTG | CTG | CAG | CTG | AAA | 720 |
| Phe | Asp | Asp | Asp | Thr | Tyr | Asp | Asn | Asp | Ile | Ala | Leu | Leu | Gln | Leu | Lys | |
| 225 | | | | | 230 | | | | | 235 | | | | | 240 | |
| TCG | GAT | TCG | TCC | CGC | TGT | GCC | CAG | GAG | AGC | AGC | GTG | GTC | CGC | ACT | GTG | 768 |
| Ser | Asp | Ser | Ser | Arg | Cys | Ala | Gln | Glu | Ser | Ser | Val | Val | Arg | Thr | Val | |
| | | | | 245 | | | | | 250 | | | | | 255 | | |
| TGC | CTT | CCC | CCG | GCG | GAC | CTG | CAG | CTG | CCG | GAC | TGG | ACG | GAG | TGT | GAG | 816 |
| Cys | Leu | Pro | Pro | Ala | Asp | Leu | Gln | Leu | Pro | Asp | Trp | Thr | Glu | Cys | Glu | |
| | | | 260 | | | | | 265 | | | | | 270 | | | |
| CTC | TCC | GGC | TAC | GGC | AAG | CAT | GAG | GCC | TTG | TCT | CCT | TTC | TAT | TCG | GAG | 864 |
| Leu | Ser | Gly | Tyr | Gly | Lys | His | Glu | Ala | Leu | Ser | Pro | Phe | Tyr | Ser | Glu | |
| | | 275 | | | | | 280 | | | | | 285 | | | | |
| CGG | CTG | AAG | GAG | GCT | CAT | GTC | AGA | CTG | TAC | CCA | TCC | AGC | CGC | TGC | ACA | 912 |
| Arg | Leu | Lys | Glu | Ala | His | Val | Arg | Leu | Tyr | Pro | Ser | Ser | Arg | Cys | Thr | |
| | 290 | | | | | 295 | | | | | 300 | | | | | |
| TCA | CAA | CAT | TTA | CTT | AAC | AGA | ACA | GTC | ACC | GAC | AAC | ATG | CTG | TGT | GCT | 960 |
| Ser | Gln | His | Leu | Leu | Asn | Arg | Thr | Val | Thr | Asp | Asn | Met | Leu | Cys | Ala | |
| 305 | | | | | 310 | | | | | 315 | | | | | 320 | |
| GGA | GAC | ACT | CGG | AGC | GGC | GGG | CCC | CAG | GCA | AAC | TTG | CAC | GAC | GCC | TGC | 1008 |
| Gly | Asp | Thr | Arg | Ser | Gly | Gly | Pro | Gln | Ala | Asn | Leu | His | Asp | Ala | Cys | |
| | | | | 325 | | | | | 330 | | | | | 335 | | |
| CAG | GGC | GAT | TCG | GGA | GGC | CCC | CTG | GTG | TGT | CTG | AAC | GAT | GGC | CGC | ATG | 1056 |
| Gln | Gly | Asp | Ser | Gly | Gly | Pro | Leu | Val | Cys | Leu | Asn | Asp | Gly | Arg | Met | |
| | | | 340 | | | | | 345 | | | | | 350 | | | |

```
ACT  TTG  GTG  GGC  ATC  ATC  AGC  TGG  GGC  CTG  GGC  TGT  GGA  CAG  AAG  GAT      1104
Thr  Leu  Val  Gly  Ile  Ile  Ser  Trp  Gly  Leu  Gly  Cys  Gly  Gln  Lys  Asp
          355                          360                     365

GTC  CCG  GGT  GTG  TAC  ACA  AAG  GTT  ACC  AAC  TAC  CTA  GAC  TGG  ATT  CGT      1152
Val  Pro  Gly  Val  Tyr  Thr  Lys  Val  Thr  Asn  Tyr  Leu  Asp  Trp  Ile  Arg
     370                          375                     380

GAC  AAC  ATG  CGA  CCG  TGA                                                        1170
Asp  Asn  Met  Arg  Pro
385
```

( 2 ) INFORMATION FOR SEQ ID NO:65:

( i ) SEQUENCE CHARACTERISTICS:
        ( A ) LENGTH: 389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:65:

```
Met  Asp  Ala  Met  Lys  Arg  Gly  Leu  Cys  Cys  Val  Leu  Leu  Leu  Cys  Gly
  1             5                        10                       15

Ala  Leu  Phe  Val  Ser  Pro  Ser  Gln  Glu  Ile  His  Ala  Arg  Phe  Arg  Arg
               20                      25                       30

Gly  Ala  Arg  Ser  Glu  Gly  Asn  Ser  Asp  Cys  Tyr  Phe  Gly  Asn  Gly  Ser
          35                       40                            45

Ala  Tyr  Arg  Gly  Thr  His  Ser  Leu  Thr  Glu  Ser  Gly  Ala  Ser  Cys  Leu
     50                            55                       60

Pro  Trp  Asn  Ser  Met  Ile  Leu  Ile  Gly  Lys  Val  Tyr  Thr  Ala  Gln  Asn
 65                       70                      75                         80

Pro  Ser  Ala  Gln  Ala  Leu  Gly  Leu  Gly  Lys  His  Asn  Tyr  Cys  Arg  Asn
                    85                           90                      95

Pro  Asp  Gly  Asp  Ala  Lys  Pro  Trp  Cys  His  Val  Leu  Lys  Asn  Arg  Arg
                100                      105                     110

Leu  Thr  Trp  Glu  Tyr  Cys  Asp  Val  Pro  Ser  Cys  Ser  Thr  Cys  Gly  Leu
               115                      120                     125

Arg  Gln  Tyr  Ser  Gln  Pro  Gln  Phe  Arg  Ile  Lys  Gly  Gly  Leu  Phe  Ala
     130                      135                      140

Asp  Ile  Ala  Ser  His  Pro  Trp  Gln  Ala  Pro  Ile  Phe  Ala  Lys  His  Arg
145                      150                      155                         160

Arg  Ser  Pro  Gly  Glu  Arg  Phe  Leu  Cys  Gly  Gly  Ile  Leu  Ile  Ser  Ser
                         165                     170                     175

Cys  Trp  Ile  Leu  Ser  Ala  Ala  His  Cys  Phe  Gln  Glu  Arg  Phe  Pro  Pro
                    180                     185                      190

His  His  Leu  Thr  Val  Ile  Leu  Gly  Arg  Thr  Tyr  Arg  Val  Val  Pro  Gly
               195                      200                     205

Glu  Glu  Glu  Gln  Lys  Phe  Glu  Val  Glu  Lys  Tyr  Ile  Val  His  Lys  Glu
     210                      215                      220

Phe  Asp  Asp  Asp  Thr  Tyr  Asp  Asn  Asp  Ile  Ala  Leu  Leu  Gln  Leu  Lys
225                      230                      235                         240

Ser  Asp  Ser  Ser  Arg  Cys  Ala  Gln  Glu  Ser  Ser  Val  Val  Arg  Thr  Val
                    245                     250                      255

Cys  Leu  Pro  Pro  Ala  Asp  Leu  Gln  Leu  Pro  Asp  Trp  Thr  Glu  Cys  Glu
               260                      265                     270

Leu  Ser  Gly  Tyr  Gly  Lys  His  Glu  Ala  Leu  Ser  Pro  Phe  Tyr  Ser  Glu
               275                      280                     285

Arg  Leu  Lys  Glu  Ala  His  Val  Arg  Leu  Tyr  Pro  Ser  Ser  Arg  Cys  Thr
```

```
                 290                         295                           300
Ser   Gln   His   Leu   Leu   Asn   Arg   Thr   Val   Thr   Asp   Asn   Met   Leu   Cys   Ala
305                           310                           315                           320

Gly   Asp   Thr   Arg   Ser   Gly   Gly   Pro   Gln   Ala   Asn   Leu   His   Asp   Ala   Cys
                        325                           330                           335

Gln   Gly   Asp   Ser   Gly   Gly   Pro   Leu   Val   Cys   Leu   Asn   Asp   Gly   Arg   Met
                  340                           345                           350

Thr   Leu   Val   Gly   Ile   Ile   Ser   Trp   Gly   Leu   Gly   Cys   Gly   Gln   Lys   Asp
            355                           360                           365

Val   Pro   Gly   Val   Tyr   Thr   Lys   Val   Thr   Asn   Tyr   Leu   Asp   Trp   Ile   Arg
      370                           375                           380

Asp   Asn   Met   Arg   Pro
385
```

( 2 ) INFORMATION FOR SEQ ID NO:66:

( i ) SEQUENCE CHARACTERISTICS:
        ( A ) LENGTH: 1170 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 1..1167

( x i ) SEQUENCE DESCRIPTION: SEQ ID NO:66:

```
ATG   GAT   GCA   ATG   AAG   AGA   GGG   CTC   TGC   TGT   GTG   CTG   CTG   CTG   TGT   GGA       48
Met   Asp   Ala   Met   Lys   Arg   Gly   Leu   Cys   Cys   Val   Leu   Leu   Leu   Cys   Gly
  1                     5                          10                          15

GCA   GTC   TTC   GTT   TCG   CCC   AGC   CAG   GAA   ATC   CAT   GCC   CGA   TTC   AGA   AGA       96
Ala   Val   Phe   Val   Ser   Pro   Ser   Gln   Glu   Ile   His   Ala   Arg   Phe   Arg   Arg
                   20                          25                          30

GGA   GCC   AGA   TCT   GAG   GGA   AAC   AGT   GAC   TGC   TAC   TTT   GGG   AAT   GGG   TCA      144
Gly   Ala   Arg   Ser   Glu   Gly   Asn   Ser   Asp   Cys   Tyr   Phe   Gly   Asn   Gly   Ser
             35                          40                          45

GCC   TAC   CGT   GGC   ACG   CAC   AGC   CTC   ACC   GAG   TCG   GGT   GCC   TCC   TGC   CTC      192
Ala   Tyr   Arg   Gly   Thr   His   Ser   Leu   Thr   Glu   Ser   Gly   Ala   Ser   Cys   Leu
       50                          55                          60

CCG   TGG   AAT   TCC   ATG   ATC   CTG   ATA   GGC   AAG   GTT   TAC   ACA   GCA   CAG   AAC      240
Pro   Trp   Asn   Ser   Met   Ile   Leu   Ile   Gly   Lys   Val   Tyr   Thr   Ala   Gln   Asn
 65                          70                          75                          80

CCC   AGT   GCC   CAG   GCA   CTG   GGC   CTG   GGC   AAA   CAT   AAT   TAC   TGC   CGG   AAT      288
Pro   Ser   Ala   Gln   Ala   Leu   Gly   Leu   Gly   Lys   His   Asn   Tyr   Cys   Arg   Asn
                         85                          90                          95

CCT   GAT   GGG   GAT   GCC   AAG   CCC   TGG   TGC   CAC   GTG   CTG   AAG   AAC   CGC   AGG      336
Pro   Asp   Gly   Asp   Ala   Lys   Pro   Trp   Cys   His   Val   Leu   Lys   Asn   Arg   Arg
                  100                         105                         110

CTG   ACG   TGG   GAG   TAC   TGT   GAT   GTG   CCC   TCC   TGC   TCC   ACC   TCC   GGC   CTG      384
Leu   Thr   Trp   Glu   Tyr   Cys   Asp   Val   Pro   Ser   Cys   Ser   Thr   Ser   Gly   Leu
            115                         120                         125

AGA   CAG   TAC   AGC   CAG   CCA   CAG   TTT   GAT   ATC   AAA   GGA   GGC   CTC   TTC   GCC      432
Arg   Gln   Tyr   Ser   Gln   Pro   Gln   Phe   Asp   Ile   Lys   Gly   Gly   Leu   Phe   Ala
      130                         135                         140

GAC   ATC   GCC   TCC   CAC   CCC   TGG   CAG   GCT   GCC   ATC   TTT   GCC   AAG   CAC   AGG      480
Asp   Ile   Ala   Ser   His   Pro   Trp   Gln   Ala   Ala   Ile   Phe   Ala   Lys   His   Arg
145                         150                         155                         160

AGG   TCG   CCC   GGA   GAG   CGG   TTC   CTG   TGC   GGG   GGC   ATA   CTC   ATC   AGC   TCC      528
Arg   Ser   Pro   Gly   Glu   Arg   Phe   Leu   Cys   Gly   Gly   Ile   Leu   Ile   Ser   Ser
                  165                         170                         175
```

| TGC | TGG | ATT | CTC | TCT | GCC | GCC | CAC | TGC | TTC | CAG | GAG | AGG | TTT | CCG | CCC | 576 |
|-----|-----|-----|-----|-----|-----|-----|-----|-----|-----|-----|-----|-----|-----|-----|-----|-----|
| Cys | Trp | Ile | Leu | Ser | Ala | Ala | His | Cys | Phe | Gln | Glu | Arg | Phe | Pro | Pro | |
| | | | 180 | | | | | 185 | | | | | 190 | | | |

| CAC | CAC | CTG | ACG | GTG | ATC | TTG | GGC | AGA | ACA | TAC | CGG | GTG | GTC | CCT | GGC | 624 |
|-----|-----|-----|-----|-----|-----|-----|-----|-----|-----|-----|-----|-----|-----|-----|-----|-----|
| His | His | Leu | Thr | Val | Ile | Leu | Gly | Arg | Thr | Tyr | Arg | Val | Val | Pro | Gly | |
| | | 195 | | | | | 200 | | | | | 205 | | | | |

| GAG | GAG | GAG | CAG | AAA | TTT | GAA | GTC | GAA | AAA | TAC | ATT | GTC | CAT | AAG | GAA | 672 |
|-----|-----|-----|-----|-----|-----|-----|-----|-----|-----|-----|-----|-----|-----|-----|-----|-----|
| Glu | Glu | Glu | Gln | Lys | Phe | Glu | Val | Glu | Lys | Tyr | Ile | Val | His | Lys | Glu | |
| 210 | | | | | 215 | | | | | 220 | | | | | | |

| TTC | GAT | GAT | GAC | ACT | TAC | GAC | AAT | GAC | ATT | GCG | CTG | CTG | CAG | CTG | AAA | 720 |
|-----|-----|-----|-----|-----|-----|-----|-----|-----|-----|-----|-----|-----|-----|-----|-----|-----|
| Phe | Asp | Asp | Asp | Thr | Tyr | Asp | Asn | Asp | Ile | Ala | Leu | Leu | Gln | Leu | Lys | |
| 225 | | | | | 230 | | | | | 235 | | | | | 240 | |

| TCG | GAT | TCG | TCC | CGC | TGT | GCC | CAG | GAG | AGC | AGC | GTG | GTC | CGC | ACT | GTG | 768 |
|-----|-----|-----|-----|-----|-----|-----|-----|-----|-----|-----|-----|-----|-----|-----|-----|-----|
| Ser | Asp | Ser | Ser | Arg | Cys | Ala | Gln | Glu | Ser | Ser | Val | Val | Arg | Thr | Val | |
| | | | | 245 | | | | | 250 | | | | | 255 | | |

| TGC | CTT | CCC | CCG | GCG | GAC | CTG | CAG | CTG | CCG | GAC | TGG | ACG | GAG | TGT | GAG | 816 |
|-----|-----|-----|-----|-----|-----|-----|-----|-----|-----|-----|-----|-----|-----|-----|-----|-----|
| Cys | Leu | Pro | Pro | Ala | Asp | Leu | Gln | Leu | Pro | Asp | Trp | Thr | Glu | Cys | Glu | |
| | | | 260 | | | | | 265 | | | | | 270 | | | |

| CTC | TCC | GGC | TAC | GGC | AAG | CAT | GAG | GCC | TTG | TCT | CCT | TTC | TAT | TCG | GAG | 864 |
|-----|-----|-----|-----|-----|-----|-----|-----|-----|-----|-----|-----|-----|-----|-----|-----|-----|
| Leu | Ser | Gly | Tyr | Gly | Lys | His | Glu | Ala | Leu | Ser | Pro | Phe | Tyr | Ser | Glu | |
| | | 275 | | | | | 280 | | | | | 285 | | | | |

| CGG | CTG | AAG | GAG | GCT | CAT | GTC | AGA | CTG | TAC | CCA | TCC | AGC | CGC | TGC | ACA | 912 |
|-----|-----|-----|-----|-----|-----|-----|-----|-----|-----|-----|-----|-----|-----|-----|-----|-----|
| Arg | Leu | Lys | Glu | Ala | His | Val | Arg | Leu | Tyr | Pro | Ser | Ser | Arg | Cys | Thr | |
| | 290 | | | | | 295 | | | | | 300 | | | | | |

| TCA | CAA | CAT | TTA | CTT | AAC | AGA | ACA | GTC | ACC | GAC | AAC | ATG | CTG | TGT | GCT | 960 |
|-----|-----|-----|-----|-----|-----|-----|-----|-----|-----|-----|-----|-----|-----|-----|-----|-----|
| Ser | Gln | His | Leu | Leu | Asn | Arg | Thr | Val | Thr | Asp | Asn | Met | Leu | Cys | Ala | |
| 305 | | | | | 310 | | | | | 315 | | | | | 320 | |

| GGA | GAC | ACT | CGG | AGC | GGC | GGG | CCC | CAG | GCA | AAC | TTG | CAC | GAC | GCC | TGC | 1008 |
|-----|-----|-----|-----|-----|-----|-----|-----|-----|-----|-----|-----|-----|-----|-----|-----|------|
| Gly | Asp | Thr | Arg | Ser | Gly | Gly | Pro | Gln | Ala | Asn | Leu | His | Asp | Ala | Cys | |
| | | | | 325 | | | | | 330 | | | | | 335 | | |

| CAG | GGC | GAT | TCG | GGA | GGC | CCC | CTG | GTG | TGT | CTG | AAC | GAT | GGC | CGC | ATG | 1056 |
|-----|-----|-----|-----|-----|-----|-----|-----|-----|-----|-----|-----|-----|-----|-----|-----|------|
| Gln | Gly | Asp | Ser | Gly | Gly | Pro | Leu | Val | Cys | Leu | Asn | Asp | Gly | Arg | Met | |
| | | | 340 | | | | | 345 | | | | | 350 | | | |

| ACT | TTG | GTG | GGC | ATC | ATC | AGC | TGG | GGC | CTG | GGC | TGT | GGA | CAG | AAG | GAT | 1104 |
|-----|-----|-----|-----|-----|-----|-----|-----|-----|-----|-----|-----|-----|-----|-----|-----|------|
| Thr | Leu | Val | Gly | Ile | Ile | Ser | Trp | Gly | Leu | Gly | Cys | Gly | Gln | Lys | Asp | |
| | | 355 | | | | | 360 | | | | | 365 | | | | |

| GTC | CCG | GGT | GTG | TAC | ACA | AAG | GTT | ACC | AAC | TAC | CTA | GAC | TGG | ATT | CGT | 1152 |
|-----|-----|-----|-----|-----|-----|-----|-----|-----|-----|-----|-----|-----|-----|-----|-----|------|
| Val | Pro | Gly | Val | Tyr | Thr | Lys | Val | Thr | Asn | Tyr | Leu | Asp | Trp | Ile | Arg | |
| | 370 | | | | | 375 | | | | | 380 | | | | | |

| GAC | AAC | ATG | CGA | CCG | TGA | | | | | | | | | | | 1170 |
|-----|-----|-----|-----|-----|-----|---|---|---|---|---|---|---|---|---|---|------|
| Asp | Asn | Met | Arg | Pro | | | | | | | | | | | | |
| 385 | | | | | | | | | | | | | | | | |

( 2 ) INFORMATION FOR SEQ ID NO:67:

( i ) SEQUENCE CHARACTERISTICS:
        ( A ) LENGTH: 389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

| Met | Asp | Ala | Met | Lys | Arg | Gly | Leu | Cys | Cys | Val | Leu | Leu | Leu | Cys | Gly |
|-----|-----|-----|-----|-----|-----|-----|-----|-----|-----|-----|-----|-----|-----|-----|-----|
| 1 | | | | 5 | | | | | 10 | | | | | 15 | |

| Ala | Val | Phe | Val | Ser | Pro | Ser | Gln | Glu | Ile | His | Ala | Arg | Phe | Arg | Arg |
|-----|-----|-----|-----|-----|-----|-----|-----|-----|-----|-----|-----|-----|-----|-----|-----|
| | | | 20 | | | | | 25 | | | | | 30 | | |

| Gly | Ala | Arg | Ser | Glu | Gly | Asn | Ser | Asp | Cys | Tyr | Phe | Gly | Asn | Gly | Ser |
|-----|-----|-----|-----|-----|-----|-----|-----|-----|-----|-----|-----|-----|-----|-----|-----|
| | | | 35 | | | | | 40 | | | | | 45 | | |

| Ala | Tyr | Arg | Gly | Thr | His | Ser | Leu | Thr | Glu | Ser | Gly | Ala | Ser | Cys | Leu |
|-----|-----|-----|-----|-----|-----|-----|-----|-----|-----|-----|-----|-----|-----|-----|-----|
| | | | 50 | | | | | 55 | | | | | 60 | | |

```
Pro  Trp  Asn  Ser  Met  Ile  Leu  Ile  Gly  Lys  Val  Tyr  Thr  Ala  Gln  Asn
65                       70                  75                           80

Pro  Ser  Ala  Gln  Ala  Leu  Gly  Leu  Gly  Lys  His  Asn  Tyr  Cys  Arg  Asn
               85                       90                       95

Pro  Asp  Gly  Asp  Ala  Lys  Pro  Trp  Cys  His  Val  Leu  Lys  Asn  Arg  Arg
               100                      105                 110

Leu  Thr  Trp  Glu  Tyr  Cys  Asp  Val  Pro  Ser  Cys  Ser  Thr  Ser  Gly  Leu
          115                      120                      125

Arg  Gln  Tyr  Ser  Gln  Pro  Gln  Phe  Asp  Ile  Lys  Gly  Gly  Leu  Phe  Ala
     130                      135                      140

Asp  Ile  Ala  Ser  His  Pro  Trp  Gln  Ala  Ala  Ile  Phe  Ala  Lys  His  Arg
145                 150                      155                           160

Arg  Ser  Pro  Gly  Glu  Arg  Phe  Leu  Cys  Gly  Gly  Ile  Leu  Ile  Ser  Ser
               165                      170                      175

Cys  Trp  Ile  Leu  Ser  Ala  Ala  His  Cys  Phe  Gln  Glu  Arg  Phe  Pro  Pro
               180                      185                      190

His  His  Leu  Thr  Val  Ile  Leu  Gly  Arg  Thr  Tyr  Arg  Val  Val  Pro  Gly
          195                      200                      205

Glu  Glu  Glu  Gln  Lys  Phe  Glu  Val  Glu  Lys  Tyr  Ile  Val  His  Lys  Glu
     210                      215                      220

Phe  Asp  Asp  Asp  Thr  Tyr  Asp  Asn  Asp  Ile  Ala  Leu  Leu  Gln  Leu  Lys
225                      230                      235                      240

Ser  Asp  Ser  Ser  Arg  Cys  Ala  Gln  Glu  Ser  Ser  Val  Val  Arg  Thr  Val
               245                      250                      255

Cys  Leu  Pro  Pro  Ala  Asp  Leu  Gln  Leu  Pro  Asp  Trp  Thr  Glu  Cys  Glu
               260                      265                      270

Leu  Ser  Gly  Tyr  Gly  Lys  His  Glu  Ala  Leu  Ser  Pro  Phe  Tyr  Ser  Glu
          275                      280                      285

Arg  Leu  Lys  Glu  Ala  His  Val  Arg  Leu  Tyr  Pro  Ser  Ser  Arg  Cys  Thr
     290                      295                      300

Ser  Gln  His  Leu  Leu  Asn  Arg  Thr  Val  Thr  Asp  Asn  Met  Leu  Cys  Ala
305                      310                      315                      320

Gly  Asp  Thr  Arg  Ser  Gly  Gly  Pro  Gln  Ala  Asn  Leu  His  Asp  Ala  Cys
               325                      330                      335

Gln  Gly  Asp  Ser  Gly  Gly  Pro  Leu  Val  Cys  Leu  Asn  Asp  Gly  Arg  Met
               340                      345                      350

Thr  Leu  Val  Gly  Ile  Ile  Ser  Trp  Gly  Leu  Gly  Cys  Gly  Gln  Lys  Asp
          355                      360                      365

Val  Pro  Gly  Val  Tyr  Thr  Lys  Val  Thr  Asn  Tyr  Leu  Asp  Trp  Ile  Arg
     370                      375                      380

Asp  Asn  Met  Arg  Pro
385
```

We claim:

1. An isolated DNA encoding a non-glycosylated tissue plasminogen activator (tPA) represented by the following amino acid sequence (I) as its primary structure (SEQ ID NO: 1):

```
                         180
R—  Glu  Gly  Asn  Ser  Asp  Cys  Tyr  Phe  Gly  Asn
                              190
          Gly  Ser  Ala  Tyr  Arg  Gly  Thr  His  Ser
                                                        200
          Leu  Thr  Glu  Ser  Gly  Ala  Ser  Cys  Leu  Pro  Trp
                                             210
                    Asn  Ser  Met  Ile  Leu  Ile  Gly  Lys  Val
                                             220
          Tyr  Thr  Ala  Gln  Asn  Pro  Ser  Ala  Gln  Ala  Leu
                                             230
                    Gly  Leu  Gly  Lys  His  Asn  Tyr  Cys  Arg
```

-continued

```
                        240
Asn  Pro  Asp  Gly  Asp  Ala  Lys  Pro  Trp  Cys  His
                             250
          Val  Leu  Lys  Asn  Arg  Arg  Leu  Thr  Trp
                        260
Glu  Tyr  Cys  Asp  Val  Pro  Ser  Cys  Ser  Thr  Cys
                                       270
                    Gly  Leu  Arg  Gln—Y—
277            280
—X— Gly  Gly  Leu  Phe  Ala  Asp  Ile  Ala  Ser  His
                             290
                    Pro  Trp  Gln  Ala  Ala  Ile
                   300
Phe  Ala  Lys  His  Arg  Arg  Ser  Pro  Gly  Glu  Arg
                                  310
          Phe  Leu  Cys  Gly  Gly  Ile  Leu  Ile  Ser
                        320
Ser  Cys  Trp  Ile  Leu  Ser  Ala  Ala  His  Cys  Phe
                        330
          Gln  Glu  Arg  Phe  Pro  Pro  His  His  Leu
                   340
Thr  Val  Ile  Leu  Gly  Arg  Thr  Tyr  Arg  Val  Val
                             350
          Pro  Glu  Glu  Glu  Glu  Gln  Lys  Phe  Glu
                        360
Val  Glu  Lys  Tyr  Ile  Val  His  Lys  Glu  Phe  Asp
                             370
          Asp  Asp  Thr  Tyr  Asp  Asn  Asp  Ile  Ala
                                  380
Leu  Leu  Gln  Leu  Lys  Ser  Asp  Ser  Ser  Arg  Cys
                        390
          Ala  Gln  Glu  Ser  Ser  Val  Val  Arg  Thr
                        400
Val  Cys  Leu  Pro  Pro  Ala  Asp  Leu  Gln  Leu  Pro
                             410
          Asp  Trp  Thr  Glu  Cys  Glu  Leu  Ser  Gly
                        420
Tyr  Gly  Lys  His  Glu  Ala  Leu  Ser  Pro  Phe  Tyr
```

```
                             430
          Ser  Glu  Arg  Leu  Lys  Glu  Ala  His  Val
                             440
Arg  Leu  Tyr  Pro  Ser  Ser  Arg  Cys  Thr  Ser  Gln
                                  450
          His  Leu  Leu  Asn  Arg  Thr  Val  Thr  Asp
                             460
Asn  Met  Leu  Cys  Ala  Gly  Asp  Thr  Arg  Ser  Gly
                             470
          Gly  Pro  Gln  Ala  Asn  Leu  His  Asp  Ala
                             480
Cys  Gln  Gly  Asp  Ser  Gly  Gly  Pro  Leu  Val  Cys
                             490
          Leu  Asn  Asp  Gly  Arg  Met  Thr  Leu  Val
                             500
Gly  Ile  Ile  Ser  Trp  Gly  Leu  Gly  Cys  Gly  Gln
                             510
          Lys  Asp  Val  Pro  Gly  Val  Tyr  Thr  Lys
                             520
Val  Thr  Asn  Tyr  Leu  Asp  Trp  Ile  Arg  Asp  Asn
                                       527
                                       Met  Arg  Pro
``` wherein R is Ser.

X is -lys-, and

Y is -TyrSerGlnProGlnPheArgIle-(SEQ ID NO: 3) or -TyrSerGlnProGlnPheAspIle-(SEQ ID NO: 4).

2. A recombinant expression vector comprising the DNA of claim 1.

3. A transformant comprising the expression vector of claim 2.

4. A process the production of tissue plasminogen activator (tPA) which comprises culturing a host cell transformed with the expression vector of claim 2 in a culture broth and recovering the resultant tPA from the broth.

* * * * *